(12) United States Patent
Trudeau et al.

(10) Patent No.: US 9,216,098 B2
(45) Date of Patent: Dec. 22, 2015

(54) INTERVERTEBRAL DISC SPACE SIZING TOOLS AND METHODS

(75) Inventors: Jeffrey L. Trudeau, Marquette, MI (US); Thomas S. Kilpela, Marquette, MI (US); Qi-Bin Bao, Marquette, MI (US); Weston Pernsteiner, Marquette, MI (US)

(73) Assignee: PIONEER SURGICAL TECHNOLOGY, INC., Marquette, MI (US)

( * ) Notice: Subject to any disclaimer, the term of this patent is extended or adjusted under 35 U.S.C. 154(b) by 1090 days.

(21) Appl. No.: 12/368,964

(22) Filed: Feb. 10, 2009

(65) Prior Publication Data

US 2009/0182343 A1 Jul. 16, 2009

Related U.S. Application Data

(63) Continuation-in-part of application No. PCT/US2007/075612, filed on Aug. 9, 2007.

(60) Provisional application No. 60/846,859, filed on Sep. 22, 2006, provisional application No. 60/826,864, filed on Sep. 25, 2006, provisional application No. 60/822,027, filed on Aug. 10, 2006, provisional application No. 61/118,904, filed on Dec. 1, 2008.

(51) Int. Cl.
*A61F 2/46* (2006.01)
*A61B 17/02* (2006.01)
*A61F 2/44* (2006.01)

(52) U.S. Cl.
CPC ....... *A61F 2/4657* (2013.01); *A61B 2017/0256* (2013.01); *A61F 2/44* (2013.01); *A61F 2002/4658* (2013.01); *A61F 2002/4666* (2013.01)

(58) Field of Classification Search
CPC .......... A61F 2/4657; A61F 2002/4658; A61B 19/46; A61B 17/025; A61B 2017/0256; A61B 2017/0262; A61B 2017/0268; A61B 2017/0275
USPC .......... 623/17.14, 17.16, 11.11, 13.11, 13.12, 623/13.13, 17.11, 17.13, 17.15; 403/16; 600/201–249; 606/99, 102, 86 R, 1, 87, 606/88, 90
See application file for complete search history.

(56) References Cited

U.S. PATENT DOCUMENTS 3,196,463 A * 7/1965 Farneth ........................... 623/49
3,969,773 A * 7/1976 Menschik .................. 623/20.24

(Continued)

*Primary Examiner* — David Bates
*Assistant Examiner* — Samuel Hanna
(74) *Attorney, Agent, or Firm* — Fitch, Even, Tabin & Flannery LLP

(57) ABSTRACT

A method and apparatus for making a size measurement within an intervertebral space by placing an expandable and contractible device into the intervertebral space, expanding the device, measuring a size characteristic of the space, contracting the device and then removing it. The measurement may be accomplished by an external x-ray or other imaging device imaging the expanded device in situ or by mechanically operated devices. An expansion and contraction mechanism such as fluid containing bladder or mechanically shifted members expands the device which later contracts in a controlled manner to the contracted size. An apparatus and method is provided for the measuring of the intervertebral space at a controlled distraction force. The apparatus includes an expandable device for providing a measurement within the intervertebral space and facilitating the measurement of the angulations of the lordotic curve of the intervertebral space.

10 Claims, 75 Drawing Sheets

(56) References Cited

U.S. PATENT DOCUMENTS

| | | | |
|---|---|---|---|
| 5,213,112 A * | 5/1993 | Niwa et al. | 600/587 |
| 5,597,379 A * | 1/1997 | Haines et al. | 606/80 |
| 5,681,316 A * | 10/1997 | DeOrio et al. | 606/88 |
| 5,931,777 A * | 8/1999 | Sava | 600/213 |
| 6,022,377 A * | 2/2000 | Nuelle et al. | 606/90 |
| 6,500,132 B1 | 12/2002 | Li | |
| 6,533,799 B1 | 3/2003 | Bouchier | |
| 6,575,975 B2 | 6/2003 | Brace et al. | |
| 6,669,697 B1 | 12/2003 | Pisharodi | |
| 7,264,621 B2 | 9/2007 | Coates et al. | |
| 2002/0143319 A1 * | 10/2002 | Brock | 606/1 |
| 2003/0069586 A1 | 4/2003 | Errico et al. | |
| 2003/0220691 A1 * | 11/2003 | Songer et al. | 623/17.14 |
| 2003/0236520 A1 * | 12/2003 | Lim et al. | 606/61 |
| 2004/0186579 A1 * | 9/2004 | Callaway et al. | 623/19.14 |
| 2005/0070918 A1 * | 3/2005 | Zwirnmann et al. | 606/104 |
| 2005/0228501 A1 * | 10/2005 | Miller et al. | 623/17.14 |
| 2006/0069436 A1 | 3/2006 | Sutton et al. | |
| 2006/0155295 A1 * | 7/2006 | Supper et al. | 606/90 |
| 2006/0247657 A1 | 11/2006 | Trieu | |
| 2007/0093838 A1 | 4/2007 | Khodadadyan-Klostermann et al. | |
| 2007/0191954 A1 * | 8/2007 | Hansell et al. | 623/17.15 |
| 2007/0213641 A1 | 9/2007 | Francis | |
| 2007/0233143 A1 * | 10/2007 | Josse et al. | 606/90 |
| 2008/0015597 A1 | 1/2008 | Whipple | |
| 2008/0114367 A1 * | 5/2008 | Meyer | 606/90 |
| 2008/0288073 A1 * | 11/2008 | Renganath et al. | 623/17.12 |

* cited by examiner

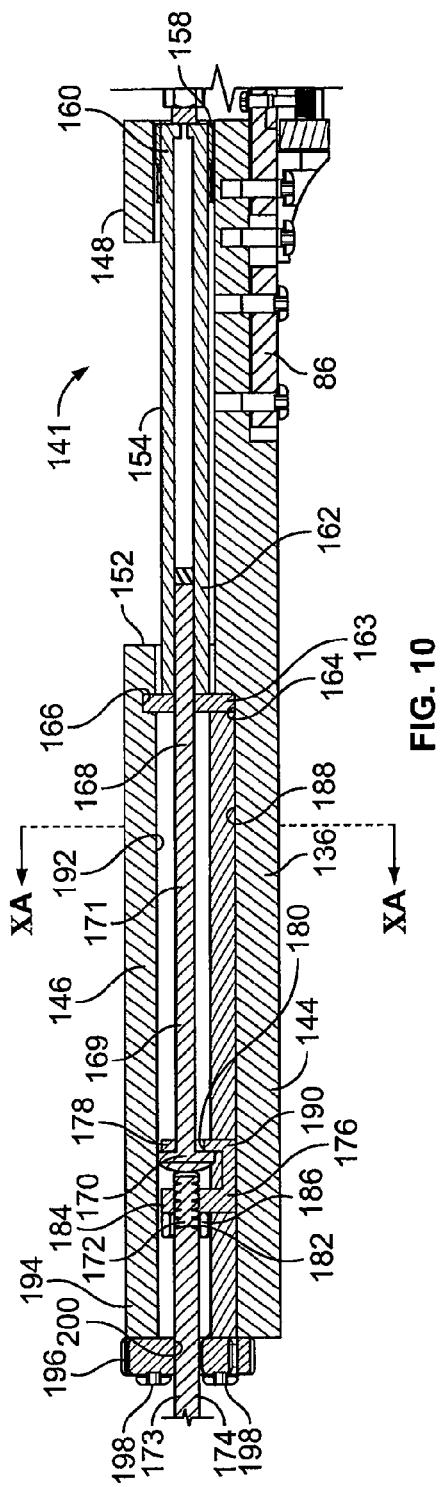
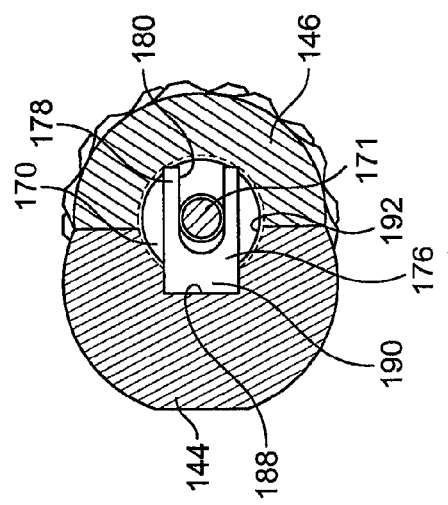
FIG. 10
FIG. 10A

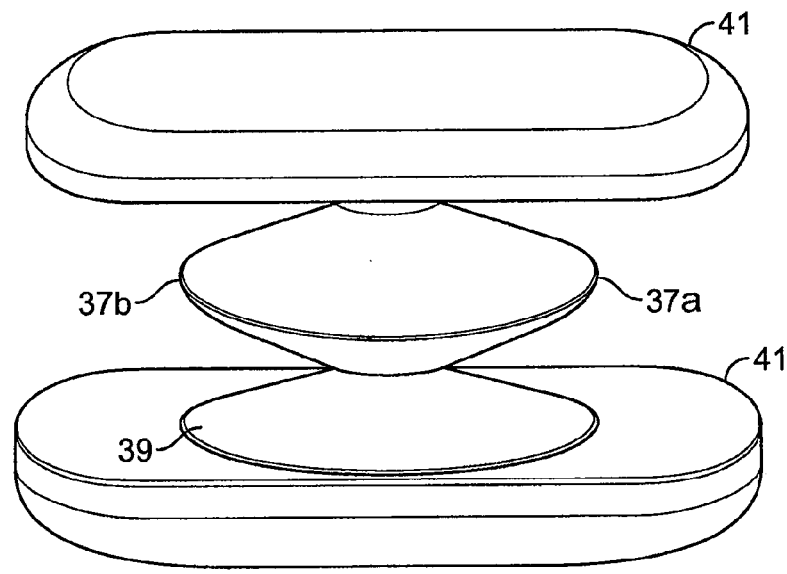
FIG. 13
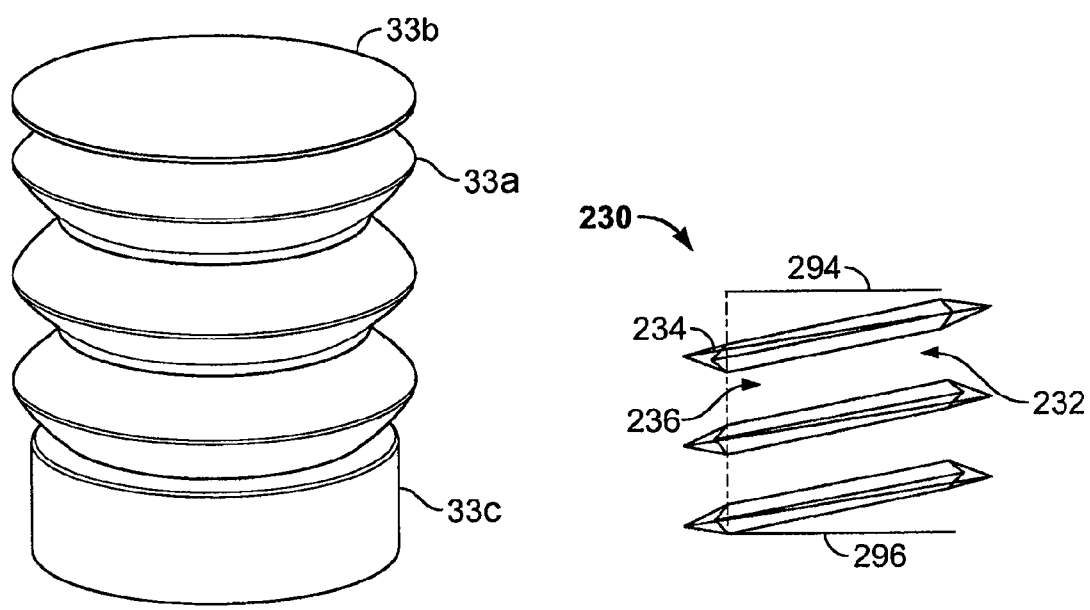
FIG. 14
FIG. 15

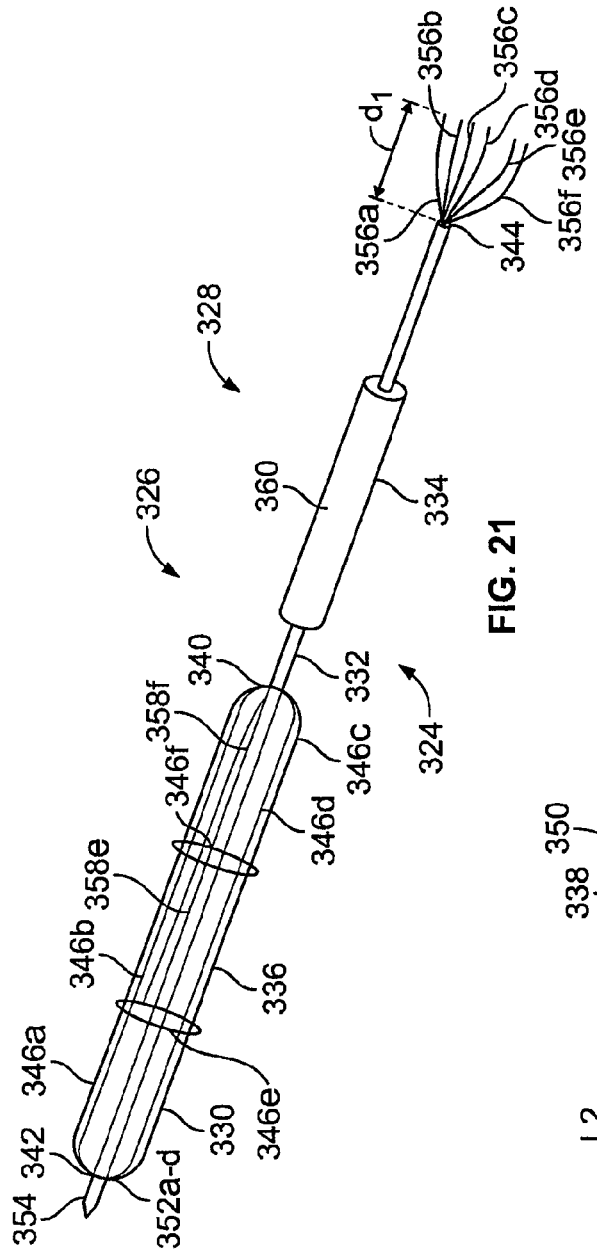
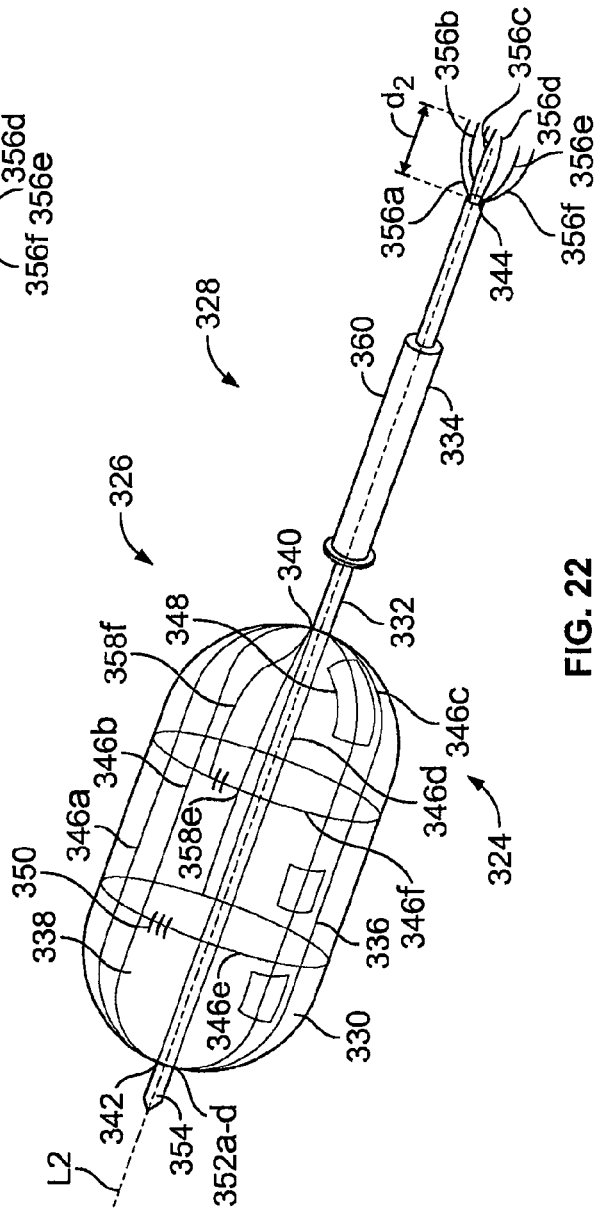
FIG. 21
FIG. 22

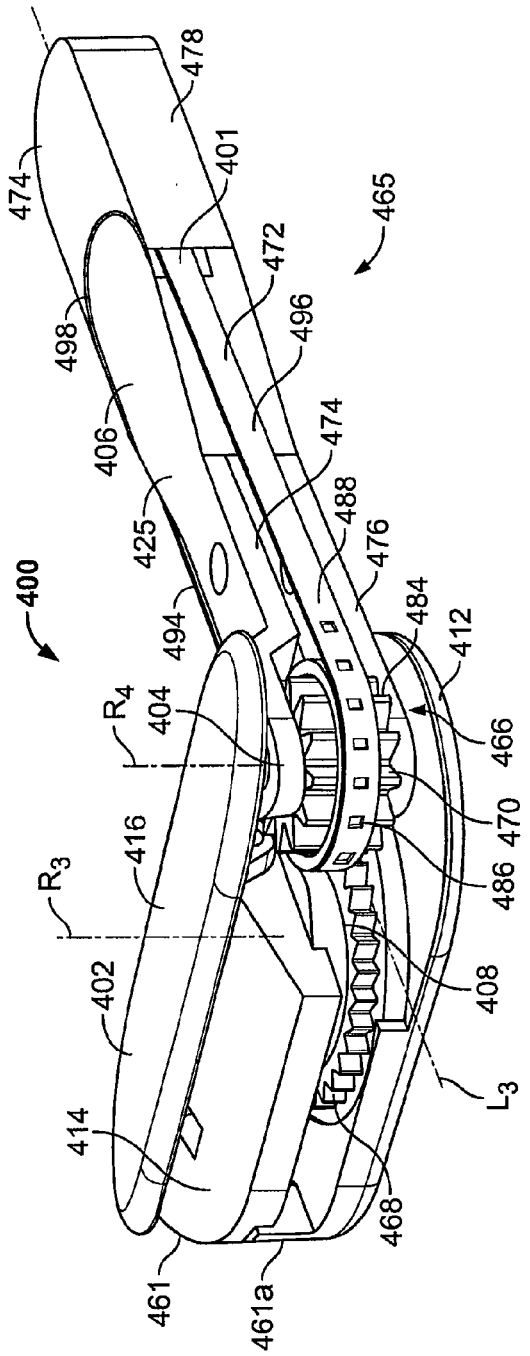
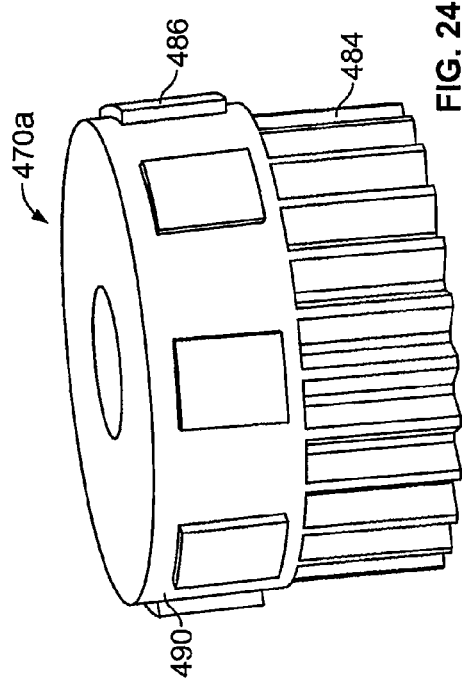

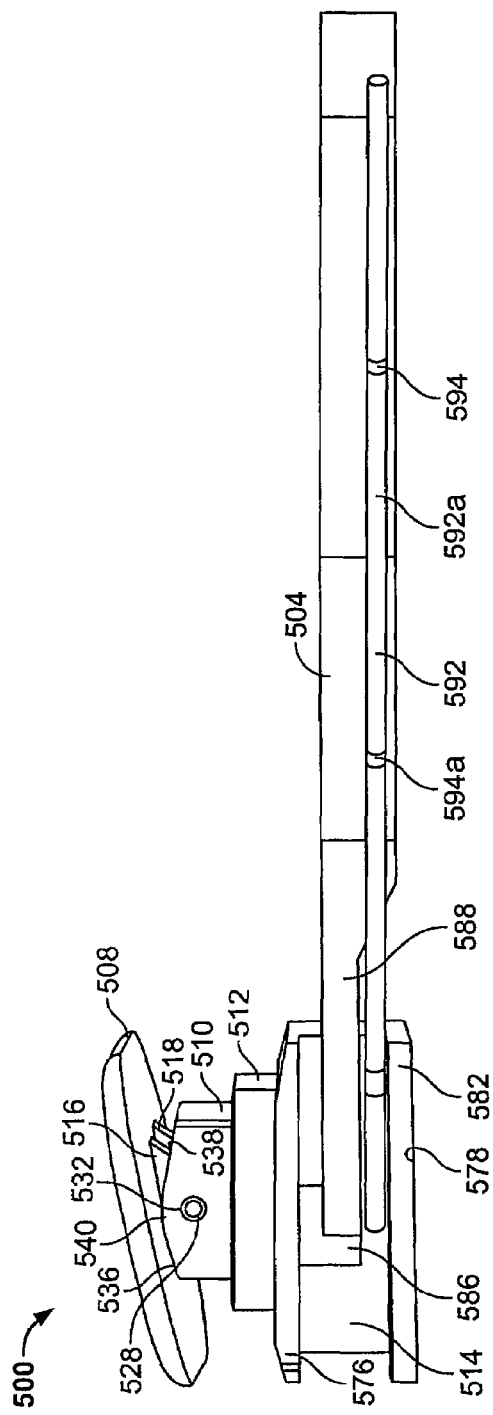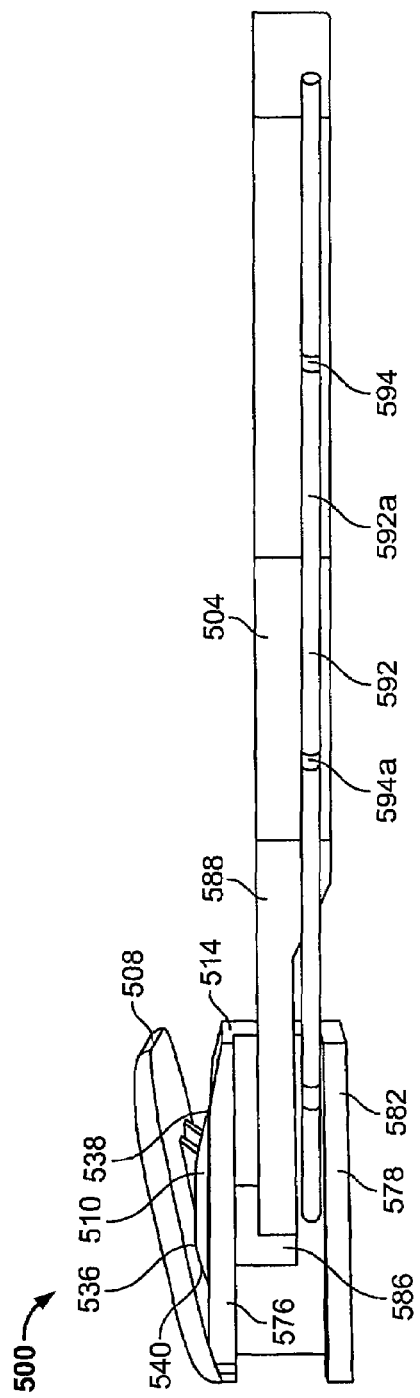

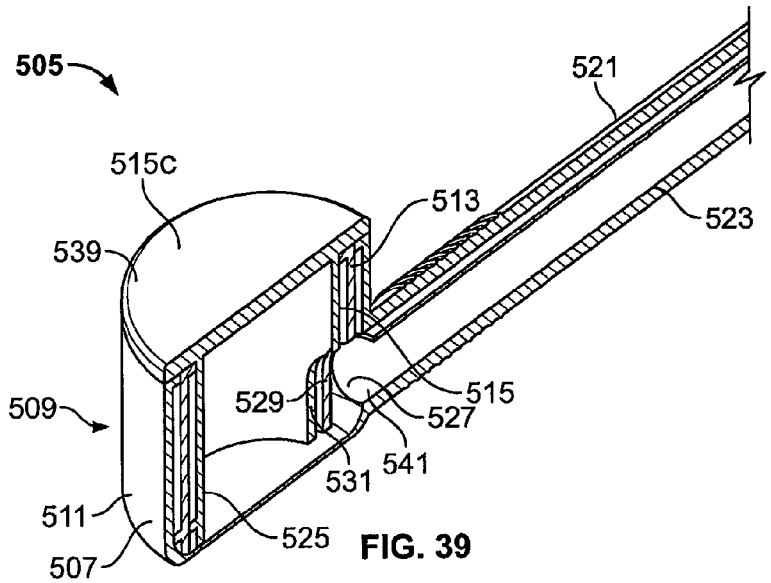
FIG. 39
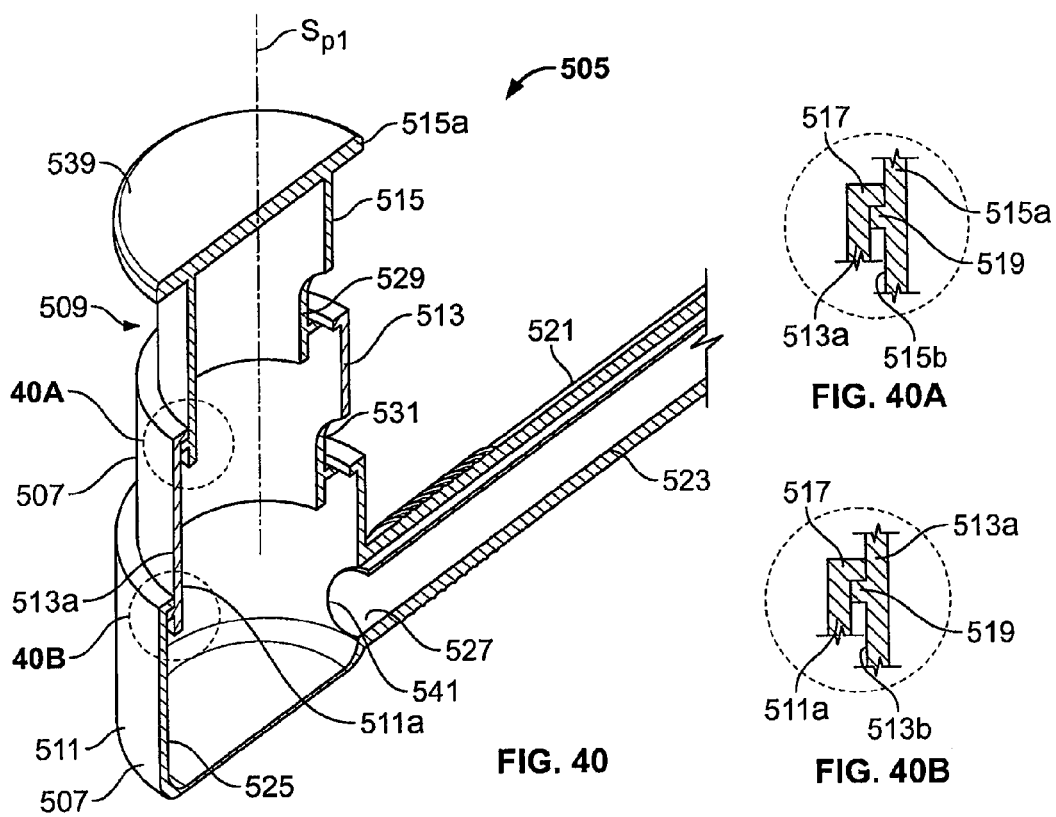
FIG. 40
FIG. 40A
FIG. 40B

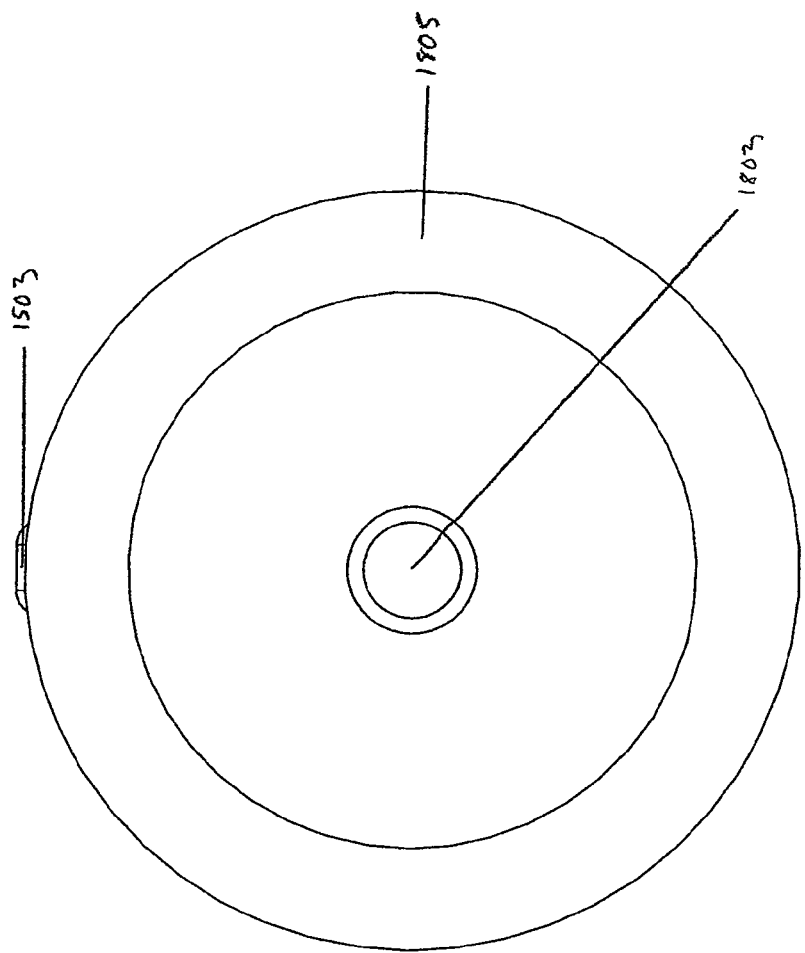
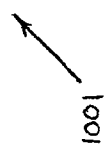
FIG. 88

INTERVERTEBRAL DISC SPACE SIZING TOOLS AND METHODS

This application is a continuation-in-part of PCT Application No. PCT/US2007/075612, filed Aug. 9, 2007, which claims priority to U.S. Provisional Patent Application No. 60/846,859, filed Sep. 22, 2006, No. 60/826,864, filed Sep. 25, 2006, and No. 60/822,027, filed Aug. 10, 2006, all of which are incorporated herein by reference in their entirety. This application also claims the benefit of U.S. Provisional Patent Application No. 61/118,904, filed Dec. 1, 2008, which is incorporated herein by reference in its entirety.

FIELD OF THE INVENTION

The present invention relates to sizing tools used to measure the space between vertebrae for placement of artificial implants therebetween, and in particular, to sizing tools that can expand within an intervertebral space and methods for their use.

BACKGROUND OF THE INVENTION

The most common orthopedic condition for which professional medical treatment is sought is lower back pain. Although many factors may be responsible for causing lower back pain, a principal factor is damage or degeneration of an intervertebral spinal disc resulting in impingement on the nerve system, specifically the spinal cord, located within the spine. Such impingement may result in, for instance, loss of mobility, urinary and fecal incontinence, and sciatica or pain experienced in the extremities.

Damage to or degeneration of a spinal disc can result from a number of factors such as abuse or age. The disc itself is composed primarily of an annulus and a nucleus contained therein. The annulus is a fibrous annular piece that connects to the adjacent vertebrae and contains the nucleus, which is in turn a gel-like viscous material capable of shock absorption and flowable to permit poly-axial rotation and resilient compression of the vertebrae and spine. Most frequently, disc degeneration results from damage occurring to the annulus such that the flowable nucleus material may leak or seep out of the annulus. Disc degeneration also can occur in other ways, such as by being deprived of nutrient flow leading to a dried disc susceptible to damage. Because the nuclear material is flowable, extensive damage to the annulus is not necessary for leakage to occur.

Currently, approaches to treatment of spinal problems directly affecting the spinal cord are numerous. For instance, immobilization and high doses of corticosteroids may be employed. The dominant surgical procedures for treatment of these problems are spinal fusion and discectomy. Fusion is a method where adjacent vertebrae are immobilized so that they permanently secure to each other by having bone growth between and to the vertebrae, while discectomy involves removal of a portion or an entirety of a spinal disc.

However, the current practice of each of these procedures typically has certain limitations. With fusion, making a portion of the spine generally rigid produces a reduction in mobility, and drastically alters normal load distribution along the spinal column. Due to these factors, the non-fused portions of the spine experience stress and strain that are significantly increased over normal physiological motions. The increased stress and strain on the non-fused portions may lead to accelerated disc degeneration of the non-fused portions, particularly the adjacent levels of the spine.

Discectomy is effective for relieving sciatic pain by removing the damaged or herniated disc tissue compressing the spinal nerves. However, current discectomy often may lead to a reduction of the disc space between adjacent vertebrae, as well as instability in the affected portion of the spine. Such long-term effects with current discectomy often result in further surgery several years after the initial discectomy surgery.

In an alternative spinal surgery, a disc arthroplasty restores or reconstructs the disc using a prosthesis to replace a portion or entirety of the damaged disc. The primary objective of disc arthroplasty is to restore or maintain the normal disc anatomy and functions, while addressing and treating the causes of the pain. However, prosthetic disc implants have problems due to the complexity of the natural disc structure and biomechanical properties of a natural spinal disc. As used herein, the term natural refers to normal tissue including portions of the spine and the disc.

Two types of prostheses for disc arthroplasty are currently believed to merit further development by medical science and research. One type is a total disc prosthesis, or TDP, where the entire spinal disc is replaced after radical discectomy. A typical TDP includes structures that attempt to together mimic the properties of a natural disc.

The other type is a disc nucleus prosthesis, or DNP, that is used to replace only the nucleus of a spinal disc after a nucleotomy while retaining the annulus of the disc and, possibly, the endplates intact. As discussed above, failure of the natural disc does not require extensive damage to the annulus. An undamaged annulus, however, would often be capable of retaining a non-flowing prosthetic nucleus. Implantation of a DNP involves making a small incision in the annulus, clearing of the natural nucleus from the annulus through the procedure known as nucleotomy, and inserting the DNP through, and then within, the annulus. Accordingly, DNPs are typically smaller and require less extensive surgery than TDPs while still mimicking some of the biomechanical properties of a natural intervertebral disc.

Implantation of most DNPs with pre-formed dimensions requires a 5-6 mm, or larger, incision in the annulus for implantation and uses minimal disc tissue resection. Moreover, recovery and post-surgical pain are minimal due to the minimal invasiveness of the procedure, and interbody fusion remains a viable revision surgery. In addition, the incision in the annulus is kept as small as possible to minimize the potential for the implant to back out through the incision. The annulus itself is used to at least aid in maintaining the implant within the nuclear space. This permits the DNP to sit in the intervertebral space without anchors that violate the endplates of the vertebrae. As the annulus does not heal well and suturing the annulus is difficult due to its tissue properties, once the incision is too large, the ability of the annulus to retain the implant is diminished if not eliminated.

The risk of enlarging the incision on the annulus in the DNP procedure is increased because sizing tools are typically also placed through the incision. The size of the implant should match the size of the natural disc and/or nuclear cavity (i.e. the height of the space between adjacent vertebrae and the width and length dimensions or the footprint of the space within the annulus). If the implant is too large or too small, the implant may cause damage to the spine or pain to the patient. In order to determine the size of the nuclear cavity, conventional sizing tools such as a set of trial spacers disclosed by U.S. Pat. No. 6,478,801 are used. Each spacer has a different size and is sequentially inserted in the nuclear space in trial and error fashion until the trial spacer fits the nuclear space which indicates the correct size of implant that should be used. Moving trial spacers in and out of the nuclear cavity numerous times, however, creates further risk of enlarging the incision or damaging the annulus, vertebral endplates and/or even other tissue around the spine whether or not the annulus is present. Also with this procedure, the surgeon wastes time by choosing and obtaining a different trial spacer multiple times and then inserting each trial spacer into the nuclear space. Thus, a need exists for a sizing tool that need not be inserted into a nuclear space multiple times in order to obtain the dimensions of the nuclear space.

Other improvements specifically for the DNP procedure would be desirable. As mentioned above, a DNP requires less extensive surgery than for a TDP since it replaces only part of the disc. Implantation of most known DNPs with pre-formed dimensions generally requires a 5-6 mm, or larger, incision in the annulus for implantation. The incision, however, should be kept as small as possible to hold the DNP within the annulus without using anchors on the DNP that extend into the endplates of the vertebrae for securing the DNP. The minimal invasiveness of the procedure results in minimal recovery and post-surgical pain, and interbody fusion remains a viable revision surgery. Thus, maintaining a small incision and keeping damage to the annulus to a minimum is a high priority. Therefore, it would be desirable to provide a DNP and trial spacer that does not require an enlarged incision and does not significantly damage the annulus or other tissue during insertion and placement of the DNP.

Other problems relate to the geometry of the intervertebral nuclear space. A natural nuclear space within the annulus has a length in the lateral direction (orthogonal to the anterior-posterior direction) that is longer than the width of the space in the anterior-posterior direction. Since it would be desirable to have the sizing tool as well as the implant match the shape of the nuclear space, some conventional sizing tools or implants are generally rectangular, oval or obround with a length greater than its width in order to more closely fit the nuclear space. In this case, the short or narrow side of the sizing tool or implant is presented as the leading edge for insertion (i.e. it faces the incision) in order to maintain a reduced incision on the annulus. This frequently requires an anterior-lateral approach to the surgical site which requires a general surgeon's service, typically in conjunction with an orthopedic surgeon or neurosurgeon, or both, which then raises the costs of the procedure.

A posterior or posterior-lateral approach, while less costly, does not typically permit the access required for inserting sizing tools, removal of the natural disc and implantation of the prosthetic device because the geometry and structure of the spine blocks or fills the path to the nuclear space that is needed for the approach. This is especially true for a sizing tool as described where the sizing tools long side would need to be presented first for insertion and extraction from a posterior approach. Therefore, a need exists for a sizing tool that is not limited to particular surgical approaches.

Some implants utilize an inflatable bladder or balloon-like structure as disclosed by U.S. Patent Publication No. 2004/0133280. These inflated structures, however, are not configured to be deflated in any controlled manner. Uncontrolled collapse of an inflated body within an annulus may result in a deflated structure that is too large or irregularly shaped to be retracted through the incision without enlarging the incision or damaging the annulus or other tissue.

Another problem occurs when the top or bottom end of a sizing tool does not match the geometry of the endplates on the opposing vertebrae which may be slanted to align with the lordotic or kyphotic curve of the spine. When a mismatch occurs, such as when the top plate of a sizing tool remains horizontal while the endplate of a vertebrae it faces is slanted, measurement readings of the height of the nuclear space may be inaccurate.

SUMMARY OF THE INVENTION

In accordance with the embodiments illustrated herein, an intervertebral space sizing method and apparatus for measuring within the intervertebral space comprises placing an expandable and contractible device into the intervertebral space and measuring a characteristic of the space using an expandable device in an expanded size and then contracting the device to a contracted size and removing it from the intervertebral space. Preferably, the expandable, contractible device is shifted to an expanded size or position, e.g., in the superior-inferior direction relative to the intervertebral space, so that the device abuts adjacent vertebrae in order to determine the distance from one vertebra to the other. In accordance with a further aspect, the expandable device is configured to measure the width or footprint of the intervertebral space or an angle of the endplate of a vertebra. The device is contracted after the measuring operation to a smaller size to be removed to lessen any damage during the withdrawal operation. A holder or support for the device is held by the surgeon to insert and remove the device. Although the intervertebral space being measured may be with or without an annulus forming a nuclear space within the annulus, the device is particularly useful for being inserted and removed through a small incision in the annulus used to remove the disc.

In the illustrated embodiments, expansion and contraction mechanisms that expand the expandable devices are configured to operate without pressing harmfully against anatomical structure such as the vertebrae, annulus or an incision on the annulus the sizing tool extends through. More specifically, it is desired that potentially harmful lateral motion of the expansion and contraction mechanism at the annulus and intervertebral space and relative to the longitudinal axis of the holder is eliminated or minimized. The expansion and contraction mechanisms are provided with a number of different configurations. For example, some have fluid delivery systems that have passageways such as tubes extending into the intervertebral space for filling the expandable device with fluid to expand it while others have axially shifting members or shafts that are operated to expand the expandable device within the intervertebral space. The members or shafts all translate longitudinally relative to the holder and while extending into an intervertebral space and also, when present, through an incision on an annulus to minimize damage to the incision, annulus or other tissue.

Once the expandable device is within the nuclear space, in the preferred method, the expandable and contractible device is oriented with its longitudinal axis extending laterally relative to the anterior-posterior direction to match the orientation of the nuclear space or the removed natural nuclear disc to obtain a more accurate measurement of the intervertebral space. In an illustrated embodiment, this is achieved by turning the device when it is entering the intervertebral space to place it in the desired orientation just mentioned. Preferably, a steering mechanism for the expandable device turns, e.g., pivots the device relative to the distal end of the holder, and this permits a surgeon to insert the expandable device 20 through an incision in the disc annulus, when the annulus is present, from any convenient surgical approach. A passive steering without a steering mechanism may also be used for the device.

In accordance with a further aspect, a measuring device is associated with the tool for measuring a space characteristic within the intervertebral space and this measuring may be accomplished with the use of imaging techniques such as x-ray, MRI, fluoroscopic or similar techniques that provide a measurable image of the expansion of the expandable device while it is positioned within the intervertebral space. In other embodiments, the pressure or volume of a fluid delivered to the expandable tool is measured to obtain a size characteristic of the intervertebral space. In further embodiments, the measuring device uses an axially shifting elongate member and the axial distance the elongate member shifts during expansion of the device corresponds to the amount the superior and inferior portions distracted in the intervertebral space. Other measuring devices and techniques may be used to measure the footprint of the space and the angle of a vertebrae endplate.

Preferably, the holder on all of the sizing tools remains connected to the expandable device so that the expandable device can be retracted from the intervertebral space after a space characteristic is measured. The expandable device is collapsed to retract it so that the expandable device fits through an annulus incision. Even if the annulus is not present, it is easier to retract the expandable device when it is collapsed. The vertebrae forming the intervertebral space apply pressure against the expandable device that could retain the expandable device within the intervertebral space. This pressure is reduced or eliminated when the expandable device is collapsed.

In the illustrated embodiment, the preferred expandable devices are configured to provide a controlled collapse into a predetermined collapsed configuration. The predetermined collapse configuration encloses whatever expansion structure the expandable device uses in order to present smooth, continuous outer surfaces on the expandable device that minimize damage to surrounding tissue during insertion and retraction into the intervertebral space. This is particularly helpful when inserting and retracting through an incision in the annulus such that the collapsed configuration of the expandable device fits through the annulus incision. In order to achieve the collapsed configurations, the expandable devices preferably have structure that connects the superior and inferior portions to each other while maintaining the superior and inferior portions laterally aligned along a common axis as the expandable device is expanded or collapsed. Thus, the sizing tool has fluid receiving expandable devices with inflatable bodies such as bladders, bellows or reinforced balloons configured to collapse while remaining aligned along a superior-inferior axis. Some of the size tools have and employ fluid receiving expandable devices with pistons that remain concentrically located on a superior-inferior axis as they collapse. Other sizing tools have and employ threaded parts connecting the superior and inferior covers to each other and that engage concentrically about the superior-inferior axis to maintain the covers along the axis. Still other sizing tools have and employ pivoting links to hold the superior and inferior portions of the expandable and contractible device in alignment or they have and employ structure on the holders to retain the expandable devices in an alignment along a superior-inferior axis.

The preferred shape of the expandable and contractible devices is obround, race-track shaped or oval to more closely match the configuration of a natural disc and a nuclear space between the vertebrae. To minimize the required size of the annulus incision, the expandable device may have an elongated shape having a narrow, distal, longitudinal end that is used to face the annulus incision and lead the expandable device as it is inserted through the incision and into a nuclear space. Preferably, the expandable device is inserted into the nuclear space while it is held on the holder in a straight, insertion or 0 degree orientation where the longitudinal axis of the expandable device extends generally parallel to a longitudinal axis of the holder to position the lead end in front of the holder. This orientation forms a generally linear configuration for the sizing tool to minimize contact with anatomical structure as the sizing tool is advanced forward to advance the expandable device into the intervertebral space.

In another aspect of the invention, a number of the sizing tools may be provided with at least passive steering but more preferably active steering of the expandable device within the intervertebral space. Preferably, the user advances the holder to press the expandable device against the back of annulus or other tissue to pivot the expandable device about the end of the holder and into the desired position. Since passive steering may damage the annulus, however, the sizing tools are preferably provided with steering mechanisms for active steering of the expandable device, as explained above. For active steering, a member pushes or pulls on a side of the expandable device while the expandable device is adjustably or pivotally held at the distal end of the holder in order to pivot the expandable device. This reduces the need to press against the back of an annulus as with passive steering.

In order to minimize the risk of damaging the annulus, annulus incision or other tissue such as the vertebrae, the steering mechanism is also configured to shift axially relative to the holder rather than laterally which could press the steering mechanism against the anatomical structure just mentioned. The steering mechanism is described in further detail below with the specific embodiments.

It will be understood that a surgeon may use both active and passive steering to pivot the expandable device. Although passive steering raises the risk of damaging an annulus, using passive steering by simply advancing the sizing tool against the annulus can be generally faster than carefully using the steering mechanism to actively pivot the expandable device. For this reason, the surgeon may use a compromise and may use passive and active steering simultaneously by pushing the expandable device against the annulus or other tissue to turn the expandable device as the surgeon also operates the steering mechanism to pivot the expandable device.

Optionally, the surgeon may use the steering modes consecutively such as by first using the steering mechanism to initially pivot the expandable device in an initial angle such as up to 45 degrees to the left or right and relative to the longitudinal axis of the holder. This initially points the expandable device toward the side of the holder it needs to turn to. Then, when less force will be applied orthogonally to a wall of the annulus due to the initial, pivoted position of the expandable device, the surgeon uses passive steering and pushes the expandable device against the annulus or other tissue to pivot the expandable device to the desired final angle.

The preferred sizing tool and method of operation employs an elongated holder having an external end gripped by the surgeon used at a location outside of the person's body and a distal end comprising the expandable and contractible device to insert and remove it from the intervertebral space. The holder may also vary the expansion and contraction device which is operated at the external device. Further, the preferred holder also carries a steering mechanism to orient the device such as by pivoting the same to turn an elongated shape of the device to the desired orientation for measuring. Herein, the longitudinal axis of the holder and the longitudinal axis of the elongated-shaped device are parallel or aligned during insertion, particularly through an incision in the annulus, and then the elongated-shaped device is turned to be at an angle to the holder when in its measuring position.

In one form, the present invention includes an intervertebral space sizing system including a sizing tool that has a holder with a distal end and an expandable device pivotally mounted on the distal end to measure an intervertebral or nuclear space. A steering mechanism on the sizing tool is connected to the expandable device to pivot the expandable device once it is located within the nuclear space in order to properly position it in the space.

In a preferred form, the expandable device is race-track shaped, oval or other similar elongated shape with a narrow end and elongated longitudinal sides. In order to maintain a small incision on an annulus, the narrow end is positioned as the leading end via the steering mechanism to face an incision in an annulus for insertion of the expandable device through the incision. If the surgeon uses a non-lateral surgical approach, once the expandable device is inserted through the incision, the steering mechanism on the sizing tool is operable outside the nuclear space to redirect the expandable device in the nuclear space, as by pivoting thereof, and relative to the distal end of the holder so that ultimately the longest dimension of the expandable device extends generally orthogonally to the posterior-anterior direction (i.e. laterally) to better correspond to the orientation of the nuclear space and natural disc that previously occupied the space. Once located within the space, the expandable device is expanded and then a measurement is taken to determine the size of the nuclear space as explained in detail below. The process is controllably reversed to retract the expandable device.

One embodiment of the steering mechanism has the expandable device pivotally mounted on the distal end of the holder to provide passive steering where the expandable device can be steered simply by pushing the expandable device against the back wall of the annulus or other anatomy around the nuclear space. In this case, the expandable device and distal end of the holder have cooperating structure such as an aperture on the expandable device that receives a boss on the distal end of the holder so that the expandable device pivots about the boss as the expandable device is pushed against the annulus.

Active steering, however, reduces the risk of damage to the annulus or other tissue by minimizing or eliminating the need to engage the annulus or other tissue to pivot the expandable device. To provide active steering where a component on the sizing tool pulls or pushes the expandable device to pivot it, the steering mechanism has an actuator connected to the expandable device such as a longitudinally translating steering shaft (longitudinal being relative to the longitudinal axis of the sizing tool) extending from the holder and to the expandable device so that moving the shaft axially rotates the expandable device. The expandable device is pivotally mounted about a boss on the distal end of the holder as with the passive steering mentioned above while the shaft is separately connected to the expandable device in order to push or pull the expandable device about the boss. To perform this, the expandable device has a slot with a predetermined orientation and that receives a pin on a distal end of the steering shaft so that the longitudinal motion of the steering shaft causes the pin to cam against an edge of the slot to pivot the expandable device about the pin as the pin shifts along or advances in the slot. This camming action also causes the expandable device to pivot about the boss holding the expandable device. The steering mechanism has a steering control device on the holder and connected to the steering actuator so that operating the control device steers the expandable device. The control device has a screw with a head used as the knob of the control device while the screw's shank extends parallel to the steering shaft and is threaded to a collar fixed on the steering shaft. So configured, adjusting the knob translates the steering shaft.

In another aspect of the invention, the expandable device has an expanded configuration for measuring the nuclear space and a collapsed configuration for insertion into, and extraction from, the nuclear space. More particularly, the expandable device is maintained in its collapsed configuration while it is inserted through the incision on the annulus and into the nuclear space. Once within the nuclear space, the expandable device is then expanded, measured or photographed in its expanded configuration to determine the size of the nuclear space, and then collapsed for retraction out of the nuclear space and back through the incision. Thus, the measurement is performed with a single insertion of the sizing tool into the intervertebral space which reduces the risk of enlarging or damaging the annulus or other tissue and eliminates the need to insert trial spacers multiple times into the nuclear space.

The present invention includes a number of alternative configurations for the sizing tool in order to accomplish the expansion of the expandable device. One preferred configuration includes an actuator such as a fluid delivery system with a fluid supply connected to an expandable device for expanding or evacuating an expandable, fluid-holding body or chamber on the expandable device to respectively expand or collapse the expandable device.

The fluid-holding body may be generally cylindrical, expandable bellows, balloons, or pistons. Most of these configurations have the expandable body disposed between a bottom member or cover connected to a distal end of a holder on the sizing tool and a top member or cover aligned with the bottom cover so that expanding the body distracts or shifts the top and bottom covers away from each other along a common axis and collapsing the expandable body shifts the top and bottom covers toward each other. In a collapsed configuration, the expandable device preferably forms a generally smooth or continuous outer surface that generally encloses the expandable body between the top and bottom covers and can easily pass an annulus or other anatomy without hooking, snagging, or catching on any of the anatomical structure.

Bellows or balloons with exterior stabilizing threads may be used to control the collapse of the expandable device. The bellows have an inner array of joints connected by folds to an outer array of joints. For circular bellows, the inner joints have a shorter uniform radius than a uniform radius of the outer joints where both radii extend from a central axis of the bellows. The joints in each array are positioned directly over each other, and the bellows controllably expand or collapse by bending at their joints so that the folds remain radially aligned with each other. This is due to the positioning of the joints and the stiffness of the folds which are made of a metal or a hard polymer that retains the joints at the uniform radii. Thus, the bellows cause one fold to lay upon the next adjacent fold when collapsed and retains the folds between the top and bottom covers so that the bellows cannot bend or entangle with other parts of the expandable device or any anatomical structures. This also applies for non-circular bellows such as generally elongate or obround bellows.

Similarly, an external, relatively rigid, spiraling or coiled thread on a cylindrical balloon causes the balloon to collapse so that one layer of the thread lays on the next layer of the thread like a coil spring. So configured, the thread retains the balloon in a generally cylindrical configuration when the balloon is collapsed. The bellows and balloons have bodies that are fluid-tight with one opening for a tube that injects or evacuates the fluid from the fluid delivery system as explained below.

In one alternative structure, a rigid, outer wall on the expandable device may be placed around at least a portion of the balloon instead of having an external thread on the balloon so that the collapsed form of the balloon is not controlled. The outer wall encloses the space between the top and bottom covers so that the expandable device has a leading distal end with a generally continuous or uninterrupted, outer, curved surface for facing an incision on an annulus and for inserting the expandable device through the incision. Since the balloon is mainly held within the outer rigid wall, it cannot interfere with the annulus or other anatomical structure.

In another alternative expandable device that uses fluid to expand it, a balloon is used as a mold to form an annular wall made of a curable material within the intervertebral space and that has a height that represents the height of the intervertebral space once cured. The annular wall is made of a compressible polymer so that it can be removed from the intervertebral space, and the annular wall is shape-retentive so that it regains the shape it had within the intervertebral space after its removal therefrom. The height of the wall can then be conveniently measured outside of the human body by rulers, gauges or imaging techniques.

More specifically, the expandable device has an outer torroidal balloon that encircles an inner balloon that is filled with fluid to act as a mold for forming the annular wall either within the outer torroidal balloon or alternatively in an annular space between the inner and outer balloons. When the annular wall is to be placed between the inner and outer balloons, both balloons are filled with fluid before the wall is formed so that both balloons act as a mold for forming opposite sides of the wall. Depending on the form mentioned, either the outer balloon or the space between the balloons is then filled with an elastic curable material such as a polymer. Once cured, the material forms an elastic, shape-retentive, annular wall that is sufficiently flexible to be removed from the human body or intervertebral space. Whichever balloons are filled with fluid are deflated to provide further clearance for the annular wall to bend and/or compress as it is removed from the intervertebral space. The balloons and annular wall may be removed together by grasping them with a surgical tool such as a pincher, clamp or similar grasping tool.

Optionally, when the outer torroidal balloon is filled with curable polymer, it may remain in situ to replace or support a weak or damaged annulus and to hold an implant placed in the core of the outer balloon previously occupied by the inner balloon. In this case, the inner balloon is inflated with fluid in the core of the outer balloon as mentioned before. The outer balloon is then filled with polymer and cured to form the annular wall. Once the wall is formed, the inner balloon is deflated and the height of the outer balloon is measured by imaging techniques while the outer balloon remains in the intervertebral space. Since the outer balloon extends from the inferior to the superior vertebrae to substantially enclose a nuclear space therebetween, to remove the inner balloon, a surgeon inserts a surgical tool such as a clamp, pincher or other tool between the vertebra facing the balloon and the top of the outer balloon. The surgeon then presses against the top of the outer balloon with the tool to compress the outer balloon away from the vertebra which provides access to the core of the outer balloon. The surgeon then uses the tool to grasp the inner balloon while still pressing against the outer balloon and retrieves the inner balloon.

Similarly, to insert the implant in the core, the surgeon may use a surgical tool to press against the outer balloon to provide access to the core and maintain the outer balloon in a compressed configuration. Simultaneously, the surgeon uses an inserter tool with an end holding the implant to advance the implant over the outer balloon and into the core of the outer balloon. Once the inserter tool releases the implant in the core and is retracted, the surgical tool holding the outer balloon is also retracted. The elastic annular wall within the outer balloon, and in turn the outer balloon itself, expand back to their original shape and enclose the implant within the core of the outer balloon.

Alternatively, instead of a second surgical tool, the lead end of the implant secured on the inserter tool could be used to provide access to the core of the outer balloon. In this case, the lead end of the implant is advanced to place it between the outer balloon and one of the vertebrae. The implant is then pressed against the outer balloon which compresses the outer balloon out of the way of the implant. This provides access to the core of the outer balloon for placement of the implant. In such a procedure, the implant would need to be sufficiently secured to the inserter tool so that the implant cannot be unintentionally released from, or pivoted on, the inserter tool while pressing it against the outer balloon.

Another alternative expandable device that receives fluid uses axially moving strings on a balloon to measure the expansion of the expandable device. The expandable device includes an elongated, three-dimensionally obround (e.g. capsule shaped) balloon that expands radially from an elongated holder extending on a central, longitudinal axis of the balloon and through the interior of the balloon. The holder has an exterior portion extending out of, and away from, the balloon. A measuring mechanism on this expandable device includes strings extending longitudinally on different sides of the balloon as well as strings wrapped circumferentially around the balloon. Ends of all of the strings extend along the exterior portion of the holder. The position of the proximal end of each string is predetermined relative to the other strings or a position on the holder. So configured, the strings are pulled axially on the holder as the balloon expands radially from its central axis so that the respective ends of the strings shift from their predetermined initial position to a sizing position when the balloon is fully inflated in the vertical space. The distance the ends of the strings have shifted represent the amount the balloon is inflated. Since the strings are spaced along a number of positions on the balloon (e.g. top, bottom and sides) both the height and width of the balloon can be measured to measure both the superior-inferior height and footprint of the nuclear space respectively.

In yet a further alternative that uses fluid, an expandable device has a hydraulic, telescoping piston. A holder is connected to a base of the expandable device which supports the piston while a superior or top cover is disposed on the piston. The piston has at least two coaxial portions that translate relative to each other and the base in a telescoping manner in order to shift the top cover closer or farther from the base in order to collapse or expand the expandable device. A fluid delivery system is connected to the piston and provides fluid to a chamber on the base. The piston portions also sit within the chamber in a collapsed configuration. So configured, the fluid flows into a space between the bottom most piston portion and a bottom surface of the chamber. At a minimum, the space is initially formed by a slight mismatch in the dimensions of the components caused by manufacturing tolerances but may be configured with predetermined dimensions. The chamber receiving the fluid may have a fluid-tight liner or balloon connected to the fluid delivery system if the collapsed configuration of the expandable device still provides space for such a liner.

In order to permit a surgeon to choose an implant that matches the lordotic or kyphotic angle of the vertebrae, the expandable device in this embodiment also preferably includes a pivoting superior cover (e.g. pivoting about a lateral axis extending orthogonal to the superior-inferior direction) that is able to slant to more closely match the lordotic or kyphotic angle of the vertebra it is pressed against when the expandable device is expanded. In one form, a laterally extending shaft pivotally connects the flat superior cover to an upper most piston portion. The top surface or edge of the upper most piston portion is generally flat and extends in a slant relative to a superior-inferior direction so that the superior cover has clearance to pivot and can rest against the top surface for support in certain slanted orientations. In this position, the angle of the cover can be measured by using imaging technology mentioned below that creates an image of the implanted cover positioned against the vertebra so that the angle of the superior cover can be measured on the image. An implant can then be chosen that has a superior portion that can be oriented in the same angle as the superior cover of the sizing tool to more closely match the shape of the nuclear space.

In another aspect of the present invention, an expansion mechanism includes an actuator used for expanding the expandable device. In one form, the expansion actuator includes a fluid delivery system with a fluid supply such as a syringe mounted on the holder. A tube connects the fluid supply to an expandable body or chamber on the expandable device and a plunger on the syringe is operated for selectively delivering the fluid to the expandable device or drawing the fluid out therefrom. In the preferred embodiment, the syringe is mounted on a proximal portion of the sizing tool and the plunger of the syringe is connected to an expansion control device for operating the syringe. In one form, the control device is a threaded shaft connected to the plunger at one end so that the shaft and plunger act as one axial member. An end of the shaft has a rotatable knob which is easier for a surgeon to grasp and manipulate than the relatively small end of the syringe plunger and provides greater precision for controlling the axial position syringe plunger and in turn the flow of fluid ejected from or drawn into the syringe. The surgeon rotates the knob in one rotating direction which causes the shaft to be driven axially in a direction toward the syringe so that the plunger of the syringe, in turn, is driven axially into the syringe barrel to eject the fluid from the barrel and inject the fluid into the fluid passage or tube that leads to the expandable device. When the knob is turned in the opposite rotating direction, the syringe draws in fluid from the expandable device, through the interconnecting fluid passage, and back into the syringe.

The fluid system also has a pressure gauge in communication with the fluid passage that extends from the syringe to the expandable device to indicate the pressure of the fluid within the expandable device. So configured, fluid can be supplied to the expandable device with precision so as to exert a pressure against vertebrae similar to the pressure exerted by a natural disc. The expandable device can then be measured by obtaining an image of the expandable device in situ by visual techniques such as fluoroscopic, x-ray, MRI, or other similar imaging techniques to determine the appropriate size for an implant to be inserted into the nuclear space.

In the alternative, or in addition, the pressure gauge in conjunction with a volume gauge on the fluid supply such as indicia on the side of the syringe can be used as a measurement mechanism when specific volumes at known fluid pressures correspond to predetermined heights on the expandable device. For this purpose, the fluid is injected until the fluid reaches the implant imitating pressure mentioned above, the surgeon senses an increase in resistance when rotating the control shaft on the sizing tool, or the surgeon observes the expansion of the expandable device visually or by an imaging technique mentioned above. The fluid volume indicated on the volume gauge may then correspond to the amount of fluid in the bellows and in turn to a height of the expandable device.

For some arthroplasty procedures, it is desirable to cause over-distraction of the vertebrae in order to stretch the soft tissue (i.e. the annulus and ligaments) in order to cause stress relaxation in that tissue. This permits more separation of the vertebrae in the superior-inferior direction than what the tissue would otherwise permit while inserting the implant and without damaging the tissue. The preferred expandable device can over-distract the vertebrae by maintaining the fluid system at a specific pressure that is much higher than the natural physiological force which is imitated by a sizing tool to measure the height of the nuclear space. This pressure is maintained for a specific time to stretch the tissue, annulus and ligaments as desired in order to provide extra height or clearance in the nuclear space for easier insertion of the implant.

Alternative sizing tools with expansion actuators other than the fluid delivery system are also contemplated. In one such embodiment, a sizing tool has a holder with a distal end connected to an expandable device that has a gear or collar mounted on a generally flat, inferior cover or base and rotates relative to the inferior cover about an axis extending in the superior-inferior direction and transversely to the inferior cover. The collar engages a threaded portion fixed to a superior cover or extending from an intermediate adjustment member disposed between the collar and the superior member so that rotating the collar shifts the threaded portion and inferior cover up and down in the superior-inferior direction relative to the inferior cover.

In one preferred form, the superior cover is pivotally mounted on the adjustment member so that the superior cover can pivot to match the lordotic or kyphotic angle of the adjacent vertebra. The superior member is connected to the adjustment member by pins extending parallel to the longitudinal axis of the expandable device so that the superior member can pivot in the anterior-posterior direction in see-saw fashion. A top surface of the adjustment member that faces the flat superior member is gabled or slanted relative to the superior-inferior direction and relative to a plane generally formed by the inferior member to provide clearance for the superior member to pivot about the pins.

An actuator or expansion mechanism includes cooperating structure on the holder and the base of the expandable device that selectively rotates the collar for expanding and collapsing the expandable device. In one instance, the cooperating structure is an elongated member such as a belt, band or chain wrapped around the collar and a pin or gear mounted on the holder so that rotating the pin or gear on the holder rotates the belt and in turn the collar. Instead of a band, the cooperating structure may be a rotatable gear on the holder and that engages the collar directly or an intermediate pinion engaging the collar. In these cases, an expansion control device is provided on the holder and is configured to selectively rotate the gear or pin on the holder.

The control device, in one example, is a finger accessible, user operated, elongated looped member wrapped around the gear or pin on the holder and extending on an exterior surface of the holder. The looped member is configured so that a user's finger on the user's hand gripping the holder can extend comfortably on the looped member. So configured, the user simply presses his finger forward or back and against the looped member to shift the looped member and operate the expandable device.

In another alternative configuration for the expansion actuator and expansion control device, the cooperating structure is a worm wheel rotatably mounted on the holder and meshed either directly with the collar or with an intermediate pinion between the worm wheel and collar. In this case, the expansion control is a rotatable shaft connected to the worm wheel and extending along the elongate holder so that rotation of the shaft rotates the worm wheel which in turn rotates the collar for expanding or collapsing the expandable device.

Another alternative sizing tool has an expandable device with superior and inferior, opposite covers connected to each other by a number of links. One of the covers is connected to a distal end of an elongated holder while the other or second cover is connected to a lever arm. The lever arm extends from the second cover and to a pivot bar that extends transversely to the longitudinal dimension formed by the holder. The pivot bar is also rotatably connected to the holder. Two links are respectively connected to the holder and lever arm at one end, and are connected to a central driving member at their opposite ends. In order to operate the expandable device, the user holds the holder with one hand and the driving member with the other hand. Shifting the driving member longitudinally relative to the holder causes the links to pivot and fold or unfold to expand or collapse the expandable member in the superior-inferior direction.

In another alternative sizing tool, an expandable device has links that connect a superior cover to an inferior cover in a "car-jack" type of linking configuration such that it includes a main, middle link spaced from an outer, middle link. Both of the middle links are connected to their own secondary links to the superior and inferior covers. To connect the middle links to the secondary links, the middle and secondary links have extensions that engage each other and are secured together by a pin forming a hinge connection. Similarly, the secondary links are connected to sidewalls on the covers by pins. Alternatively, living hinges may connect the links to each other.

To expand or collapse the expandable device, a driving member extends from a holder, through the middle, main link and connects to the outer, middle link so that shifting the driving member longitudinally shifts the middle links closer or farther from each other. The shifting of the middle links rotates the secondary links relative to the middle links and the superior and inferior covers, which in turn shifts the covers closer or farther from each other to expand or collapse the expandable device. In one form, the driving member is threaded to the middle, main link so that rotating the driving member forces the middle, main link closer or farther from the middle, outer link.

In another aspect of this embodiment, the expandable device pivots relative to the holder for positioning the expandable device in the nuclear space. For this purpose, the holder has a tubular shaft for holding the driving member and is pivotally mounted to the middle, main link on the expandable device by a rigid, pivoting, stabilizing arm extending laterally from the holder. The arm provides at least passive steering so that pressing the expandable device against an annulus wall or other anatomical structure pivots the expandable device relative to the stabilizing arm and holder. The stabilizing arm is dimensioned to maintain the holder, and in turn the driving member, at a predetermined alignment to minimize shifting or bending of the driving member in undesirable directions. The portion of the driving member that bends when the expandable device is pivoted is covered by a compressible sleeve to attempt to minimize debris connecting to the driving member and interfering with the bending or axial translation of the driving member. The middle, main link also has a laterally extending brace with a curved, outer periphery for receiving the guide sleeve and/or distal end of the holder. The outer periphery has a predetermined radius or curvature to maintain the sleeve and/or holder, and in turn the driving member, along a predetermined corresponding path during the pivoting of the expandable device so that the driving member does not bend in undesirable directions that could make the driving member difficult to operate.

In yet another alternative sizing tool that uses links, an expandable device eliminates the need to be pivoted about the superior-inferior axis. Here, a generally cylindrical expandable device with circular domed ends is held by an actuator within an annular, insertion end of a holder that forms a through-hole. In this case, the outer diameter of the annular insertion end of the holder is about the same as the narrow width of the elongated, obround expandable devices described above. Thus, the insertion end and circular expandable device are not elongated to correspond to the longer dimension of the natural nuclear disc and nuclear space. So configured, a surgeon can insert the expandable device into a nuclear space within an annulus without the need to steer or pivot the expandable device when the expandable device is within the annulus. This is true no matter which surgical approach relative to the anterior-posterior direction is used.

In order to ensure further accurate measurement of the height of the intervertebral space, the expandable device has distracting superior and inferior covers with domed external surfaces that form a relatively constant diameter from domed surface to domed surface similar to the diameter of a sphere and when the expandable device is in an expanded configuration. With this structure, the expandable device can be tilted or askew from perfectly vertical where its central axis of curvature is substantially parallel to the superior-inferior direction of the nuclear space and still provide an accurate height measurement. As long as each domed surface abuts an opposing vertebra that forms the intervertebral space it is within, the diameter from one domed surface to the other domed surface sufficiently represents the height of the intervertebral space.

In another aspect of this embodiment, the expandable device has a linkage mechanism operable to expand or collapse the expandable device. For this purpose, the linkage mechanism has a main rotatable link connected to the superior and inferior covers by oppositely extending secondary links. The actuator is connected to the main rotatable link so that operating the actuator to cause rotation of the main link will expand or collapse the expandable device. The circular covers of the expandable device have the same diameter and each form a circumference and walls spaced along the circumference. In one form, each cover has three walls alternately extending between the three walls from the opposite cover. The walls also extend vertically or in a superior-inferior direction and into the through-hole on the annular end of the holder. The spaced walls abut the interior surface of the holder forming the though-hole so that the walls are retained by the interior surface and to extend in a superior-inferior direction. This restrains the covers on the expandable device so that they do not rotate with the rotation of the main rotatable link thereby causing the secondary links to shift the superior and inferior covers between an expanded and a collapsed configuration.

In a collapsed configuration, the covers are positioned generally flush with outer surfaces of the holder forming a configuration with a relatively continuous or smooth surface to limit damage to anatomical structure. The insertion end of the holder is also provided without any sharp breaks that could catch on anatomical structures during insertion, for example, so that it can form the leading end of the sizing tool for insertion through the anatomical structure and an incision on an annulus of a nuclear space.

In a further alternative aspect of the invention, a sizing tool has an expandable device mounted on the end of an elongate holder for insertion into an intervertebral space. The expandable device includes a wedge disposed between distractible opposing portions such as superior and inferior covers so that shifting the wedge moves the superior and inferior covers closer or farther from each other to collapse or expand the expandable device and along a superior-inferior axis orthogonal to a longitudinal axis of the holder. To accomplish this, inclined surfaces on the wedge engage inclined surfaces on the opposing portions so that all four of the inclined surfaces are slanted relative to the superior-inferior axis. The inclined surfaces also all slant either toward or away from a user end of the holder where a user can grasp the holder and toward the longitudinal axis of the holder. The wedge is connected to a driving member that extends longitudinally on the holder and translates axially thereto in order to shift the wedge longitudinally. So configured, shifting the driving member axially causes the wedge to shift axially so that it slides or cams against at least one of the opposing portions to shift the opposing portions closer or away from each other.

In one preferred form, the holder is configured to maintain the wedge and opposing portions in alignment with the longitudinal axis of the holder as well as maintain the opposing portions one above the other and in an alignment along the superior-inferior axis while the wedge shifts longitudinally and the opposing portions shift transversely along the superior-inferior axis. For these purposes, the holder has a U-shaped support member with the wedge positioned between, and slidingly engaging, two longitudinally extending arms of the 'U' configuration. The arms also have guide posts extending in the superior-inferior direction and engaging the opposing portions. With this configuration, shifting the wedge longitudinally translates the wedge longitudinally forward along the arms while the opposing portions distract and slide along the guide posts in a superior-inferior direction to an expanded or collapsed configuration.

In yet a further aspect of the invention, an elongated measuring member is connected to an expandable device and is used to determine the distance or height the expandable device expands by determining the longitudinal distance the measuring member translated during expansion of the expandable device. For this purpose, a sizing tool has an expandable device mounted on a distal end of a holder and has a superior cover that moves relative to an inferior cover (or vice versa) connected to the holder. The measuring mechanism is connected to the expandable device and extends over the holder to measure how far the superior and inferior covers are distracted. Specifically, the measuring mechanism has an elongated, bendable measuring member such as a cable or coil spring with a distal end that is connected to the superior cover. The cable or coil spring is used because it bends. The measuring member has a first portion that extends parallel to a superior-inferior axis and toward the inferior cover and a second portion that extends along the holder. While the total length of the measuring member does not change, the lengths of the first and second portions of the measuring member varies depending on the position of the superior cover relative to the inferior cover. The expandable device and holder have cooperating structure such as a bar or shaft around which the bendable member is bent into the variable length second portion. The second portion is redirected laterally (relative to the superior-inferior axis) away from the expandable device and to extend longitudinally along the holder.

So configured, when the expandable device expands, the first portion of the measuring member is drawn axially and upward with the superior cover and the second portion of the measuring member is drawn longitudinally along the holder. In this expanded configuration, the distance the measuring member was drawn is determined by comparing the final position of an end of the second portion of the measuring member extending on the holder to a predetermined initial, position of the end of the second portion. The axial or longitudinal difference between the initial and final positions of the end of the second portion is determined either visibly or by mechanisms connected to the end of the second portion such as gauges. The distance the elongated member is drawn indicates the amount of expansion. This measuring mechanism may be placed on any of the embodiments with a superior cover that moves relative to an inferior cover (or vice versa).

In one configuration, the elongated measuring member also operates as the driving member for expanding and collapsing the expandable device. In this case, the elongated member includes a coil spring, such as along a portion of its length, so that the elongated member can bend to provide expansion in the superior-inferior direction while being controlled in a lateral direction orthogonal to the superior-inferior direction. This permits a surgeon to control the expandable device from outside of the intervertebral space and annulus while the expandable device is disposed within the intervertebral space and annulus.

An end of the elongated member is connected to a control device operative for advancing the elongated member axially to expand the expandable device. The elongated member has an opposite end that is connected to a superior cover that moves up and down in a superior-inferior direction and relative to an inferior cover. So configured, the advancing of the elongated member drives the superior cover away from the inferior cover. In this embodiment, the superior cover is a platform that slides upon poles that extend from the inferior cover and in the superior-inferior direction. The inferior cover has a bore with an approximately 90° curve so that the bore extends in the superior-inferior direction and opens toward the superior cover. The bore receives the coil spring from the holder and redirects the coil spring upward toward the superior cover. The control device may be threaded and rotatable so that rotating the control device within the bore moves the elongated member axially. The control device may also have predetermined positions to indicate the distance the elongated member translated in order to determine the distance of expansion of the expandable device.

In accordance with another aspect of the present invention, an apparatus and method are disclosed for sizing an implantable space within a patient. The implantable space in a preferred form is an intervertebral space. Preferably, a measuring instrument is implemented in the form of an expandable intervertebral sizing instrument. Many features of the expandable intervertebral sizing instrument are applicable to surgical instruments in general, but in a preferred form, the intervertebral sizing instrument according to the present invention is particularly suited for determining the size and lordotic angle at a set distraction force of an intervertebral space to appropriately size spinal implants such as spinal cages, VBR/IBFs, and motion preservation implants such as TDPs, or DNPs.

The expandable sizing instrument has a mechanism in the form of a measuring head configured to expand within an intervertebral space, i.e. the space between vertebrae of the spine, with a controlled amount of force or pressure to measure the space within the intervertebral space. In a preferred form, the force exerted on the vertebrae adjacent the intervertebral space is held constant throughout the range of motion of the measuring head. The measuring head includes a spacer mechanism which preferably includes a pair of pads that can toggle or pivot to effectively conform to the configuration of the vertebral surfaces including the lordotic angles thereof to facilitate accurate measurement of the space between the vertebrae. Furthermore, the pads may be radio-opaque, which allows the exact angle of the vertebral surfaces to be determined via fluoroscopy or x-ray imaging while the pads are positioned within the intervertebral space in an expanded configuration.

In one form, the expandable sizing instrument has a thin curved outer shaft to reach within the narrow confines of the intervertebral space from a variety of surgical approaches, i.e. angles of entry. However, the outer shaft could also be straight for conventional surgical approaches. Inside the outer shaft is the drive mechanism that drives the spacer mechanism by applying force thereto. The outer shaft also preferably includes an indicator mechanism that displays a visual indication of the amount of space or height within the intervertebral space, which corresponds to the distance between the outer surfaces of the pads, which abut the inner surfaces of the adjacent vertebrae when the measuring head is in an expanded configuration.

Preferably, the expandable sizing instrument has a handle mechanism which has an adjustable force-setting mechanism including a compressible spring that creates the amount of force used to distract the vertebrae, i.e. the distraction force. The amount of force is controlled by the force adjustment mechanism in the form of a knob which can set the desired amount of distraction force via rotation thereof. A certain amount of distraction force is required to slightly distract the adjacent vertebrae so that when the implant is inserted, there is sufficient compressive force exerted on the implant by the vertebrae to keep the implant from slipping out of place. Using an inadequate amount of distraction force while sizing the intervertebral space can result in undersizing the implant, because the implant will not fit snugly between the vertebrae. Using an excessive amount of force can result in excessive distraction of the vertebrae, which may cause the selection of an implant that is too large for the space, and can damage the vertebral surfaces, endplates, or connective tissues in and around the spinal joint. Thus, via the adjustable force-setting mechanism, a user may reliably set the distraction force of the sizing instrument and thereby avoid excessive risk of inaccurately sizing the implant or causing injury to the patient.

In a preferred form, the expandable sizing instrument is operated by adjusting the force adjustment mechanism, and positioning or placing the tip of the inserter within the intervertebral space. An actuator mechanism, such as a trigger or lever operably connected to the spacer mechanism, is operable to cause the spacer mechanism to expand or contract. When the actuator mechanism is moved to a first position, the spacer mechanism expands and the indicator mechanism indicates the size of the intervertebral space corresponding with the expanded size of the spacer mechanism. The spacer mechanism may be contracted by moving the actuator mechanism to a second position, which corresponds to an insertion or removal configuration of the measuring head.

One advantage of the expandable sizing instrument is the ability to eliminate multiple insertions of different sized trial spacers to determine the correct size implant. The elimination of multiple insertions into the narrow confines of the intervertebral space reduces the time required for the surgery and amount of time the patient is under anesthetic. The reduction of time under anesthetic correspondingly reduces the health risk and the recovery time of patients due to the surgery and anesthetic.

Another advantage of the expandable sizing instrument is the ability to reduce the potential of tissue damage to the remaining annulus fibrosus or disc during the implantation of a disc nucleus prosthesis, or DNP. The repeated insertion and removal of static trial spacers can cause damage to the annulus, because the remaining annulus is generally stretched each time a spacer is inserted or removed. By eliminating the need for repeated insertion and removal of trial spacers, the expandable sizing instrument has the advantage of minimizing tissue damage to the annulus.

Finally, an additional advantage of the expandable sizing instrument is the ability to improve consistency and reliability of the insertion of spinal implants such as spinal cages, VBR/IBFs, TDPs, or DNPs. The expandable sizing instrument allows the accurate and consistent sizing of intervertebral implants in an objective measurable way. The precise measurement of the intervertebral space reduces reliance upon the subjective manner in which surgeons determine the correct implant size based on the subjective "feel" of the fit of a trial spacer and hence reduces human error. The objective measurement provided by an expandable sizing instrument according to the present invention allows for more consistency and reliability in the implantation of correctly sized spinal implants. Moreover, the expandable sizing instrument saves labor because there is less training required to size implants and a lessened likelihood of subsequent revision surgeries.

Additional advantages and features of the invention will become apparent from the following description and attached claims taken in combination with the accompanying drawings.

BRIEF DESCRIPTION OF THE DRAWINGS

FIG. 10 is a top, cross-sectional view of a proximal portion of the sizing tool showing the actuator and components of the fluid delivery system;

FIG. 10A is a cross-sectional view taken along line XA-XA on FIG. 10 and showing a clip holding a plunger for the fluid delivery system;

FIG. 13 is a side, perspective view of another alternative expandable device with a single complete bellow in an expanded configuration;

FIG. 14 is a side, perspective view of a further alternative expandable device with circular bellows in an expanded configuration;

FIG. 15 is an elevational view of an further alternative expandable device with a side wall that has a spiraling thread;

FIG. 21 is a side perspective view of a further alternative expandable device showing size measuring strings extending along a balloon in a collapsed configuration and a holder connected to the balloon;

FIG. 22 is a side perspective view of the expandable device of FIG. 21 and showing size measuring strings extending along a balloon in an expanded configuration and a holder connected to the balloon;

FIG. 23 is a perspective view of an alternative sizing tool in accordance with the present invention and showing a holder connected to an expandable device in a collapsed configuration and having a gear with a centrally located sprocket;

FIG. 24 is a side perspective view of an alternative gear with a sprocket for the sizing tool of FIG. 23;

FIG. 37 is a left-side view of the sizing tool of FIG. 32 showing the expandable device in an expanded configuration and the top cover in a slanted position;

FIG. 38 is a left-side view of the sizing tool of FIG. 32 showing the expandable device in a collapsed configuration and the top cover in a slanted position;

FIG. 39 is a left-side, cross-sectional view of another alternative sizing tool showing an expandable device with a hollow piston in a collapsed configuration and connected to a holder;

FIG. 40 is a left-side, cross-sectional view of the sizing tool of FIG. 39 showing an expandable device with a hollow piston in an expanded configuration and connected to a holder;

FIGS. 88 and 89 are rear views of the expandable sizing instrument in respective closed and opened configurations thereof showing the adjustment knob disposed on the handle.

DESCRIPTION OF THE PREFERRED EMBODIMENTS

Figure 1:
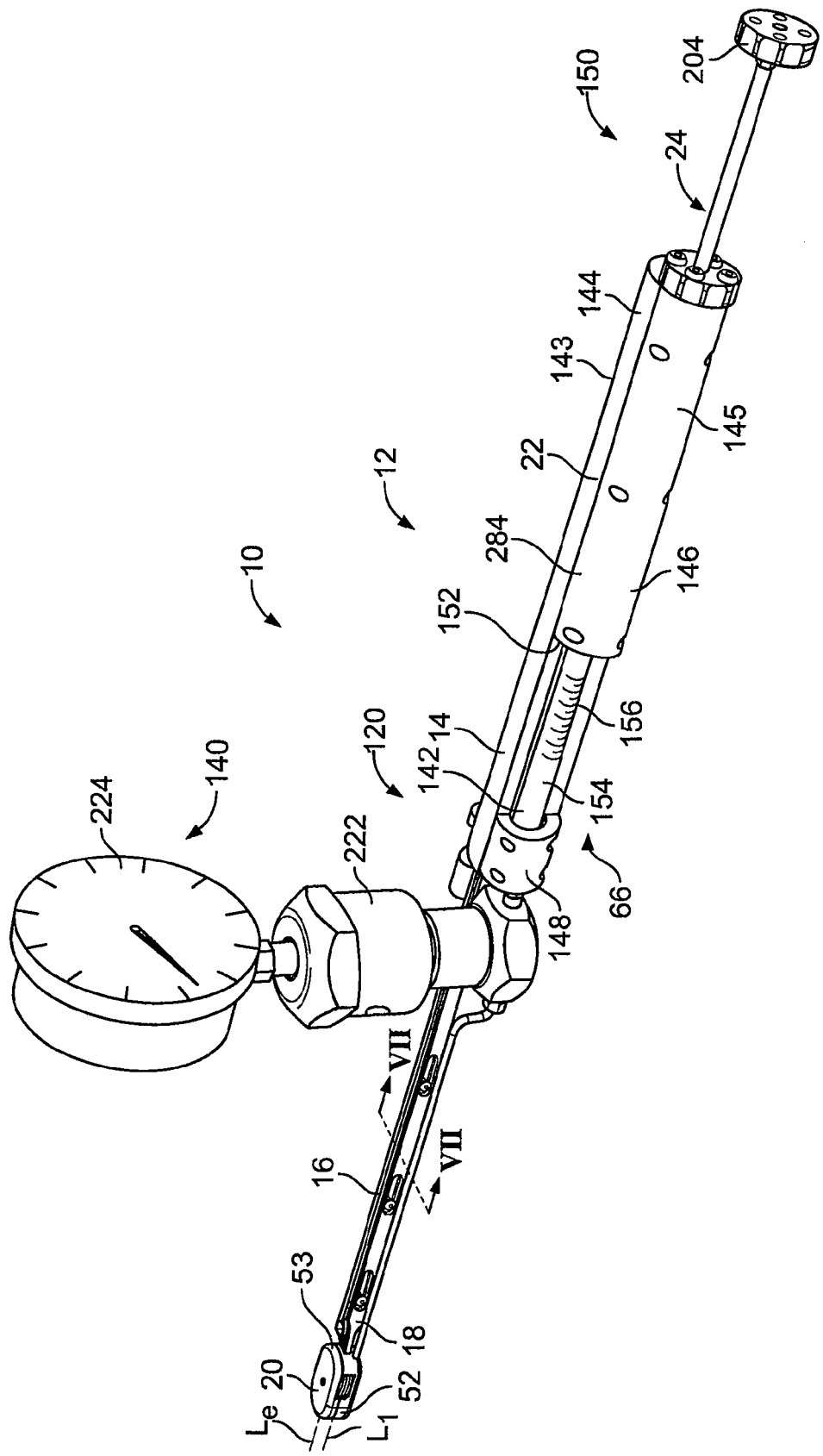
FIG. 1 is a perspective view of a sizing tool with an expandable device on the end of a holder in accordance with the present invention.

A system for replacing a spinal disc from an intervertebral space between adjacent, superior and inferior vertebrae includes a number of alternative sizing tools described herein and used for determining the size of the intervertebral space. After the size is determined using the sizing tools described herein, an artificial disc implant with an appropriate size that fits the measured space can be implanted so that the relatively complicated procedure for implanting the disc does not need to be repeated. The sizing tools may be used for implantation of either a disc nucleus prosthesis (DNP) or a total disc prosthesis (TDP).

The sizing tools described herein have a holder with a distal end connected to an expandable device that is placed within the intervertebral or nuclear space. The illustrated expandable device, except for one configuration described below, has a superior cover or portion that can be shifted closer to or farther from an inferior cover or portion by an expansion mechanism connected to the expandable device. The expansion mechanism is provided on the sizing tools for expanding the expandable device in a superior-inferior direction and within the intervertebral space so that the expandable device abuts both vertebrae forming the space to determine the distance or height from one vertebra to the other. A number of the expandable devices are also configured to determine the width or footprint of the intervertebral space when it is expanded. This, however, may require that the sizing tool and expandable device be held on its side to expand in a lateral or anterior-posterior direction within the intervertebral space depending on the configuration of the sizing tool. It should be noted that wherever the term intervertebral space is mentioned it includes the space with or without an annulus forming a nuclear space.

The expansion mechanisms for expanding the expandable devices are all configured to operate without pressing harmfully against anatomical structure such as the vertebrae, annulus or an incision on the annulus the sizing tool extends through. Thus, potentially harmful lateral motion of the expansion mechanism at the annulus and intervertebral space and relative to the longitudinal axis of the holder is eliminated or minimized. The expansion mechanisms are provided with a number of different configurations to perform this function. Sizing tools 10, 239, 300, 324, 500 and 505 described below have fluid delivery systems that have passageways such as tubes extending into the intervertebral space for filling the expandable device with fluid to expand it. The other illustrated sizing tools 400, 403, 431, 551, 600, 700, 800 and 900 all have axially shifting members or shafts that are operated to expand the expandable device within the intervertebral space. The members or shafts all translate longitudinally relative to the holder and while extending into an intervertebral space or through an incision on an annulus to minimize damage to the incision, annulus or other tissue.

Figure 16:
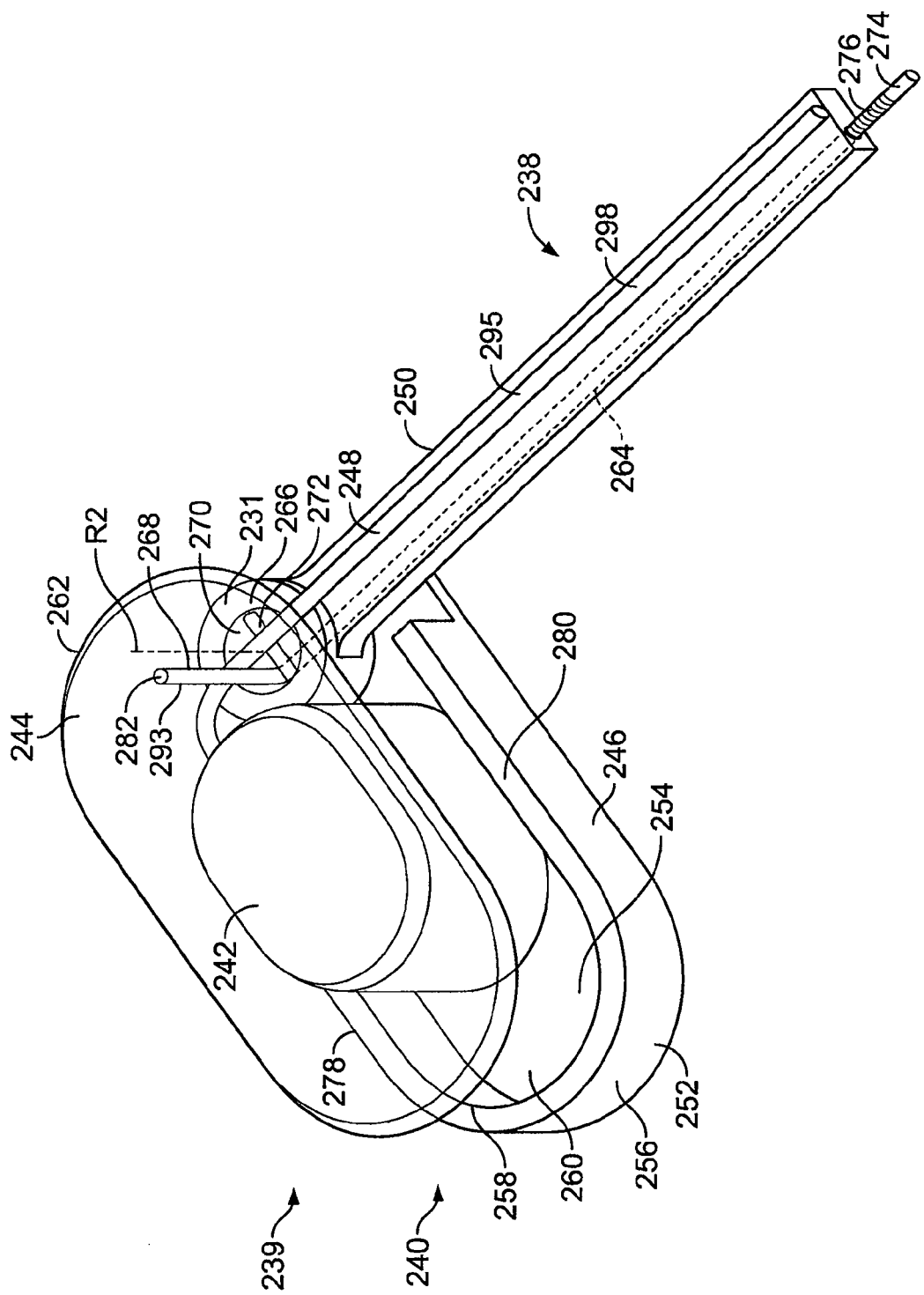
FIG. 16 is a top, perspective view of an alternative expandable device and distal end of a holder showing a rigid outer wall placed around an expandable balloon in an expanded configuration.
Figure 17:
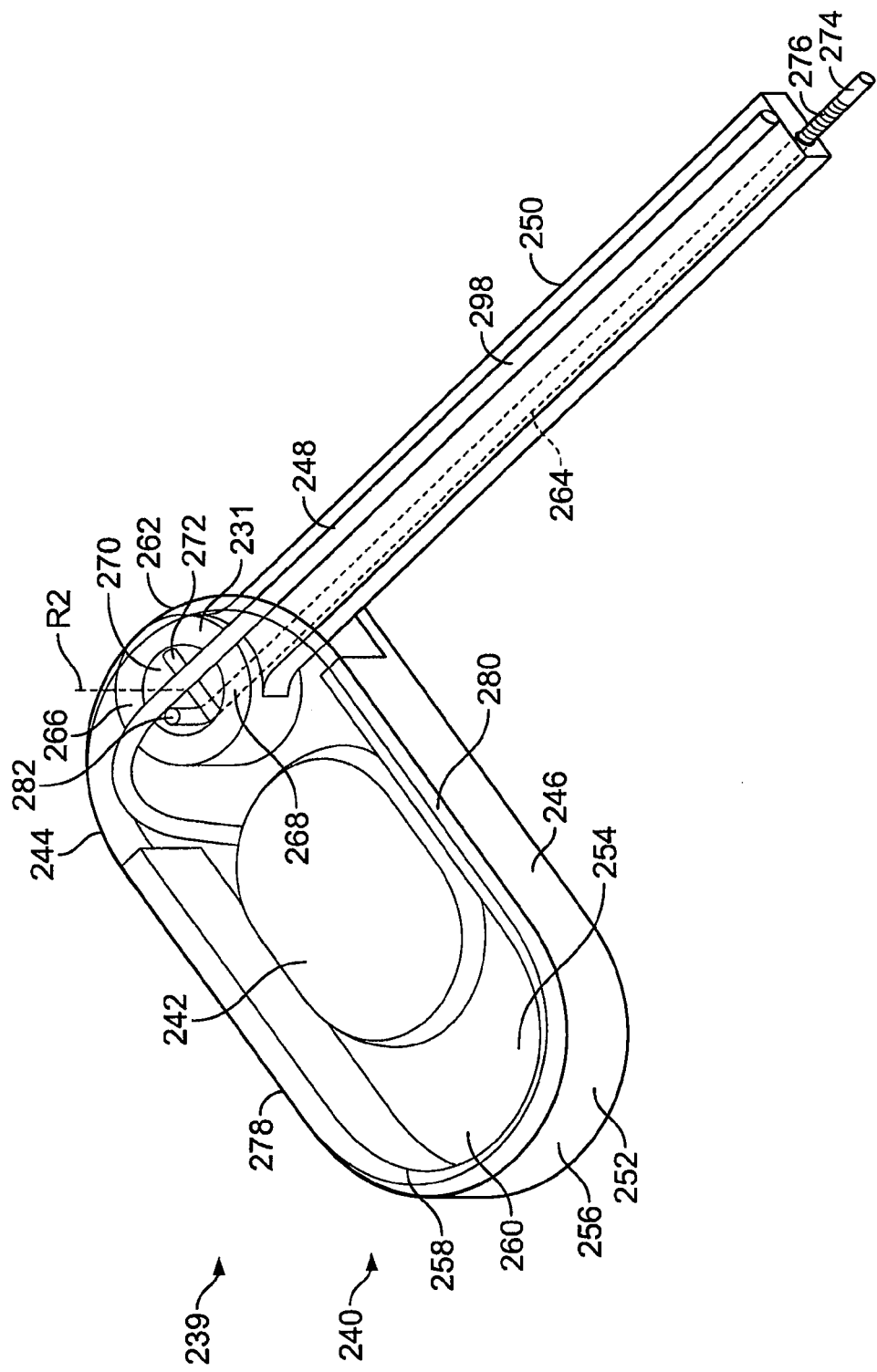
FIG. 17 is a top, perspective view of the expandable device of FIG. 16 shown in a collapsed configuration.

Once the expandable device is expanded within an intervertebral space for any of the embodiments, a measurement mechanism may include measuring the height of the expandable device by imaging techniques such as x-ray, MRI, fluoroscopic or similar techniques that provide a measurable image of the expansion of the expandable device while it is positioned within the intervertebral space. An alternative measurement mechanism 264 as shown in FIGS. 16-17 that may be used by any of the sizing tools with a superior portion and an inferior portion includes an axially shifting elongate member 268 that extends from one of the superior and inferior portions and toward the opposite portion. The member 268 bends to extend away from the expandable device and along the holder. The axial distance the elongate member 268 shifts during expansion of the device corresponds to the amount the superior and inferior portions distracted in the intervertebral space. The measurement mechanism 264 is described in greater detail below. Other methods for measuring the expandable device described below are particular to the type of expansion mechanism that is used.

Preferably the holder on the sizing tool remains connected to the expandable device so that the expandable device can be retracted from the intervertebral space after the space is measured. The expandable device is collapsed to retract it so that the expandable device fits through an annulus incision. Even if the annulus is not present, it is easier to retract the expandable device when it is collapsed. The vertebrae forming the intervertebral space apply pressure against the expandable device that could retain the expandable device within the intervertebral space. This pressure is reduced or eliminated when the expandable device is collapsed.

Most of the expandable devices that have a superior and inferior portion are configured to provide a controlled collapse into a predetermined collapsed configuration. The predetermined collapse configuration preferably encloses whatever expansion structure the expandable device uses in order to present smooth, continuous outer surfaces on the expandable device that minimize damage to surrounding tissue including the annulus and so that the expandable device fits through the annulus incision. In order to achieve the collapsed configurations, the expandable devices have structure that connects the superior and inferior portions to each other while maintaining the superior and inferior portions laterally aligned along a common axis as the expandable device is expanded or collapsed. Thus, sizing tool 10 has fluid receiving expandable devices with inflatable bodies such bellows or reinforced balloons configured to collapse while remaining aligned along a superior-inferior axis. Sizing tools 500 and 505 have fluid receiving expandable devices with pistons that remain concentrically located on a superior-inferior axis as they collapse. Sizing tools 400, 403 and 431 have threaded parts connecting the superior and inferior covers to each other and that engage concentrically about the superior-inferior axis to maintain the covers along the axis. Sizing tools 600 and 700 have pivoting links to hold the superior and inferior portions in alignment while sizing tools 800 and 900 have structure on the holders to retain the expandable devices in an alignment along a superior-inferior axis.

In another aspect of the invention, a number of the sizing tools may be provided with at least passive steering but more preferably active steering of the expandable device within the intervertebral space. In order to better measure the intervertebral space, a number of the expandable devices described below are obround, race-track shaped or oval to more closely match the configuration of a natural disc and a nuclear space between the vertebrae. To minimize the required size of the annulus incision, the expandable device may have an elongated shape having a narrow, distal, longitudinal end that is used to face the annulus incision and lead the expandable device as it is inserted through the incision and into a nuclear space. The expandable device is inserted into the nuclear space while it is held on the holder in a straight, insertion or 0 degree orientation where the longitudinal axis of the expandable device extends generally parallel to a longitudinal axis of the holder to position the lead end in front of the holder. This orientation forms a generally linear configuration for the sizing tool to minimize contact with anatomical structure as the sizing tool is advanced forward to advance the expandable device into the intervertebral space.

Once the expandable device is within the nuclear space, it is usually desirable to orient the expandable device with its longitudinal axis extending laterally relative to the anterior-posterior direction to match the orientation of the nuclear space or the removed natural nuclear disc to obtain a more accurate measurement of the intervertebral space. For convenience and adaptability, it may also be desirable to pivot the expandable device as it is held within the intervertebral space to place it in the desired orientation just mentioned. Providing an expandable device that pivots relative to the distal end of the holder permits a surgeon to insert the expandable device 20 from any convenient surgical approach including more posterior approaches.

For passive steering, the user advances the holder to press the expandable device against the back of annulus or other tissue to pivot the expandable device about the end of the holder and into the desired position. Since passive steering may damage the annulus, however, the sizing tools may be provided with steering mechanisms for active steering of the expandable device. For active steering, a member may push or pull on a side of the expandable device while the expandable device is adjustably or pivotally held at the distal end of the holder in order to pivot the expandable device. This reduces the need to press against the back of an annulus as with passive steering.

In order to minimize the risk of damaging the annulus, annulus incision or other tissue such as the vertebrae, the steering mechanism may also be configured to shift axially relative to the holder rather than laterally which could press the steering mechanism against the anatomical structure just mentioned. The steering mechanism is described in further detail below with the specific embodiments.

It will be understood that a surgeon may use both active and passive steering to pivot the expandable device. Although passive steering raises the risk of damaging an annulus, using passive steering by simply advancing the sizing tool against the annulus can be generally faster than carefully using the steering mechanism to actively pivot the expandable device. For this reason, the surgeon may use a compromise and may use passive and active steering simultaneously by pushing the expandable device against the annulus or other tissue to turn the expandable device as the surgeon also operates the steering mechanism to pivot the expandable device.

Optionally, the surgeon may use the steering modes consecutively such as by first using the steering mechanism to initially pivot the expandable device in an initial angle such as up to 45 degrees to the left or right and relative to the longitudinal axis of the holder. This initially points the expandable device toward the side of the holder it needs to turn to. Then, when less force will be applied orthogonally to a wall of the annulus due to the initial, pivoted position of the expandable device, the surgeon uses passive steering and pushes the expandable device against the annulus or other tissue to pivot the expandable device to the desired final angle.

Referring now to the specific embodiments that provide the advantages mentioned above, as illustrated in FIG. 1, one system 12 for replacing a spinal disc has a sizing tool 10 with a holder 14. The holder 14 has a distal portion 16 for adjustably holding an expandable device 20 that expands within an intervertebral space or a nuclear space within an annulus. The sizing tool 10 also has a steering mechanism 120 with a steering actuator 94 mounted along the distal portion 16 of the holder 14 and that connects to the expandable device 20 for actively pivoting the expandable device. The steering actuator 94 operates by shifting axially or longitudinally relative to a main shaft 86 holding the expandable device 20 so that it minimizes lateral pressure against an annulus incision as the actuator extends through the incision. The sizing tool 10 also has an expansion mechanism 150 connected to the expandable device for expanding and collapsing the expandable device 20.

In one form, the expansion mechanism 150 of the sizing tool 10 includes a fluid delivery system 66 that extends through the incision on an annulus and is connected to the expandable device 20. The system 66 fills the expandable device with fluid to expand it and empties the expandable device 20 of fluid to collapse it. An expansion control device 24 on a proximal portion 22 of the holder 14 is used to operate the fluid delivery system 66. The expandable device 20 is provided in a number of different forms that receive the fluid and are described below. It should be noted that the terms distal and proximal used herein for all of the embodiments, unless noted, are relative to the user end (end closest to the user) of the sizing tools.

Further, the sizing tool 10 may use a measuring mechanism 140 which is connected to the fluid delivery system 66 and used to indicate the amount of expansion of the expandable device 20 while the expandable device resides within the intervertebral space. In one embodiment, the measuring mechanism 140 includes a pressure gauge 222 that measures the pressure of the fluid in the fluid delivery system 66 and within the expandable device 20 which in turn corresponds to the pressure the expandable device exerts on adjacent vertebrae.

In one technique for measuring the amount of expansion on expandable device 20, the fluid is injected into the expandable device until a pressure is indicated on gauge 222 that imitates the physiological pressure that a natural disc applies on the vertebrae, such as generally about 30-40 psi (generally about 0.2-0.3 Mpascal). The collapsed configuration of the expandable device 20 has a height (about 6-7 mm) that is about the same or less than the desired height of the implant. Thus, it is assumed that an expanded expandable device 20 that attains the same pressure that a natural disc exerts is about the same height of the natural disc as well as the desired height of the implant. In one alternative, the height of the expandable device 20 is then measured by imaging techniques as mentioned above.

In an alternative technique, the fluid volume at a particular pressure corresponds to predetermined heights for the expandable device 20. In this case, the fluid delivery system 66 has a fluid supply 142 mounted on the holder 14 for supplying the expandable device with fluid and a fluid volume gauge 156 on the fluid supply. The expandable device 20 is expanded until it abuts both vertebrae at a generally desired height. This may be indicated by the fluid reaching the imitated pressure mentioned above, an increase in resistance in expanding the expandable device, or by visual observation. Once it is determined that the expandable device reached a desirable height, the fluid volume as indicated on volume gauge 156 corresponds to a predetermined height of the expandable device.

Figure 2:
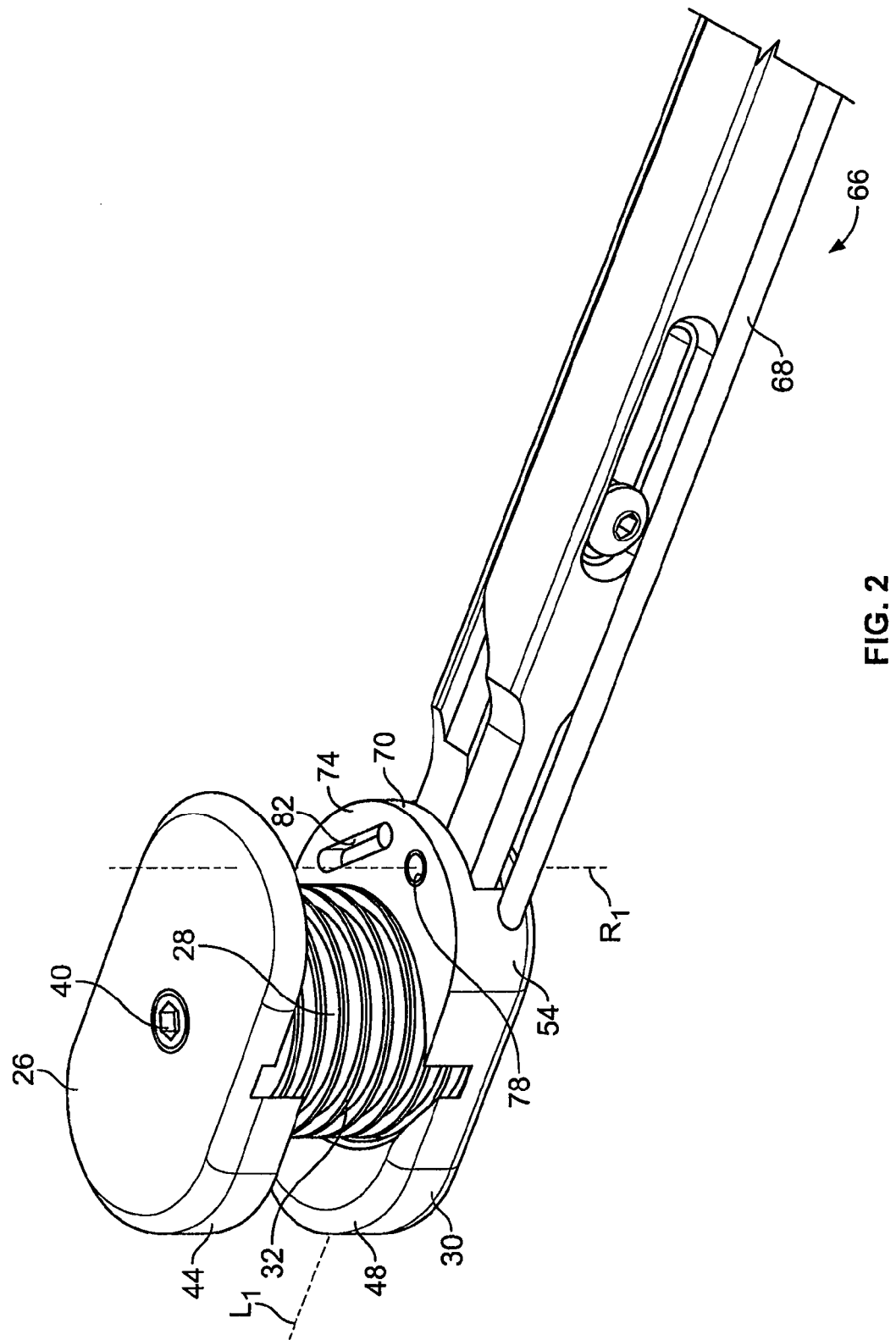
FIG. 2 is an enlarged perspective view of the sizing tool of FIG. 1 showing an expandable body in an expanded configuration and the connection of an expandable device to a distal end of a holder.
Figure 3:
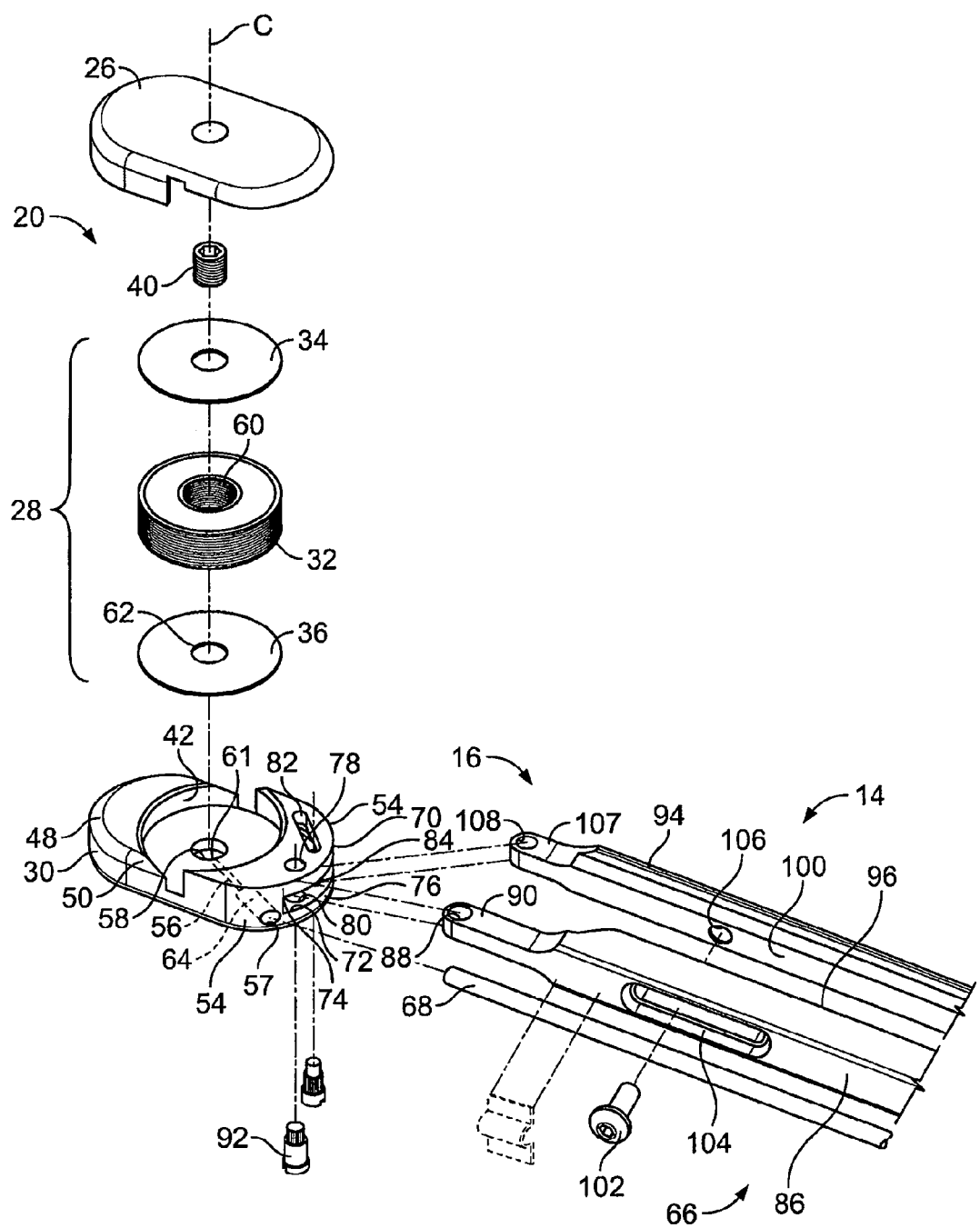
FIG. 3 is an exploded, perspective view of the expandable device and the distal end of the sizing tool showing the components for expanding and pivoting the expandable device.
Figure 3A:
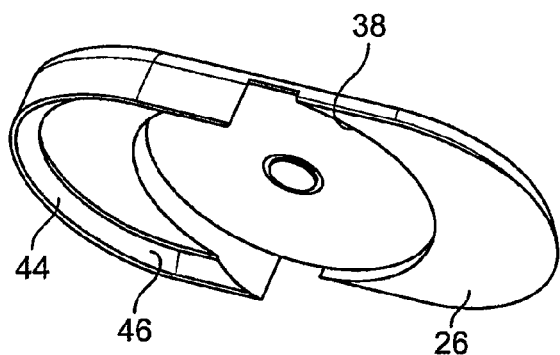
FIG. 3A is a bottom perspective view of a top cover of the expandable device showing mating surfaces for connection to an expandable body and a bottom cover of the expandable device.
Figure 3B:
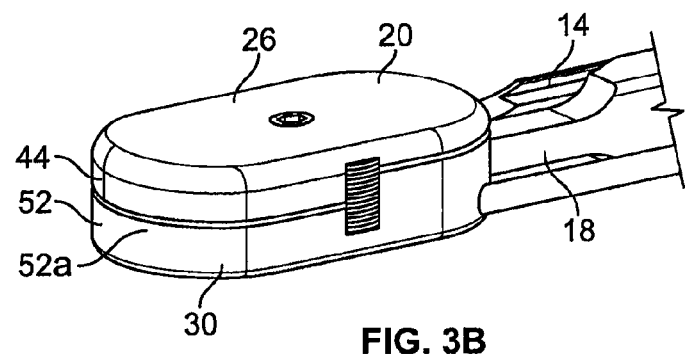
FIG. 3B is a left side perspective view of the distal end of the holder and expandable device showing the expandable device in a collapsed configuration.
Figure 4:
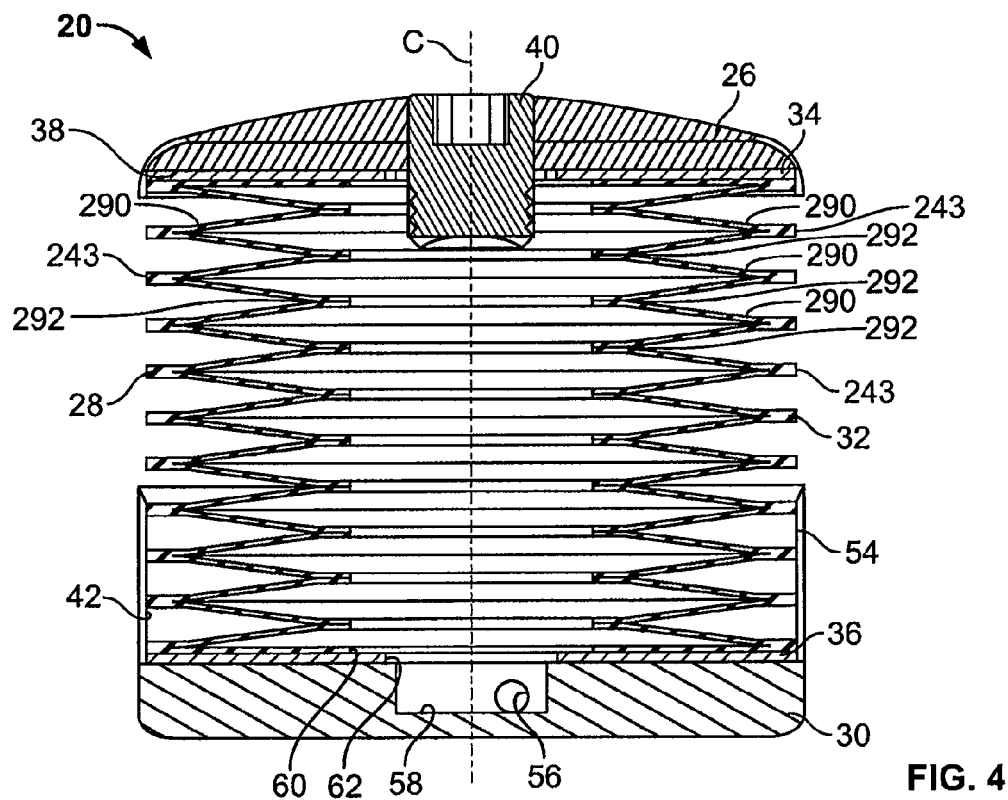
FIG. 4 is a cross-sectional view of the expandable device showing an expandable body in an expanded configuration and with bellows connected to top and bottom covers.

With regard to FIGS. 2-4 for describing the expandable device 20 in greater detail, expandable device 20 has a superior member or cover 26 placed over a fluid-holding body 28 which in turn is positioned over an inferior member or cover 30 supporting the body 28. As shown in FIG. 3B, the expandable device 20 has a predetermined collapsed configuration, which is the same as the insertion configuration, where a fluid-holding body 28 is generally enclosed by the inferior and superior covers 26 and 30. In this configuration, the covers 26 and 30 form a smooth, curved body with a minimum of rough edges that could damage soft tissue, such as ligaments or the annulus as the expandable device 20 is inserted into a human body and/or through an incision on the annulus.

Referring to FIGS. 3-4, the fluid-holding body 28 is preferably configured to provide a controlled collapse that ensures that it will be generally enclosed within the superior and inferior covers 26 and 30 while the expandable device 20 is collapsed. This minimizes the risk of the body 28 causing damage to any anatomical structure around the intervertebral space. Thus, the fluid-holding body 28 in one form is an inflatable yet relatively rigid body such as a generally cylindrical bellows 32. The bellows 32 are connected by solder, living hinges, or adherent to a top plate 34 and a bottom plate 36. The top plate 34 is disposed within a downwardly accessible, circular recess 38 (shown in FIG. 3A) formed by the superior cover 26 and fastened to the superior cover 26 by a threaded fastener 40. The bottom plate 34 sits within an upwardly accessible, circular recess 42 formed by the inferior cover 28. The inferior cover 28 is welded, adhered or fit tightly to the recess 42. With this structure, the covers 26 and 30 are sufficiently secured to the expandable body 28 so that pivoting the inferior cover 30 will also pivot the expandable body 28 and the superior cover 26.

In order to control the collapse of the expandable device 20, the bellows 32 form a relatively rigid structure. Thus, the bellows 32 are formed by an array of rigid folds 290 connected to each other by an array of inner joints 292 and an array of outer joint 243. For circular bellows as shown, the inner joints 292 have a uniform radius from a central axis of curvature C (shown on FIG. 3) which is shorter than a uniform radius of the outer joints 243. The folds 290 each extend from an inner joint 292 to an adjacent outer joint 243 and are sufficiently stiff to maintain the joints at their uniform radii. In one form, the folds 290 of the bellows 32 are made of a hard polymer or metal and in the preferred embodiment the folds 290 are titanium connected together by silver solder at the joints 292 and 243.

Once placed within the intervertebral space, the bellows 32 may be expanded or collapsed by bending at the joints 292 and 243. The rigidity of the folds 290 forces the folds 290 to lay one upon the other coaxially about central axis C as the bellows 32 are collapsed. With such a controlled collapse, the expandable device 20 can regain a generally solid collapsed configuration after expansion and that substantially covers the bellows 32 for retraction of the expandable device 20. Such a structure is less prone to folding over, bending, and extending out from between the superior and inferior covers 26 and 30. Thus, the risk of the bellows 32 entangling with itself, other parts of the sizing tool and/or the anatomical structure within or surrounding the intervertebral space during retraction is minimized.

Figure 12:
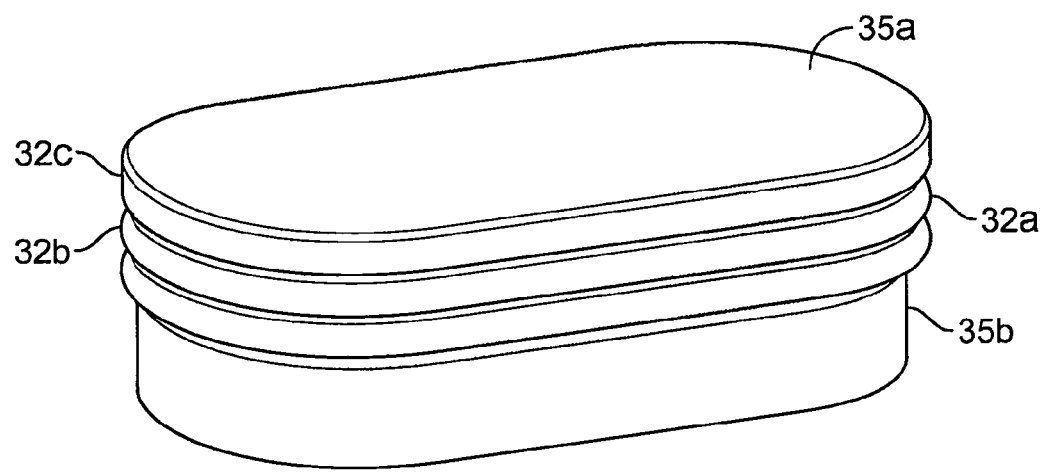
FIG. 12 is a side, perspective view of an alternative expandable device showing elongated bellows in a collapsed configuration.

Referring to FIGS. 12-14, alternative configurations for the bellows 32 provide added stability for the upper covers of the expandable device as the expandable device is being expanded in the intervertebral space. For instance, obround bellows 32a has an upper and lower cover 35a and 35b. An outer periphery 32b of obround bellows 32a is generally configured to match the longitudinal and lateral dimensions of an outer periphery 35c of the upper cover 35a. This configuration minimizes the overhang of the periphery 35c of the upper cover outwardly and past the periphery 32b of the bellows 32a which minimizes the ability of the upper cover 35a to pivot or tip relative to the top of the bellows while the bellows are being expanded or collapsed. The circular bellows 33a is configured with upper and lower covers 33b and 33c for the same reason.

As shown by bellows 37a, however, the bellows 37a may have very few folds such as a single convex fold 37b connected to two opposite cone-shaped bellows 39 (only one is shown) and that are connected to the covers 41.

Referring again to FIG. 3, in order to fill the expandable device 20 with fluid, a proximal end 54 of the inferior cover 30 forms a fluid passage 56 with one end 57 opening on an exterior surface 70 of the proximal end 54. Another end 61 of the fluid passage 56 opens to a central recess 58 disposed within, and extending downward from, the circular recess 42 on the inferior cover 30. The central recess 58 communicates with an interior 60 of the bellows 32 through an opening 62 on the bottom plate 36.

A widened portion 64 of the passage 56 receives part of fluid delivery system 66 such as a tube 68 that provides fluid for inflating the bellows 32. The tube 68 may be secured by adherent, interference fit, or threaded connection that limits axial motion of the tube 68 within passage 56 in which case the tube 68 is provided with enough slack to permit rotation of the expandable device 20. Alternatively, the tube 68 may be free to translate axially within the widen portion 64 a sufficient distance to permit the rotation of the expandable device 20 without disconnecting the tube 68 from the inferior cover 30.

Referring now to FIG. 3, the expandable device 20 is obround, race-track shaped or oval for the reasons mentioned above and forms a longitudinal axis $L_e$. The expandable device 20 has a narrow, distal, longitudinal end 52 that is used to face the annulus incision and be the lead end during insertion. In the collapsed configuration, lead end 52 is provided with a generally continuous, curved, smooth outer surface 52a with minimal openings and no sharp edges for facing the annulus and leading the expandable device 20 during insertion. The continuous outer surface 52a is cooperatively formed by providing the superior and inferior covers 26 and 30 with corresponding and mating shapes and surfaces. For instance, the superior cover 26 has a downwardly extending peripheral wall 44 with a beveled interior edge 46 (shown in FIG. 3A) that mates with a beveled peripheral corner 48 on a distal end 50 of the inferior cover 30 (as shown in FIG. 3). The expandable device 20 is inserted into the nuclear space in the straight orientation (shown in FIGS. 1-2) where the longitudinal axis $L_e$ of the expandable device 20 extends generally parallel to a longitudinal axis $L_1$ of the holder 14 to position the lead end 52 in front of the holder 14.

Figure 8:
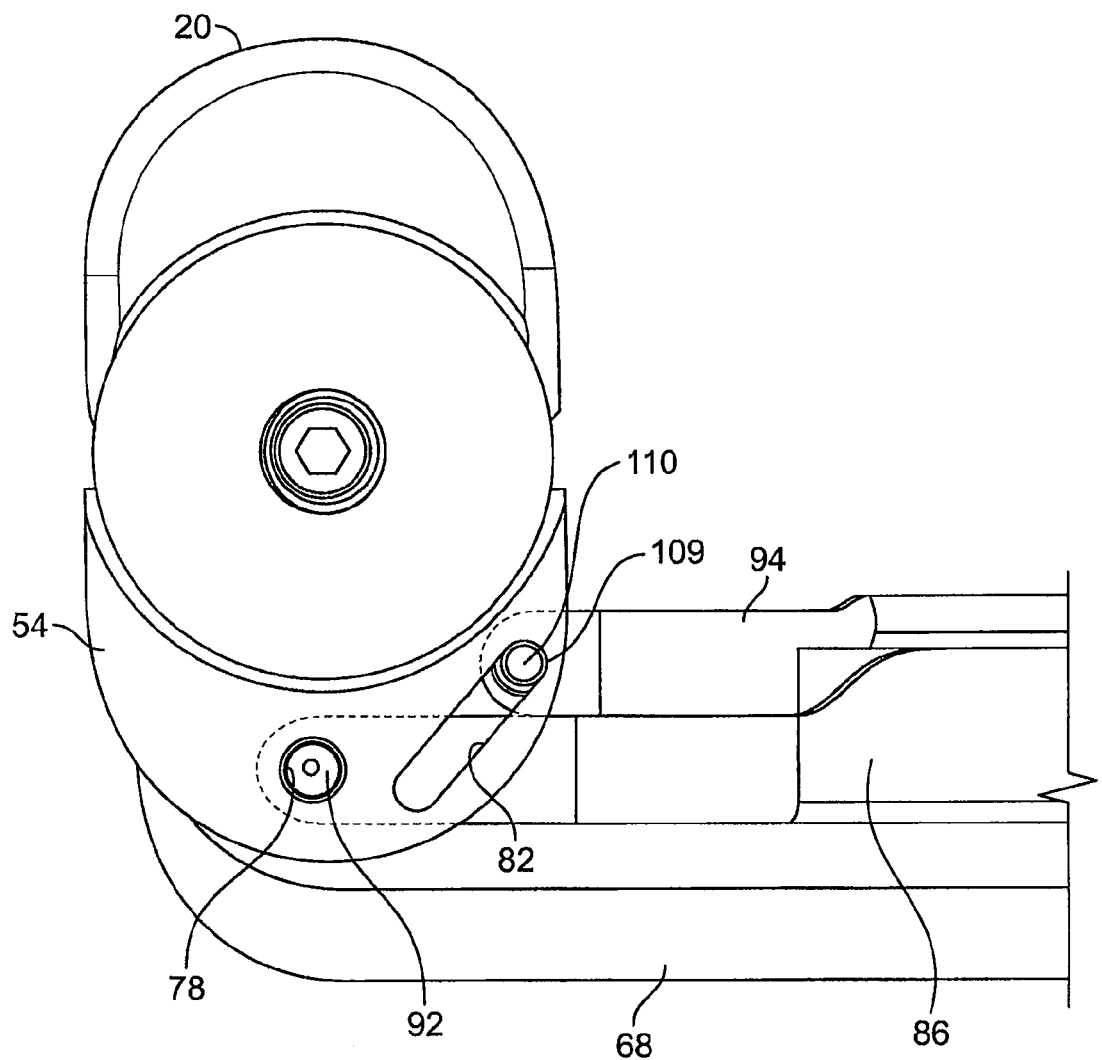
FIG. 8 is a top view of the distal end of the holder and expandable device with its top cover removed and showing the pin-slot connection between the expandable device in a pivoted orientation and the holder.

To provide active steering, the steering mechanism 120 has a steering control device 112 disposed on the holder 14 remotely from the expandable device 20 and that controls the steering actuator 94. The steering actuator 94 extends along the distal portion 16 of the sizing tool 10 and connects to the expandable device 20. So configured, operating the steering control device 112 pivots the expandable device 20 between the straight orientation and a pivoted orientation to the right of longitudinal axis $L_1$ to about 90 degrees as shown in FIG. 8. While the expandable device 20 is shown to pivot to the right of the holder 14, it will be appreciated that the holder could be configured to pivot the expandable device 20 to the left instead.

Still referring to FIG. 3, in order to pivot the expandable device 20, the inferior cover 30 is configured to connect to, and pivot relative to, a distal end 18 of the holder 14. Generally, the holder 14 has a main shaft 86 that secures the expandable device 20 longitudinally while permitting it to pivot about a pin 92 that secures the main shaft 86 to the expandable device. The steering actuator or shaft 94 has a pin 110 connected to aligned slots 82 and 84 on the expandable device 20. The slots extend diagonally relative to the longitudinal axis $L_1$ so that axially translating the steering shaft 94 relative to the main shaft 86 causes the pin 110 to slide in the slots 82 and 84. The pin 110, therefore, cams against the slots 82 and 84 and forces the expandable device 20 to pivot about pin 92 at the main shaft 86.

More particularly, the proximal end 54 of the inferior cover 30 has a transversely extending main slot 72 (where transverse is relative to the longitudinal axis $L_e$ of the expandable device 20). The main slot 72 opens proximally on the exterior surface 70 of the proximal end 54. The main slot 72 also is formed by spaced, opposing, top and bottom walls 74 and 76. The top and bottom walls 74 and 76 have respective, concentric apertures 78 and 80 and the slots 82 and 84 aligned one above the other and that all open to the main slot 72.

In order to hold the inferior cover 30, the main shaft 86 has a first end 90 that extends into the main slot 72. The main shaft 86 as well as most of the main components of the sizing tool 10 and the sizing tools in the embodiments described herein are made of a sufficiently strong and hard polymer or metal, such as stainless steel.

The first end 90 of the main shaft 86 has an opening 88 disposed concentrically with the apertures 78 and 80 on the inferior member 30. A snap-in, tight fit or threaded locking pin 92 extends through the opening 88 and apertures 78 and 80 to rotatably mount the expandable device 20 on the main shaft 86. Thus, the pin 92 secures the inferior cover 30 laterally and longitudinally to the main shaft 86. The pin 92 and openings/apertures 78, 80, and 88 generally form the axis of rotation $R_1$ for the expandable device 20 (shown in FIG. 2) extending in the superior-inferior direction and transverse to the longitudinal axis $L_1$ of the holder 14.

Although not preferred, the connection of the main shaft 86 and expandable device 20 to pin 92, and omitting the steering mechanism 120, permits the expandable device 20 to be steered passively by using the holder 14 to advance the expandable device 30 against anatomical structure such as the annulus to pivot the expandable device about axis $R_1$. This will position the longitudinal axis $L_e$ of the expandable device to extend laterally or orthogonally to the anterior-posterior direction.

Figure 6:
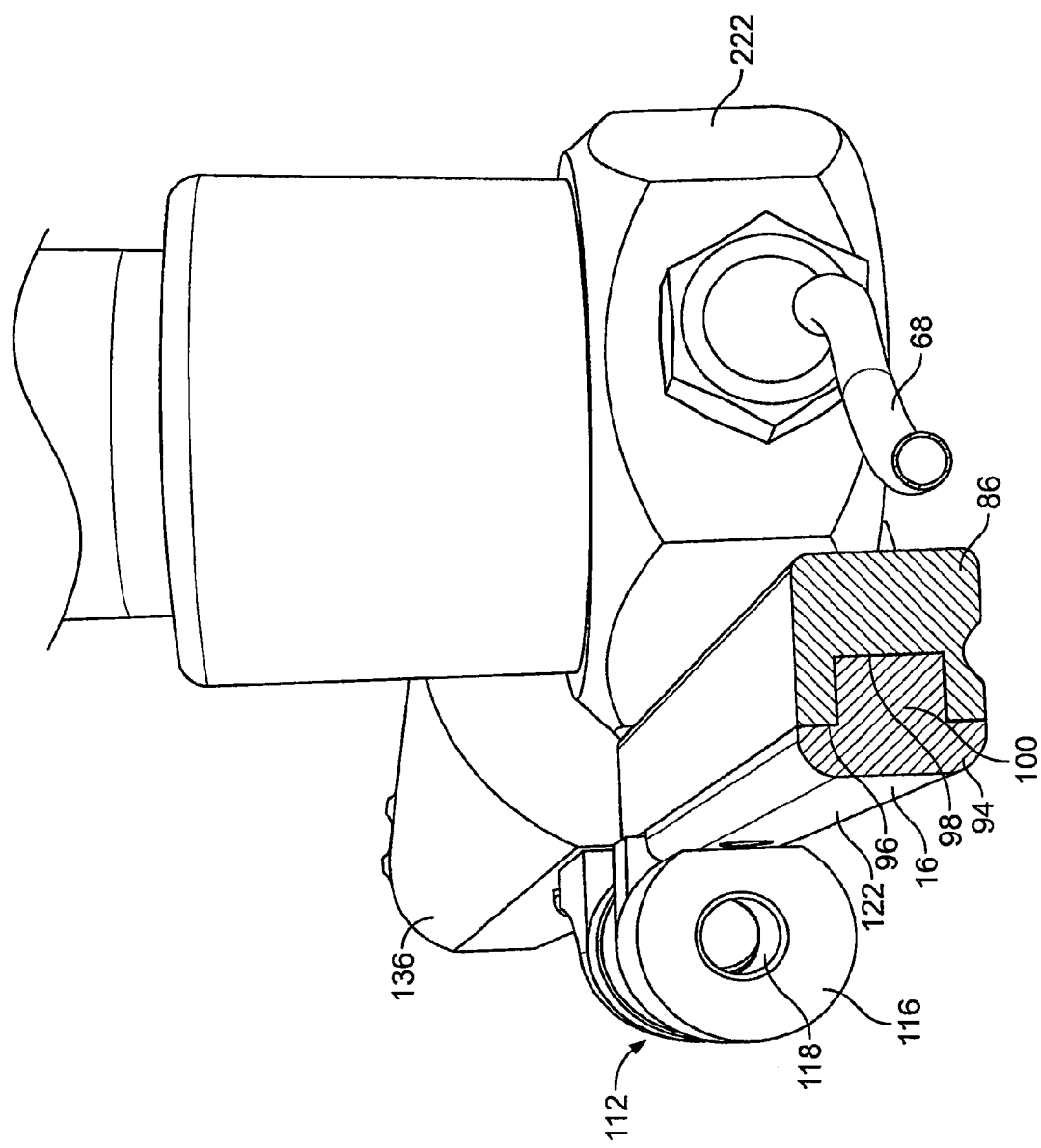
FIG. 6 is a cross-sectional view taken along line VI-VI on FIG. 1 showing the connection between a steering actuator and the side of the sizing tool.

In the preferred embodiment, however, and as mentioned above, the steering mechanism 120 provides active steering with the steering shaft 94. As shown on FIG. 6, in order to hold the steering shaft 94 on the main shaft 96 while permitting the shaft 94 to translate axially relative to the main shaft 86, the steering shaft 94 has a reclining T-shaped cross section where the bottom of the 'T' forms an elongate rail 100 that extends generally parallel to longitudinal axis $L_1$. The rail 100 is received by, and translates within, an elongate groove 98 on the right side 96 of the main shaft 86.

Figure 5:
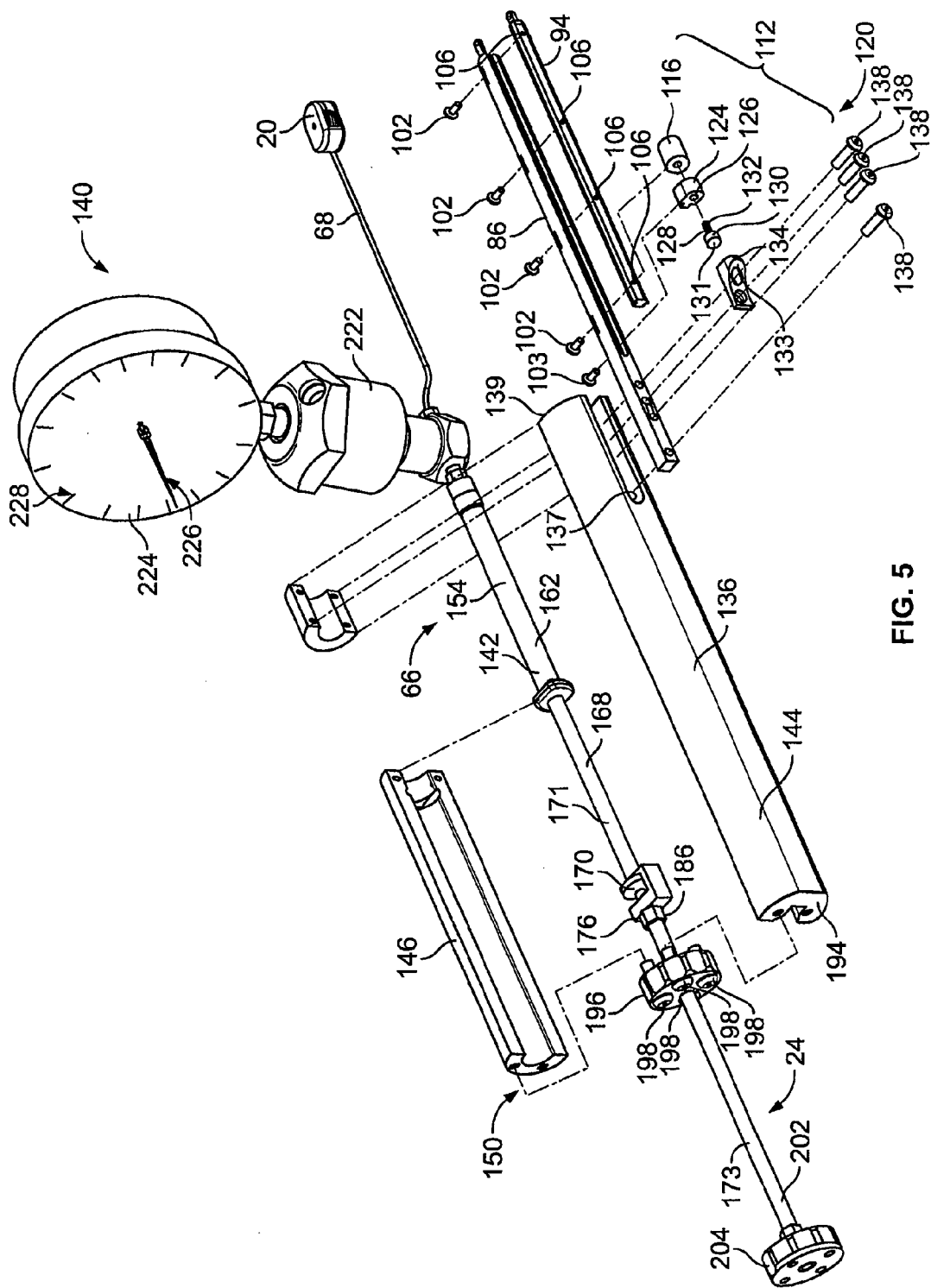
FIG. 5 is an exploded, perspective view of the sizing tool of FIG. 1 showing the components of a steering mechanism, handle portion, and fluid delivery system.

As shown in FIGS. 3 and 5, the steering shaft 94 is laterally secured to the main shaft 86 (to the left and right relative to the holder 14) by a plurality of screws 102. Each screw 102 is received by longitudinally extending slots 104 on the main shaft 86 that are aligned with openings 106 on the steering shaft 94. The axial length of the slots 104 are set to limit the distance the steering shaft 94 is permitted to translate on the main shaft 86.

As shown in FIG. 3, to connect the steering shaft 94 to the inferior cover 30, a distal end 107 of the steering shaft 94 has an aperture 108 extending in the superior-inferior direction. The distal end 107 is received by main slot 72 for aligning the aperture 108 with the diagonal slots 82 and 84. The pin 110 has similar structure to that of pin 92 and is placed through the slots 82 and 84 and aperture 108 for securing the steering shaft 94 to the expandable device 20.

Figure 7:
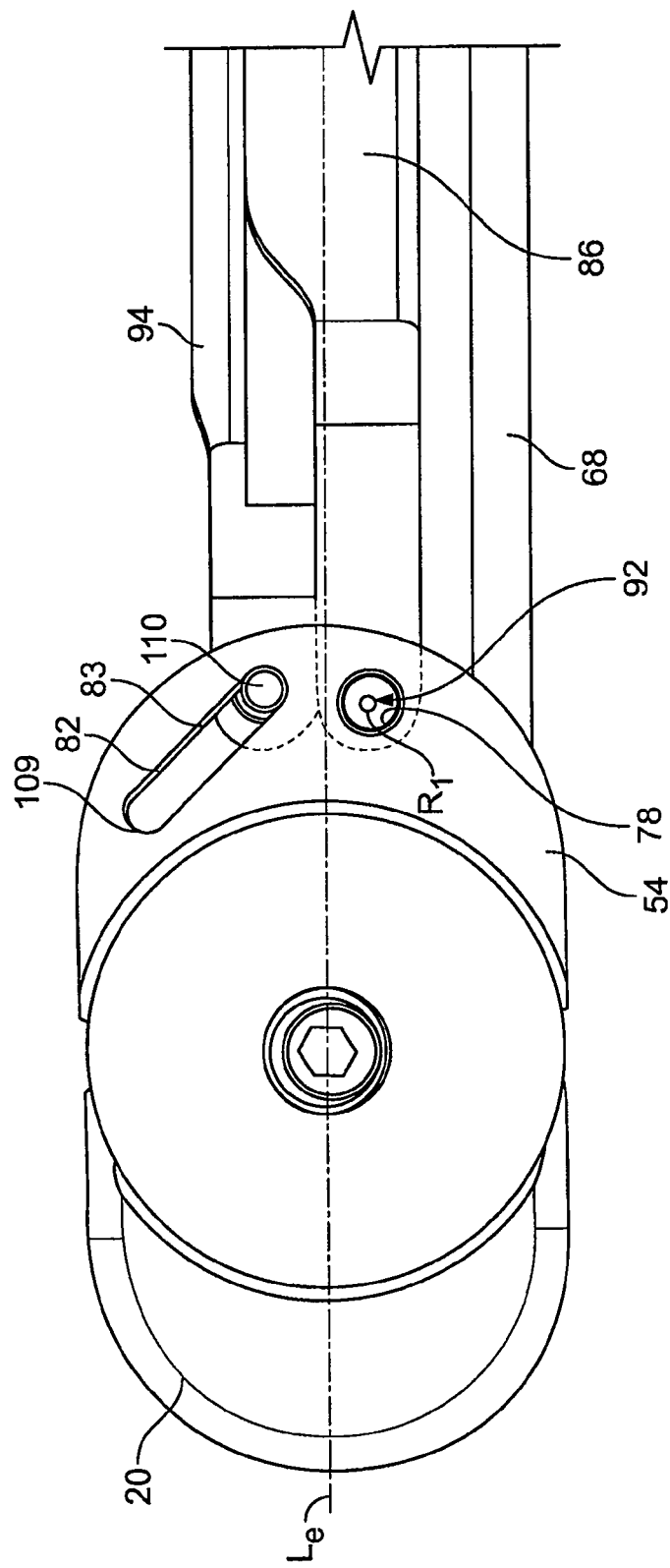
FIG. 7 is a top view of the distal end of the holder and expandable device with its top cover removed and showing a pin-slot connection between the expandable device in a non-pivoted orientation and the holder.

Referring to FIGS. 7-8, in order to pivot the inferior cover 30, the steering shaft 94 is retracted longitudinally and proximally toward the user which causes the pin 110 to slide along the slots 82 and 84 (only one is shown). Since the pin 92 retains the proximal end 54 of the inferior member 30 in a fixed axial position relative to pin 110, the axial motion of the pin 110 causes the pin 110 to cam against at least one edge 83 of the slots 82 and 84 to pivot the inferior cover 30 about both pin 92 and pin 110. The direction and length the diagonal slots 82 and 84 extend controls the direction and amount of pivoting of the inferior cover 30. Here, with the inferior cover 30 at a neutral or straight orientation shown in FIG. 7, the slots 82 and 84 extend distally from the pin 110 at a 45 degree angle relative to the longitudinal axis $L_e$ of the expandable device 20. The slots 82 and 84 are long enough to permit the expandable device 20 to be pivoted to the right up to approximately 90 degrees upon proximal translation of the steering shaft 94 and until pin 110 abuts an outer end 109 of the slots 82 and 84 as shown in FIG. 8. This configuration also permits the inferior cover 30 to be pivoted slightly to the left (less than 45 degrees) when the steering shaft 94 is translated distally to pivot the expandable device 20 until the pin 110 abuts the distal end 109 of the slots 82 and 84.

It will be appreciated that a mirrored structure to that presented here will allow the inferior cover 30 to be mainly rotated to the left up to 90 degrees rather than to the right. Additionally, the slots 82 and 84 could extend in other directions, or in additional directions, in order to accommodate about 180 degrees of rotation although the inferior cover 30 may need to be extended to provide such slots.

Figure 9:
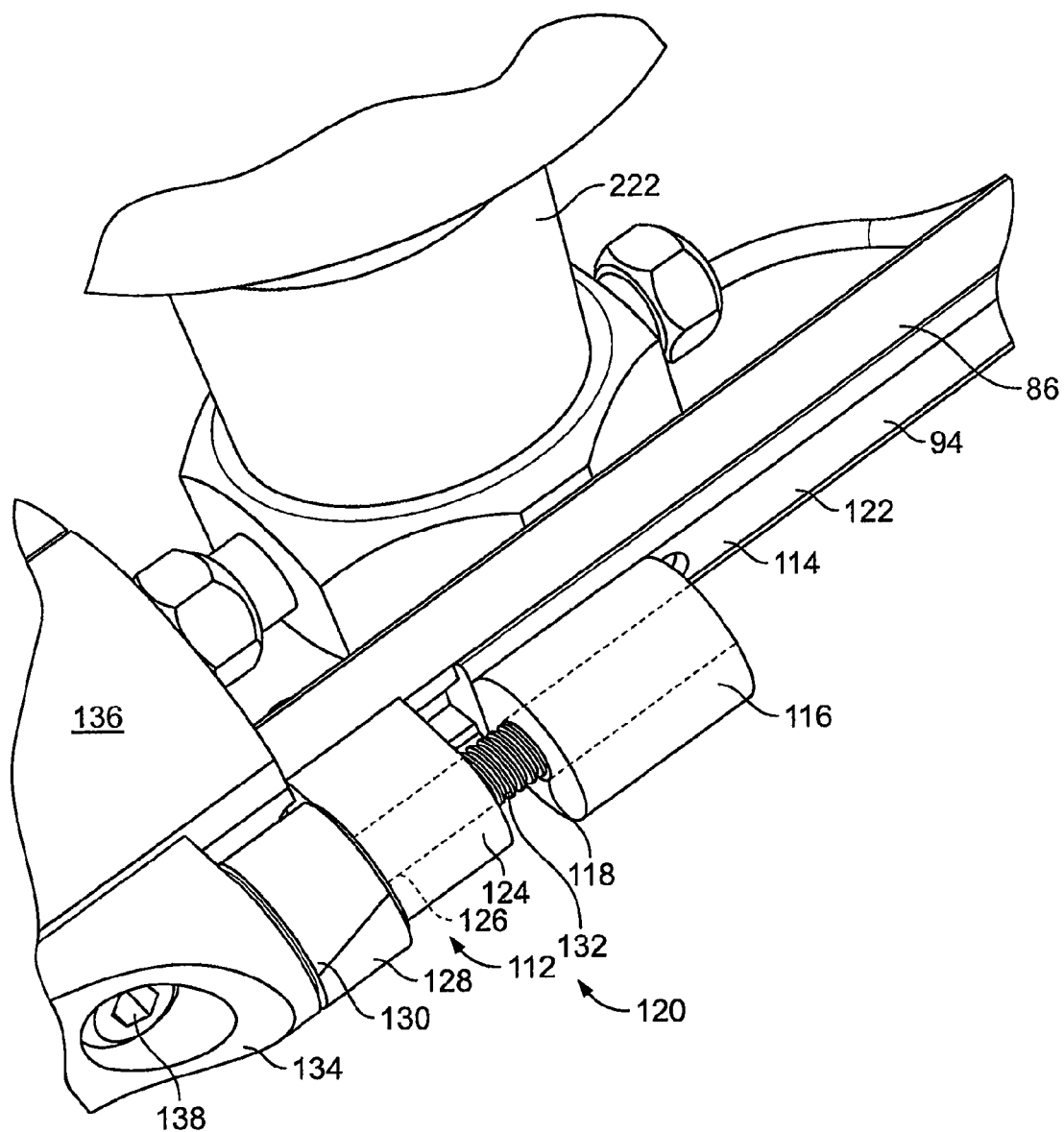
FIG. 9 is an enlarged, right-side perspective view of the sizing tool showing a steering control.

Referring to FIG. 9, in order to translate the steering shaft 94, the steering control device 112 is disposed at a proximal end 114 of the steering shaft 94. The control device 112 has a control screw 128 with a knob 130 and that is laterally and longitudinally secured to the main shaft 86. The control screw 128 also generally extends parallel to the longitudinal axis $L_1$. The control screw 128 is threadedly mated in a bore 118 on a collar 116. The collar 116 is secured to a right side 122 of the steering shaft 94 so that axially shifting the collar 116 also shifts the steering shaft 94 axially. So configured, rotating the knob 130 axially shifts the collar 116 and in turn steering shaft 94.

Referring to FIGS. 5 and 9, a securing block 124 for laterally securing the control screw 128 to the holder 14 is mounted on the groove 90 on the right side 96 of the main shaft 86 by a fastener 103. The block 124 is disposed between the knob 130 and the collar 116. The control screw 128 has a shank 132 extending from the knob 130, through a longitudinally extending, non-threaded bore 128 on block 124, and into the collar 116.

To ensure the control screw 128 cannot be unintentionally removed from the block 124 and collar 116, a retainer 134 is also mounted on the main shaft 86 and behind the knob 130 so that the knob 130 is secured axially between the retainer 134 and the block 124. For this reason, the retainer 134 has an enlarged forward end 133 that extends laterally from the main shaft 86 to closely oppose and substantially cover a rear face 131 of the knob 130 so that the knob 130 does not have clearance to shift distally or laterally.

Fasteners 138 secure the retainer 134 and main shaft 86 to a generally cylindrical main body 136 that forms the proximal portion 22 of the holder 14. The main body 136 also provides a handle 284 for a user to grasp the holder 14. The main body 136 has a longitudinally extending slot 137 extending from a forward end 135 of the main body that receives the proximal end 139 of the main shaft 86.

In operation, rotating the knob 130 rotates the shank 132 within bore 118 which longitudinally shifts the collar 116 and in turn translates steering shaft 94. Turning the knob 130 in one direction, such as counter-clockwise, translates the collar 116 and steering shaft 94 proximally or forward to drive pin 110 within slots 82 and 84 forward as described above to pivot the expandable device 20 to the left. Rotating the knob 130 clockwise will retract the collar 116, steering shaft 94 and in turn drive pin 110 in slots 82 and 94 to pivot the expandable device 20 to the right.

Referring again to FIGS. 5 and 11, as mentioned previously, a fluid delivery system 66 may be used to expand and collapse the expandable device 20 while the expandable device is located within the intervertebral space. The fluid delivery system 66 includes an expansion actuator 141 with a syringe as the fluid supply 142 and that is held by the main body 136. A fluid channel 208, formed by a valve body 210 described below, extends forward from the syringe 142 and to the fluid conduit or tube 68 which connects to the expandable device 20 to provide fluid to the expandable device. The expansion control device 24 on the proximal portion 22 of the holder 24 is operatively connected to the syringe 142 to eject fluid from the syringe 142 to expand the expandable device 20 or to draw the fluid back into the syringe 142 to collapse the expandable device.

In order to hold the syringe 142, the main body 136 is provided in three generally semi-cylindrical pieces. An elongate, main right-side shell 144 forms the right side 143 of the main body 136 while a proximal left-side shell 146 and a distal left-side shell 148 forming the left side 145 of the main body 136. Fasteners connect the left shells 145 and 146 to the right shell 144. A gap 152 (shown best on FIGS. 1 and 10) is formed on the left side 145 of the main body 136 and longitudinally between the left proximal shell 146 and the left distal shell 149. The gap 152 is spanned by a translucent or transparent, tubular barrel 154 of the syringe 142 that holds the fluid so that the contents of the barrel 154 are visible to determine the volume of fluid in the expandable device 20.

As shown in FIG. 1, the syringe 142 has the volume gauge 156 with scale indicia 155 displayed along the side of the barrel 154 in a longitudinally extending array to indicate the amount of fluid within the syringe. The indicia 155 may run the entire length of the gap 152 or just portions thereof as needed. The fluid is preferably a liquid approved for use within the human body such as saline.

Referring to FIGS. 5 and 10, the barrel 154 has a nozzle end 160 connected with channel 208 for delivering fluid. The barrel 154 also has an opposite plunger end 162 that reciprocally receives a syringe plunger 168 that ejects fluid from, or draws fluid into, the barrel 154. A generally cylindrical luer lock 158 is threaded or snap-fit on the nozzle end 160 of the syringe 142 for securing the nozzle end 160 to the shell pieces 144 and 148. The luer lock 158 is secured either by a threaded fit or interference fit with the main body 136 that secures the syringe 142 to the main body 136. In order to secure the plunger end 162 on the main body 136, the plunger end 162 of the barrel 154 has a radially and transversely extending flange 163 received by corresponding interior grooves 164 and 166 respectively on the opposing shell pieces 144 and 146.

In order to operate the fluid delivery system 66, the expansion control device 24 includes a main plunger 174 that is accessible to the user and that is connected to the syringe plunger 168 so that the two plungers operate as a single axially translating device. The main plunger 174 is provided because the main plunger has a large gnarled knob 204 that is easier to grasp than a head 170 on the syringe plunger 168. The main plunger 174 also provides a threaded connection to main body 136 for greater precision in controlling the flow of the fluid by rotating the knob 204 than is possible by pressing or pulling the head 170 of the syringe plunger. Thus, the plungers 168 and 174 are configured so that rotating the knob 204 in one direction advances the main plunger 174 and syringe plunger 168 to deliver fluid to the expandable device 20. Rotating the knob 204 in the other direction retracts the main plunger 174 and syringe plunger 168 to draw fluid from the expandable device.

To connect the syringe plunger 168 to the main plunger 174 so that the two plungers act as a single member, a bracket 176 connects to, and shifts axially with, a distal end 172 of the main plunger and a proximal end 169 of the syringe plunger. Due to the fluid pressure in the barrel 154, the syringe plunger 168 is always biased distally toward the main plunger 174 so that the bracket 176 mainly maintains the two plungers 168 and 174 generally along the same longitudinal axis.

In further detail, the syringe plunger 168 has a rod 171 extending from a head 170 and into the barrel 154. The main plunger 174 has a threaded rod 173 extending forward from knob 204. The bracket 176 abuts the head 170 against a distal end 172 of the threaded rod 173. The bracket 176 is generally U-shaped with opposing, forward and rear legs 178 and 184 connected to each other on one side by an axially extending bridge 190.

As shown in FIG. 10A, the forward leg 178 of the bracket 176 is itself also U-shaped and has an opening 180 that receives the rod 171 of the syringe plunger 168 for placing the head 170 between the bracket legs 178 and 184. Rear leg 184 of the bracket 176 has an unthreaded bore 182 for receiving the distal end 172 of the threaded rod 173 of the main plunger 174 and that permits the rod 173 to rotate within the bore 182.

The head 170 fits tightly between the forward leg 178 of the bracket 176 and the distal end 172 of the rod 173.

In the preferred embodiment, the threaded rod 173 extends rearwardly from the bracket 176 and through a threaded opening 200 on a cap 196 connected to a rear end 194 of the main body 136. This threaded connection longitudinally secures rod 173 to the main body 136 so that the rod 173 will not shift axially unless the knob 204 is rotated. Since the syringe plunger 168 is biased distally against the distal end 172, axially shifting the rod 173 forward or rearward will also axially shift the syringe plunger 168 forward or rearward.

A locking nut 186 is threaded on the rod 173 and disposed against the rear side of the bracket 176 to abut and advance the bracket 176 as the control 24 is moved distally or forward to move the syringe plunger 168 distally. The locking nut 186 also retains the bracket 176 as the rod 173 is shifted proximally. A plastic ring may be placed around nut 186 and leg 184 of the bracket 176 to further secure the nut and rod 173 to the bracket. So configured, the two plungers 168 and 174 are secured to each other so that they translate distally and proximally together.

The main body's shell pieces 144 and 146 cooperatively form a longitudinally extending, main bore 192 that is dimensioned to permit the longitudinal translation of the bracket 176 within it. The bore 192 includes an elongate, longitudinally extending groove 188 (shown best in FIG. 10A) that receives the bridge 190 of the bracket 176. The groove 188 circumferentially secures the bracket relative to longitudinal axis $L_1$ and so that the bracket does not rotate about the plunger rods 171 and 173 as the rod 173 is rotated.

The main bore 192 is covered at the rear end 194 of the main body 136 by the cap 196 which is secured by fasteners such as screws 198 to the main body 136. As mentioned above, the threaded rod 173 of the main plunger 174 extends through a threaded opening 200 on the cap 196

Figure 11:
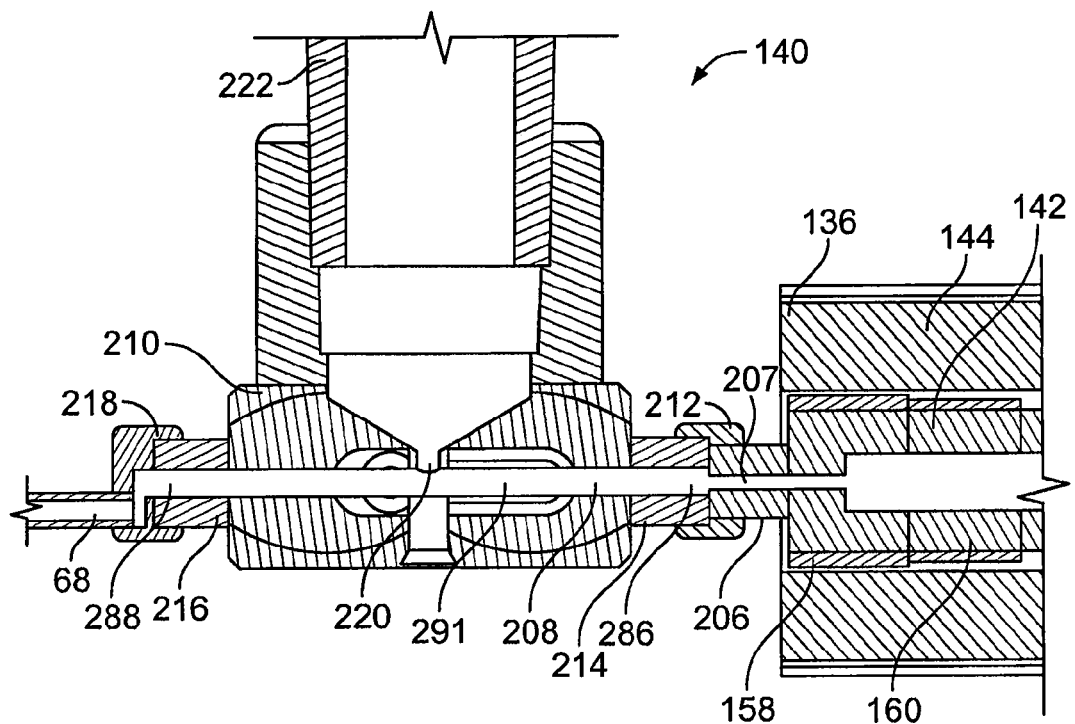
FIG. 11 is a left-side, cross-sectional view of a central portion of the sizing tool showing the internal paths of the fluid delivery system.

Referring now to FIG. 11, the illustrated fluid delivery system 66 includes a valve body 210 that connects the syringe 142 and the measuring device 140 to the expandable device 20. The valve body 210 provides an inverted T-shaped fluid passage 291 with the main longitudinal channel 208. A proximal end 286 on channel 208 is connected to the syringe 142 and a distal end 288 of channel 208 is connected to the tube 68 that is in turn connected to the expandable device 20. A branching, upwardly extending channel 220 of the inverted T-shaped passage 291 is connected to a pressure gauge 222 such that the valve body 210 is a base for the gauge 222.

The valve body 210 has a proximally extending stem 214 connected to a distally extending nose 206 on the nozzle end 160 of the syringe 142. A bushing 212 secures the nose 206 to the stem 214, and the nose 206 has a narrow passage 207 that opens to the channel 208. The valve body 210 also has a distally extending stem 216 that is connected to the flexible tube 68 by a bushing 218 that secures the tube 68 to channel 208 for supplying the fluid to the expandable device 20.

Referring to FIGS. 1 and 5, the pressure gauge 222 may be a floating diaphragm type gauge or similar type of pressure gauge that indicates the pressure of the fluid in the fluid channels 208 and 220 and in turn the pressure of the fluid in the expandable body 28. A face 224 of the gauge 222 here shows a rotating pointer 226 and a circular array of indicia 228 as shown in FIG. 5. The face 224 may show fluid pressure in psi, Mpascals or other units and could alternatively show an electronic, analog or digital read-out to indicate the pressure of the fluid in the fluid system 66.

In the preferred embodiment the surgeon injects fluid to expand the expandable device 20 until it is determined that the expandable device is about the height of the natural disc. This may be done using the pressure gauge as described above. Other ways of determining that the expandable device 20 has reached a desired height in the intervertebral space is for the surgeon to sense increased resistance to rotating the knob 204, or to observe that the expandable device is expanded against both adjacent vertebrae either visually or through the imaging techniques mentioned previously. For the use of imaging techniques, the threaded rod 173 holds the position of the syringe plunger 168 to maintain the fluid at the desired pressure until the control 24 is moved again.

As mentioned above, one alternative way to measure the expansion is to use the volume gauge 156. Predetermined fluid volumes may correspond to specific expansion amounts. Thus, the height of the expandable device 20 corresponds to the volume of fluid injected into the expandable device 20 as indicated on the volume gauge 156 on the barrel 154 of the syringe 142. The volume of fluid within the expandable device may be directly indicated by the indicia 155 or may be indirectly indicated by indicia displaying the amount of fluid within the syringe barrel 154 so that a certain reduction of fluid from the barrel 154 indicates the amount of fluid delivered to the expandable device 20. Once the volume is known, a corresponding height of the expandable device and in turn height of the implant can be determined.

Once the height of the expandable device 20 is determined, the knob 204 is rotated to draw the syringe plunger 168 rearward to draw the fluid from the expandable device 20 and back into the syringe barrel 154. Once collapsed, the expandable device 20 is pivoted back to a straight orientation by rotating the knob 130 on the steering control device 112 so that the expandable device's longitudinal axis $L_e$ is parallel to the longitudinal axis $L_1$ of the holder 14. The expandable device 20 is then retracted out of the nuclear or intervertebral space without damaging or enlarging an annulus incision.

Alternatively to retracting the expandable device 20 after its expansion has been measured, the pressure may be increased even further for a short period of time, such as to 100 psi (as indicated by pressure gauge 222) for 5 minutes, to over-distract and stretch the soft tissue such as the ligaments and annulus in order to provide extra height of the intervertebral space for insertion of the implant.

In alternative configurations for sizing tool 10, it will be understood that parts of the fluid delivery system 66 and/or measurement mechanism 150 may be separate from the sizing tool 10. In such a case, the system 12 has tube 68 still connected to the expandable device 20, distal and/or proximal portions 16, 22 of the sizing tool 10 but then lead to a fluid supply and/or pressure gauge maintained in a remote location from the sizing tool 10.

Referring now to FIG. 15, instead of bellows 32, a number of other embodiments include inflatable, elastic balloons or bladders for expanding and collapsing an expandable device. In one embodiment, expandable device 20 may be provided with an alternative expandable, inflatable body 230 made of elastic material such as a polymer balloon 232 that may be more cost efficient than bellows. Balloon 232 has a helical, rigid thread 234 mounted on a cylindrical, outer surface 236 of the balloon to control the expansion and collapse of the balloon, similar to bellows 32. The thread 234 is biased to fold its coils one on top of another to maintain a generally cylindrical shape and a concentric alignment about a superior-inferior axis. This minimizes the risk of the balloon extending from between superior and inferior cover pieces and damaging the annulus or other anatomical structure. The thread 234 may be integrally formed with the balloon 232 or connected by adherent, welding or other similar techniques.

The balloon 232 has a top 294 that may be completely closed and adhered to top plate 34 or directly to the superior cover 26 of expandable device 20. As an alternative, the top 294 may have an opening to receive fastener 40 shown in FIG. 3. A bottom 296 of the balloon has an opening to receive the fluid from the fluid delivery system 66 but is otherwise adhered to the bottom plate 36 or directly to the inferior cover 30 of expandable device 20.

Referring to FIGS. 16-17, in an alternative embodiment, a sizing tool 239 may be provided with an expandable device 240 that uses a peripheral wall 252 between superior and inferior covers 244 and 246 to generally enclose a balloon 242 therebetween rather than using reinforcing structure attached to the balloon. Thus, the inferior cover 246, which is held at an end 231 of a holder 250, has a peripheral wall 252 that extends upward from a top surface 254 of the inferior cover 246 and toward the superior cover 244. As shown in FIG. 17, in the collapsed configuration, the wall 252 engages the superior cover 244 to substantially cover the height between the superior cover 244 and the top surface 254 of the inferior cover 246. The wall 252 extends at least around a distal, leading end 256 of the expandable device 240 and preferably at sides 278 and 280 of the expandable device 240. This protects the balloon 242 while the leading end 256 of the expandable device is placed in front of the expandable device 240 during insertion of the expandable device 240 into an intervertebral space and through an annulus incision. The wall 252 stops short of a proximal end 262 of the expandable device 240 in order to provide clearance for the distal end 231 of the holder 250, a collar 266 and the measurement mechanism 264.

In another aspect of this embodiment, the measuring mechanism 264, mentioned above, is provided to measure the distance the superior cover 244 distracts from the inferior cover 246. The measuring mechanism 264 includes the elongate member 268 which may be a cable. The elongate member 268 has a holder portion 293 that extends longitudinally along the holder 250 and onto the inferior cover 246 where it is bent into an expansion portion 295. The expansion portion 295 extends upward from the holder portion 293 and in a superior-inferior direction to the superior cover 244 where a distal end 282 of the cable 268 is secured. The cable 268 is bent around a bar or beam 272 which extends transversely to the longitudinal dimension of the holder 250 in order to transition from the expansion portion 295 to the holder portion 293. The beam 272 extends across a bore 270 of the collar 266 that itself extends in the superior-inferior direction and connects the inferior cover 246 to the distal end 231 of the holder 250 as explained further below.

With this configuration, filling the balloon 242 distracts the superior cover 244 away from the inferior cover 246 which in turn axially shifts the distal end 282 of the cable 268 upward and distally. This varies the length of the expansion portion 295 and in turn changes the length of the holder portion 293 of the cable 268. As a result, a proximal end 274 of the cable 268 is axially shifted from a predetermined initial axial position to a sizing position. The difference or distance between the two positions indicates the length the height of the expandable device 240 has changed during its expansion.

The proximal end 274 of the cable 268 may be visible along the holder 250 or at an end of the holder. Thus, the amount of expansion can be indicated by, for example, a visual inspection of the cable 268 by indicia 276 on the cable. Optionally, an indicator such as a gauge or other similar device may be connected to the proximal end 274 of the cable 268 and that indicates the change in distance from the initial position to the sizing position of the cable 268.

In order to expand the balloon 242, a fluid delivery system 238 connected to the expandable device 240 has an expansion actuator 298 including a tube 248 that extends along the holder 250 and is connected to the balloon 242 in order to fill the balloon 242 with fluid and to alternatively evacuate the fluid from the balloon 242. The fluid delivery system 238 may have the same or similar expansion control device to that provided for fluid delivery system 66 on sizing tool 10. Other than the connection to tube 248, the balloon 242 has no other opening and may be adhered or fastened to the superior and inferior covers 244 and 246.

In order to at least provide passive steering of the expandable device 240, the collar 266 may be part of the holder 250 and rotatably mounted on the inferior cover 246. In this case, the collar 266 may be rotatably mounted on a boss, pin or other similar connector extending upward from the inferior cover 246. Alternatively, the bottom of the collar 266 may have a downwardly extending boss received by an aperture in the inferior cover 246 instead. In another alternative, the distal end 231 of the holder 250 may have a ring rotatably mounted on the collar 266 which would be secured to the inferior cover 246. These structures permit the expandable device 240 to pivot relative to the distal end 231 of the holder 250 and about a rotational axis $R_2$ extending in a superior-inferior direction at the center of collar 266. It will also be understood, however, that the expandable device 240 and holder 250 may be modified with the structure of the steering mechanism 150 on sizing tool 10 to provide active steering.

Figure 18:
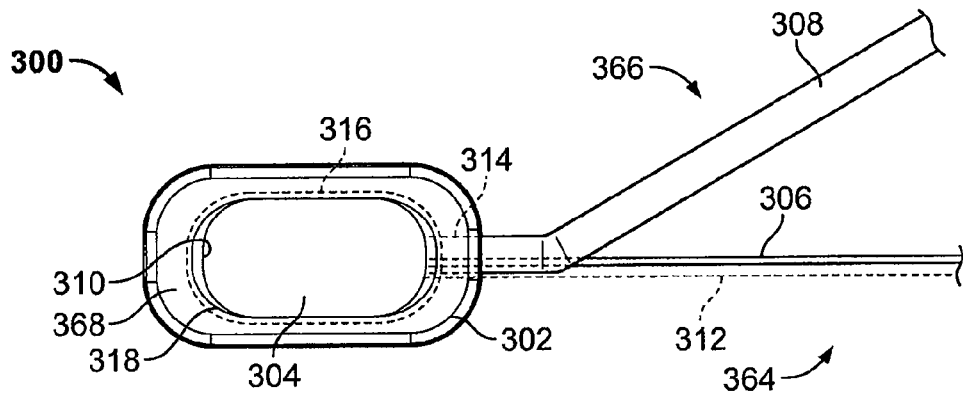
FIG. 18 is a top view of yet another alternative expandable device with a torroidal balloon and a distal end of a fluid delivery system in accordance with the present invention.
Figure 19:
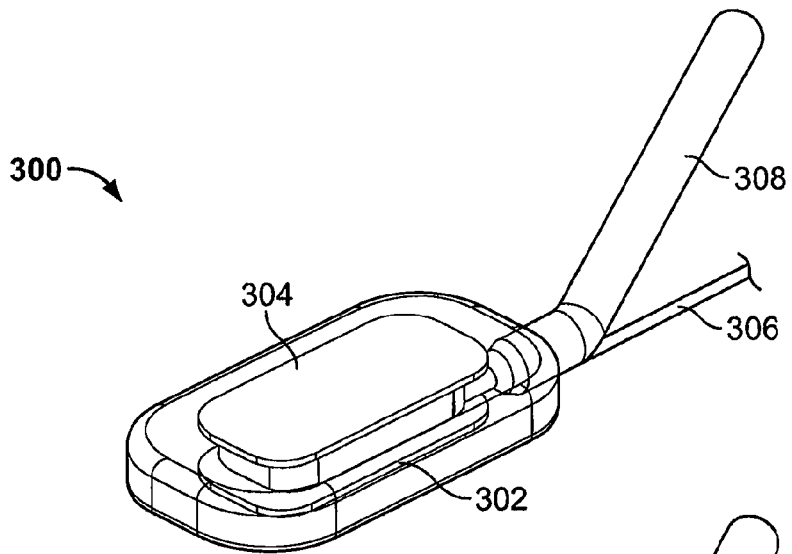
FIG. 19 is a side perspective view of the expandable device of FIG. 18 showing the expandable device in a collapsed configuration and the fluid delivery system.
Figure 20:
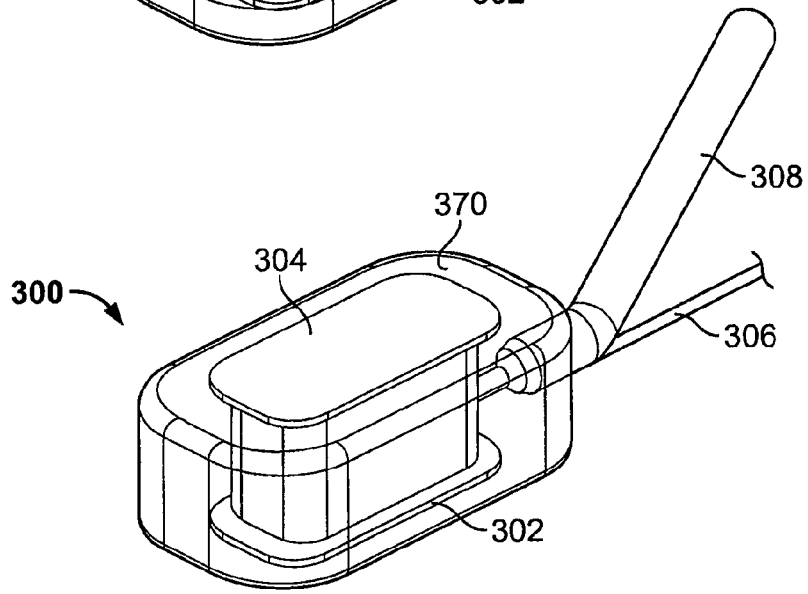
FIG. 20 is a side perspective view of the expandable device of FIG. 18 showing the expandable device in an expanded configuration and the fluid delivery system.

With reference now to FIGS. 18-20, to increase accuracy in measuring the height of the intervertebral space, an alternative expandable device 300 for placement in an intervertebral space uses a curing material to form a measurable, shape-retentive annular wall that may be removed from the intervertebral space so that it can be measured ex situ. The expandable device has an outer, generally torroidal balloon 302 that encircles a generally obround, inner balloon 304 for a number of different configurations for forming the annular wall.

In one configuration, the inner balloon 304 is used as a form or mold while the annular wall is created in the outer balloon 302. For this configuration, the inner balloon is first inflated with a fluid such as saline through a fluid tube 306 of a fluid delivery system 364 the same or similar to fluid delivery system 66. The fluid tube 306 either passes through the outer balloon 302 or passes around the top or bottom of the outer balloon to connect to the inner balloon 304. Once the inner balloon 304 is inflated, the inner balloon 304 can then be used as a form or mold for an interior surface of the annular wall and outer balloon 302.

The outer balloon 302 is connected to a tube 308 of a curing material delivery system 366 for filling the balloon 302 with a soft deformable, elastic curing material such as polymer, polyvinylsiloxane and similar materials that will cure after placement of the curing material in balloon 302. The outer balloon 302 has a predetermined, generally fixed width and length while its height is variable. Thus, the outer balloon 302 may be inflated with curing material until it abuts superior and inferior vertebrae and forms an annular wall 368 within the balloon 302.

Once inflated as shown in FIG. 20, the outer balloon 302 can be removed from the intervertebral space in order to measure the height of the outer balloon which indicates the height of the intervertebral space. In order to remove the outer balloon 302 from the intervertebral space, once the polymer in the outer balloon 302 is cured, the inner balloon 304 is deflated by drawing the fluid as explained for fluid delivery system 66. The deflation of the inner balloon 304 provides the outer balloon 302 with enough flexibility and deformability to be compressed for retracting the outer balloon 302 from the intervertebral space. The surgeon may use a pinching or grasping tool to pull the inner and or outer balloons out of the intervertebral space.

The curable material is shape-retentive so that once the outer balloon 302 is released from the intervertebral space, the outer balloon 302, and in turn the annular wall 368 of cured material, will change back to the shape it had within the intervertebral space. The outer balloon 302 can then be measured ex situ to measure the height of the intervertebral space.

In an alternative configuration for the expandable device 300, the outer balloon 302 remains permanently in the intervertebral space to either support the annulus if present or to replace the annulus. Thus, the outer balloon 302, and in turn the height of the intervertebral space, is measured by imaging or other methods as mentioned above while the outer balloon 302 is within the intervertebral space. The outer balloon 302 then remains within the intervertebral space while the inner balloon 304 is deflated and removed and an implant is put in its place.

To provide access to a core or opening 310 that the outer balloon 302 encircles and where the inner balloon 304 resides the outer balloon is shifted away from an adjacent vertebra since the outer balloon 302 extends from the inferior to the superior vertebrae to substantially enclose a nuclear space therebetween. Thus, to remove the inner balloon 304, a surgeon inserts a surgical tool such as a clamp or pincher between a top 370 of the outer balloon 302 facing an adjacent vertebra and the adjacent vertebra. The surgeon then presses against the top 370 of the outer balloon 302 with the tool to compress the outer balloon and the cured annular wall 368 within it and presses it in a direction away from the vertebra which provides access to the core 310 of the outer balloon 302. The surgeon then uses the tool to grasp the inner balloon 304 within the core 310 while still pressing against the outer balloon 302 to retrieve the inner balloon.

Similarly, to insert an artificial disc implant or similar device in the core 310, the surgeon may use a surgical tool to press against the outer balloon 302 to provide access to the core 310 and maintain the outer balloon in a compressed configuration. This provides a passage to the core 310 between the outer balloon 302 and the adjacent vertebra. Simultaneously, the surgeon uses an inserter tool with an end holding the implant to advance the implant over the outer balloon 302 and into the core 310. Once the inserter tool releases the implant in the core and is retracted, the surgical tool holding the outer balloon 302 is also retracted. The annular wall 368 expands back to its original shape to enclose the implant within the core 310 of the outer balloon 302.

Alternatively, instead of a second surgical tool, a lead end of the implant secured on the inserter tool could be configured and used to provide access to the core 310 of the outer balloon 302. In this case, the lead end of the implant is advanced to place it between the outer balloon 302 and one of the vertebra. The implant is then pressed against the outer balloon 302 which compresses the outer balloon out of the way of the implant so that the implant can be advanced into the core 310. In such a procedure, the implant would need to be sufficiently secured to the inserter tool so that the implant cannot be unintentionally released from the inserter tool or pivoted on the insertion tool while pressing it against the outer balloon 302.

It is also contemplated that the inflated outer balloon 302 could be removed from the intervertebral space with the inner balloon 304. Then, the inner balloon 304 could be removed from the outer balloon 302 and replaced with an implant ex situ. The outer balloon 302, held by an insertion tool as the balloon 302 surrounds the implant, could then be placed back into the intervertebral space.

Referring to FIG. 18, in yet another alternative configuration, both balloons 302 and 304 can be used as molds to form a compressible, shape-retentive, annular wall 318 (shown in dashed line) between them. Since the wall 318 is so thin, it gains substantially in flexibility and compressibility for easy removal from the intervertebral space.

For this configuration, both the outer balloon 302 and the inner balloon 304 are filled with saline by either placing a hole or branch tube on the fluid tube 306 that opens to the interior of the outer balloon 302 or by providing a second fluid tube 312 (shown in dashed line) that opens to the outer balloon 302. For this configuration, the tube 308 for the curing material has an extension 314 (shown in dashed line) that communicates with a generally cylindrical, relatively thin opening 316 (also shown in dashed line) between the outer and inner balloons 302 and 304.

After the balloons 302 and 304 are inflated, the curing material is delivered to the annular opening 316 by the tube 308 and forms the thin cylindrical or annular wall 318 between the inflated balloons 302 and 304 when cured. The balloons 302 and 304 can then be deflated in order to compress and then remove the wall 318 from the intervertebral space with the balloons. Once removed, the annular wall is shape-retentive to regain its originally cured shape for measurement ex situ.

Referring to FIGS. 21-22, in another aspect of the invention, a sizing tool 324 has an expandable device 328 with a measuring mechanism 326. The measuring mechanism 326 includes a plurality of strings 346a-f that extend along an inflatable body 336 such as a three-dimensionally obround balloon 330. Thus, inflating the balloon 330 shifts the strings 346a-f axially along the balloon. The axial distance the strings shift indicates the amount of expansion of the balloon and in turn a corresponding size of the intervertebral space it is placed within.

In order to measure the expansion of the balloons, the plurality of strings 346a to 346f extend on different parts of the balloon 330 so that the axial distance any one string shifts along the balloon 330 corresponds to the amount of expansion on the part of the balloon that the string is attached to. Thus, a change in length of top and bottom strings indicates the height of the balloon and in turn the height of the intervertebral space. Similarly, a change in length of strings extending longitudinally on the left and right sides of the balloon as well as strings extending circumferentially around the balloon indicates the width of the balloon or the footprint of the intervertebral space.

In greater detail, the expandable device is held on a holder 360 that cooperatively forms a longitudinal central axis $L_2$ with balloon 330. The balloon 330 is made of an elastic material and widens radially away from longitudinal axis $L_2$. Holder 360 has an elongate, main member 332 that extends along the longitudinal central axis $L_2$, and through an interior 338 of the balloon body 330. The main member 332 extends from a proximal end 340 of the balloon and through a distal end 342 of the balloon 330 for holding the balloon 330 at the balloon's proximal and distal ends 340 and 342. The main member 332 also forms an elongate exterior portion 362 that extends outwardly from the proximal end 340 of the balloon 330. The exterior portion 362 is mounted within a tubular shaft 334. The shaft 334 is sufficiently rigid to aid in holding the main member 332 for guiding the balloon 330 as the shaft 334 is manipulated to place the balloon within an intervertebral space. The ends 340 and 342 of the balloon 330 are connected and sealed to the main member 332 by adherent, welding or other similar methods.

The strings 346a-f may be connected to the balloon 330 by a covering layer 348 or transverse strips 350, hooks or other fastening devices that at least permits the strings 346a-f to translate axially while securing the strings radially and/or laterally to the balloon 330.

Four of the strings 346a-d extend longitudinally on the balloon 330 and relative to longitudinal axis $L_2$. The strings 346a-d have distal ends 352a-d that are connected to the distal end 342 of the balloon 330 or to a distal end 354 of the main member 332. The strings 346a-d run also extend off of the balloon 330 and into the shaft 334 until they terminate at proximal ends 356a-d in initial, predetermined positions in the vicinity of a proximal end 344 of the main member 332.

Two of the strings 346e-f extend around at least a portion of the circumference of the balloon and longitudinal axis $L_2$ before turning to extend parallel to the holder 360. In the preferred form the strings 346e-f form one full rotation around the balloon. The strings 346e-f have holder portions 358e-f that extend longitudinally within shaft 334 and terminate at ends 346e-f that form initial, predetermined positions along with the other longitudinal strings 346a-d as shown in FIG. 21.

Referring to FIG. 21, in the collapsed or non-inflated state of the balloon, the strings 346a-f and their longitudinal or holder portions 358a-f have a predetermined length so that their predetermined initial positions are a distance 'd1' from a proximal reference end 344 of the main member 332 or other stationary marker or predetermined axial position on the sizing tool 300. After insertion into an intervertebral space, the balloon 330 is then inflated with fluid as described above for expandable device 20 on sizing tool 10 until the balloon 330 abuts superior and inferior vertebrae or other anatomical forming the intervertebral space. Optionally, the balloon 330 is inflated until the fluid reaches a predetermined pressure as explained previously which is known to configure the balloon so that it abuts the vertebrae.

During inflation, the strings 346a-f shift axially on the balloon while the balloon grows radially from the longitudinal axis $L_2$. This action retracts the proximal ends 356a-f of the strings 346a-f distally and toward the balloon until the ends 356a-f are placed at a new sizing position a distance d2 from the proximal, reference end 344 of the main member 332. The difference between the distances d1 and d2 indicates the expanded height or width of the balloon 336, and therefore, the height and width of the intervertebral or nuclear space.

The proximal ends of the strings 356a-d may be positioned remotely from the balloon 330 so that the change in distances from d1 to d2 is observed upon a visual inspection of the strings 346a-d and main member 332. Holder 360 may have a comparison window in order to observe the difference in length of the strings. The strings 346a-f may be color coded or have other configurations, indicia or indicators that represent whether it is a longitudinal string 346a-d or a circumferential string 346e-f and in turn which dimension of the intervertebral space the string measures. Alternatively, the main member 332 and strings 346a-f may be connected to one or more mechanical indicators or gauges on the holder 360 that indicates the amounts of d1 and d2 and/or the difference between d1 and d2 to a user so that a corresponding dimension of the intervertebral space can be determined. In other forms, such an indicator may instead or additionally indicate the size or dimension of the intervertebral space directly.

It will be understood that more or less than four longitudinal and two circumferential strings may be used. Other alternative configurations for the expandable device 328 are contemplated such as locating the balloon 330 between top, bottom and/or side covers more similar to expandable device 20. Such a configuration can permit the expandable device 328 to be passively or actively steered as described for sizing tool 10.

Referring to FIGS. 23-29, in another form of the invention, a sizing tool 400 has an expandable device 402 that expands and collapses by using mechanical moving parts other than an inflatable body for insertion into an intervertebral space in order to determine the size of the space. The expandable device 402 is also adjustably held on an elongate holder 406 to at least provide passive steering for positioning the expandable device 402 in the desired position described above to imitate the orientation of a natural nuclear disc and space.

Figure 25:
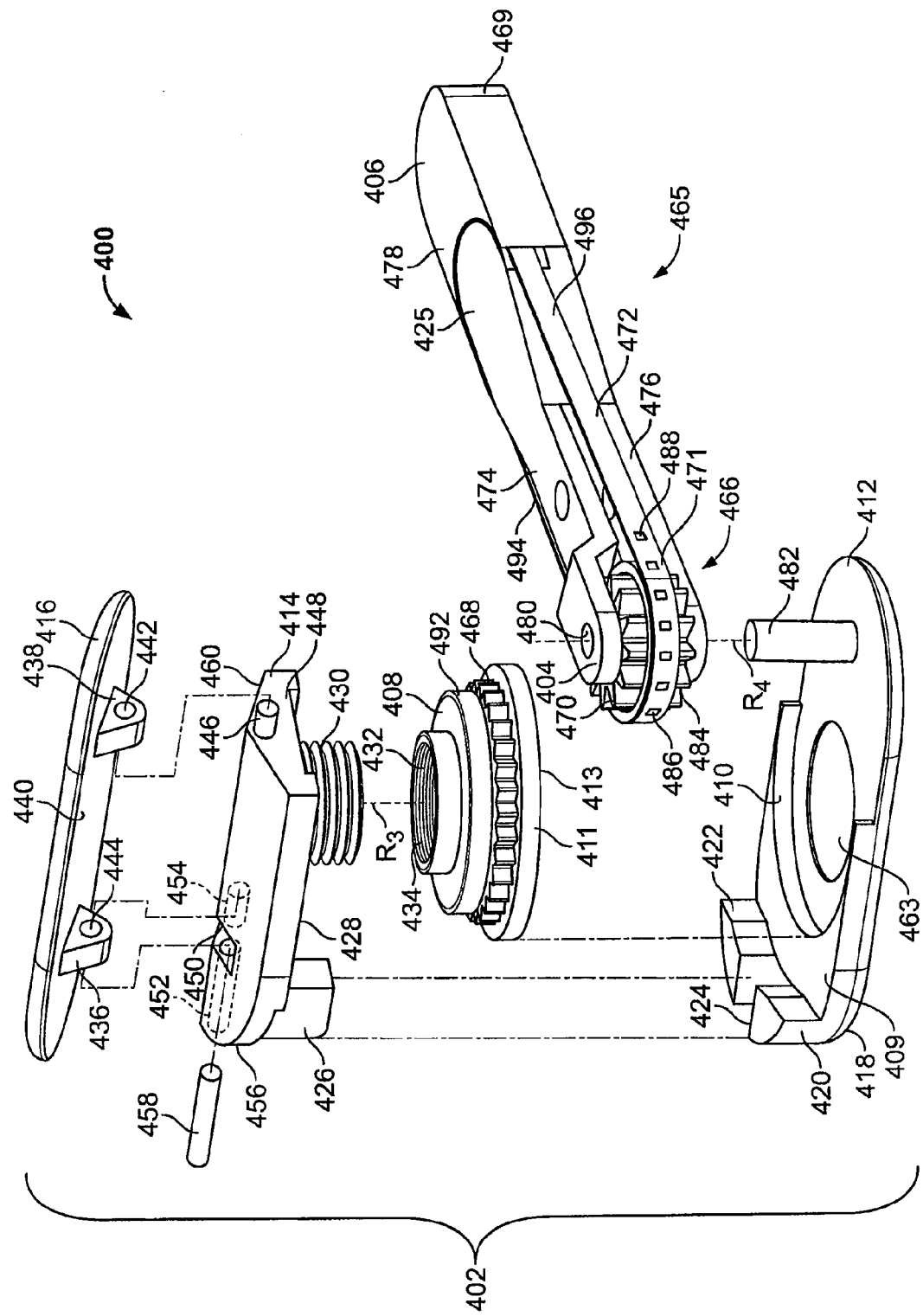
FIG. 25 is an exploded perspective view of the sizing tool of FIG. 23 and showing the components for expanding the expandable device, and for tipping the top cover of the expandable device.

Referring to FIGS. 23 and 25, in order to expand and collapse the expandable device 402, generally, a first portion or collar 408 is pivotally mounted on an inferior cover 412 while a superior cover 416 is connected to a second portion 430 threaded into the collar 408 and extending in a superior-inferior direction. Both the first portion and the second portion are concentric to the same superior-inferior axis $R_3$. With this configuration, the superior cover 416 is maintained in alignment with the inferior cover 412 and the axis $R_3$ to provide a controlled collapse of the expandable device 402.

Rotating the collar 408 on the inferior cover 416 shifts the second portion 430 axially to shift the superior cover 416 closer or farther from the inferior cover 412 to expand or collapse the expandable device 402. An expansion actuator or mechanism 466 is mounted on holder 406 and connects to the collar 408 in a number of different configurations of cooperating structure explained below for rotating the collar 408. An expansion control device 465 is mounted on the holder 406 for selectively operating the expansion mechanism 466. The expansion mechanism 466 is also pivotally connected to the expandable device 402 and about a rotational axis $R_4$ to provide the passive steering as well as to operate the collar 408.

In further detail, the expandable device 402 is pivotally connected to a distal end 404 of the holder 406 that generally forms a longitudinal axis $L_3$ as shown in FIG. 23. The expandable device 402 has an elongate, generally obround shape forming a longitudinal axis $L_4$ and has a narrow distal end 461 used as the lead end for insertion. While FIGS. 23-29 show the expandable device 402 pivoted about 90 degrees relative to the distal end 404 of the holder 406, it will be understood that the expandable device 402 is preferably inserted into the intervertebral space with its longitudinal axis $L_4$ generally parallel to the holder's longitudinal axis $L_3$.

In order to provide the expandable device 400, and in turn narrow end 461, with a relatively low profile to facilitate insertion through an annulus incision, the inferior cover 412 (also referred to as a base) and the superior cover 416 are generally flat and extend in planes parallel to the longitudinal axes $L_4$ and transverse to the superior-inferior direction in an insertion orientation.

As shown on FIGS. 23 and 25, in order to expand and collapse the expandable device 402, the collar 408 is internally threaded and mounted within a partially-circular recess 410 formed on an upwardly facing surface 409 on inferior cover 412. The collar 408 is free to rotate with in the recess 410 and coaxially about an axis $R_3$ that extends in the superior-inferior direction.

An adjustment member 414 is disposed between the collar 408 and the superior cover 416 and has the second portion 430 in the form of an externally threaded projection. The projection 430 extends downward from a downwardly facing surface 428 on the adjustment member 414 and that faces the inferior cover 412. The threaded projection 430 is fixed to the adjustment member 414 and is received by, and threadedly engages, the collar 408 so that rotation of the collar shifts the projection 430 axially, and in turn, raises or lowers the adjustment member 414 and superior cover 416 along the superior-inferior axis $R_3$ in order to expand or collapse the expandable device 402.

Figure 26:
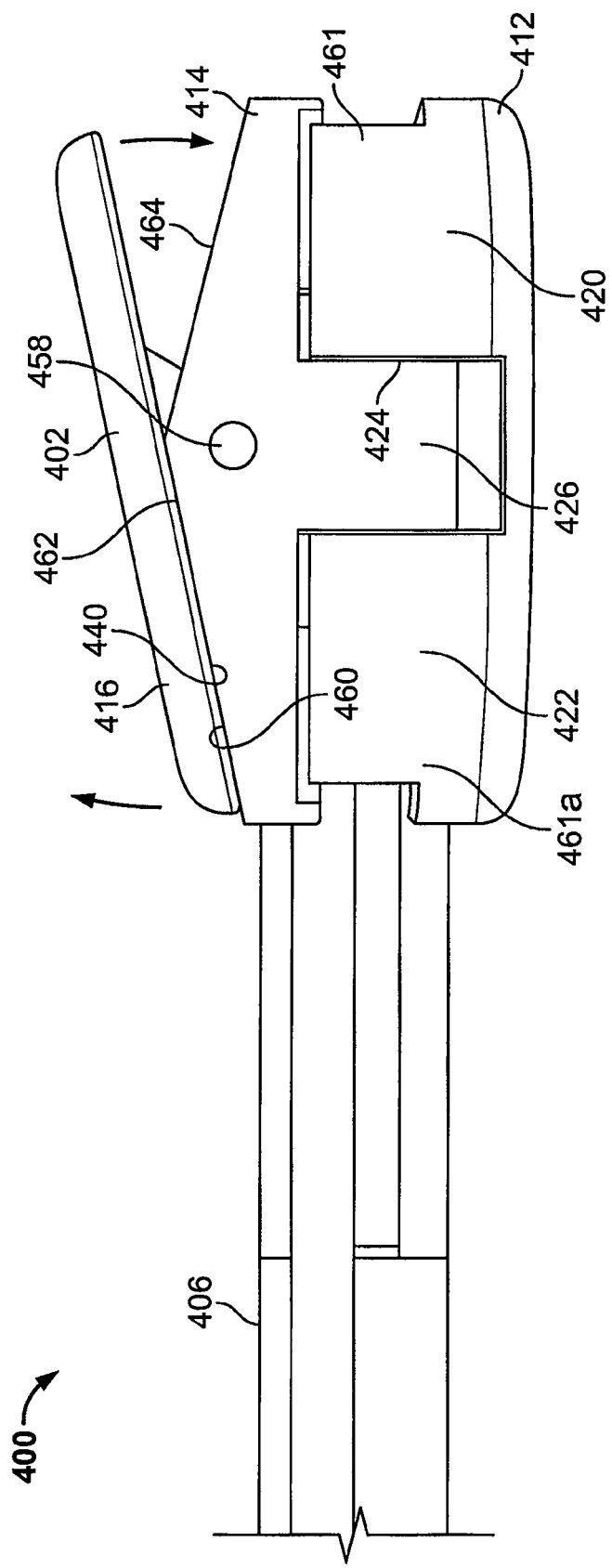
FIG. 26 is an enlarged, right-side elevational view of the sizing tool of FIG. 23 showing the top cover of the expandable device in a slanted orientation.

Referring to FIGS. 25-26, three interlocking walls 420, 424 and 426 form a smooth, continuous outer surface 461a on lead end 461 while also retaining the adjustment member 414 as the collar 408 pivots. The inferior cover 412 has a distal end 418 forming a portion of the lead end 461 with two of the walls 420 and 422 extending upward from the upwardly facing surface 409. The walls 420 and 422 form a slot 424 therebetween for receiving alignment wall 426 extending downward from the bottom surface 428 of the adjustable member 414. The configuration of the three walls 420, 422 and 426 forms the lead end 461.

In order to create the axial motion of the adjustment member 414 and superior cover 416 in the superior-inferior direction, the adjustment member 414 and in turn the threaded projection 430 is secured circumferentially while the collar 408 is permitted to rotate about the threaded projection 430. For this reason, the slot 424 retains the alignment wall 426 and in turn the adjustment member 416 along a fixed radius relative to the axis $R_3$ as the collar 408 is rotated about the projection 430.

Referring to FIG. 25, in order to secure the collar 408 to the inferior cover 412, rims, lips, ledges and/or retainers may be provided and that extend from the upwardly facing surface 409 of the inferior cover 412 and over an outer rim 411 of the collar 408. With such structures, the collar 408 is free to rotate within recess 410 while being secured to the inferior cover 412. Alternatively, the collar 408 may have a base that it rotates upon and that is adhered or otherwise fastened to, or through, a bottom 463 of the recess 410 on the inferior cover 412.

Referring again to FIGS. 23 and 25, the expansion mechanism 466 for rotating the collar 466 in a first form has cooperating structure that includes radially and outwardly extending gear teeth 468 on the collar 408 that meshes with a rotating gear 470 rotatably mounted on the forward end 404 of the holder 406. The expansion control device 465 has an elongated member 472 such as a chain, belt or looped band wrapped around the gear 470 and extending on the holder 406 so that rotating the elongated member 472 rotates the gear 470 which in turn rotates the collar 408.

In more detail, the holder 406 includes two generally flat, upper and lower arms 474 and 476 extending longitudinally and distally from a proximal portion 478 of the holder 406. Both arms 474 and 476 have concentric apertures 480 (only one is shown) at the distal end 404 of the holder 406. The gear 470 is positioned between the arms 474 and 476 and concentrically with apertures 480 to be pivotally and coaxially mounted on a post 482 extending upward from upwardly facing surface 409 on the inferior cover 412. This configuration forms a rotational axis $R_4$ upon which the expandable device 402 pivots relative to the distal end 404 of the holder 406 in order to provide passive steering as discussed below. The post 482 may be integrally formed with the inferior cover 412 or otherwise screwed or fastened to the inferior cover.

Outwardly extending teeth 484 on the gear 470 are configured to mesh with the teeth 468 of the collar 408. The gear 470 also has a ring of sprockets 486 for engaging an array of openings 488 on at least a distal portion 471 of the elongated member 472 although the openings may be spaced along the whole elongated member. The openings 488 and sprockets 486 have corresponding shapes such as square or other shapes that provide sufficient engagement so that shifting the elongated member 472 will rotate the gear 470.

It will also be appreciated that while the ring of sprockets 486 is placed around a central area on the gear 470, it may be placed anywhere along the height of the gear such as closer to, or on, the gear's upper end 490 as shown on alternative gear 470a in FIGS. 24 and 27-29. In either case, the collar 408 has a shoulder 492 stepped back from the teeth 468 in order to provide clearance for the ring of sprockets 486 as shown best in FIGS. 27-28.

Figure 27:
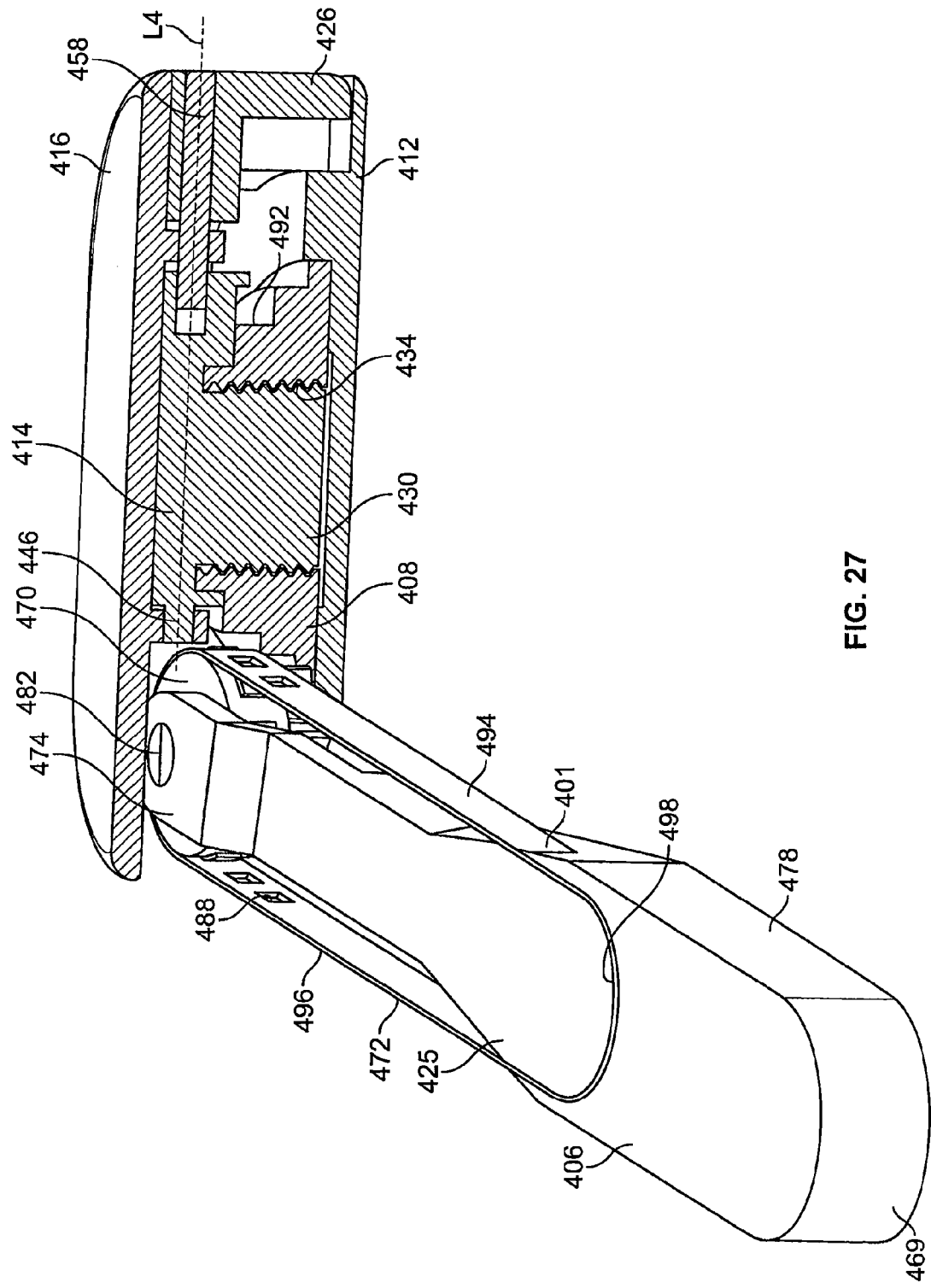
FIG. 27 is a rear, partially cross-sectional view of the sizing tool of FIG. 23 showing the gears of the expandable device in a collapsed configuration.
Figure 28:
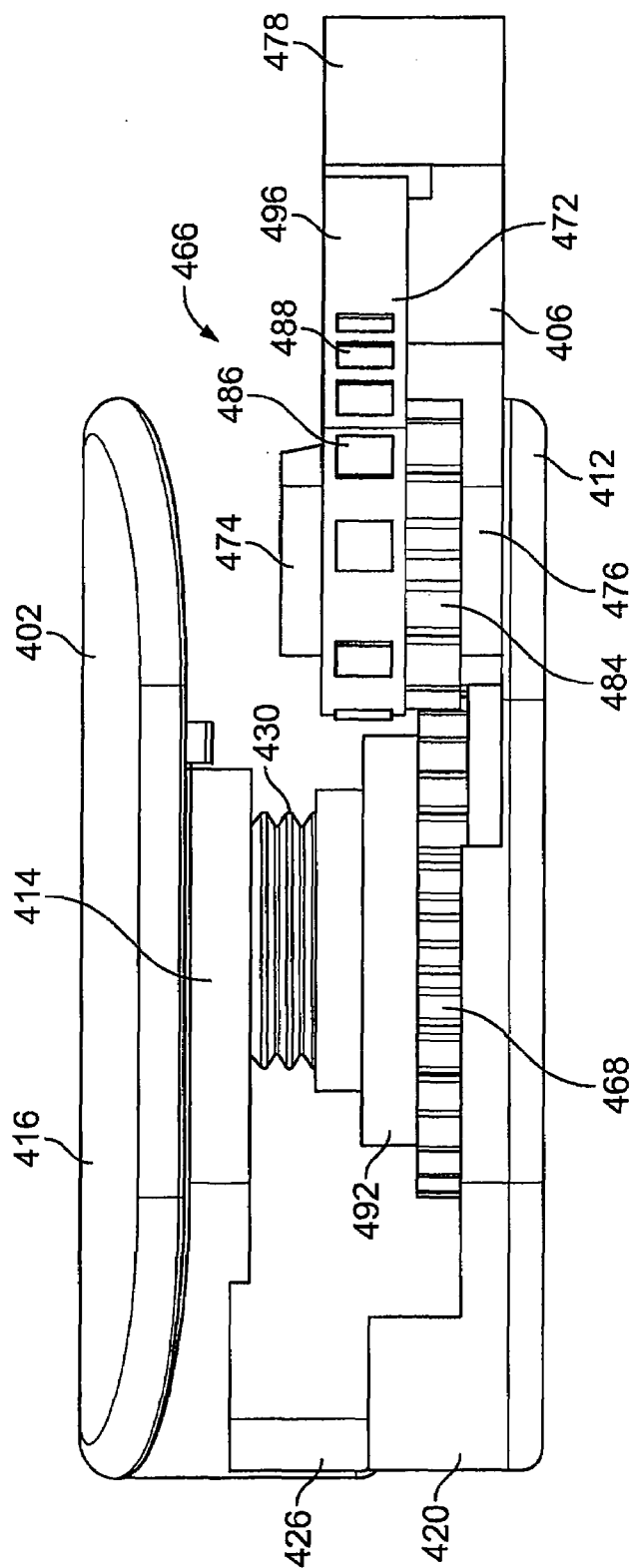
FIG. 28 is a front, elevational view of the sizing tool of FIG. 23 showing the gears of the expandable device in an expanded configuration.

As shown on FIG. 27, the elongate member 472 is positioned where it is accessible to a user's finger so that a user may shift the elongate member 472 by comfortably pressing a finger against the elongate member 472 where the finger is on the user's hand gripping the holder 406. To be accessible to a user's finger, sides 494 and 496 of the elongated member 472 are spaced laterally outward from the arms 474 and 476 of holder 406 as the sides 494 and 496 span from the gear 470 to the proximal portion 478 of the holder 406.

In order to hold a proximal portion 401 of the elongated member 472, the holder 406 has a curved slit 498 for receiving proximal portion 401 and sized to permit the elongated member 472 to slide axially within the slit. As shown in FIG. 23, the slit 498 may be open to a top surface 425 of the holder 406 for easier assembly of the elongated member 472 to the holder 406 although in the alternative it need not be as shown in FIG. 25. In one form, the slit 498 is semicircular to receive elongated member 472 and to position the elongated member 472 in an obround or race-track shape.

In operation, a user or other mechanism may grasp the holder 406 and position the expandable device 402 in its collapsed insertion configuration where the longitudinal axis $L_4$ of the expandable device 402 is parallel to the longitudinal axis $L_3$ of the holder 406. This will position the leading end 461 to face an annulus incision if present as the sizing tool 400 is thrust forward between the vertebrae.

Once positioned between vertebrae, if the surgical approach was other than a lateral approach, the expandable device 402 may be pivoted by passive steering and about pin 482 to position its longitudinal axis $L_4$ to extend laterally relative to the anterior-posterior direction. It will be appreciated, however, that expandable device 402 and holder 406 could be modified to add the steering mechanism on sizing tool 10 in order to provide active steering.

Once the expandable device 402 is properly positioned within the intervertebral space, the elongated member 472 is shifted by a user's finger or other mechanism that can engage the elongated member 472 on the holder 406. The openings 488 of the elongated member 472 will force the sprockets 486, and gear 470 to rotate which in turn will rotate the collar 408 due to the meshing of the collar's teeth 468 and the gear's teeth 484. The rotation of the collar 408 axially moves the threaded projection 430 and in turn the adjustable member 414 and superior cover 416 axially upward and away from the collar 408 and inferior cover 412.

Figure 29:
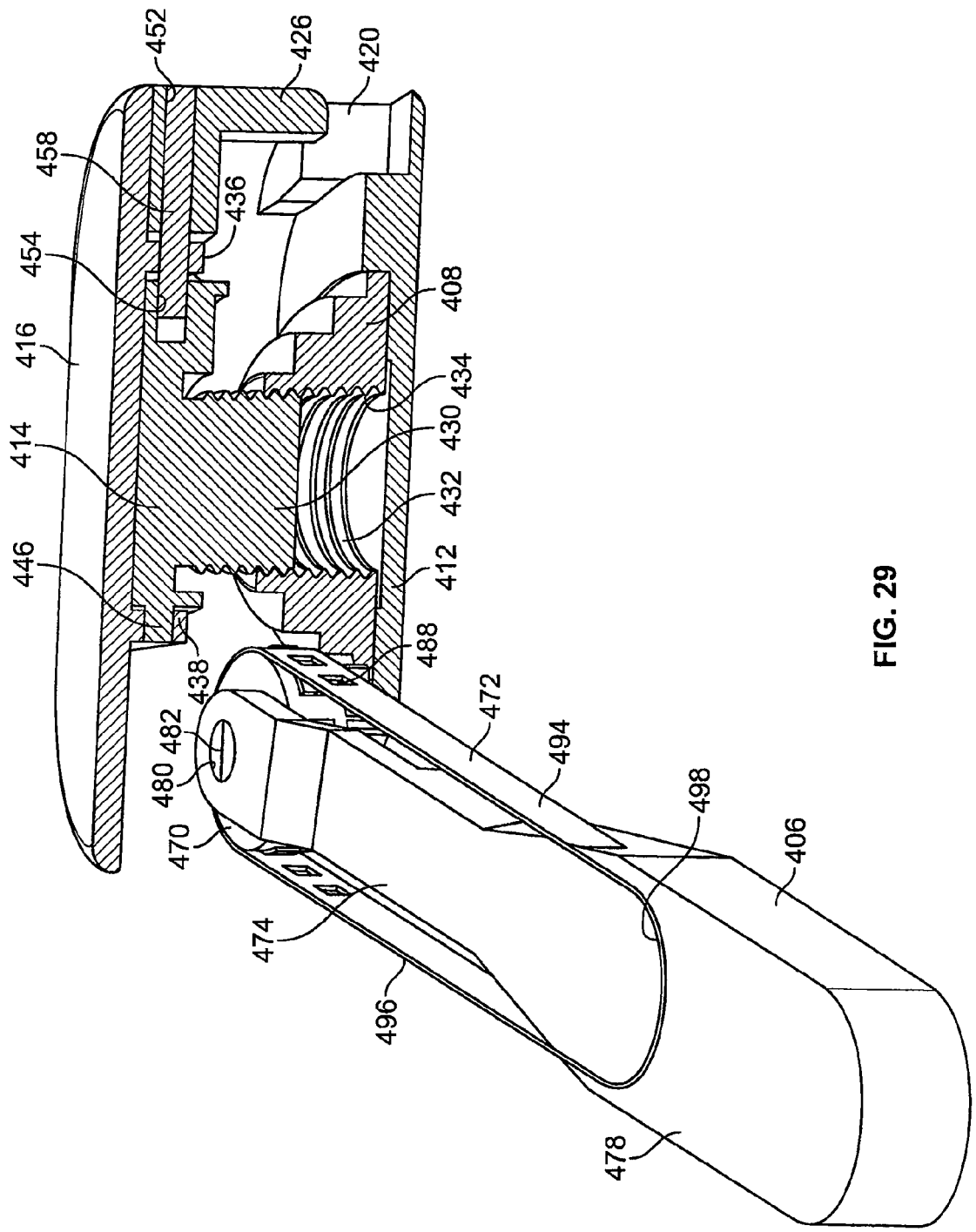
FIG. 29 is a rear, partially cross-sectional view of the sizing tool of FIG. 23 showing the gears of the expandable device in an expanded configuration and showing alignment structure of the expandable device.

After the expandable device 402 is expanded as shown in FIG. 29, the height of the intervertebral or nuclear space may be measured by the methods mentioned above such. Alternatively, a general determination of the distance the expandable device expanded may be indicated on the holder 406 by the position of the elongated member 472 such as by the use of indicia, visual coding or other indicators at least along a portion of the elongated member 472 that may align with pointers on the holder 406 or vice-versa.

Figure 30:
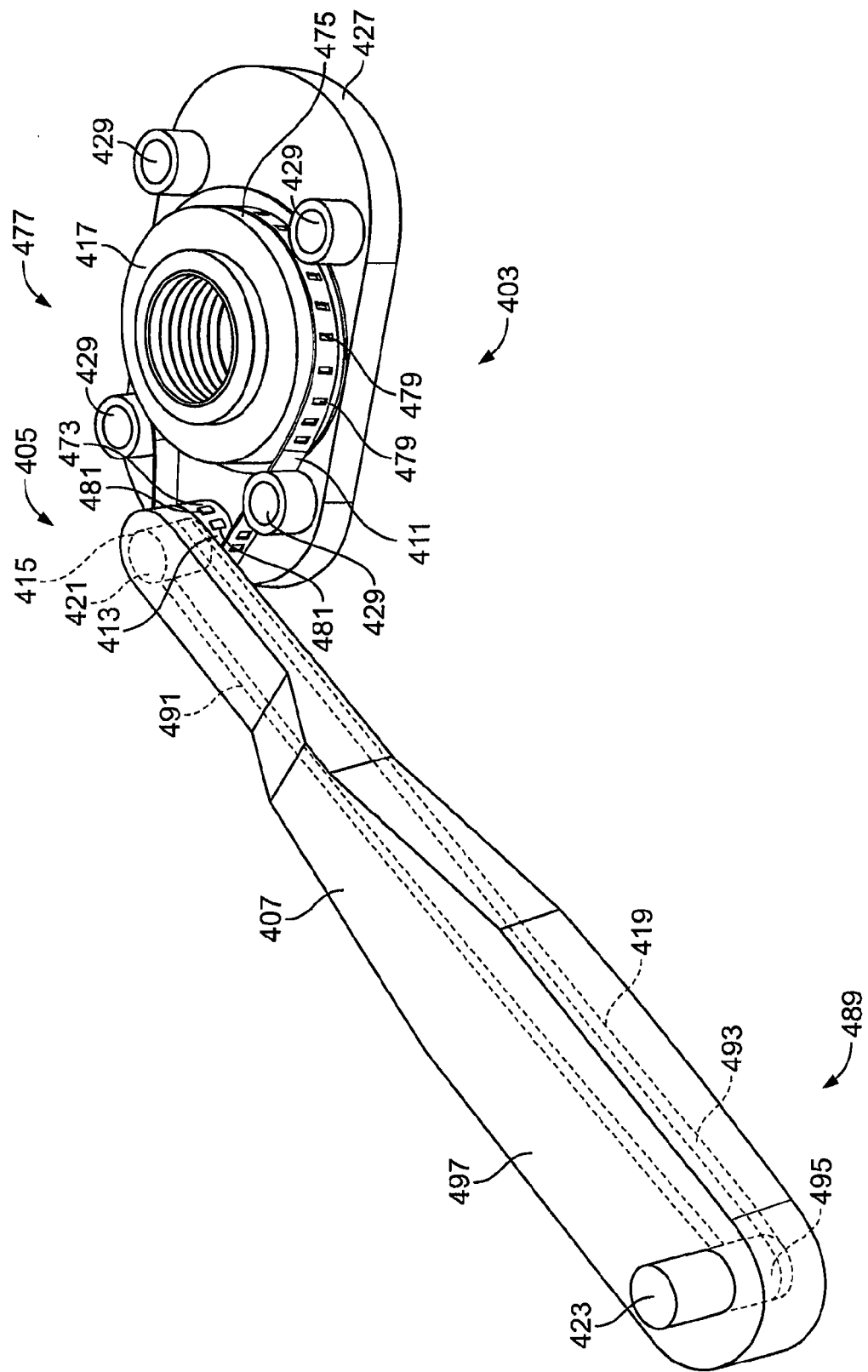
FIG. 30 is a top, perspective view of an alternative sizing tool showing a bottom portion of an expandable device with a band connected to a sprocket on a holder connected to the expandable device.

Referring now to FIG. 30, an alternative sizing tool 403 has an expansion actuator or mechanism 405 that uses an endless member in the form of a loop, or a looped member 411 rather than a gear to rotate a collar 417 disposed on the inferior cover 427. In more detail, the expansion mechanism 405 is disposed on an expandable device 477 for insertion into an intervertebral space. Similar to sizing tool 400, the expandable device 477 of sizing tool 403 is pivotally mounted on a distal end 415 of a holder 407, and the collar 417 is mounted on the inferior cover 427 in the same way collar 408 is mounted on inferior cover 412. In this configuration, however, the elongated first looped member 411 such as a chain, belt or band is wrapped around the collar 417. The first looped member 411 is also wrapped around a rotatable pulley such as a pinion 413 that is rotatably mounted on the distal end 415 of the holder 407 by a pin or similar mechanism so that the expandable device 477 pivots relative to the holder 407. With this structure, at least passive steering is provided although the sizing tool 403 could be modified to provide active steering similar to that provided for sizing tool 10.

The first looped member 411 has an array of openings 479 that engage a ring of outwardly and radially extending sprockets 499 on an outer rim 475 on the collar 417. The looped member 411 also has an array of openings 481 that engage a ring of outwardly and radially extending sprockets 487 on an outer rim 473 of the pinion 413. Alternatively, the first looped member 411 may operate by friction such that it either engages tautly against the rims 473 and 475 or the rims and looped member 411 have high-friction or coarse surfaces so that rotating the first looped member 411 rotates the collar 417.

An expansion control 489 for operating the expansion mechanism 405 includes a second endless or looped member 419 (shown in dashed line) that extends longitudinally along holder 407. So positioned, the second looped member 419 may be controlled remotely from an intervertebral space that the expandable device 477 is positioned within. The second looped member 419 has the end 491 wrapped around an upper end 421 of the pinion 413 and another end 493 wrapped around a portion 495 of a proximal dial 423 that is disposed within the holder 407. The dial 423 extends through a top surface 497 of the holder 407 to be accessible to the user so that rotating the dial 423 rotates the pinion 413. The second looped member 419 may engage the pinion 413 and dial 423 by friction or sprockets as mentioned for the first looped member 411.

With this configuration, turning the dial 423 rotates the second looped member 419 which in turn rotates the pinion 413. The pinion 413 then rotates the collar 417 by rotating the first looped member 411. The other features of the sizing tool 403 are the same or similar to the features on the sizing tool 400 except that instead of the slot and pin connection on the distal end 418 of the inferior cover 412, here the inferior cover 427 may have four support or base collars 429 for receiving support columns that extend downward from a superior cover or adjustable member. Otherwise, the collar 417 here is internally threaded to rotate about an externally threaded projection extending downward from an adjustable member or a superior cover as mentioned for collar 408 on sizing tool 400 above.

Figure 31:
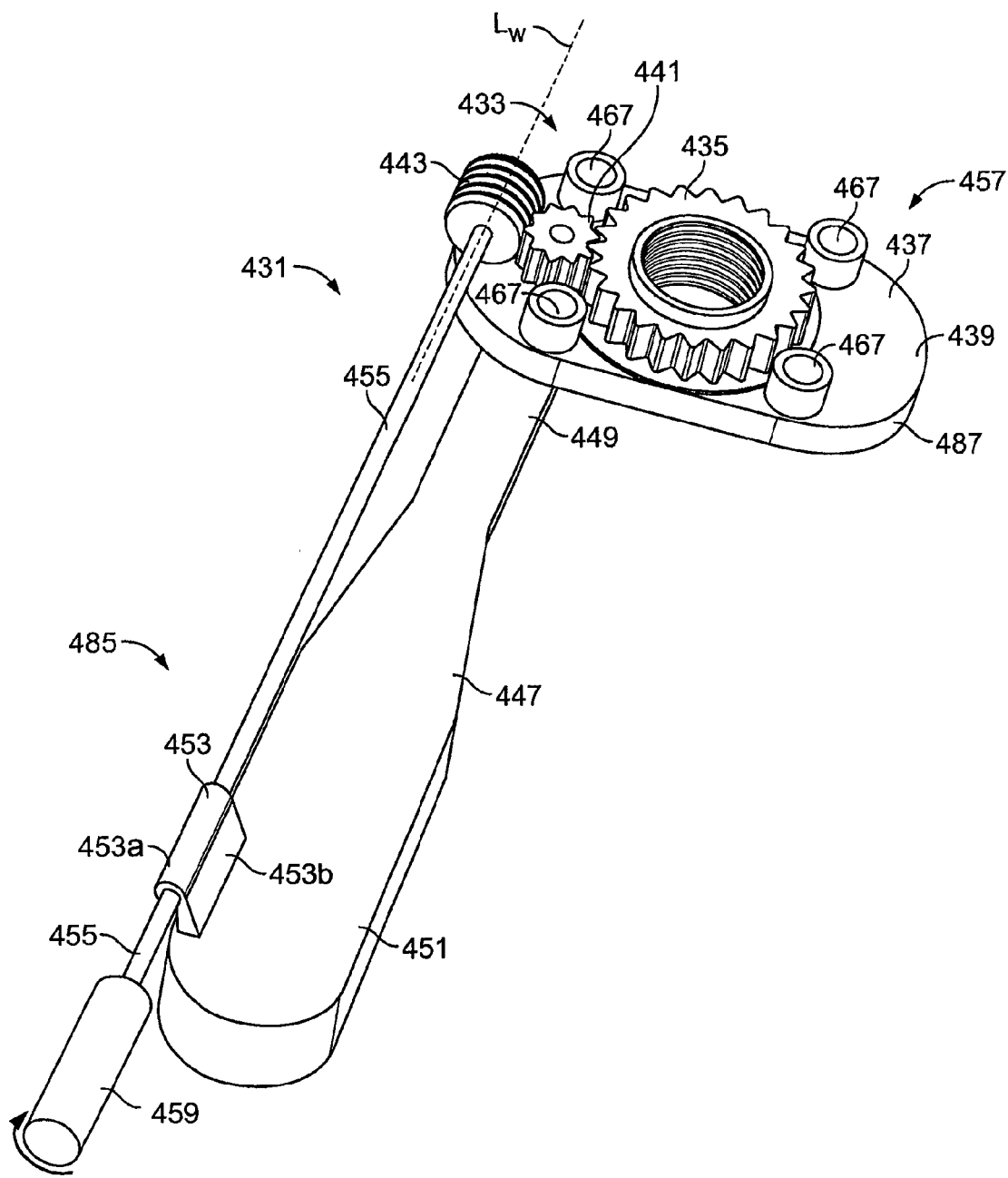
FIG. 31 is a top, perspective view of another alternative sizing tool showing a bottom portion of an expandable device with gears connected to a worm wheel and having a handle extending to a holder connected to the expandable device.

Referring now to FIG. 31, another alternative sizing tool 431, also similar to sizing tools 400 and 403, has an expansion mechanism 433 that that uses a threaded worm wheel 443 to rotate a collar 435 on an inferior cover 437 of an expandable device 457 in order to expand and collapse the expandable device 457. In further detail, the expandable device 457 is pivotally mounted on a distal end 449 of a holder 447. The distal end 449 of the holder 447 may be connected to a bottom of the inferior cover 437 by a boss-aperture type of connection in order to provide passive steering.

The expansion actuator or mechanism 433 engages the collar 435 which is disposed on an upwardly facing surface 439 on the inferior cover 437 of the expandable device 457 so that the collar 435 is free to rotate upon the inferior cover. In this alternative configuration, the expansion mechanism 433 has a toothed pinion 441 rotatably mounted on the inferior cover 437 between the collar 435 and the worm wheel 443. An expansion control 485 includes an elongate, rotatable bar 445 connected to the worm wheel 443 for rotating the worm wheel about a longitudinal axis $L_w$ that extends generally parallel to a longitudinal dimension of the holder 447. The bar 445 extends longitudinally over the holder 447 and to a proximal end 451 of the holder 447 where the bar 445 is held by a stand or holding member 453. The stand 453 includes a collar 453a with a base 453b that can laterally secure the bar 451 to the holder 447 while permitting the bar to rotate about longitudinal axis $L_w$. A proximal end 455 of the bar 451 has a knob or handle 459 or may be connected to another control.

So configured, the expandable device 457 is inserted into a nuclear space as explained above for the other sizing tools 400 and 403. The expandable device 457 here is inserted into an intervertebral space until the distal end 449 of the holder 447 that is disposed underneath the inferior cover 437 abuts the vertebrae, annulus or other tissue. Once the expandable device 457 extends between the vertebrae, the surgeon can rotate the handle 459 to rotate the worm wheel 443 which in turn meshes with and rotates the pinion 441. The pinion 441 then meshes with and rotates the collar 435. It will be understood, however, that pinion 441 may be eliminated so that the worm wheel 443 directly engages the collar 435 to rotate the collar.

The rotation of the collar 435 moves an engaging externally threaded projection received by the collar 435 and extending from an adjustable member or superior cover to move the superior cover in the superior-inferior direction as described for expandable device 402 on sizing tool 400 (FIG. 23). Otherwise, the structure of the expandable device 457 may include the same modifications as the expandable device 477 on sizing tool 403 (FIG. 30) including an inferior cover that uses support collars 467 adapted to receive columns to add further support to a superior cover.

In order to provide at least passive steering, the expandable device 457 on sizing tool 431 is rotatable by making the worm wheel 433 rotate about either pinion 441 if present or collar 435 so that bar 445 can rotate with the holder 447. The sizing tool 431 could be modified, however, to add an active steering mechanism similar to that described for sizing tool 10.

Referring again to FIGS. 23-29, in another aspect of the sizing tool 400, the superior cover 416 pivots to more closely align with the lordotic or kyphotic angle of an endplate of an opposing vertebra. This is provided in order to obtain a measurement of the angle the vertebra endplate extends relative to a plane formed by lateral and anterior-posterior axes. Once measured, an implant can be chosen that matches the angle of the endplate for a better fitting implant.

For this purpose, the superior cover 416 has at least one projection although two projections 436 and 438 are shown here and extend downward from a bottom surface 440 of the superior cover. The projections 436 and 438 are spaced longitudinally relative to axis $L_4$ of the expandable device 402 and each projection 436 and 438 respectively has a bore 444 and 442 with central axes both extending parallel to the longitudinal axis $L_4$. The more proximal projection 438 is rotatably mounted on a longitudinally extending pin 446 (shown on FIG. 27) extending rearwardly from a rear end 448 of the adjustable member 414.

The more distal projection 436 is received by an upwardly accessible opening 450 that is open to a top surface 460 of the adjustment member 414. The adjustment member 414 has longitudinally extending, concentric bores 452 and 454 that open to opposite sides of the opening 450. So configured, while the projection 436 is disposed within opening 450, the bore 444 on the projection 436 concentrically aligns with bores 452 and 454 on the adjustment member 414. The bore 452 opens to a forward end 456 of the adjustable member 414 for receiving a locking dowel 458 that fits within the bores 444, 452, and 454 and is secured therein by tight-fit or threaded connection to one of the bores.

This configuration pivotally secures the projections 436 and 438 to the adjustable member 414 so that the superior cover 416 is permitted to pivot or swing in see-saw fashion transversely to the longitudinal axis $L_4$. This configuration also permits the superior cover 416 to slant in the anterior-posterior direction of the intervertebral space while the longitudinal axis $L_4$ of the expandable device 402 extends laterally relative to the anterior-posterior direction. This permits the superior cover 416 to lie flush against an angled vertebra abutting the superior cover 416 while the superior cover 416 is longitudinally and transversely secured to the adjustable member 414. The dowel 458 is sized to close the end of bore 452 to present the relatively continuous, smooth leading end 461 for insertion as shown on FIG. 26.

Referring to FIGS. 26-27, in order to provide clearance for the superior cover 416 to pivot, the top surface 460 of the adjustable member 414 is angled relative to the plane formed by lateral and anterior-posterior axes. In the preferred form, top surface 460 is gabled or slanted to accommodate the superior cover 416 slanting to the left or right of the expandable device 402. In other words, this permits the superior cover 416 to slant inferiorly in either an anterior or posterior direction. The top surface 460 is symmetrical relative to longitudinal axis $L_4$ and has two sides 462 and 464 both slanting downward as they extend away from each other to permit the superior cover 416 to pivot to both the left and right of expandable device 402.

The slanted surfaces 462 and 464 may also be used to support the superior cover 416 in either a left or right leaning position as shown on FIG. 26. The slanted surfaces 462 and 464 also limit further pivoting of the inferior cover 416 and therefore may be set to extend at angles relative to the plane of the inferior cover that match the expected range of angles formed by the vertebrae.

Referring now to FIGS. 32-38, a sizing tool 500 has an expandable device 502 to be inserted into an intervertebral space for determining the size of the space. The expandable device 502 uses a combination of rigid, moving mechanical parts and a fluid-tight chamber to expand and collapse the expandable device 502 within the intervertebral space. The expandable device 502 includes a telescoping hydraulic piston 506 that remains aligned with a superior-inferior axis during a controlled collapse and expansion of the expandable device 502.

Figure 32:
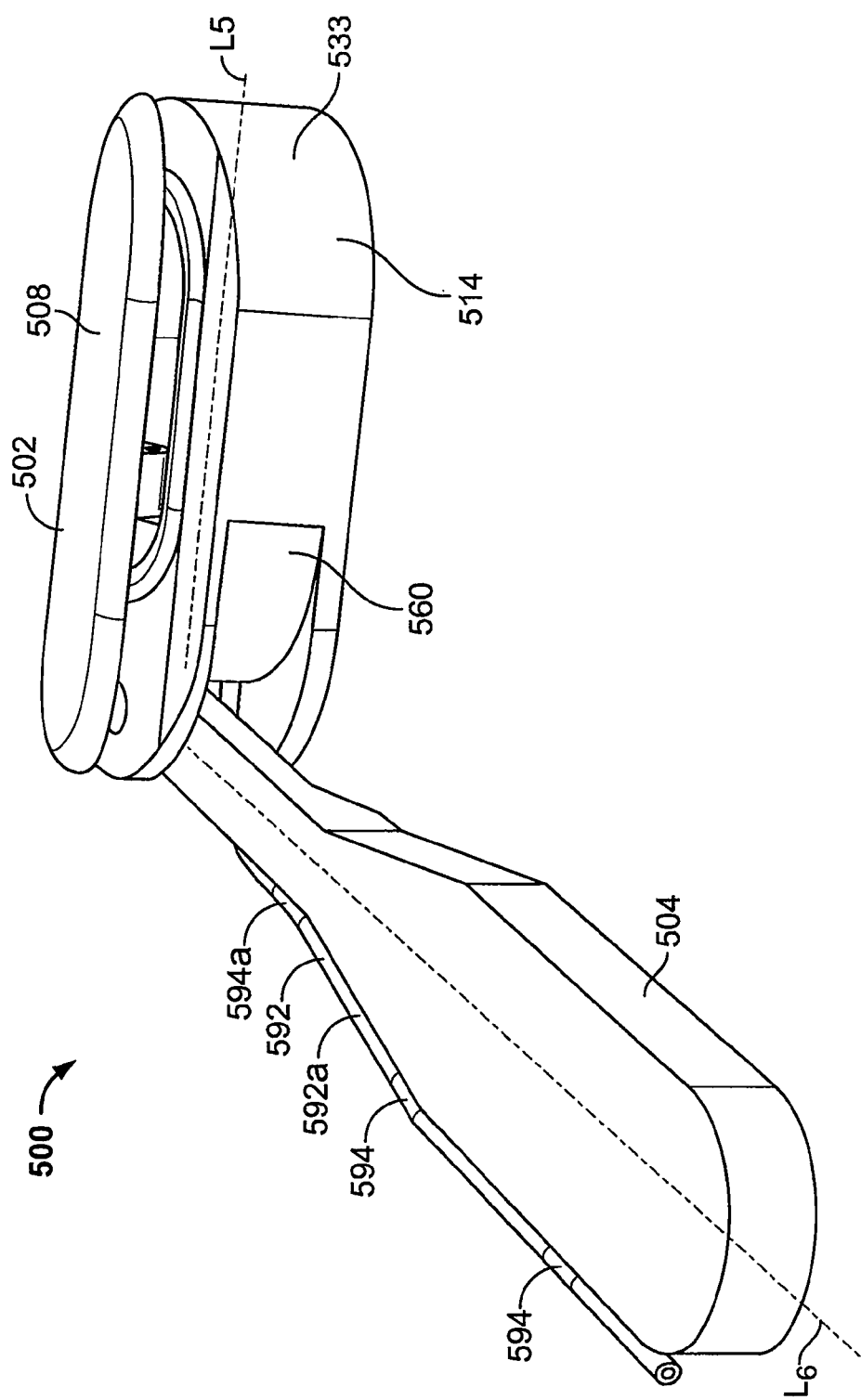
FIG. 32 is a rear, perspective view of yet a further alternative sizing tool showing an expandable device with a piston in a collapsed configuration and a fluid delivery system connected to a holder.
Figure 33:
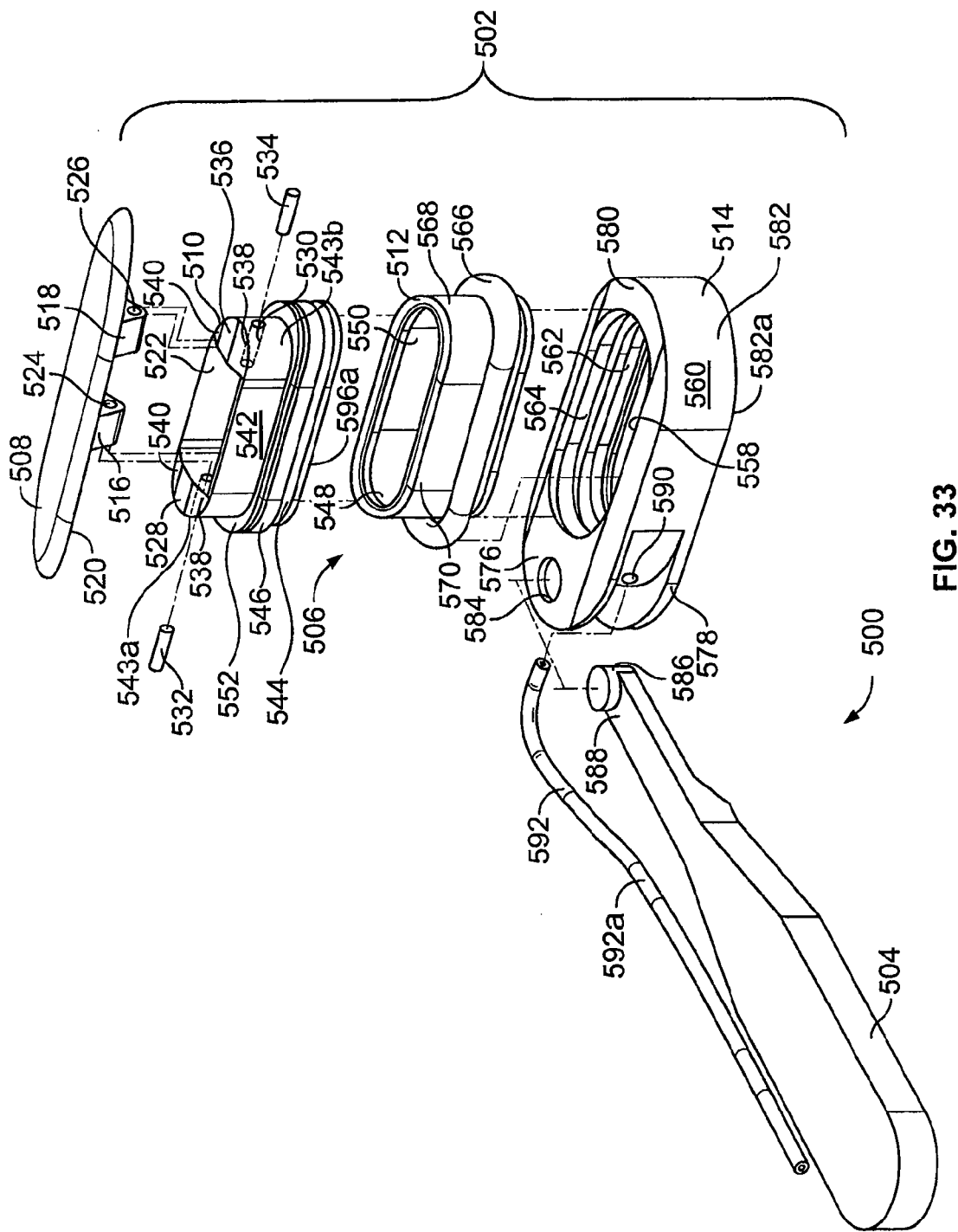
FIG. 33 is an exploded perspective view of the sizing tool of FIG. 32 and showing the components of a piston on the expandable device.
Figure 34:
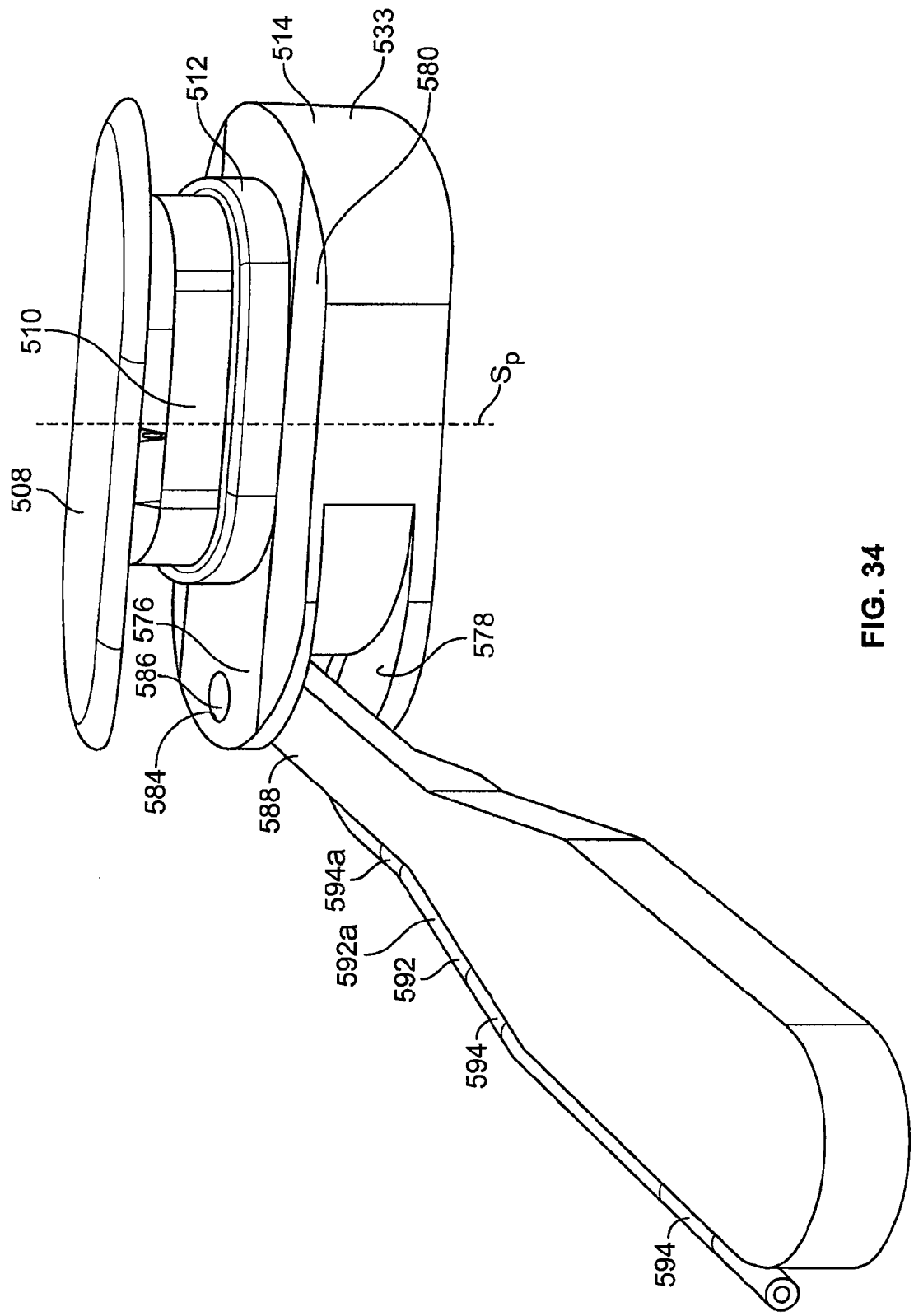
FIG. 34 is a rear perspective view of the sizing tool of FIG. 32 and showing the expandable device in an expanded configuration and a fluid delivery system connected to the holder.

In detail and while referring to FIGS. 32-33, expandable device 502 is pivotally mounted on a distal end 588 of a holder 504 and is generally elongated or obround from a top view to provide a narrow, distal lead end 533. As shown in FIG. 33, in order to expand and collapse the expandable device 502, the hydraulic piston 506 on the expandable device 502 has at least one but preferably more telescoping portions. More specifically, in the preferred form, the expandable device 502 has a superior cover 508 mounted on an upper piston portion 510 that is in turn mounted within a slightly larger, lower piston portion 512. The lower piston portion 512 is in turn mounted within a base or inferior cover 514 that is slightly larger than the lower piston portion 512. In a telescoping manner, the upper piston portion 510 translates within, and relative to, the lower piston portion 512 while the lower piston portion 512 translates within, and relative to, the inferior cover 514. Both piston portions 512 and 514 as well as the superior cover 508 are disposed coaxially and raise and lower along a superior-inferior axis $S_P$ shown on FIG. 34. A top surface 537 of the superior cover 507 and a bottom surface 582a formed by a bottom wall 582 of the inferior cover 514 are generally flat and engage the endplates of the vertebrae forming the intervertebral space.

The piston portions 510 and 512 and the inferior cover 514 all have a generally similar shape with a generally annular or obround sidewall 542, 570 and 560 respectively and that extend generally parallel to the superior-inferior axis $S_P$. The sidewall 542 on the upper piston portion 510 extends upward from a generally flat bottom wall or base 596 while the sidewall 560 on the inferior cover 514 extends upward from the bottom wall or base 582. Both bases 596 and 582 extend in planes transverse to the superior-inferior axis $S_P$. The sidewalls 542, 570 and 560 also respectively form upwardly accessible openings 522, 550 and 558 in order to respectively receive the superior cover 508, piston portion 510 and piston portion 512 that extends into and above the openings to form the piston 506 as described in further detail below.

Figure 35:
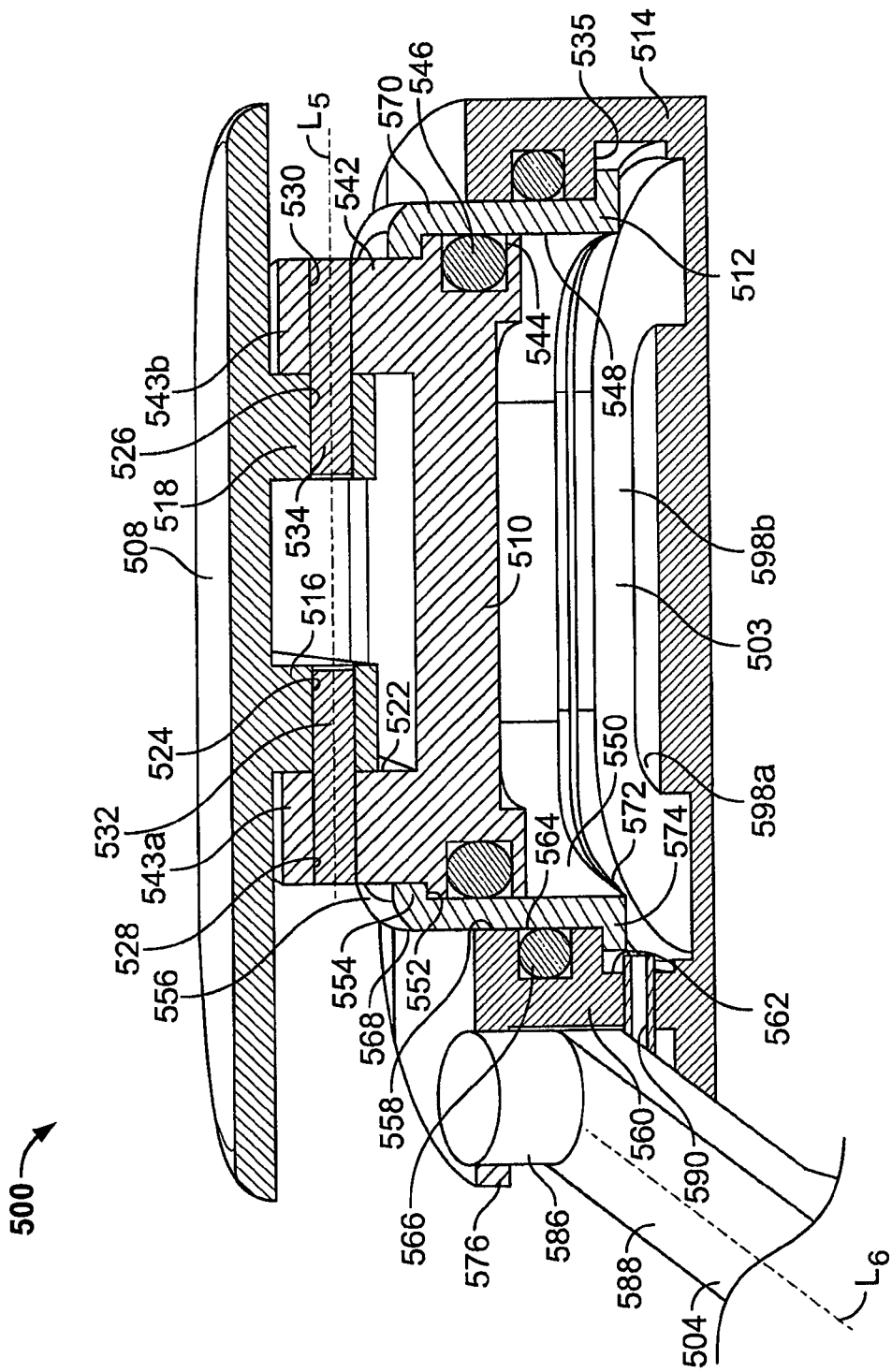
FIG. 35 is a rear, partially cross-sectional view of the sizing tool of FIG. 32 showing a fluid chamber and the piston components of the expandable device in an expanded configuration.

Referring to FIGS. 33 and 35, in order to secure the superior cover 508 to the upper piston portion 510 while permitting the superior cover 508 to pivot to better correspond to the lordotic or kyphotic angle of an adjacent vertebra, similar to superior cover 416 on sizing tool 400, the superior cover 508 is relatively flat and extends in a plane transverse to the axis $S_P$. At least one projection although two projections 516 and 518 are shown here and extend downward from a bottom surface 520 of the superior cover 508. The projections 516 and 518 are spaced along a longitudinal axis $L_5$ shown on FIG. 35 and have longitudinally extending apertures 524 and 526 respectively.

The projections 516 and 518 extend downward and into upwardly accessible opening 522 formed by sidewall 542 on the upper piston portion 510. The sidewall 542 also forms two concentrically disposed bores 528 and 530 that are positioned on opposite longitudinal ends 543a and 543b of the sidewall 542 relative to longitudinal axis $L_5$. The bores 528 and 530 extend longitudinally and through the sidewalls 542 so that they both open to opening 522. The projections 516 and 518 are disposed within opening 522 so that their apertures 524 and 526 respectively align concentrically with the bores 528 and 530.

Figure 36:
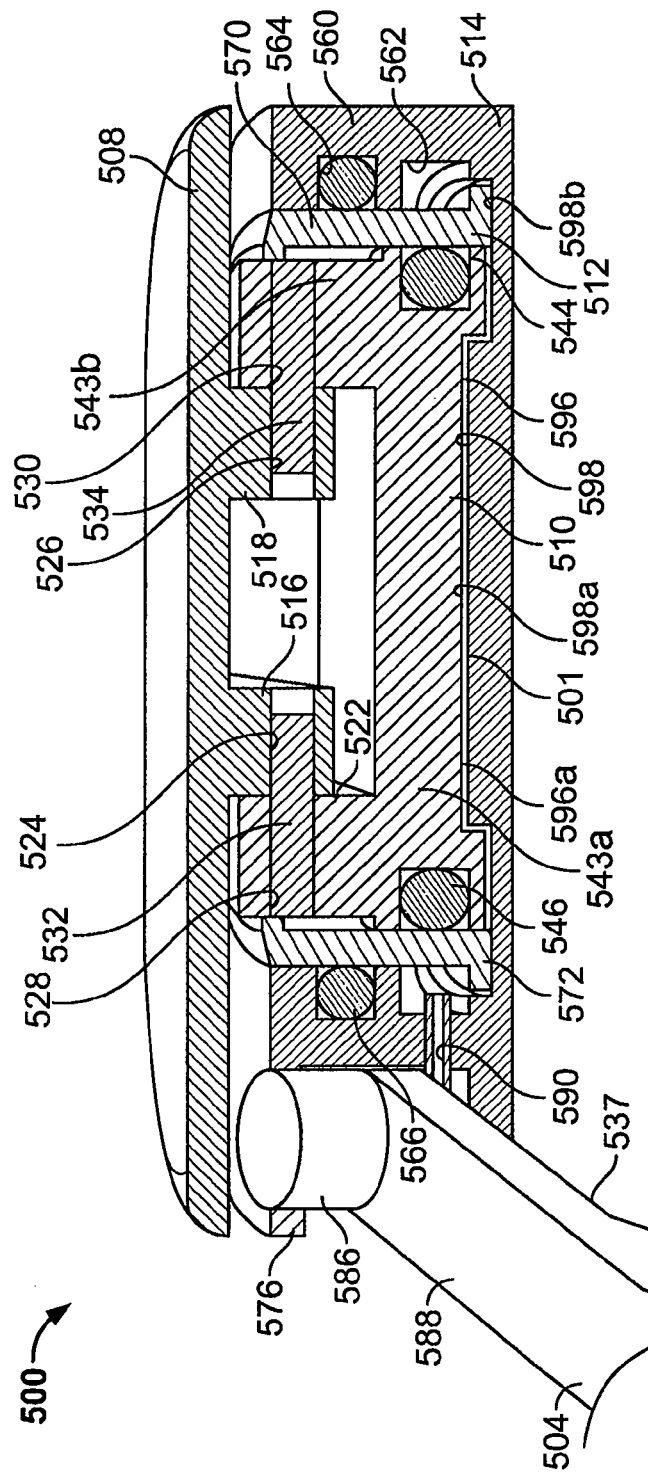
FIG. 36 is a rear, partially cross-sectional view of the sizing tool of FIG. 32 showing the piston components of the expandable device in a collapsed configuration and the fluid pathways in the piston.
Figure 41:
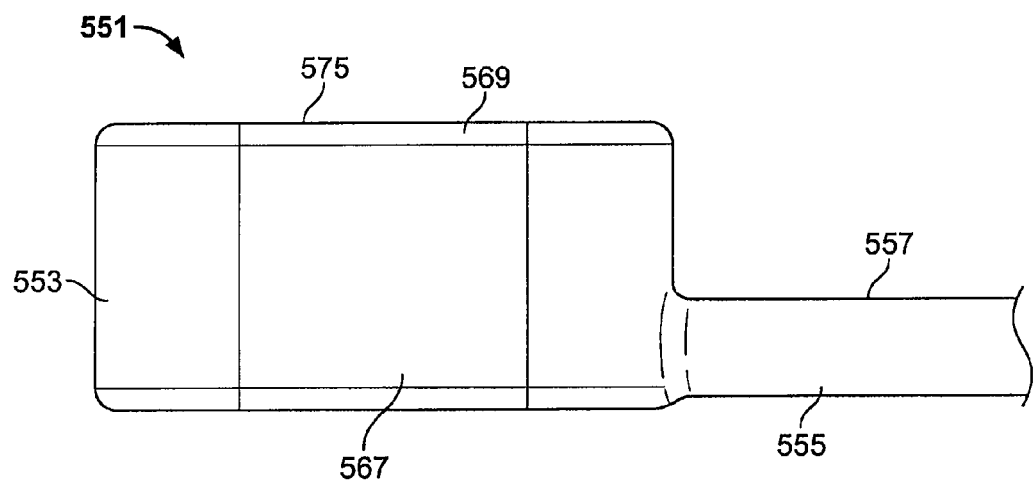
FIG. 41 is a left-side elevational view of an alternative sizing tool showing the shape of an expandable device connected to a distal end of a holder in accordance with the present invention.
Figure 42:
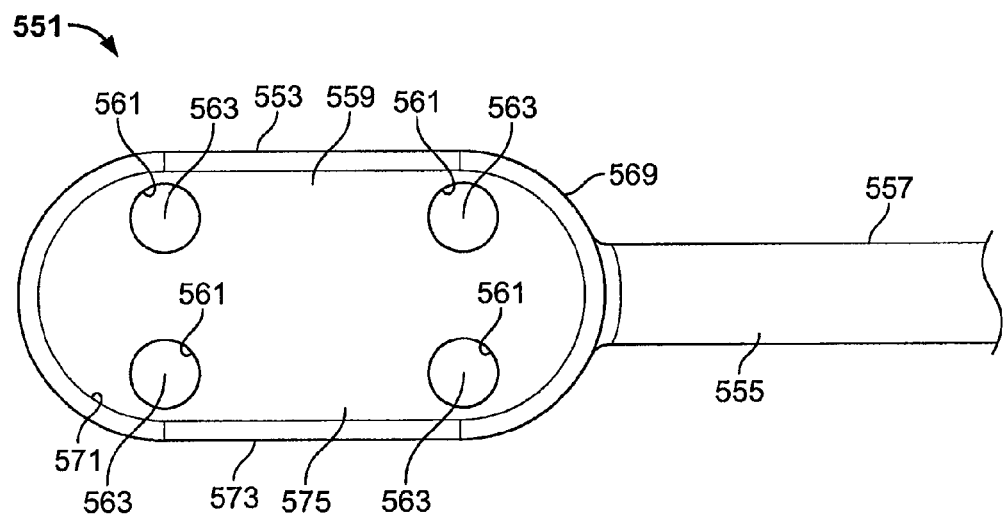
FIG. 42 is a top view of the sizing tool of FIG. 41 showing the race-track shape of the expandable device.

As shown on FIGS. 35-36, pins 532 and 534 extend respectfully through the apertures 524 and 526 and bores 528 and 530 to secure the superior cover 508 to the upper piston portion 510. The pins 532 and 534 extend orthogonally to the superior-inferior direction and longitudinally relative to the expandable device 502 and longitudinal axis $L_5$. This permits the superior cover 508 to pivot about the pins 532 and 534 in the anterior-posterior direction as described for sizing tool 400. Also similar to sizing tool 400, and as shown in FIGS. 37-38, in order to support the superior cover 508 while providing clearance for the superior cover 508 to pivot anteriorly or posteriorly, a top surface 536 of the upper piston portion 510 has two slanted surfaces 538 and 540 on both longitudinal ends 543a and 543b of the upper piston portion 510.

As shown in FIG. 33, in order to minimize fluid leaking from the piston, the expandable device has first and second O-rings 546 and 566 to seal the spaces between the piston portions and inferior cover. Thus, to seal the area between the upper piston portion 510 and the lower piston portion 512, the sidewall 542 of the upper piston portion 510 has an outwardly facing groove 544 extending around the sidewall 542 for holding the first O-ring 546. The O-ring 546 abuts an interior surface 548 of the sidewall 570 while the lower piston portion 512 is disposed within opening 550. Similarly, to seal the area between the lower piston portion 512 and the inferior cover 514, the sidewall 560 forming the opening 558 on the inferior cover 514 also forms an annular, inwardly facing, upper groove 564 accessible through opening 558 and that receives the second O-ring 566. The second O-ring 566 abuts an exterior surface 568 of the sidewall 570 while the lower piston portion 512 is disposed within opening 558.

Referring to FIGS. 35-36, filling the piston 506 with fluid causes the upper piston portion 510 to translate upwardly relative to the lower piston portion 512 and the lower portion 512 to translate upwardly relative to the inferior cover 514 until an expanded orientation is reached. The piston 506 is configured to retain the piston portions 510 and 512 in the expanded orientation so that the parts do not disconnect from each other or the inferior cover 514. Thus, in order to retain the upper portion 510 on the lower piston portion 512, an obround shoulder 552 extends outwardly from sidewall 542 on the upper piston portion 510. The shoulder 552 is sized to extend underneath and abut an annular, interiorly extending lip 554 on an upper rim 556 of the lower piston portion 510 and that forms the opening 550 on the lower piston portion 512. Since the shoulder 552 does not have clearance to avoid the lip 554 as the shoulder is translated toward the lip 554 with the upper piston portion, the lip 554 on the lower piston portion 512 retains the shoulder 552, and in turn the bottom 596 of the upper piston portion 510, within the opening 550 on the lower piston portion 512.

Likewise, in order to secure the lower piston portion 512 within the opening 558 of the inferior cover 514, the sidewall 560 of the inferior cover 514 has an annular or obround lower groove 562 disposed below the upper groove 564 holding the second O-ring 566. The lower groove 562 opens to the opening 558 to face the sidewall 570 of the lower piston portion 512. The top of the lower groove 562 is formed by an upper wall 535 that separates the lower groove 562 from the upper groove 564.

A bottom rim 572 on the sidewall 570 of the lower piston portion 512 has an obround, outwardly extending lip 574 that is sized to extend into groove 562 and underneath upper wall 535 so that the lip 574 engages the upper wall 535 while piston 506 expands. Since the lip 574 does not have clearance to escape the groove 562, the top wall 535 retains the lip 574, and in turn the lower piston portion 512, within the opening 558 on the inferior cover 514.

Referring to FIGS. 33-36, in order to permit at least passive steering where the expandable device 502 pivots relative to the holder 504, the inferior cover 514 has rearwardly extending, upper and lower, parallel flanges 576 and 578 that also extend longitudinally relative to axis $L_5$ and respectively from a top surface 580 and the bottom surface 582 of the inferior cover 514. The top flange 576 has a bore 584 for receiving an upwardly extending boss 586 on the distal end 588 of the holder 504. The boss 586 is secured in the superior-inferior direction within the bore 584 while the boss 586 is dimensioned to rotate within bore 584 to permit the expandable device 502 to pivot relative to the distal end 588 of the holder 504.

To provide sufficient clearance for connecting the distal end 588 of the holder 504 while still retaining the distal end 588 of the holder between the flanges 576 and 578, the flanges are spaced a sufficient distance apart from each other and flex slightly to permit the distal end 588 of the holder 504 to squeeze between the flanges to align the boss 586 with the bore 584. Once aligned with the bore 584, the boss 586 snaps into the bore 584. Once connected to the bore 584, the boss 586 does not have clearance to be pulled out of the bore 584 and between the flanges unintentionally. The boss 586 can be separated from bore 584 by using a relatively substantial force applied downward on the boss 584 to press and flex the lower flange 578 away from the upper flange 576 to provide clearance between the flanges to remove the holder 504. In order to further reduce the risk of damage to the annulus or other tissue, translating shafts, pins and slots or similar structure as described for sizing tool 10 could be added to the sizing tool 500 to form an active steering configuration.

Referring to FIGS. 32-33, in order to deliver fluid to the piston 506 to expand the piston, a fluid delivery system 592 has a fluid supply tube 592a that extends longitudinally along the holder 504 and connects to the expandable device 502. The tube 592a is connected to a fluid supply and a control device for injecting the fluid preferably at predetermined pressures. The fluid delivery system 592 may be similar to fluid delivery system 66 for sizing tool 10 and holder 504 may be modified to accommodate such a system.

Referring to FIGS. 35-36, the fluid delivery tube 592a enters the expandable device 502 through a bore 590 that extends through sidewall 560 on the inferior cover 514 and between the flanges 576 and 578. The bore 590 opens to the groove 562 on the interior of the sidewall 560. As shown on FIG. 32, the tube 592a is secured laterally to the holder 504 by clips or similar fasteners 594 although the tube 592a could be maintained separate from the holder 504 so that it hangs loose and extends to a fluid supply separate from the sizing tool 500. In order to accommodate rotation of the holder 504 relative to the expandable device 502, the bore 590, the fasteners 594 or both permit the tube 592a to translate axially and the tube 592a is provided with sufficient length so that it will not separate from the bore 590. Alternatively, the tube 592a may be provided with enough slack between the proximal-most fastener 594a on the holder 504 and the bore 590 to accommodate the pivoting of the expandable device 502 relative to the holder 504 while the tube 592a is fixed to the bore 590.

Referring again to FIGS. 36 and 38, in the collapsed configuration, the lower and upper piston portions 512 and 510 are disposed almost entirely in the opening 558 of the inferior cover 514. In order to expand the expandable device 502 from the collapsed configuration, fluid is injected through tube 592 according to the methods mentioned previously such as injecting fluid until a certain fluid pressure or a certain amount of resistance is reached. The fluid is injected into the opening 558 which first fills groove 562 and flows into a space 501 between the bottom rim 572 of the lower piston portion 512 and an upwardly facing bottom surface 598 that forms the bottom of the opening 558 on the inferior cover 514. The fluid then flows between the bottom surface 596a of the upper piston portion 510 and the bottom surface 598 of the inferior cover 514.

In order to maintain the upper and lower piston portions 510 and 512 in lateral and longitudinal alignment with the inferior cover 214 in a collapsed configuration shown on FIG. 36, the upwardly facing, bottom surface 598 of the inferior cover 214 has a central, raised, generally obround platform 598a encircled by a recessed ring 598b. The ring 598b receives an outer rim 596b of the bottom surface 596a of the upper piston portion and the bottom rim 572 of lower piston portion 512 to hold them in the collapsed configuration.

To receive the fluid while the piston 506 is in a collapsed configuration, the space 501 may be a predetermined depth. Thus, the piston portions 510 and 512 and/or inferior cover 514 may have preconfigured recesses for forming the space. The space 501 here, however, is otherwise sufficiently formed by the typical spaces found between adjacent abutting metal and/or polymer components due to manufacturing tolerances in the dimensions of the components manufactured for the medical purposes described herein.

Referring to FIG. 35, the fluid entering space 501 lifts the upper piston portion 510, and in turn the lower piston portion 512 either by advancing it upward under the bottom rim 572 of the lower piston portion 512 or by the upper piston portion 510 drawing the lower piston portion 510 upward by shoulder 552. The fluid can lift the piston portions 510 and 512 upward creating a fluid chamber 503 and until the fully expanded configuration is reached as shown in FIGS. 35 and 37. The O-rings 546 and 566 retain the fluid within the chamber 503.

It will be appreciated that the height of the sidewalls 542, 570 and 560 may be lower or higher than that shown and is otherwise selected in order to provide the expandable device 502 with a predetermined total height of expansion and/or collapse. It will also be appreciated that the space 501 and chamber 503 could be dimensioned to hold a flexible, stretchable inflatable body such as a balloon or a fluid-holding liner connected to tube 592 to hold the fluid.

Once the expandable device 502 is expanded within an intervertebral space, the height of the space may be measured by the methods mentioned above. After measurement or imaging of the expandable device 502, the expandable device 502 is collapsed and retracted out of the intervertebral space.

With regard to FIGS. 39-40, an alternative sizing tool 505 has an expandable device 507 with an expansion actuator or mechanism 509 such as a telescoping shell piston 539 that has relatively little internal structure so that it either has fluid-tight joints or can hold an inner liner or balloon 525. The expandable device 507 has an inferior portion 511 in telescoping relation with at least one intermediate portion 513 and a top superior portion 515. All the portions 511, 513, 515 respectively have sidewalls 511a, 513a, and 515a that are cylindrical or elongated (e.g. obround) shapes and are coaxial to a superior-inferior axis $S_{P1}$.

The superior portion 515 has a slightly smaller width or diameter than that of the intermediate portion 513 so that the superior portion fits and translates within the intermediate portion 513 and along superior-inferior axis $S_{P1}$ while the intermediate portion 513 similarly has a smaller diameter or width than that of the inferior portion 511 so that the intermediate portion 513 fits and translates within the inferior portion 511 and along axis $S_{P1}$.

In order to support the expandable device 509, a holder 521 has a distal end 541 connected to the expandable device 509 and has a fluid supply tube 523 that runs longitudinally along the holder 521 and is connected to the balloon 525. The tube 523 may be connected to a fluid delivery system such as that described for sizing tool 10 above.

As shown in FIG. 39, in a collapsed configuration, the tube 523 extends though a hole 527 on the inferior portion 511 and through grooves 529 and 531 on the intermediate and superior portions 513 and 515 respectively. The grooves 529 and 531 align with tube 523 to provide clearance for the tube 523 while the piston 539 is in the collapsed configuration.

Referring to FIG. 40, in order to expand the piston 539, filling the piston with fluid causes the fluid to press upward against a top wall 515c of the superior portion 515 which in turn causes the superior portion to draw the intermediate portion 513 upward until it is retained by the inferior portion 511. The intermediate piston portion 513 also retains the superior portion 515 on the piston 539 once the piston 539 is fully expanded.

In order to maintain the piston portions 511, 513 and 515 in connection with each other and to permit the superior portion 515 to draw the intermediate portion 513 upward for expanding the piston 539, the portions 511, 513 and 515 are secured to each other by retaining structure on the walls 511a, 513a, 515a. More particularly, both the inferior portion 511 and the intermediate portion 513 have annular, upper rims 517 extending interiorly from sidewalls 511a and 513a, respectively. Both the intermediate portion 513 and the superior portion 515 have annular ledges 519 extending exteriorly from an exterior surface 513b and 515b of the sidewalls 513a and 515a, respectively.

In order to secure the superior portion 515 to the intermediate portion 513, and in turn to permit the superior portion 515 to draw the intermediate portion 513 upward during expansion, the upper rim 517 on the intermediate portions 513 extends over the ledge 519 of the superior portion 515. Since the ledge 519 does not have sufficient clearance to shift past the rim 517, the rim 517 retains the ledge 519, and in turn the superior portion 515, from further axial upward motion past the ledge and retains the superior portion 515 within the intermediate portion 513. So configured the superior portion 515 is free to translate upward within the intermediate portion 513 until the ledge 519 of the superior portion 515 engages the intermediate portion 513. Even after ledge 519 of the superior portion 515 engages the rim 17 on the intermediate portion 513, the superior portion 515 is still permitted to shift upward as long as the intermediate portion 513 shifts upward with the superior portion 515 until the intermediate portion 513 is retained by the inferior portion 511.

To retain the intermediate portion to the inferior portion 511, the rim 517 on the inferior portion 511 extends over the ledge 519 on the intermediate portion 513. This configuration permits the intermediate portion 513 to translate upward within the inferior portion 511 until the ledge 519 on the intermediate portion 513 engages the rim 517 of the inferior portion 511.

To maintain a sealed interior for the piston 539, the grooves 529 and 531 that provide the tube 523 access to the interior of the piston 539 while the piston 539 is in a collapsed state are covered while the piston 539 is in an expanded state. Thus, the ledges 519 and rims 517 respectively extend circumferentially around the sidewalls 511a, 513a, and 515a just above grooves 531 and 529 on the superior and intermediate portions 515 and 513 so that the piston 539 cannot be expanded further which could expose the interior of the piston through one of the grooves 529 and 531. With such a configuration, in the fully expanded state, the groove 529 on the superior portion 515 is completely covered by the sidewall 513a on the adjacent intermediate portion 513 while the groove 531 on the intermediate portion 513 is completely covered by the sidewall 511a on the inferior portion 511. Thus, the balloon 525 may be eliminated if the portions 511, 513, 515 are sealed tightly enough to hold the fluid that fills the piston 539. A sealant such as an O-ring may be placed between each engaging rim 517 and ledge 519 in order to seal the piston 539 further.

In operation, the expandable device 507 may be inserted into an intervertebral space and through an incision on an annulus in a collapsed configuration as shown in FIG. 39. Once placed within the intervertebral space, the expandable device 539 is expanded as shown in FIG. 40 until it abuts the adjacent vertebrae facing the intervertebral space. The amount of expansion and height of the space may then be measured by the methods described above. The expandable device 507 is then collapsed and retracted from the annulus or intervertebral space.

Referring now to FIGS. 41-44, in a different embodiment, a sizing tool 551 has an expansion actuator 549 that includes an elongate actuator member 581 connected to an expandable device 553 so that shifting the actuator member 581 axially expands and collapses the expandable device 553. The actuator member 581 is at least partially bendable so that it can extend in a superior-inferior direction on the expandable device in order to shift a superior portion 559 closer or farther from an inferior portion 567 forming the expandable device 553. The actuator member 581 is also configured to measure the amount of expansion of the expandable device 553.

The expandable device 553 is mounted on a distal end 555 of a tubular holder 557 and that expands in a superior-inferior direction within an intervertebral space for measuring the intervertebral space. The expandable device 553 is also generally obround.

In order to provide a controlled collapse of expandable device 553 that maintains a superior platform or portion 559 with an inferior portion 567, the superior portion 559 has four bores 561 extending in the superior-inferior direction for receiving four guide poles or posts 563 that extend upward from a top surface 565 of the inferior portion 567. The posts 563 secure the superior portion 559 laterally and longitudinally to the inferior portion 567 while permitting the superior portion 559 to translate in the superior-inferior direction and upon the posts 563.

The inferior portion 567 has a raised outer, peripheral wall 569 for forming a recess 571 therein to receive the superior portion 559. A top rim 573 of the outer wall 569 is level with a top surface 575 of the superior portion 559 when the expandable device 553 is in the collapsed configuration as shown in FIG. 43.

The holder 557 has a longitudinally extending bore 575 that opens to a bore 577 on the inferior portion 567. The bore 577 has at least one bend 583 that turns upward about 90 degrees to a superior-inferior direction from longitudinal and coaxial to bore 575 on holder 557. The bore 577 is coextensive to a collar 579 that extends the bore 577 upward and superiorly from the top surface 565 of the inferior portion 567.

Figure 44:
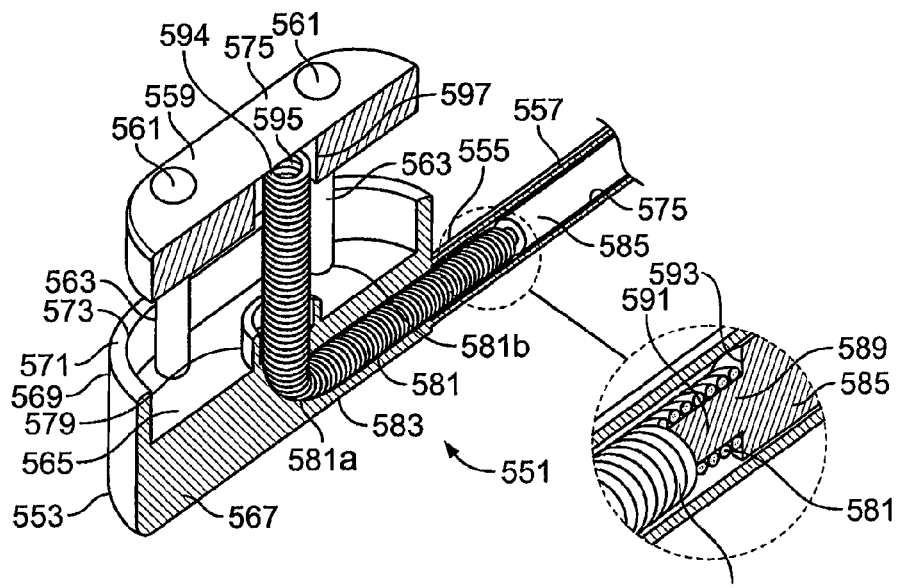
FIG. 44 is a left side, cross-sectional, perspective view of the sizing tool of FIG. 41 showing the expandable device in an expanded configuration with a sliding platform lifted off of a base.
Figure 45:
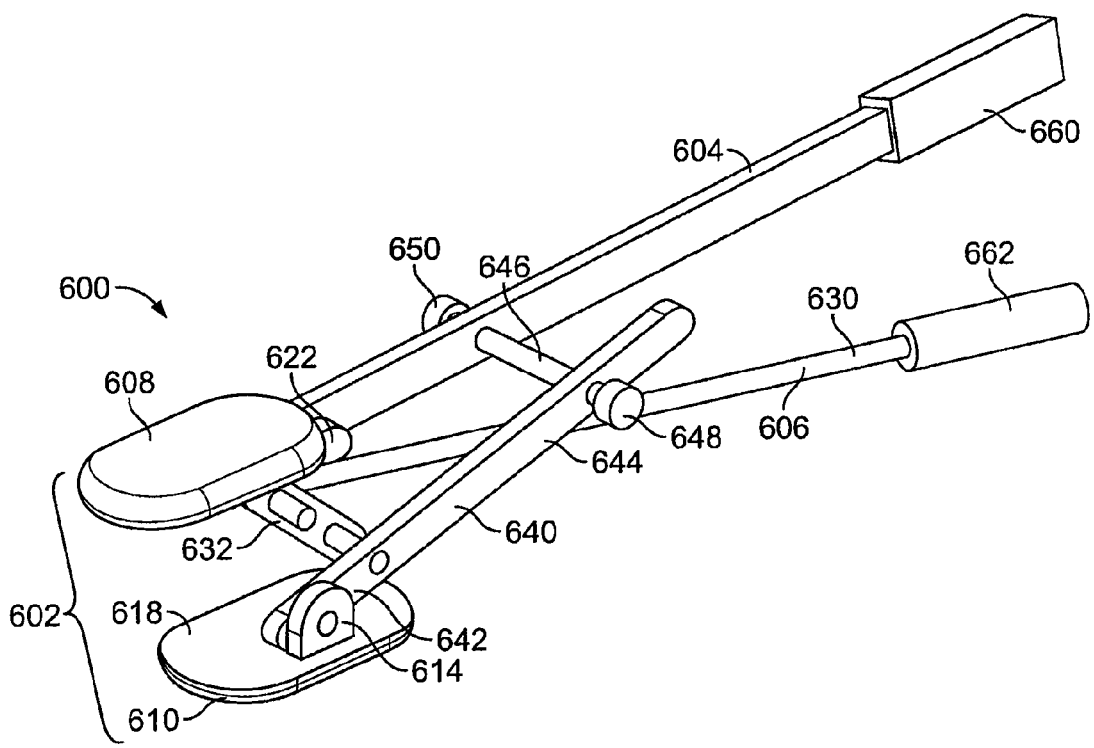
FIG. 45 is a left-side perspective view of a further alternative sizing tool showing an expandable device with top and bottom covers connected to each other by links and connected to a holder.

In order to expand and collapse expandable device 553 by raising or lowering the superior portion 559, the actuator member 581 of the expansion actuator 549 extends from an expansion control device 547 on the holder 557, through the bores 575 and 577 and connects to the superior portion 559. The actuator member 581 with at least one bendable portion such as a helical coil spring 581*a* that can shift axially through bend 583 and has sufficient stiffness to be both advanced and drawn axially through bores 575 and 577. The actuator member 581 has a superior-inferior portion 581*b* that has sufficient rigidity to generally maintain a linear configuration as it extends from the superior portion 559 and down to the inferior portion 567 when the device 553 is expanded as shown in FIG. 44.

Figure 43:
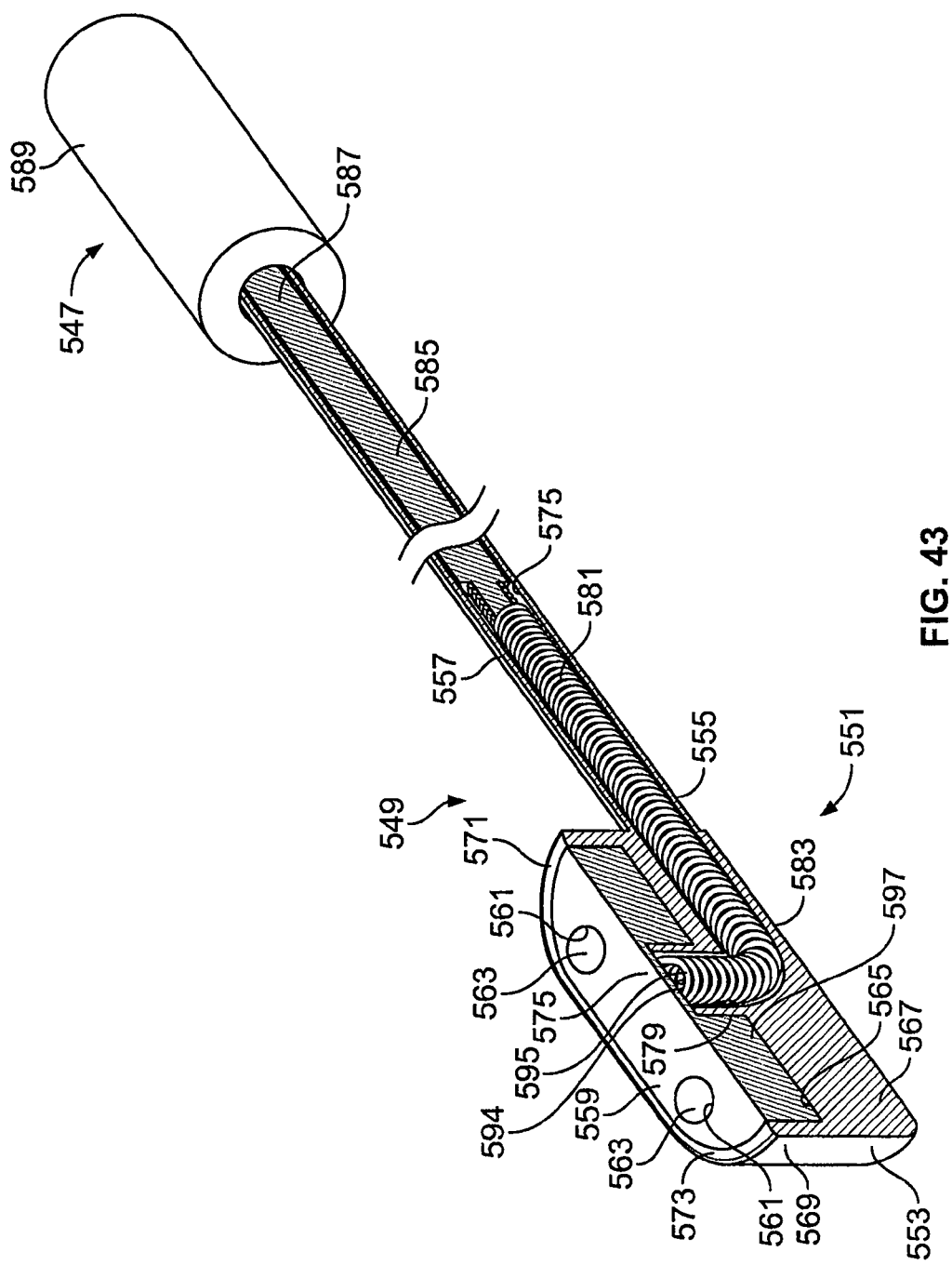
FIG. 43 is a left-side, cross-sectional, perspective view of the sizing tool of FIG. 41 showing the expandable device in a collapsed configuration and an axially moving coil spring connected to a sliding platform on the expandable device.

Referring to FIG. 43, in order to control the actuator member 581, the expansion control device 547 has an elongate drive shaft 585 that extends through the bore 575 on the holder 557 and has a proximal end 587 with a handle 589 to axially translate the actuator member 581 and a distal end 589 connected to the actuator member 581. In one form, drive shaft 585 and bore 575 are threaded so that rotating the drive shaft in the bore 575 by rotating the handle 589 shifts the actuator member 581 axially within bore 577. Rotating the handle permits the user to shift the drive shaft 585 in small amounts for greater precision. The distal end 589 of the drive shaft 585 has a pin 591 extending axially and within a proximal end 545 of the actuator member 581. The distal end 589 of the drive shaft 585 also has a shoulder 593 at the base of the pin 591 and that abuts the proximal end 545 of the actuator member 581 so that shifting the drive shaft 585 and shoulder 593 axially forward or distally advances the actuator member 581 forwardly within bore 577. In order for the drive shaft 585 to draw the actuator member 581 rearward or proximally as the drive shaft shifts rearward, the pin 591 of the drive member 585 is connected to the proximal end 545 of the actuator member 581 by a tight fit or a transversely extending fastener so that the drive shaft 585 draws the actuator member 581 rearward.

For the actuator member 581 to shift the superior portion 559 of the expandable device 553, a distal end 595 of the actuator member 581 abuts an interior surface 599 of the superior portion 559 within a downwardly extending opening 597. As shown in FIG. 43, the opening 597 also receives the raised collar 579 while the expandable device is in a collapsed configuration.

So configured, in order to expand the expandable device 553, the handle 589 is operated to shift the drive rod 585 and in turn the actuator member 581 axially and forward. The forward shifting of the actuator member 581 causes the coil spring 581*a* to bend as it shifts axially through the bend 583 of bore 577 and turns to extend in the superior-inferior direction from the bend 583 to the superior portion 559. As the superior-inferior portion 581*b* of the spring 581*a* is shifted upward against the interior surface 599 of the superior portion 559, the superior portion 559 is shifted upward or superiorly along the posts 563 and away from the inferior portion 567. The expandable device 553 can be expanded from the collapsed configuration (FIG. 43) and up to a fully expanded configuration (FIG. 44).

In order to determine the amount the expandable device 507 is expanded within the intervertebral space, the drive shaft 585 may have an indicator such as a display of indicia or a connection to a gauge that indicates the amount the drive shaft 585 and the actuator member 581 have shifted longitudinally which in turn indicates the distance the superior portion 559 has shifted along the superior-inferior direction. The measuring mechanisms may also include the techniques described above of the other embodiments.

In order to collapse the device 553 once expanded, either the guide posts 563 and collar 579 are sized so that the superior portion 559 falls inferiorly and into the collapsed configuration when the actuator member 581 is retracted proximally or the superior portion 559 has a pin or other structure that secures the distal end 595 of the actuator member 581 within opening 597 so that the actuator member 581 can draw the superior portion 559 downward and into the collapsed configuration.

In another form of the invention, a number of expandable devices are configured to have superior and inferior covers that are connected to each other by a plurality of links so that shifting the links shifts the covers closer or farther apart to expand or collapse the expandable device. In order to provide a controlled collapse of the expandable device with these configurations, either the holder holding the expandable device or the links themselves have structure to maintain the superior and inferior portions in alignment with a superior-inferior axis while the links are pivoted to shift the covers. These linking sizing tools also have control devices connected to the links that either move axially or rotate about their own axes to shift the links in order to minimize harmful lateral pressure against the annulus, ligaments or the vertebrae.

Referring now to FIGS. 45-48, a sizing tool 600 with links has an expandable device 602 with superior and inferior covers or portions 608 and 610 that are connected to each other by pivoting links 620 and 632. This embodiment is generally in the form of a scissors and has a holder 604 connected to one of the links 620 or 632 and to one portion 608 or 610. A lever arm 640 is connected to the other portion 608 or 610 and one of the links 620 or 632 so that pivoting the lever arm 640 relative to the holder shifts the two portions 608 and 610 closer together or farther apart. The lever arm 640 and holder 604 also maintain the portions 608 and 610 in alignment along a superior-inferior axis in order to provide a controlled collapse.

In order to minimize lateral pivoting of the lever arm 640 against an annulus or other tissue that could be damaged, the lever arm 640 is cut short (e.g. it has no handle portion). Instead, the sizing tool 600 also has a control device 606 with a control member 630 that is connected to the links and shifts axially in order to pivot the links. So configured, a surgeon holds the holder 604 stationary in one hand in order to hold one of the superior and inferior portions 608 and 610 stationary while shifting the control device 606 axially in the other hand to pivot the links 620 and 632 and shift the superior and inferior portions 608 and 610 closer or farther apart.

Now in more detail, the superior and inferior portions 608 and 610 are both generally obround to match the shape of a nuclear space. The superior and inferior portions 608 and 610 are also both generally flat and extend transversely to the superior-inferior direction of the intervertebral space the portions 608 and 610 are to be placed within.

Figure 48:
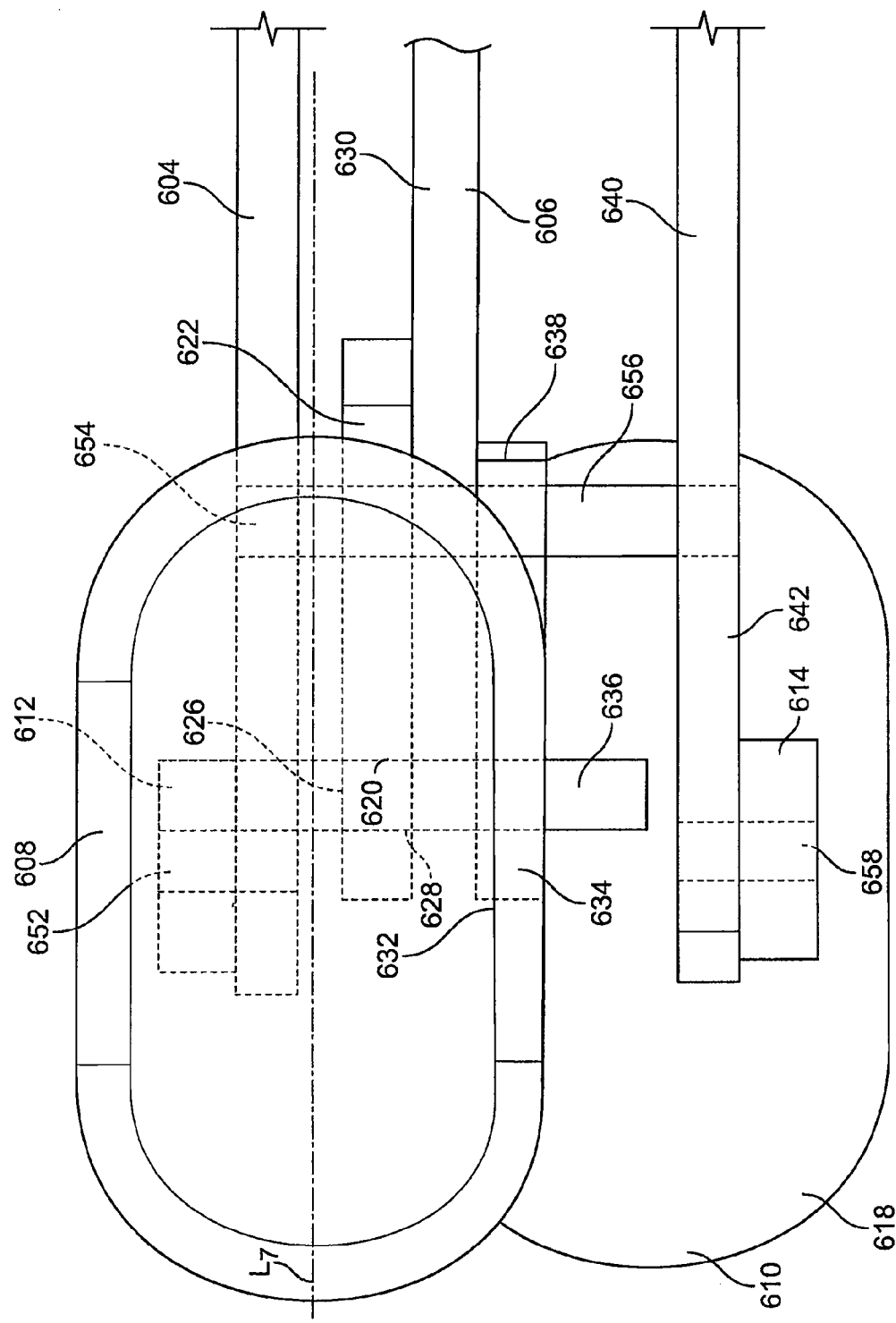
FIG. 48 is a top view of the sizing tool of FIG. 45 showing the links and connections to the holder between the top and bottom covers of the expandable device.

The superior portion 608 is pivotally connected to the elongate holder 604 and has at least one off-center projection 612 where off-center is relative to a central longitudinal axis $L_7$ of the expandable device 602 as shown in FIG. 48. The projection 612 extends downward from a downwardly facing surface 616 that also faces the inferior portion 610. The projection 612 on the superior portion 608 is pivotally connected to the holder 604 by a pin 652 (shown in dash line on FIG. 48).

Similarly, the inferior portion 610 has at least one off-center projection 614 relative to longitudinal axis $L_7$ and extending upward from an upwardly facing surface 618 on the inferior portion 610 for connection to the lever arm 640. The projections 612 and 614 are disposed on opposite sides of the longitudinal axis $L_7$ so that all of the links and members connecting the superior and inferior portions 608 and 610 to each other will fit between the projections 612 and 614 in a collapsed configuration and so that the superior and inferior portions 608 and 610 will be disposed directly above each other. It should be noted that FIG. 48 shows the superior and inferior portions 608 and 610 laterally misaligned and the lateral lengths of the members, such as arms 626 and 636 on the control member 630 for example, exaggerated for descriptive purposes.

In order to minimize the lateral motion of the members against an incision on an annulus or other anatomical structure while the expandable device 602 is being expanded within a nuclear or intervertebral space, the control member 630 is disposed to extend generally parallel to longitudinal axis $L_7$ and to shift axially to pivot the links 620 and 632. This structure reduces the amount of clearance in the superior-inferior direction that is needed to shift the control member 630 and holder 604 to operate the sizing tool 600 compared to known scissors-type sizing tools.

The control member 630 has a T-shaped distal end 628 with the two arms 626 and 636 extending oppositely while each arm is pivotally connected to one of the links 620 and 632 respectively. In order to connect the superior portion 608 to the inferior portion 610, the first link 620 has one end 622 pivotally connected to the holder 604 by a pin 654 and an opposite end 624 rotatably mounted on arm 626 of the control member 630. The second link 632 has one end 634 rotatably mounted on the remaining arm 636 of the control member 630 and an opposite end 638 connected to the lever arm 640 by a pin 656.

In order to maintain the superior and inferior portions 608 and 610 in longitudinal alignment and generally along the same superior-inferior axis, the lever arm 640 has a distal end 642 connected to the projection 614 on the inferior portion 610 by a pin 658 and a proximal end 644 connected to a main pivot bar 646. The pivot bar 646 extends laterally (left and right) relative to the longitudinal axis $L_7$ and connects to the holder 604 to secure the end 644 of the lever arm 640 at a fixed axial position relative to the holder. This maintains the inferior cover 610 at the distal end 642 of the lever arm 640 at about the same distance from the pivot bar 646 as the superior cover 608. The pivot bar 646 also terminates with caps 648 and 650 for securing the lever arm 640 and holder 604 to the pivot bar 646.

The four pins 652, 654, 656, 658 provide pivoting connections that secure the holder 604 and lever arm 640 to the projections 612 and 614, and secure the links 620 and 632 respectively to the holder 604 and lever arm 640. The pins 652, 654, 656, 658 may be threaded or configured to snap-fit or may be integrally formed with one of the pieces from which it extends.

Figure 46:
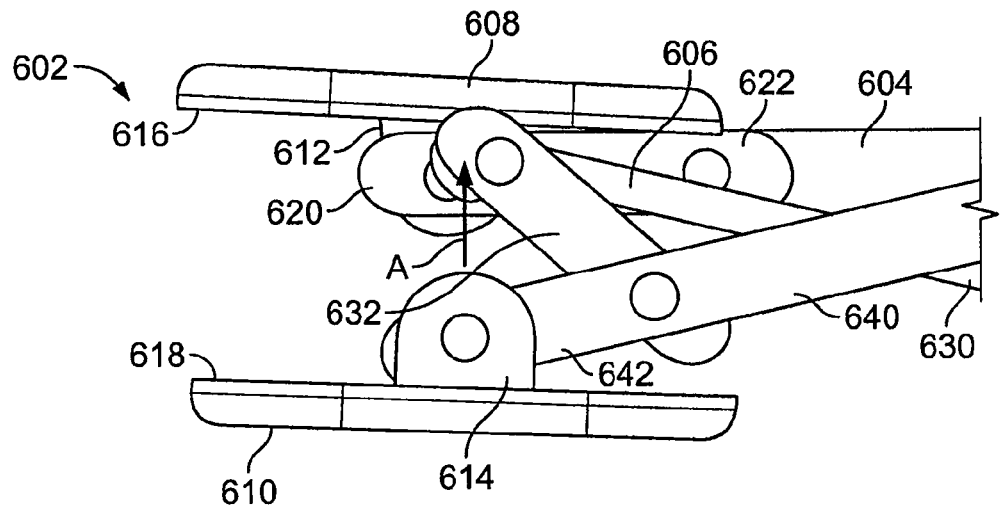
FIG. 46 is a left-side elevational view of the sizing tool of FIG. 45 showing the expandable device in a collapsed configuration.
Figure 47:
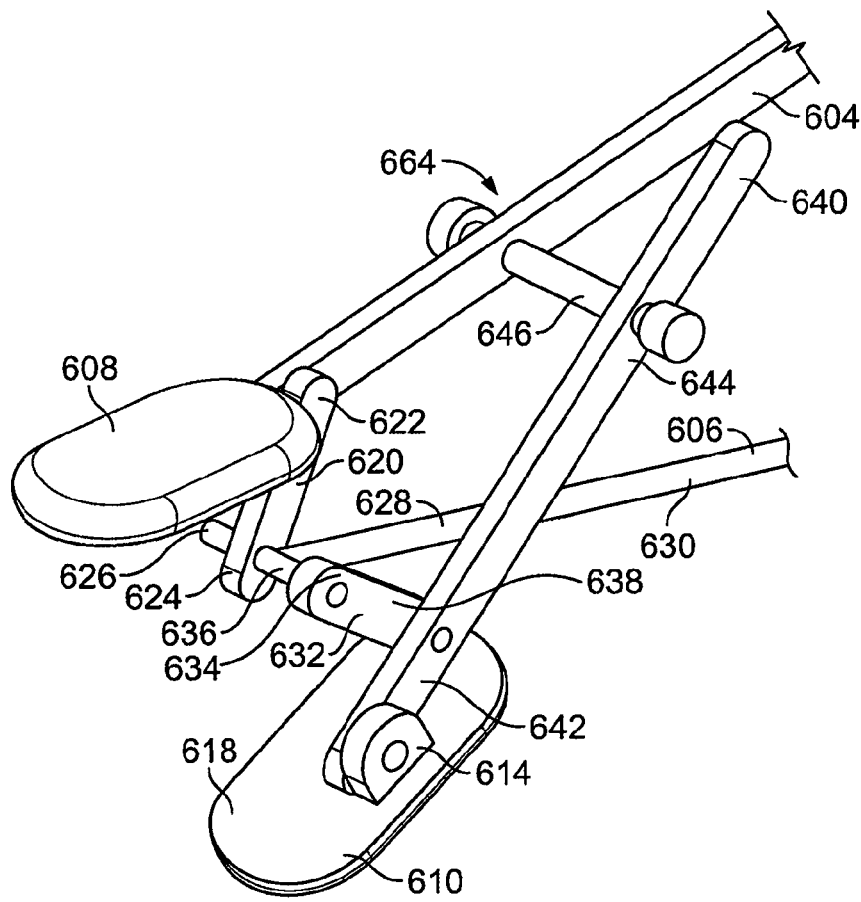
FIG. 47 is a left perspective view of the sizing tool of FIG. 45 showing the expandable device in an expanded configuration.

In operation, a surgeon grasps a handle 660 on the holder 604 with one hand and a handle 662 on the control member 630 with the other hand. The surgeon maintains the control member 640 in a forward or distal position relative to the holder 604 in order to maintain the expandable device 602 in a collapsed configuration as shown in FIG. 46. In the collapsed configuration, the links 620 and 632 are held in a generally longitudinally extending orientation, and as shown by arrow A on FIG. 46, the inferior portion 610 may be shifted toward the superior portion 608 by moving the control member 630 forward until the projection 614 on the inferior portion 610 contacts or nears the superior portion 608. So configured, the links 620 and 632, lever arm 640, holder 604 and control member 630 all extend between the projections 612 and 614 which provides the expandable device 602 with a low profile collapsed configuration for insertion into an annulus incision or intervertebral space.

Once the expandable device 602 is inserted into an intervertebral or nuclear space, the control member 630 can be drawn axially and rearward. This pivots the first and second links 620 and 632 about the arms 624 and 632 at the control member 630 and about pins 654 and 656 respectively connecting the links to the holder 604 and lever arm 640. This pivoting action causes the holder 604 to pivot about pin 652 at projection 612 and the lever arm 640 to pivot about pin 658 at projection 614 thereby causing the superior and inferior portions 608 and 610 to distract from each other generally in a superior-inferior direction to expand the expandable device 602.

Once expanded, the dimensions of the intervertebral space may be measured by methods mentioned above. The operation is then reversed for collapsing the expandable device 602.

It will be understood that the holder 604 and the control member 630 could be connected to a single body or handle of the sizing tool 600 for easier manipulation of the members 604 and 630. Such a body may permit the control member 630 to translate generally longitudinally for operation of the expandable device 602 while securing the holder 604.

It will also be understood that the expandable device 602 may be used to measure the width or footprint or other dimension of the intervertebral space rather than just the height of the space by placing the sizing tool 600 in the intervertebral space on its side.

Referring now to FIGS. 49-53, in a further alternative embodiment, a sizing tool 700 has an expandable device 702 with a superior cover 708 that is connected to an inferior cover 710 by a number of links disposed between the superior and inferior covers 708 and 710 and configured in a "car-jack" type of structure. So configured, to expand the expandable device 702, an expansion actuator 754 is operated to shift two, opposing middle links 726 and 730 closer to each other which causes the superior and inferior covers 708 and 710 to distract. To collapse the expandable device, the middle links 726 and 730 are shifted farther from each other to shift the superior and inferior covers 708 and 710 closer to each other. This configuration of rigid inks connected by pins as described below maintains the superior and inferior covers 708 and 710 in alignment with each other and along a common superior-inferior axis to provide a controlled collapse. This embodiment also permits the sizing tool 700 to provide at least passive steering by having a holder 706 that is pivotally connected to one of the links 730.

Figure 50:
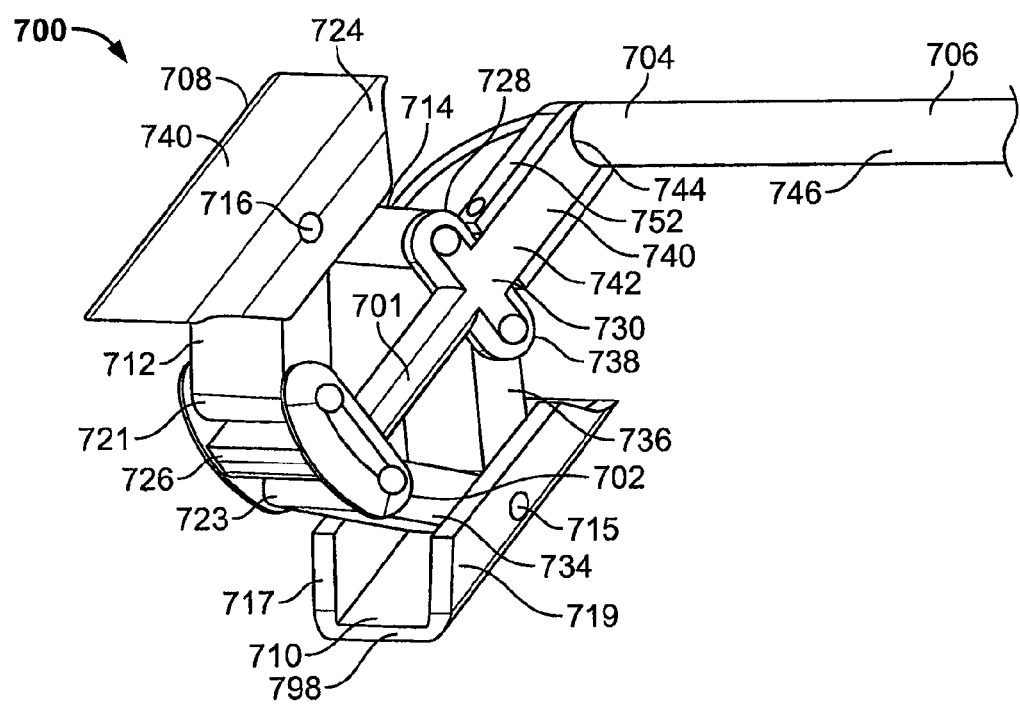
FIG. 50 is a left-side, perspective view of the sizing tool of FIG. 49 showing the expandable device in an expanded configuration and in a pivoted orientation.
Figure 51:
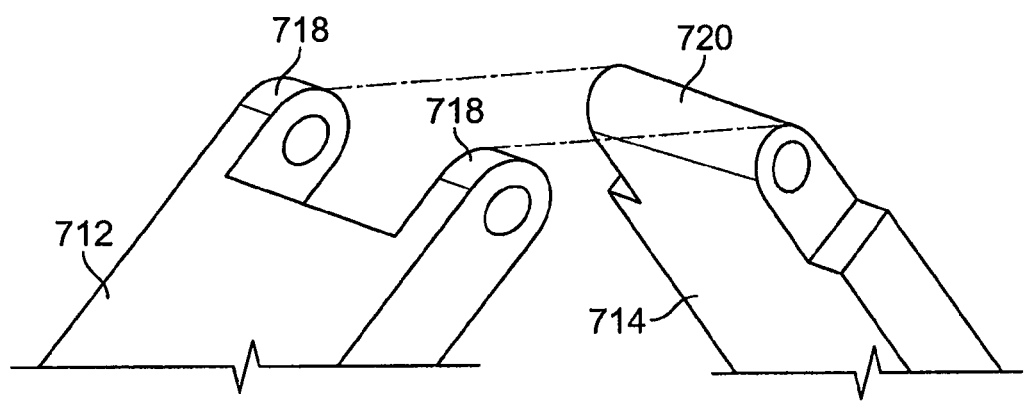
FIG. 51 is an enlarged, exploded perspective view of a link connection on the expandable device of the sizing tool of FIG. 49.

Referring to FIGS. 50-51, in further detail, the expandable device 702 is connected to a distal end 704 of holder 706 and the superior and inferior covers 708 and 710 are generally rectangular or obround for the reasons mentioned above. The superior cover 708 has a flat top wall 740 that generally extends in a plane transverse to a superior-inferior direction and has two opposing, lateral (right and left) sidewalls 722 and 724 extending downward from opposite, right and left sides of the top wall 740. The superior cover 708 is connected to two upper links 712 and 714 by a pin 716 that extends transversely to a longitudinal axis $L_8$ of the expandable device 702. The links 712 and 714 respectively have protrusions 718 and 720 that extend toward the superior cover 708 and between the right and left sidewalls 722 and 724 of the superior cover 708. The pin 716 extends though the protrusion 718 and 720 and the sidewalls 722 and 724 to form a hinge-type connection.

Referring to FIG. 50, the inferior cover 710 has right and left sidewalls 717 and 719 extending upwardly from right and left sides of a flat bottom wall 798 that extends transversely to the superior-inferior direction. The inferior cover 710 is connected to two, lower links 734 and 736 by a pin 715 in the same way that the superior cover 708 is connected to the upper links 712 and 714 by pin 716. The two, more forward or outer links 734 and 712 are connected to the middle, outer link 726, and the other two, more rearward links 714 and 736 are connected to the middle, main link 730.

The middle, outer link 726 is generally H-shaped with upper arms 721 and lower arms 723. The upper link 712 is connected to upper arm 721 by a pin 762 that extends through the link 712 while the lower link 734 is connected to the lower arms 723 by a pin 764 that extends through the link 734. Similarly, the middle, main link 730 has oppositely extending lower and upper extensions 738 and 728 respectively connected to the lower and upper links 736 and 714 by pins 766 and 768 that extend through the links 736 and 714.

Figure 49:
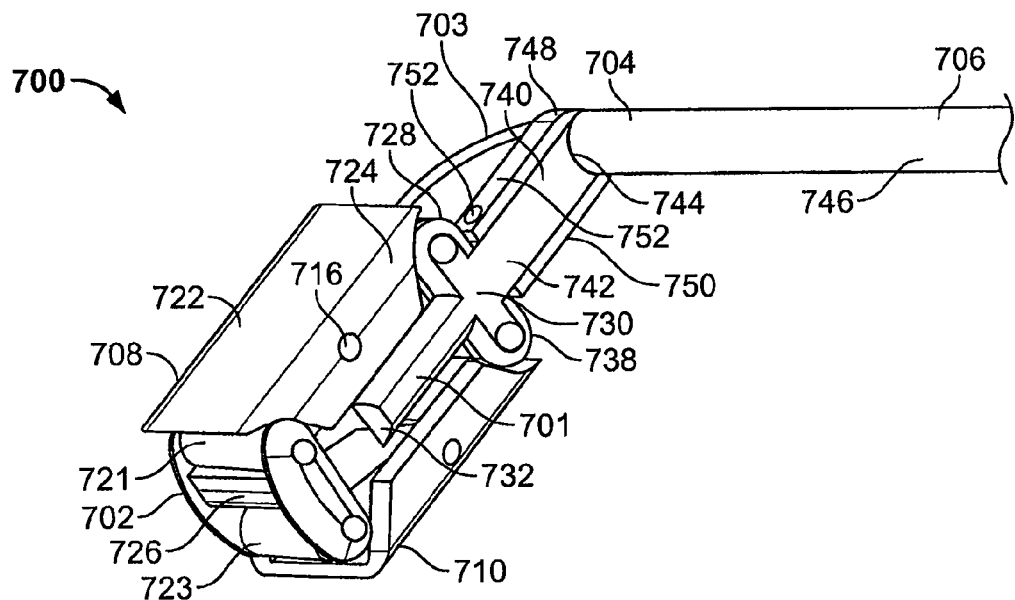
FIG. 49 is a left-side, perspective view of an alternative sizing tool showing an expandable device in a collapsed configuration and in a pivoted orientation.
Figure 52:
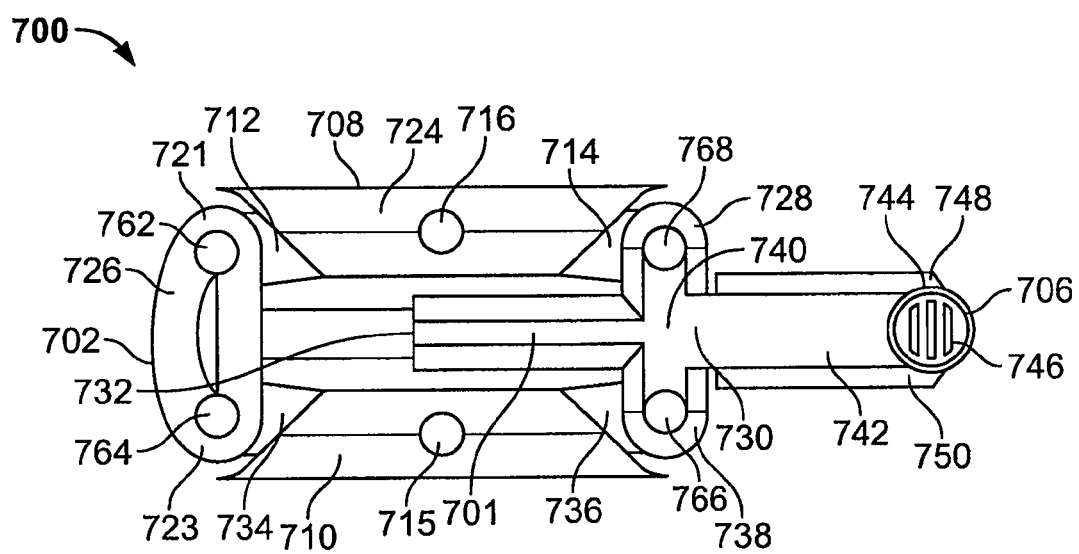
FIG. 52 is a left-side, elevational view of the sizing tool of FIG. 49 showing the expandable device and its links in a collapsed configuration and in a pivoted orientation.

With this configuration, shifting the middle links 726 and 730 toward each other causes the pins 762 and 768 to shift toward each other. This in turn causes the upper links 712 and 714 to pivot upward since the links 712 and 714 are longitudinally fixed to pin 716. Shifting pin 716 upward causes the superior cover 708 to shift upward and away from the middle links 726 and 730. The lower links 734 and 736 are caused to pivot in the same way to shift pin 715 downward instead of upward. Thus, the pivoting of the links 712, 714, 734 and 736 causes the pins 716 and 715, and in turn the superior and inferior covers 708 and 710 connected to the pins, to shift away from each other to expand the expandable device 702 as shown in FIG. 50. The process is reversed to collapse the expandable device until the links 712, 714, 734, 736 lay flat as shown in FIGS. 49 and 52. In the collapsed configuration, the links 712, 714, 734, 736 extend parallel to the longitudinal axis $L_8$ of the expandable device 702 to provide the expandable device 702 with a low profile for insertion into an intervertebral or nuclear space.

In order to limit further distraction of the superior and inferior covers 708 and 710 beyond a fully expanded orientation, the middle, main link 730 has a flat, longitudinally and forwardly extending wall 701 with a free distal end 732 that acts as a retainer. The distal end 732 faces the middle, outer link 726 and is positioned to abut the middle, outer link 726 when the expandable device 702 is in the fully expanded configuration as shown in FIG. 50.

Figure 53:
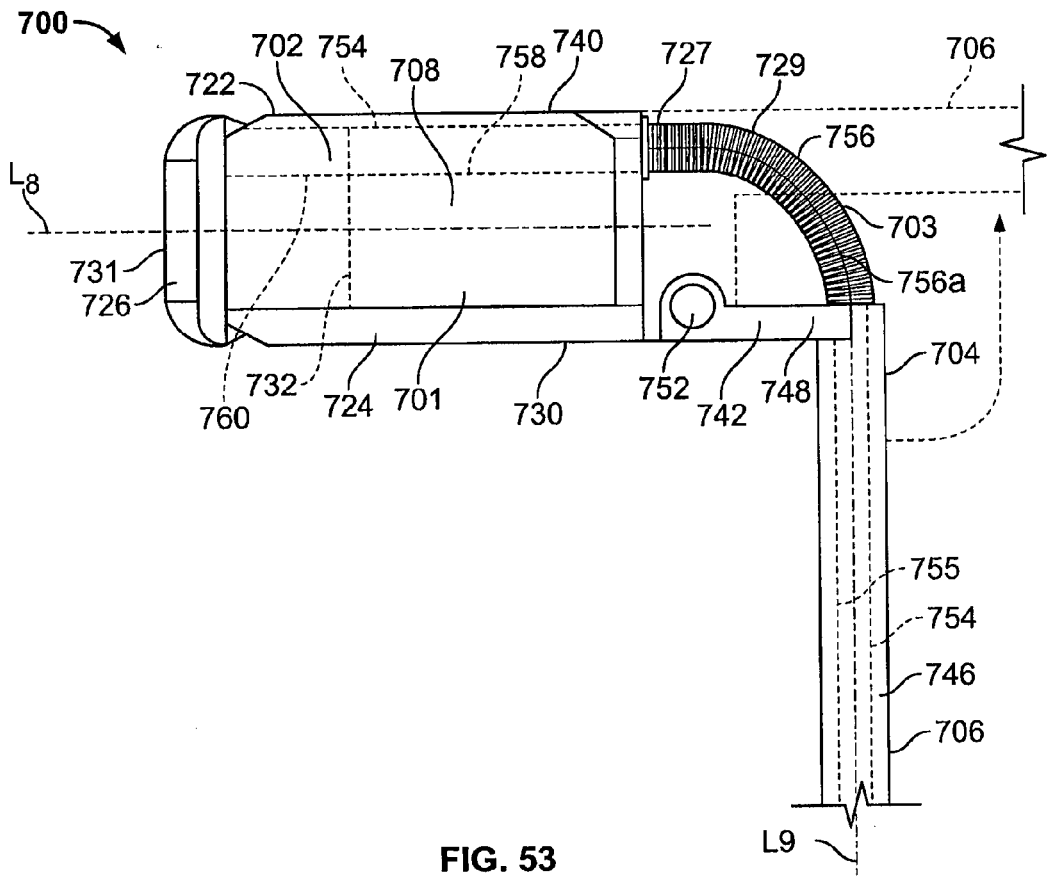
FIG. 53 is a top view of the sizing tool of FIG. 49 showing the expandable device in a pivoted orientation and the steering actuator connected to the expandable device.

Referring to FIGS. 52-53, in order to at least provide passive steering, the main link 730 also has a flat, rearwardly extending brace wall 742 that supports the holder 706. The holder 706 has a tubular shaft 746 for holding the actuator 754 and has two rigid, parallel, arms 748 and 750 extending laterally from the shaft 746. The arms 748 and 750 are respectively mounted to the top and bottom of the brace wall 742. A fastener 752 secures the arms 748 and 750 to the brace wall 742 and extends parallel to the superior-inferior direction for permitting the expandable device 702 to rotate about the fastener 752. The rigid support arms 748 and 750 respectively slide over and under the brace wall 742 while the expandable device 702 is pivoting about fastener 752 and relative to the holder 706. Thus, the expandable device 702 can be placed in a straight orientation where the longitudinal axis $L_8$ on the expandable device 702 is parallel to the longitudinal axis $L_9$ on the holder 706 (as shown in dashed line on FIG. 53) for insertion of the expandable device 702 through an annulus. The expandable device 702 can then be pivot to a 90 degree angle relative to the holder 706 for positioning the expandable device 702 within a nuclear space as shown in FIGS. 49, 50 and 52.

In order to expand or collapse the expandable device 702, the actuator 754 has an elongate member 755 and extends through the shaft 746, around the brace wall 742 while the expandable device 702 is in a pivoted orientation, and through a longitudinally extending bore 758 (shown in dashed line on FIG. 53) on the forward wall 701 of the main link 730. A distal end 760 of the actuator member 755 is connected to the middle, outer link 726 in order to shift the link 726 closer to or farther from the main link 730.

A number of alternative configurations are possible for expanding or collapsing the expandable device 702 by shifting the actuator member 755 axially. In one form, the expandable device 702 is biased in the collapsed position by a resilient member extending between the middle links 726 and 730. In such a configuration, the actuator member 755 need only have tensile properties to draw the middle link 726 toward the main link 730 to expand the expandable device 702. In this case, the actuator member 755 may be any string, rope, thread or cable that can be drawn proximally for expansion and slowly released for controlling the biased collapse of the expandable device.

In another form, the actuator member 755 is a cable or flexible rod that has sufficient compression abilities so that the actuator member is drawn axially and proximally for expanding the device 702 and advanced axially for collapsing the expandable device 702.

In yet another form, the actuator member 755 is at least partially threaded and threaded to the middle outer link 726 while being axially fixed within bore 758. In the alternative, the actuator member 755 is threaded within bore 758 while being fixed axially to the middle, outer link 726. In either of these two configurations, rotating the actuator member 755 shifts the rod axially to shift the middle links 726 and 730 closer or farther from each other to expand or collapse the expandable device 702. In this configuration, the actuator member 755 would have a straight threaded rod portion wherever it is maintained in a threaded connection and a separate bendable portion that would connect to an end of the rod portion for bending around brace wall 742 while the expandable device 702 is in a pivoted orientation.

In order to minimize the risk that the actuator member 755 bends, kinks or shifts in undesirable directions that could hamper the pivoting operation of the sizing tool 700, a proximal end 703 of the brace wall 742 is configured to guide the actuator member 755 along a predetermined, smooth, transition curve. The transition curve is cotangent with a line parallel to the longitudinal axis $L_9$ of the holder 706 on one end and remains cotangent with a line parallel to the longitudinal axis $L_8$ of the expandable device 702 on the other end (and along its length as the holder 706 pivots).

For this purpose, the proximal end 703 of the brace wall 742 has a convex curvature (shown in a top view on FIG. 53) providing about a 90 degree curve for engaging and guiding a compressible sleeve 756. The actuator member 755 extends axially through the sleeve 756 so that it is maintained along the same lateral alignment as the sleeve and along the proximal end 703. The proximal end 703 of the brace wall 742 has a concave, grooved edge 744 that receives the generally cylindrical body 756a of the sleeve 756 as well as the distal end 704 of the shaft 746. The grooved edge 744 transversely secures the sleeve 756, shaft 746 and actuator member 754 while the expandable device 702 pivots relative to the distal end 704 of the shaft 706 and about pin 752.

In order to maintain a straight, non-pivoted orientation where the longitudinal axis $L_9$ of the holder 706 is parallel to the longitudinal axis $L_8$ of the expandable device 702, the sleeve 756 is corrugated with ribs or folds so that it can compress circumferentially (relative to the curved end 703) between the distal end 704 of the holder 706 and a surface 727 that forms the opening of the bore 758 on the middle main link 730. The sleeve 756 expands circumferentially along end 703 as the expandable device 702 is pivoted relative to the holder 706.

It will be appreciated that the proximal end of the holder 706 and actuator member 755 may have an expansion control such as a handle for grasping the tool 700 and for operating the actuator member 755. Indicators on the holder 706 may represent the change in length or the amount of rotation of the actuator member 755 to indicate a distance of expansion on the expandable member 702 (although this may be performed separately by imaging technology or other methods described previously).

While a passive steering system is shown, it will be understood that an active steering system with steering shafts as described for sizing tool 10 could be added to sizing tool 700 as well as by modifying main link 730 to connect to a steering mechanism.

Figure 54:
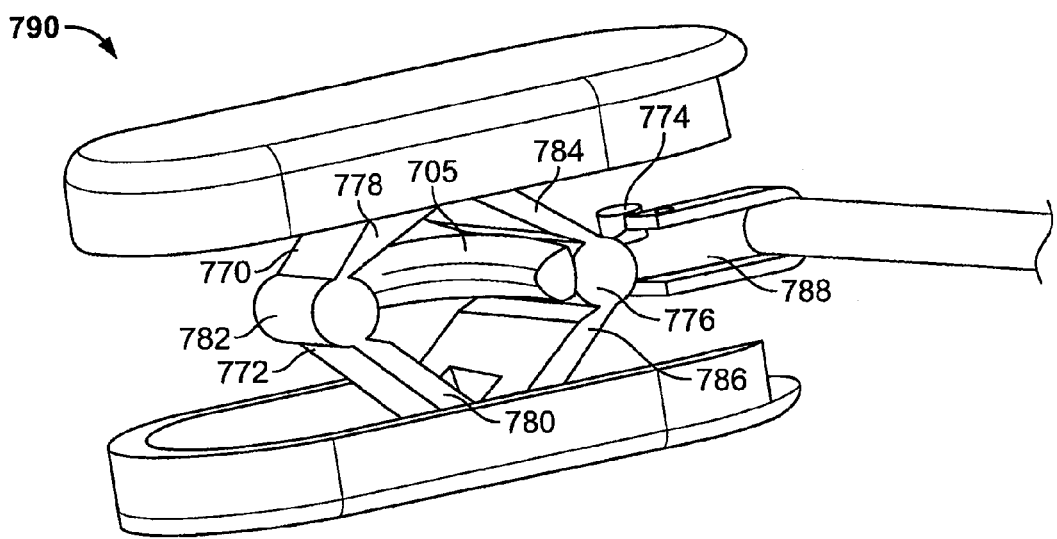
FIG. 54 is a left-side, perspective view of an alternative expandable device with alternative linking structure for the sizing tool of FIG. 49.

Referring now to FIG. 54, in an optional configuration for an expandable device 790 that is similar to expandable device 702, the pins or sizing tool 700 are replaced by living hinges 770, 772, 774, 776. In such a system, at least outer, upper and lower links 778 and 780 are integrally formed with an outer, central link portion 782. Upper and lower links 784 and 786 may be integrally formed with a main, central link 788. Otherwise, the parts of expandable device 790 are the same or similar to that of expandable device 702.

Figure 55:
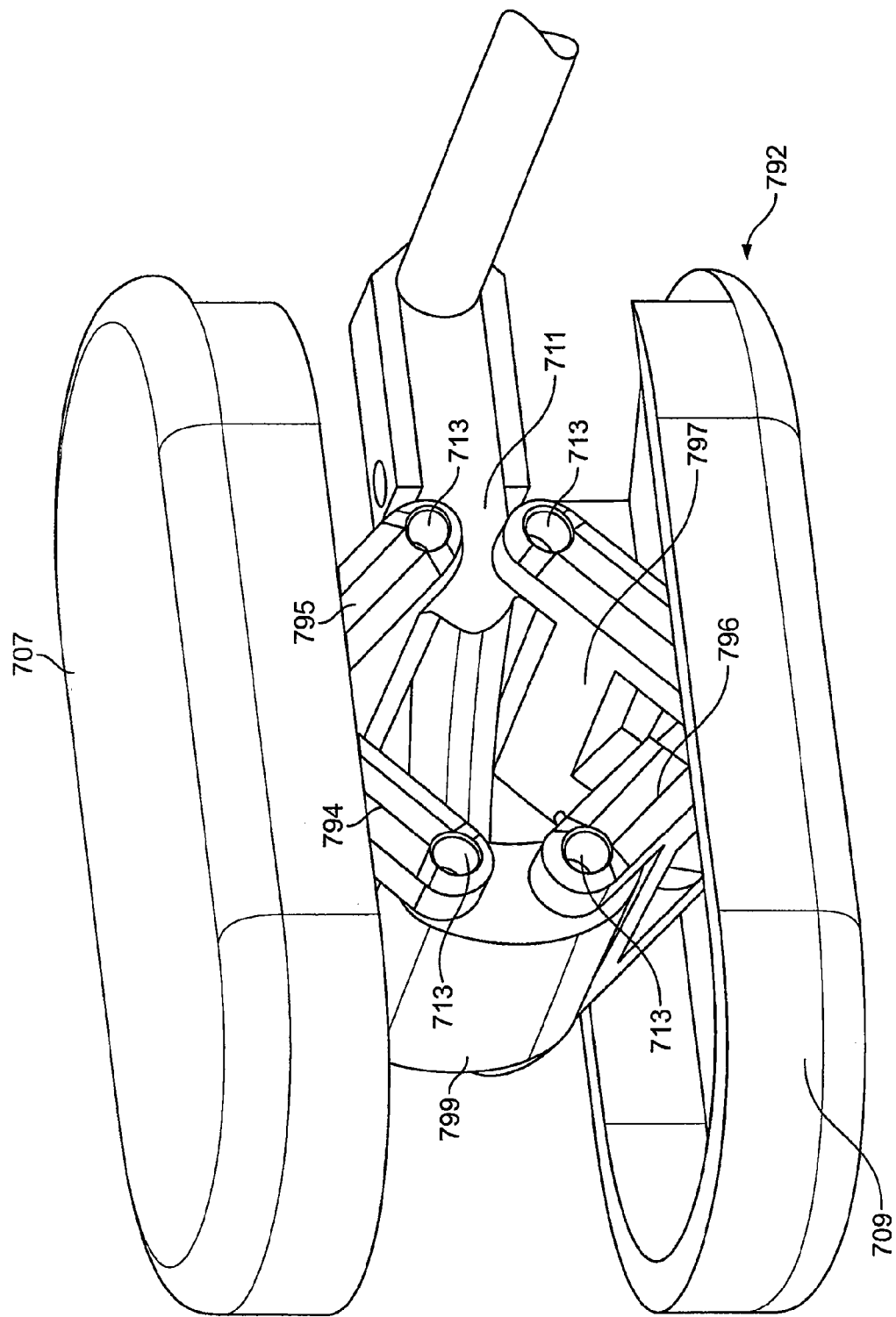
FIG. 55 is left-side, perspective view of yet a further alternative expandable device with alternative linking structure for the sizing tool of FIG. 49.

Referring to FIG. 55, instead of an H-shaped central link 726 and extensions 728 and 738 on main link 730 of expandable device 702, a similar expandable device 792 has H-shaped lower and upper links 794-797 that connect to the superior and inferior covers 707 and 709 while a middle, outer link 799 and a middle, main link 711 simply provide bores for receiving pins 713 to engage the links 794-797. Otherwise, expandable device 792 has similar structure to that of expandable device 702.

Referring now to FIGS. 56-62, a sizing and distracting tool 800 has a circular expandable device 802 with a main rotatable link 836 and pivoting links 838 and 840 that connect a superior cover 812 to an inferior cover 814 and that shift to move the covers closer together or farther apart from each other. The expandable device 802 is disposed within and engages an annular distal end 804 of a holder 806 so that the holder maintains the covers 812 and 814 in alignment with each other and along a common superior-inferior axis C (shown in FIG. 61) to provide a controlled collapse and predetermined collapsed configuration for the expandable device 702. The annular distal end 804 retains the covers along the axis C while the pivoting of links 836, 838 and 840 urges the covers 812 and 814 to shift transversely. This configuration causes the covers to shift along the axis C instead as explained in further detail below.

An expansion actuator 807 such as an elongate member or shaft 808 extends from an expansion control 810 and through the holder 806 to engage the expandable device 802. The shaft 808 holds the expandable device 802 in the annular distal end 804 of the holder 806. The shaft 808 is also connected to the main rotatable link 836 on the expandable device 802 and disposed between superior and inferior covers 812 and 814 so that rotating the link 836 shifts the covers 812 and 814 closer together or farther apart.

In another aspect of the present embodiment, convenience and speed of use of sizing tool 800 is increased by having the distal end 804 of the holder 806 include a diameter 'D' (shown on FIG. 56) about the same length as the narrow width of the leading distal ends of the elongated, rectangular or obround expandable devices described above. With such a structure, the distal end 804 of the holder 806 is inserted into an intervertebral space and through an incision on an annulus without the need for steering or pivoting the expandable device 802. This expandable device 802 measures the height of the nuclear space with sufficient accuracy but sacrifices accuracy that might have been gained by having an elongate expandable device that imitates the shape of the natural nuclear disc or the nuclear space. So configured, the distal end 804 of the holder 806 can be inserted into an intervertebral space and annulus from one of multiple surgical approaches without the need to be pivoted to match the orientation of the nuclear space.

Figure 61:
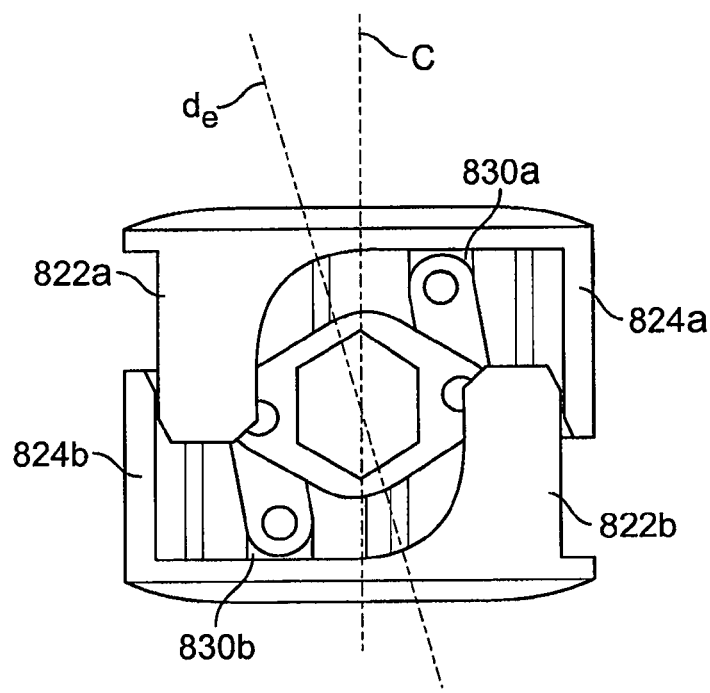
FIG. 61 is a rear, elevational view of the expandable device of the sizing tool of FIG. 56 showing the overlapping pattern of the sidewalls of the expandable device in an expanded configuration.

In yet another aspect of the present embodiment, in order to increase the accuracy of measurement of the height of the intervertebral space, both the superior and inferior covers 812 and 814 have outwardly facing, domed, exterior surfaces 818a and 818b respectively. In this form, the expandable device provides a relatively accurate measurement of the height of an intervertebral space even when the expandable device sits askew of a superior-inferior axis. This may occur when the central axis C of the expandable device 802 as shown on FIG. 61 is not parallel to the superior-inferior axis of adjacent vertebrae and the intervertebral space therebetween. In this case, the domed surfaces 818*a* and 818*b* provide a relatively constant diameter $d_e$ as shown in FIG. 61 and similar to the diameter of a sphere. The diameter $d_e$ extends from one domed surface 818*a* and 818*b* to the other domed surface so that even if the expandable device 802 sits at an angle within an intervertebral space, the distance diameter $d_e$ from dome to dome that is parallel to the superior-inferior axis on the expandable device 802 will still accurately represent the height of the intervertebral space.

Figure 58:
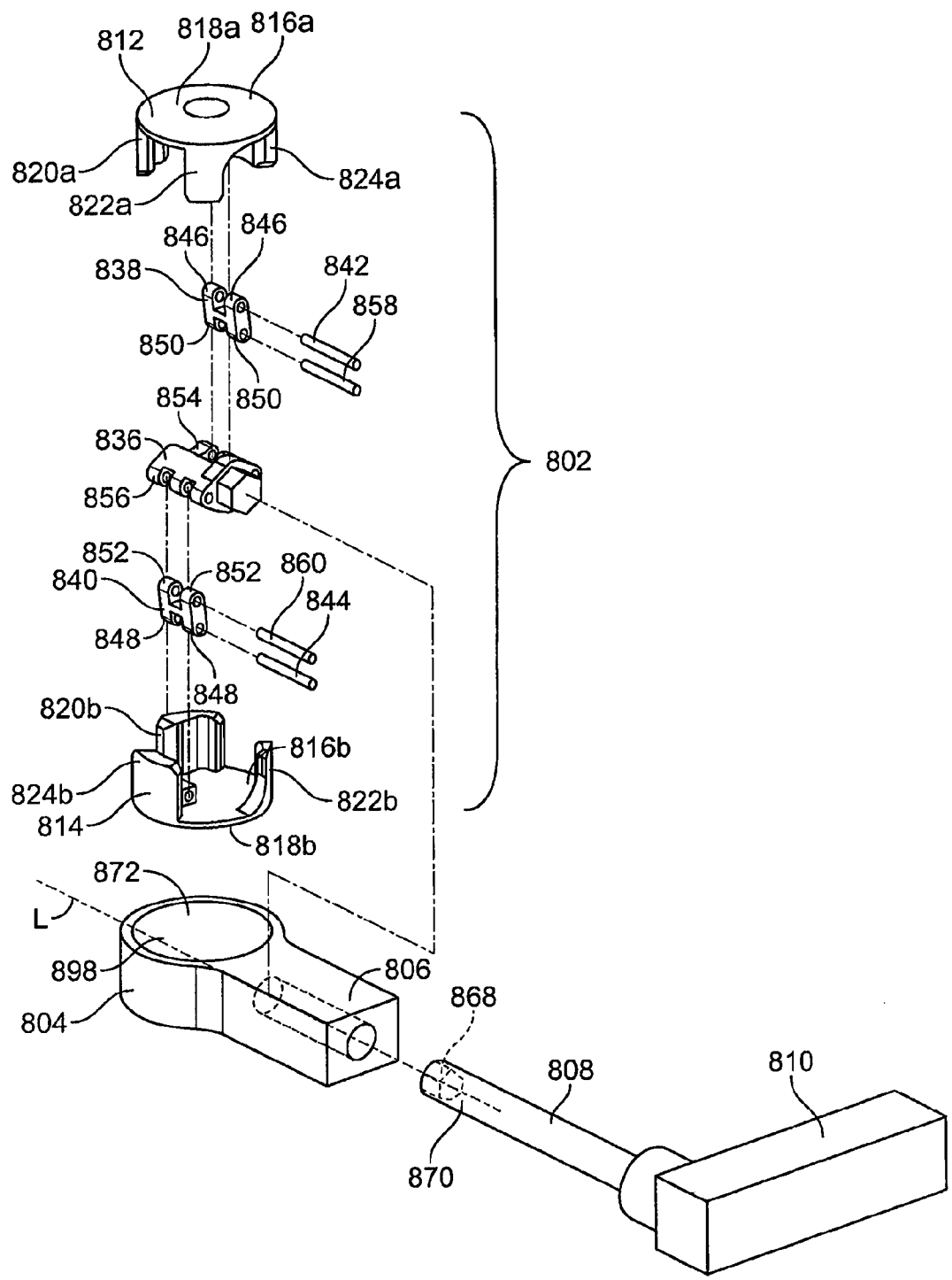
FIG. 58 is an exploded, perspective view of the sizing tool of FIG. 56 showing the components linking the top and bottom covers of the expandable device and the expansion actuator connecting to the expandable device.

Now in more detail, in order to expand and collapse the expandable device 802, the annular, distal end 804 of the holder 806 is configured to limit rotation of the covers 812 and 814 as shown in FIG. 58. As mentioned above, the holder 806 also retains the covers along the superior-inferior axis when the shaft 808 and main rotatable link 836 are rotated. The superior cover 812 has the same or similar structure as inferior cover 814. Both covers 812 and 814 respectively have a generally circular endplate 816*a* and 816*b* and form the domed exterior surfaces 818*a* and 818*b*.

Figure 59:
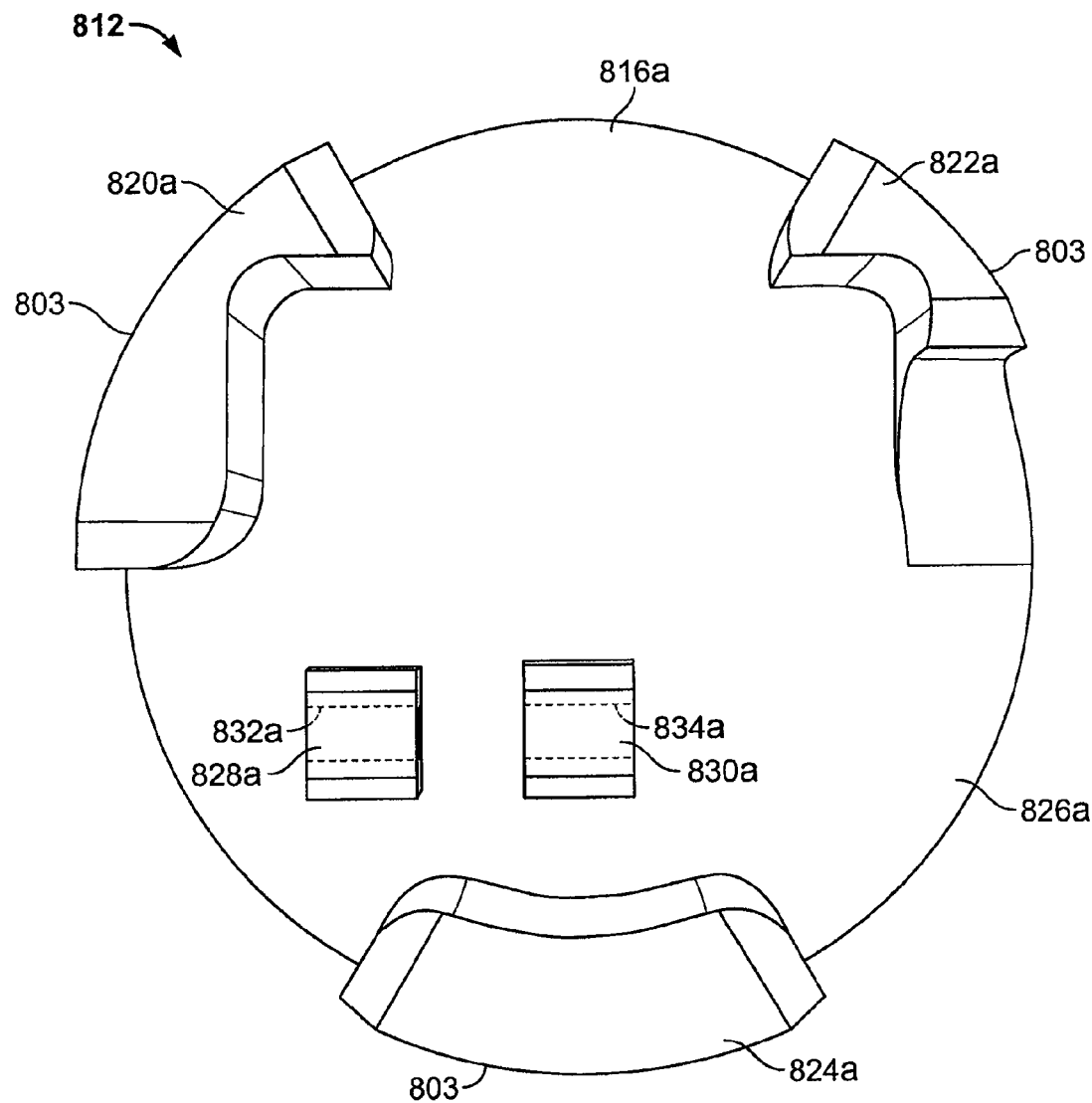
FIG. 59 is a top perspective view of either of the covers of the expandable device on the sizing tool of FIG. 56 showing the sidewall configuration of the covers.

As shown in FIG. 59, for superior cover 812 (inferior cover 814 has the same structure labeled with 'b' instead of 'a') three circumferentially spaced, arcuate sidewalls 820*a*, 822*a*, and 824*a* extend interiorly from an interior surface 826*a* on the endplate 816*a* and extend toward the opposite cover 814. The sidewalls 820*a*, 822*a*, and 824*a* are shaped to provide clearance for the internal structure of the expandable device 802 as well as engage the annular end 804 of the holder 806. The covers 812 and 814 are disposed in opposing positions relative to each other so that their sidewalls extend over alternating, circumferential positions around the expandable device 802. For example, each sidewall 820*a*, 822*a* and 824*a* on the superior cover 812 extends between two adjacent sidewalls 820*b*, 822*b* or 824*b* on the inferior cover 814.

Two anchoring protrusions 828*a* and 830*a* also extend interiorly from the interior surface 826*a* on the endplate 816*a* as shown on FIGS. 58-59 for connecting the covers 812 and 814 to the links 838 and 840 that in turn connect to the main link 836. The protrusions 828*a* and 830*a* respectively form apertures 832*a* and 834*a* that extend longitudinally relative to a longitudinal axis L (shown in FIG. 58). As shown in FIG. 61, in a rear view, the opposing positions of the covers 812 and 814 place the protrusions 828*a* and 830*a* on the right of the central axis C of the expandable device 802 while the protrusions 828*b* and 830*b* on the inferior cover 814 are located in an opposing location on the left of the central axis C to align with links 838 and 840.

Referring to FIG. 58, the covers 812 and 814 are connected to opposite sides of the main rotatable link 836 by at least one H-shaped link 838 or 840 respectively. Upper link 838 engages protrusions 828*a* and 830*a* on the superior cover 812 with a pin 842 while lower link 840 engages protrusions 828*b* and 830*b* on the inferior cover 814 with a pin 844. The links 838 and 840 are shown with two arms 846 or 848 to connect to their corresponding protrusions but may have more or less arms to engage at least one protrusion.

Figure 60:
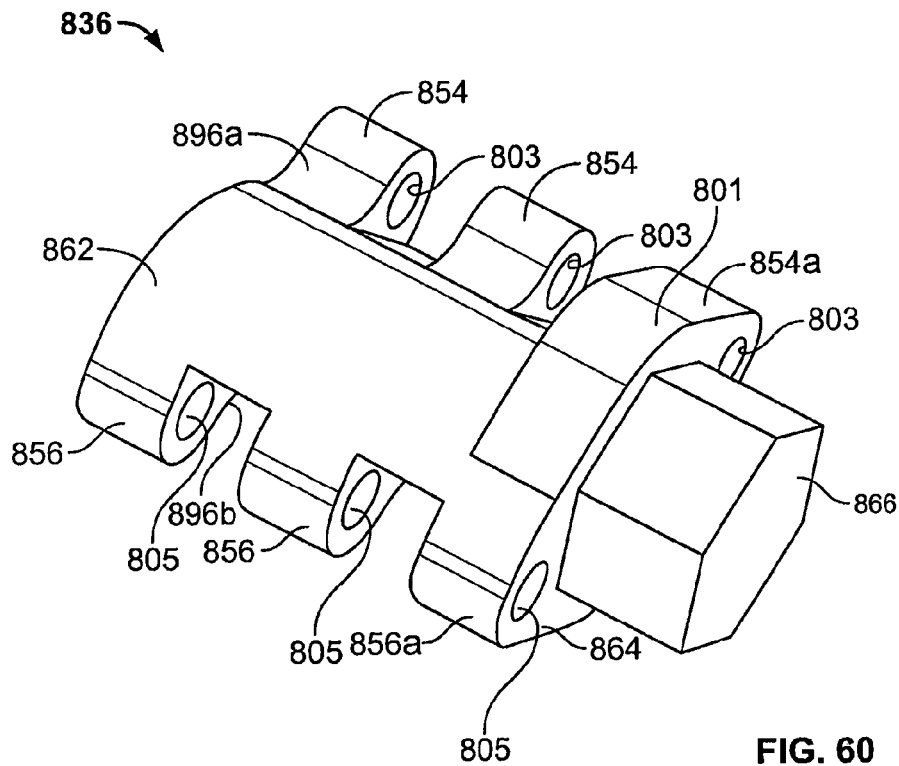
FIG. 60 is an enlarged, perspective view of a linking component of the expandable device of the sizing tool of FIG. 56 showing its arms and showing an end that connects to the expansion actuator.

Referring to FIGS. 58 and 60, two parallel, spaced arms 850 extend downwardly on upper link 838 to connect to three parallel arms 854 on the rotatable link 836 by a pin 858 extending through apertures 803. Similarly, two spaced, parallel arms 852 extend upwardly on lower link 840 to connect to three parallel arms 856 on the rotatable link 836. A pin 860 extending through apertures 805 connects the three arms 856 to the two arms 852 on the lower link 840. The arms 854 and 856 on the rotatable link 836 extend in opposite lateral directions relative to longitudinal axis L.

Figure 62:
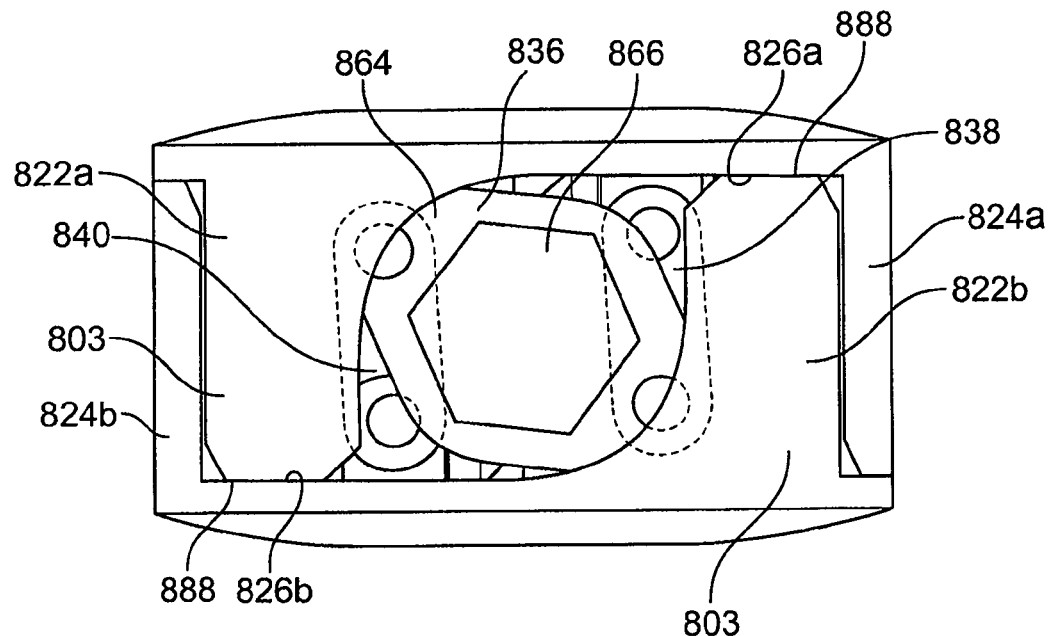
FIG. 62 is a rear, elevational view of the expandable device of the sizing tool of FIG. 56 showing the overlapping pattern of the sidewalls of the expandable device in a collapsed configuration.

In order to provide clearance for the links 838 and 840 in a collapsed configuration as shown in FIG. 62, the arms 854 have grooved sides 896*a* (shown on FIG. 60) so that the arms 854 are slanted to extend slightly upward toward upper link 838 and superior cover 812. Similarly, the arms 856 have grooved sides 896*b* so that they are slanted to extend slightly downward toward lower link 840 and the inferior cover 814 as shown on FIG. 60. This configuration permits the links 838 and 840 to abut the rotatable link 836 in a tight, reclining, Z-shaped orientation to hold the expandable device 802 in a collapsed configuration shown in FIG. 62.

Figure 60A:
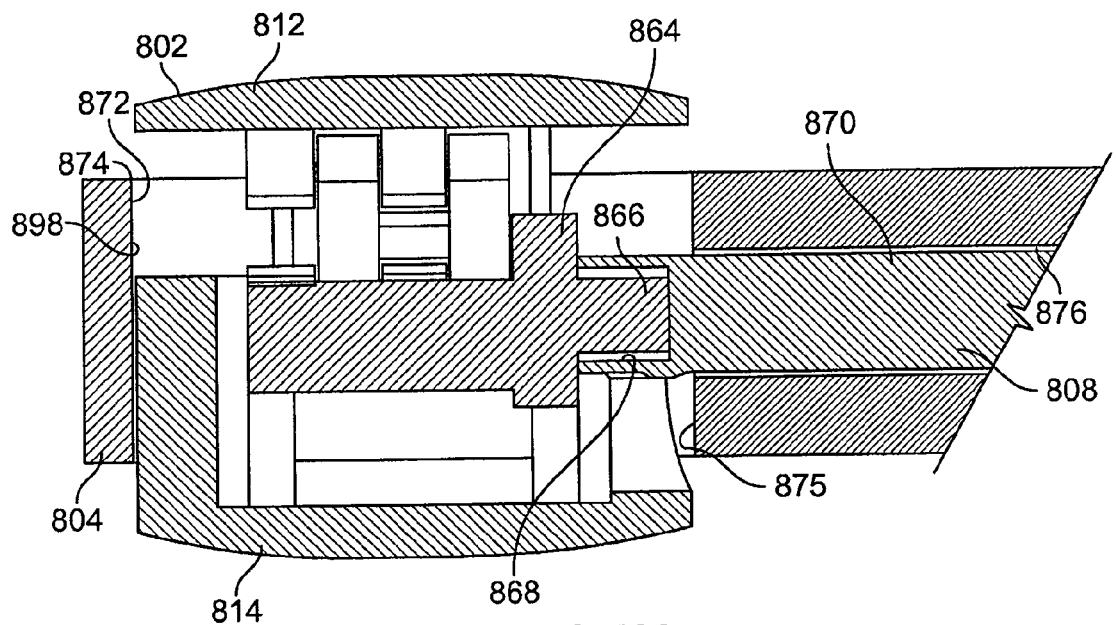
FIG. 60A is a left-side, cross-sectional view of the expandable device within the holder on the sizing tool of FIG. 56 showing the connection of the linking component to the expansion actuator and the expandable device in an expanded configuration.

Referring to FIG. 60, the arms 854 and 856 on the rotatable link 836 extend oppositely from a main body 862 of the rotatable link 836. The main body 862 has a rear end 801 that forms a generally diamond shaped flange 864 cooperatively with the two rear most arms 854*a* and 856*a*. A head 866 extends proximally from the flange 864 for receipt within a socket 868 on a distal end 870 of the shaft 808 as shown in FIG. 60A. The head 866 and corresponding socket 868 shown here are hexagonal but may be other shapes as long as the shaft 808 can engage and rotate the head 866.

Referring to FIGS. 58 and 60A, the expandable device 802 is positioned within a main through-hole 872 on the distal end 804 of the holder 806 so that the covers 812 and 814 are free to extend out of opposite openings 874 and 875 of the through-hole 872. A longitudinal bore 876 extends from a rear end 878 of the holder 806 and opens to the through-hole 872. The shaft 808 extends through bore 876 and engages head 866 while the expandable device 802 is disposed in the through-hole. Thus, the shaft 808 also retains the expandable device in the through-hole. The shaft 808 may abut the flange 864 for further longitudinal support as shown in FIG. 60A. It will be understood that bore 876 and shaft 808 may be threaded or may have an interference fit so that the bore will hold the shaft 808 in a rotated position in order to hold the expandable device 802 in a desired expanded configuration.

Figure 56:
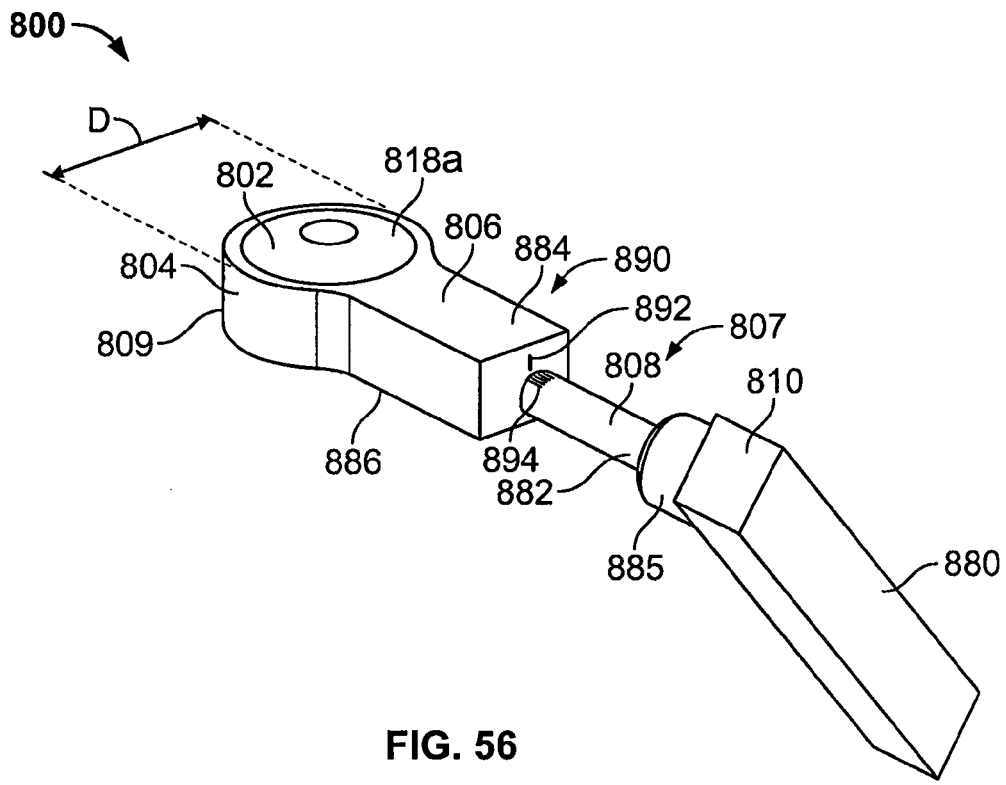
FIG. 56 is a left-side, perspective view of an alternative sizing tool in accordance with the present invention and showing an expandable device in a collapsed configuration within a holder.
Figure 57:
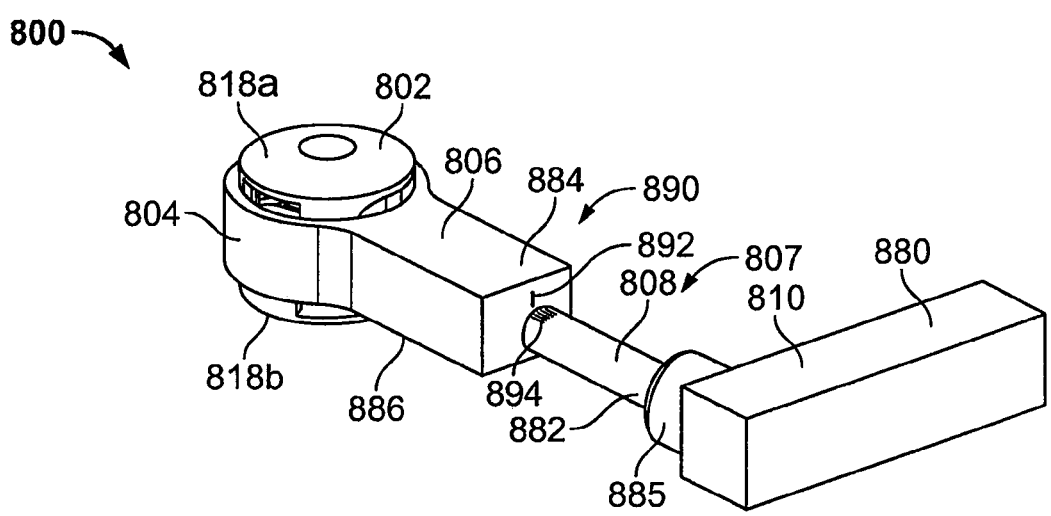
FIG. 57 is a left-side, perspective view of the sizing tool of FIG. 56 and showing the expandable device in an expanded configuration and extending out of a holder.

Referring to FIGS. 56-58, the expansion control 810 includes a bar 880 which extends radially relative to longitudinal axis L and is fixed to a proximal end 882 of the shaft 808 to function as a handle. While the shaft 808 is shown to have a locking collar 885 for securing the shaft 808 to the bar 880, the bar 880 and shaft 808 may be permanently secured or integrally formed with each other as long as the connection permits the rotation of the shaft 808.

As shown in FIG. 56, for insertion between vertebrae, the sizing tool 800 is maintained in a collapsed configuration in which the top surfaces 818*a* and 818*b* (only 818*a* is shown) of the covers 812 and 814 are generally flush with the outer surfaces 884 and 886 of the holder 806 providing the holder 806 with a low insertion profile and at least generally enclosing the expandable device 802 within the through-hole 872. The annular distal end 804, with the expandable device 820 enclosed, presents a smooth, curved lead end 809 for facing an incision on an annulus and forming the forward end for insertion of the expandable device 802. The surgeon holds the holder 806 with one hand and the control 810 with the other hand as the distal end 804 is inserted from one of a variety of different surgical approaches since the expandable device 802 does not need to be pivoted once it is within the intervertebral or nuclear space.

Referring to FIGS. 57 and 61, once the expandable device 802 is disposed within an intervertebral or nuclear space, the surgeon rotates the bar or handle 880 to rotate shaft 808 which in turn rotates rotatable link 836. The rotation of the link 836 pivots the links 838 and 840 which in turn urges the sidewalls 820a-b, 822a-b, and 824a-b to pivot with the links 838 and 840 and shift transversely relative to the superior-inferior axis C.

In order to maintain the alignment of the covers 812 and 814 and to counter the transverse forces from the links 838 and 840, the sidewalls 820a-b, 822a-b, and 824a-b are retained transversely and in coaxial alignment to the central axis C by an interior cylindrical surface 898 that forms the through-hole 872 of the holder 806. With the covers 812 and 814 so restrained, the upper link 838 is forced to shift upward and the lower link 840 is forced to shift downward which shifts the covers 812 and 814 and their sidewalls 820a-b, 822a-b, 824a-b in opposite superior and inferior directions until the covers 812 and 814 are in an expanded orientation and/or are in contact with opposing vertebrae. In order to maintain the covers 812 and 814 aligned with central axis C no matter how far the covers have distracted, the sidewalls 820a-b, 822a-b, 824a-b extend a sufficient length in the superior-inferior direction to maintain engagement with the interior surface 898 of the distal end 804 of the holder 806 even when the expandable device 802 is fully expanded.

Once the expandable device 802 is expanded to contact the vertebrae or the surgeon senses increased resistance in distracting the covers 812 and 814, the amount of expansion can be measured by having a measuring mechanism such as an indicator 890 that may include a pointer 892 on the holder 806 that is aligned with indicia 894 on the shaft 808 as shown on FIGS. 56-57. Instead of the proximal end 882 of the holder 806, the indicator 890 may be formed by a window or opening over other parts of the shaft 808 within the holder 806. Measurements may also be taken by visual observation, imaging or other techniques as mentioned above. Once measured, the control 810 is rotated to collapse the expandable device 802 which then may be retracted from the intervertebral space and back through the incision on the annulus if present.

Referring now to FIGS. 63-67, an alternative sizing tool 900 is configured to provide a controlled collapse of an expandable device 902. Expandable device 902 has a wedge 912 held by the holder 906. The expandable device 902 is configured so that shifting the wedge 912 longitudinally along a longitudinal axis $L_{HW}$ of the holder 906 shifts the superior and inferior portions 908 and 910 along a superior-inferior axis orthogonal to the longitudinal axis $L_{HW}$.

In order to provide a controlled collapse and a predetermined collapsed configuration for the expandable device 902, the holder 906 has a longitudinally extending support member 942 that retains the wedge 912 along the longitudinal axis $L_{HW}$. For this purpose, the support member 942 has arms 954 and 956 that connect to the left and right sides 958 and 960 of the wedge 912 so that the wedge can translate longitudinally upon the arms while being transversely secured between them. The support member 942 also has guide posts 958 and 960 that extend in the superior-inferior direction and connect to the left and right sides 946 and 948 of the superior and inferior portions 908 and 910. The guide posts 958 and 960 maintain the portions 908 and 910 in alignment with each other and along the same superior-inferior axis $S_1$.

In more detail, the expandable device 902 is connected to a distal, wedge end 904 of the elongate holder 906 for insertion of the expandable device 902 into an intervertebral space. The superior cover or portion 908 is disposed above the inferior cover or portion 910 which are both generally the shape of truncated cylinder ends. The wedge 912 is positioned between the two portions 908 and 910 so that shifting the wedge longitudinally cams the wedge against the inferior and superior portions 908 and 910. This shifts the portions 908 and 910 closer to, or farther from, each other and in opposite superior and inferior directions along axis $S_1$ to expand the expandable device 902.

Figure 65:
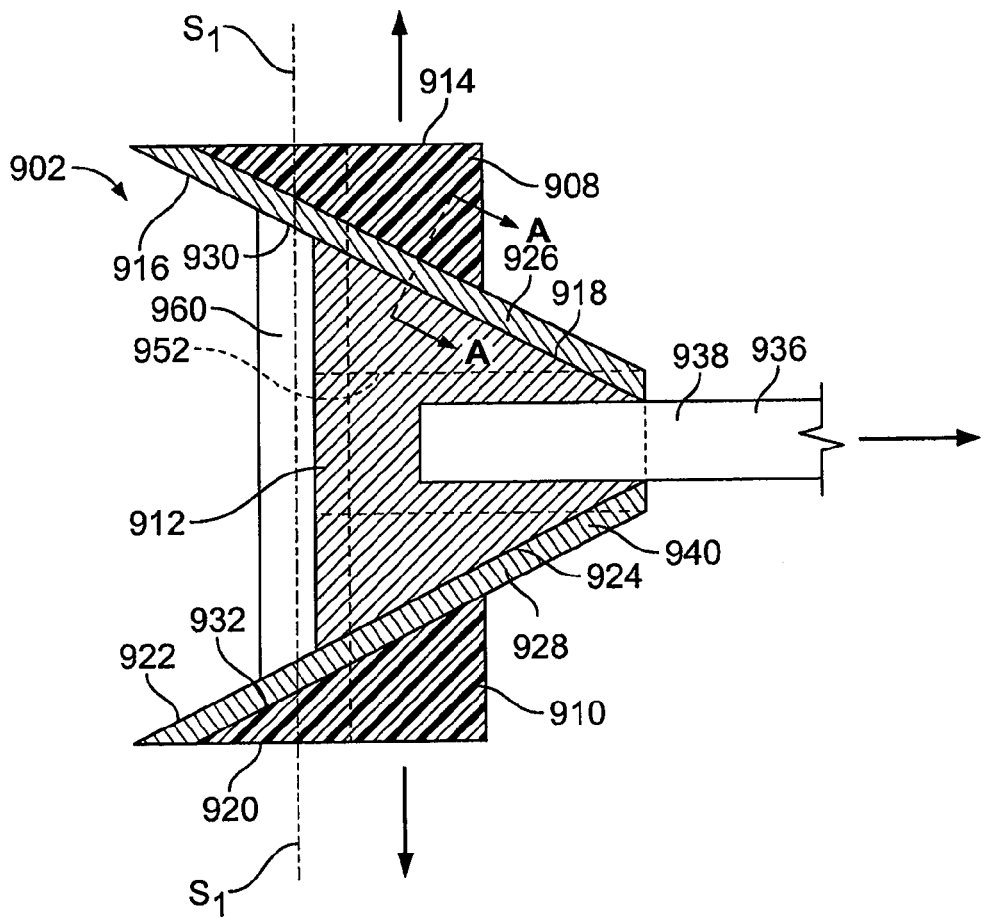
FIG. 65 is a left-side, cross-sectional view of the expandable device of the sizing tool of FIG. 63 showing the expandable device in an expanded configuration and slanted mating surfaces on the wedge and top and bottom covers of the expandable device.

Referring to FIG. 65, the superior portion 908 has a generally flat, generally obround, top surface 914 that extends parallel to the longitudinal axis $L_{HW}$. The superior portion 908 also extends in a plane transverse to the superior-inferior direction for engaging one of the vertebra that form the intervertebral space. Similarly, inferior portion 910 has a generally flat, generally obround bottom surface 920 that extends in a plane parallel to the plane of the top surface 914 for engaging a vertebra forming the intervertebral space.

In order to provide for the camming action of the wedge 912 against the opposing portions 908 and 910, the wedge 912 and opposing portions 908 and 910 have mating, inclined surfaces that are all slanted toward the longitudinal axis $L_{HW}$ and at an angle relative to the superior-inferior axis $S_1$. More specifically, an inclined bottom surface 916 on the superior portion 908 is opposite the top surface 914 and translates on a corresponding, upper, inclined surface 918 of the wedge 912. In one form, the inclined surfaces 916 and 918 slant downward toward the longitudinal axis $L_{HW}$ as the inclined surfaces extend toward a proximal, user end 974 of the holder 906.

The inferior portion 910 has a top inclined surface 922 opposite the bottom surface 920 and that translates on a corresponding, lower, inclined surface 924 on the wedge 912. The inclined surfaces 922 and 924 slant upward toward the longitudinal axis $L_{HW}$ as the surfaces 922 and 924 extend toward the user end 974 of the holder 906.

With this configuration, shifting the wedge 912 axially along longitudinal axis $L_{HW}$ and toward the user end 974 of the holder 906 causes the wedge 912 to press or cam the wedge surfaces 918 and 924 respectively against the opposing inclined surfaces 916 and 922 of the superior and inferior portions 908 and 910. This motion causes the superior and inferior portions 908 and 910 to shift away from each other and distract in opposite superior and inferior directions along axis $S_1$.

Figure 68:
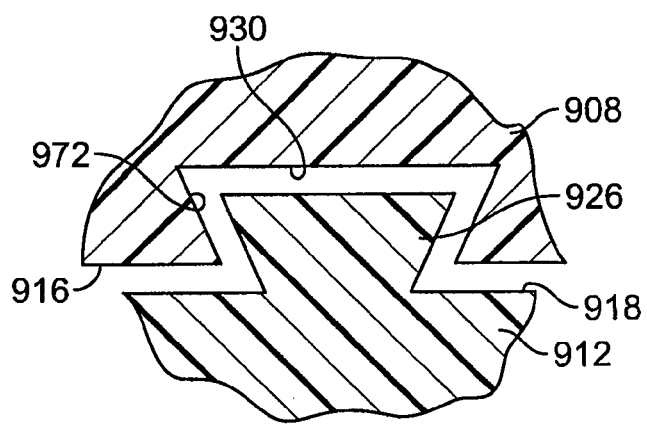
FIG. 68 is a cross-section taken along the line A-A on FIG. 68 and showing a slot-rail connection holding a wedge piece on a superior or inferior portion.

To maintain lateral alignment between the wedge 912 and the portions 908 and 910, both inclined surfaces 918 and 924 of the wedge 912 respectively have an elongate, longitudinally extending rail 926 and 928 for respectively engaging opposing elongate grooves 930 and 932 on the inclined surfaces 916 and 922. As shown in FIG. 68, to maintain the superior and inferior portions 908 and 910 in connection with the wedge 912, the rails 926 and 928 and the grooves 930 and 932 may also have a generally trapezoidal cross section transverse to their longitudinal dimensions. Thus, grooves 930 and 932 have inclined sidewalls 972 that extend inward to respectively retain the rails 926 and 928 within the grooves 930 and 932 in the superior-inferior direction.

Figure 63:
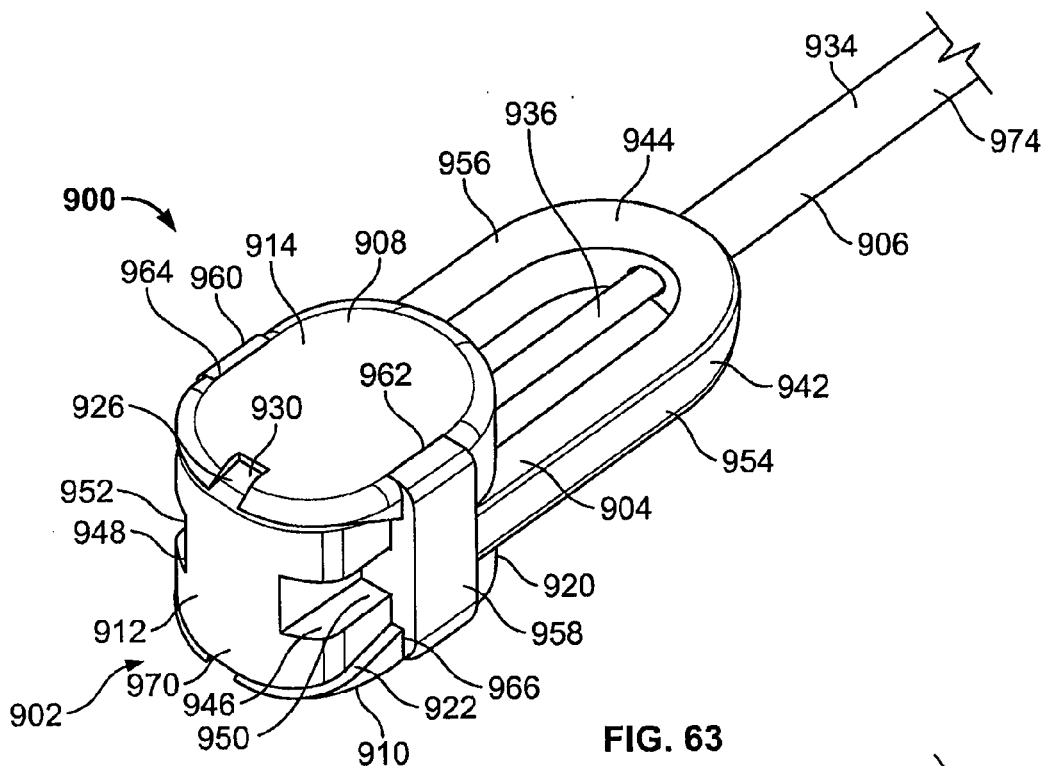
FIG. 63 is a perspective view of an alternative sizing tool in accordance with the present invention and showing an expandable device in a collapsed configuration and connected to a holder.
Figure 64:
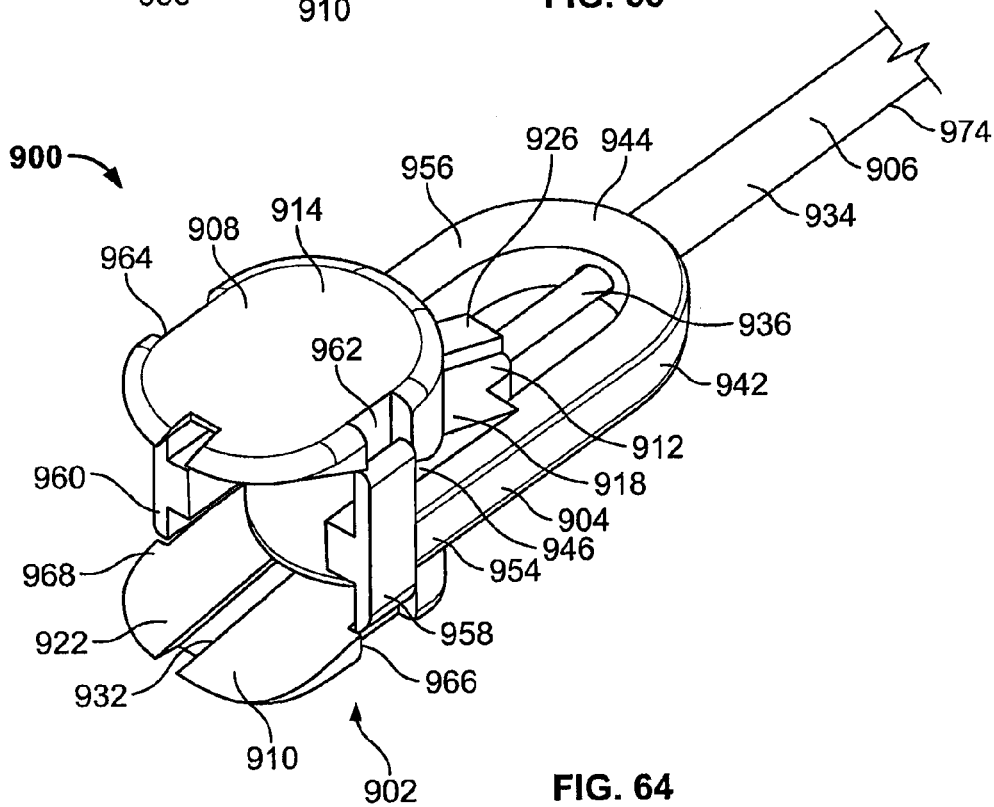
FIG. 64 is a perspective view of the sizing tool of FIG. 63 showing the expandable device with top and bottom covers separated by a wedge in an expanded configuration and connected to a holder.
Figure 66:
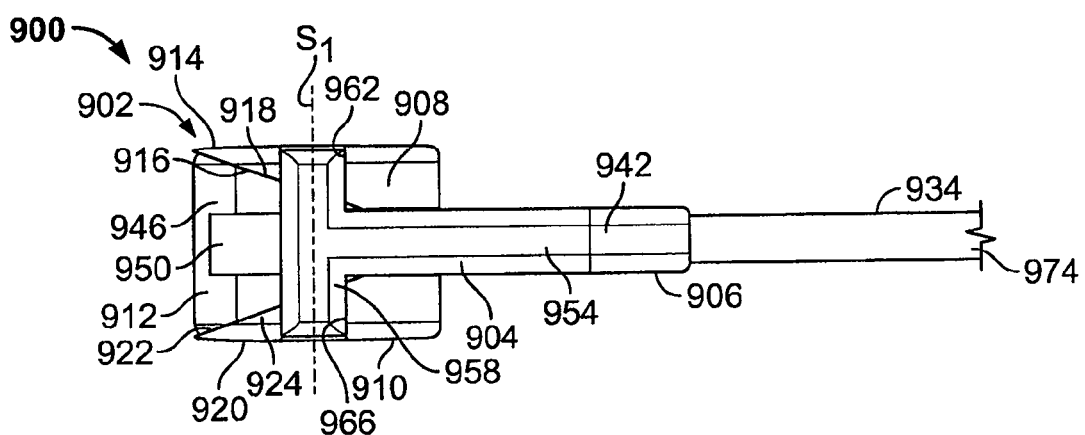
FIG. 66 is a left side elevational view of the sizing tool of FIG. 63 showing the expandable device in a collapsed configuration and connected to a holder.

With such a configuration, shifting the wedge 912 forward or distally and away from the user end 974 of the holder 906 causes the rails 926 and 928 of the wedge 912 to draw the superior and inferior portions 908 and 910 toward each other and to a collapsed configuration (shown in FIGS. 63 and 66). In an alternative form, pressure from the vertebrae may also press the superior and inferior portions 908 and 910 toward each other as the wedge 912 is shifted forward or distally. The shifting of the wedge 912 provides clearance for the superior and inferior portions 908 and 910 to shift toward the wedge and each other.

Figure 67:
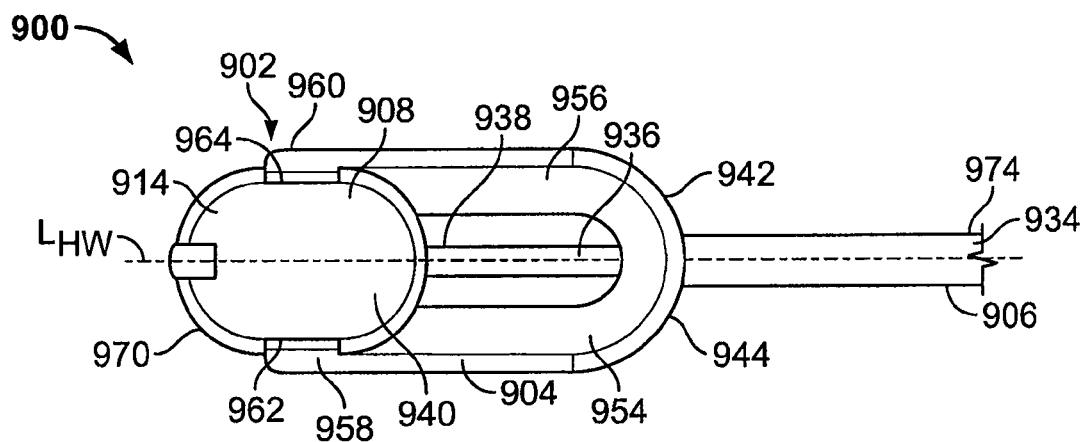
FIG. 67 is a top view of the sizing tool of FIG. 63 showing the U-shaped structure of the holder and expansion actuator connected to the expandable device.

Referring to FIGS. 65 and 67, in order to hold and shift the wedge 912, the holder 906 has a cylindrical shaft 934 that holds an expansion actuator such as an elongate drive rod 936. The rod 936 extends through the shaft 934 and can translate axially within the shaft. A distal end 938 of the drive rod 936 is connected to the rear, pointed end 940 of the wedge 912. The rod 936 may be threadedly connected to wedge 912 and to shaft 934 so that rotating the rod 936 shifts the rod and in turn the wedge longitudinally. Instead, the rod 936 and wedge 912 may have an interference fit or other connection that secures the rod 936 longitudinally to the wedge 912 so that advancing and/or drawing the rod 936 longitudinally also shifts the wedge 912 and in turn expands or collapses the expandable device 902.

Referring to FIG. 66-67, in order to maintain the wedge 912 in alignment with the longitudinal axis $L_{HW}$, the support member 942 extends forward from the shaft 934 and has a U-shaped fork or beam 944 that connects to both the left and right sides 946 and 948 of the wedge 912. The sides 946 and 948 of the wedge 912 respectively have a longitudinally extending slot 950 and 952 for respectively and slidingly engaging the corresponding arms 954 and 956 of the support member 942. So configured, the wedge 912 cannot disengage from the arms 954 and 956 in a transverse direction relative to the longitudinal axis $L_{HW}$.

In an additional aspect of the invention, in order to maintain the superior and inferior portions 908 and 910 in alignment with each other and along the superior-inferior axis $S_1$, the guide posts 958 and 960 respectively extend on the left and right of the expandable device 902 and from the arms 954 and 956 of the support member 942. Both guide posts 958 and 960 extending generally parallel to the superior-inferior axis $S_1$.

The guide posts 958 and 960 also respectively engage left and right indents 962 and 964 on the superior portion 908 and left and right indents 966 and 968 on the inferior portion 910. So configured, the guide posts 958 and 960 retain the superior and inferior portions 908 and 910 in lateral and longitudinal alignment with each other since the superior and inferior portions 908 and 910 do not have clearance to disengage from the guideposts 954 and 956. While the guide posts 954 and 956 permit the portions 908 and 910 to shift in the superior-inferior direction, the superior and inferior portions 908 and 910 are still retained on the guide posts 958 and 960 in the superior and inferior direction by the groove-slot connections between the superior and inferior portions 908 and 910 and the wedge 912 described above.

In operation, the user manipulates the holder 906 to place the expandable device 902 in an intervertebral or nuclear space while in a collapsed configuration as shown in FIGS. 63 and 66. While the expandable device 902 could be modified to include the active or passive steering mechanism described above, in its current configuration, it is desirable to use a more lateral approach to properly place the obround expandable device 902 within an intervertebral or nuclear space so that its longitudinal dimension extends laterally relative to the anterior-posterior direction.

In the collapsed configuration, a distal, leading end 970 of the wedge 912 is curved to match the obround shape of the top and bottom surfaces 914 and 920 of the superior and inferior portions 908 and 910. The leading end 970 generally provides a smooth, generally continuous surface to lead the expandable device 902 into an intervertebral space and through an annulus. Once disposed between the vertebrae, the surgeon operates the rod 936 by either rotating the rod or shifting the rod rearward to shift the wedge 912 proximally which in turn distracts the superior and inferior portions 908 and 910 along the guide posts 958 and 960. The surgeon distracts the portions 908 and 910 until a desirable expanded configuration is obtained and then measured as explained above for the other embodiments. Once the measurements or an image of the expandable device 902 are taken, the surgeon operates the rod 936 to shift the rod and in turn the wedge 912 distally to collapse the expandable device 902 and retract it from the intervertebral space and back through the incision on an annulus.

Figure 69:
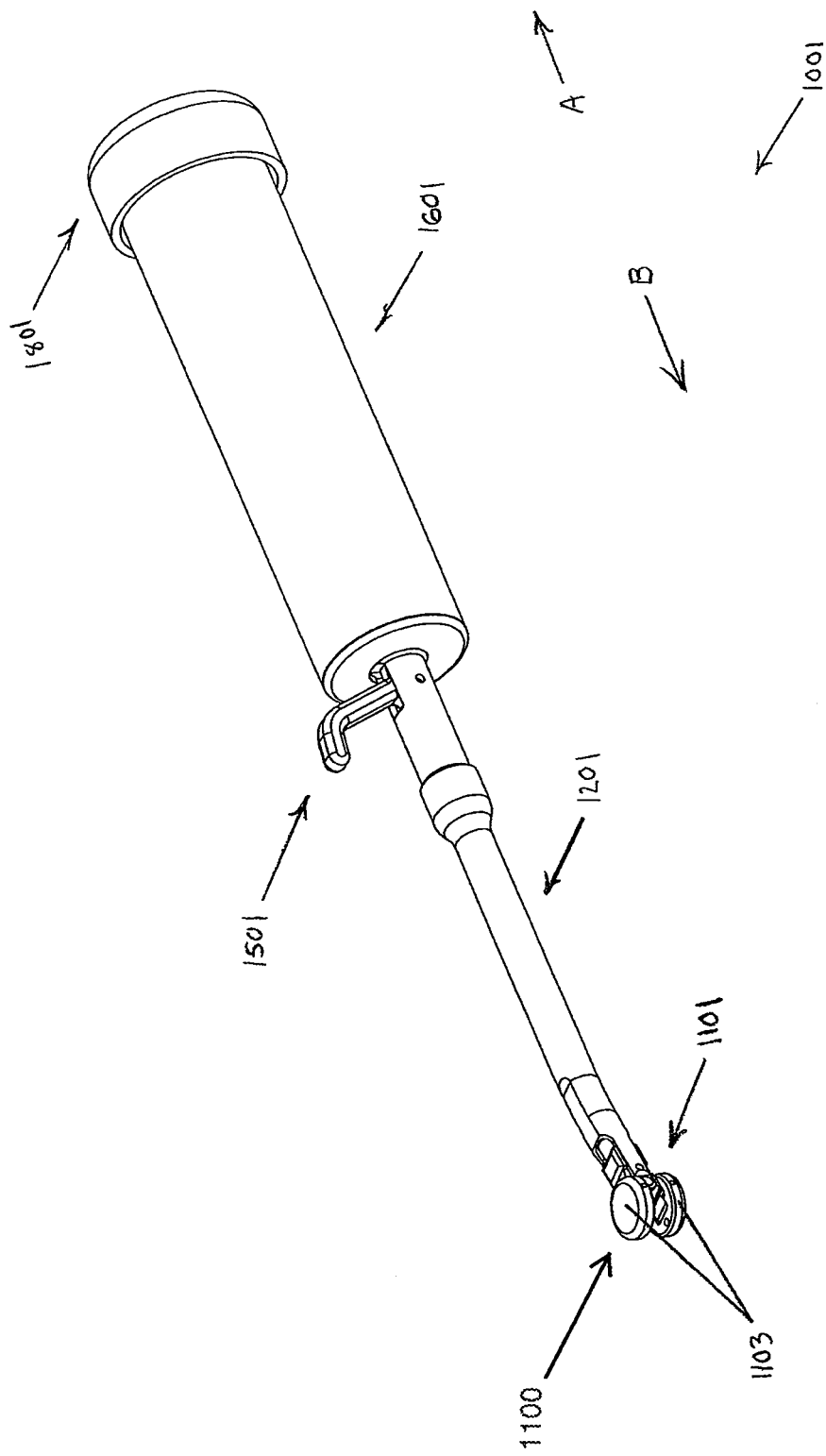
FIG. 69 is a perspective view of an alternate expandable sizing instrument in accordance with the present invention showing a pair of pad members of a measuring head in an open configuration thereof.
Figure 70:
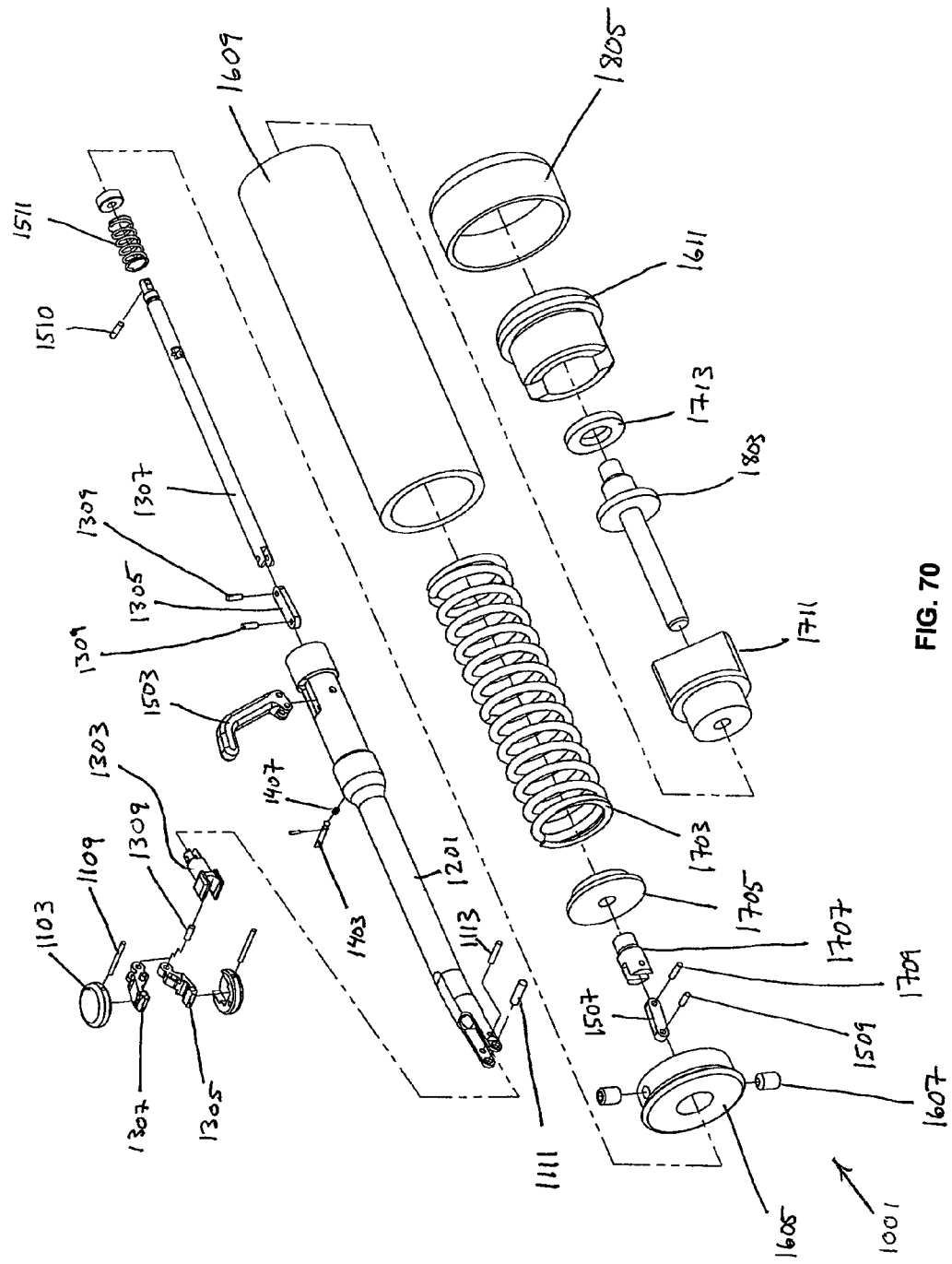
FIG. 70 is an exploded perspective view of the expandable sizing instrument of FIG. 69.

The following location and direction convention will be used throughout the description of the sizing instrument 1001 of FIGS. 69-95. The term "proximal" refers to a direction of the instrument away from the patient and towards the user while the term "distal" refers to a direction of the instrument towards the patient and away from the user. Typically, and as shown in FIG. 69, the "proximal end" of the expandable sizing instrument 1001 is shown on the top right of the figure shown as direction A. The "proximal direction" is referring to any motion toward the user and in FIG. 69 is toward the top right in direction A. The "distal end" of the inserter 1001 is shown on the bottom left of FIG. 69. The "distal direction" is referring to any motion toward the patient and in FIG. 69 is toward the bottom left shown as direction B in FIG. 69.

Figure 80:
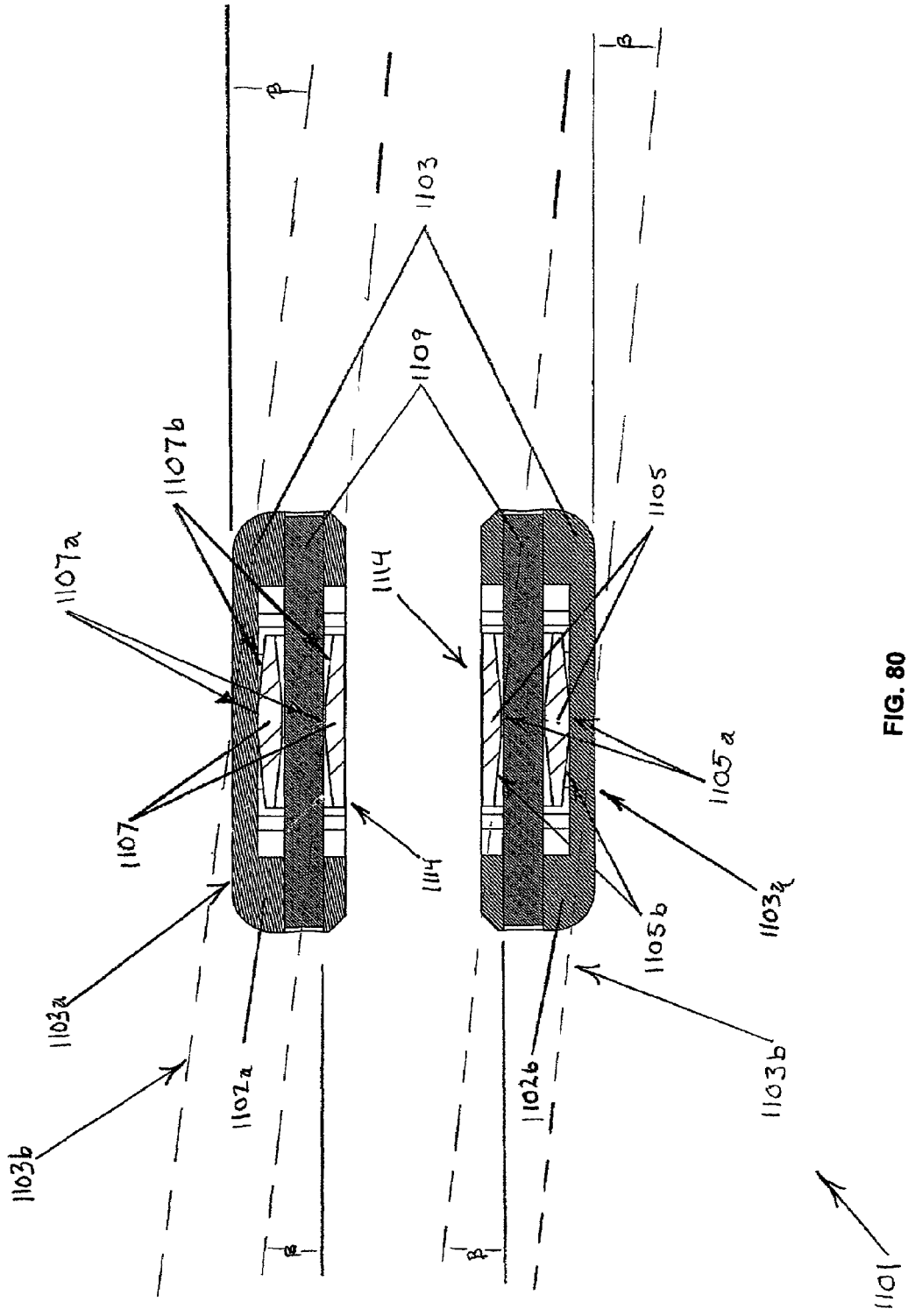
FIG. 80 is an enlarged, fragmentary cross-sectional view of the pads in the opened configuration, showing the pivotable bearing system with pins disposed in the throughbores of the upper and lower linkages having central narrow portions and outer portions having expanded configurations, which allow the pad members to pivot in a plurality of directions.
Figure 91:
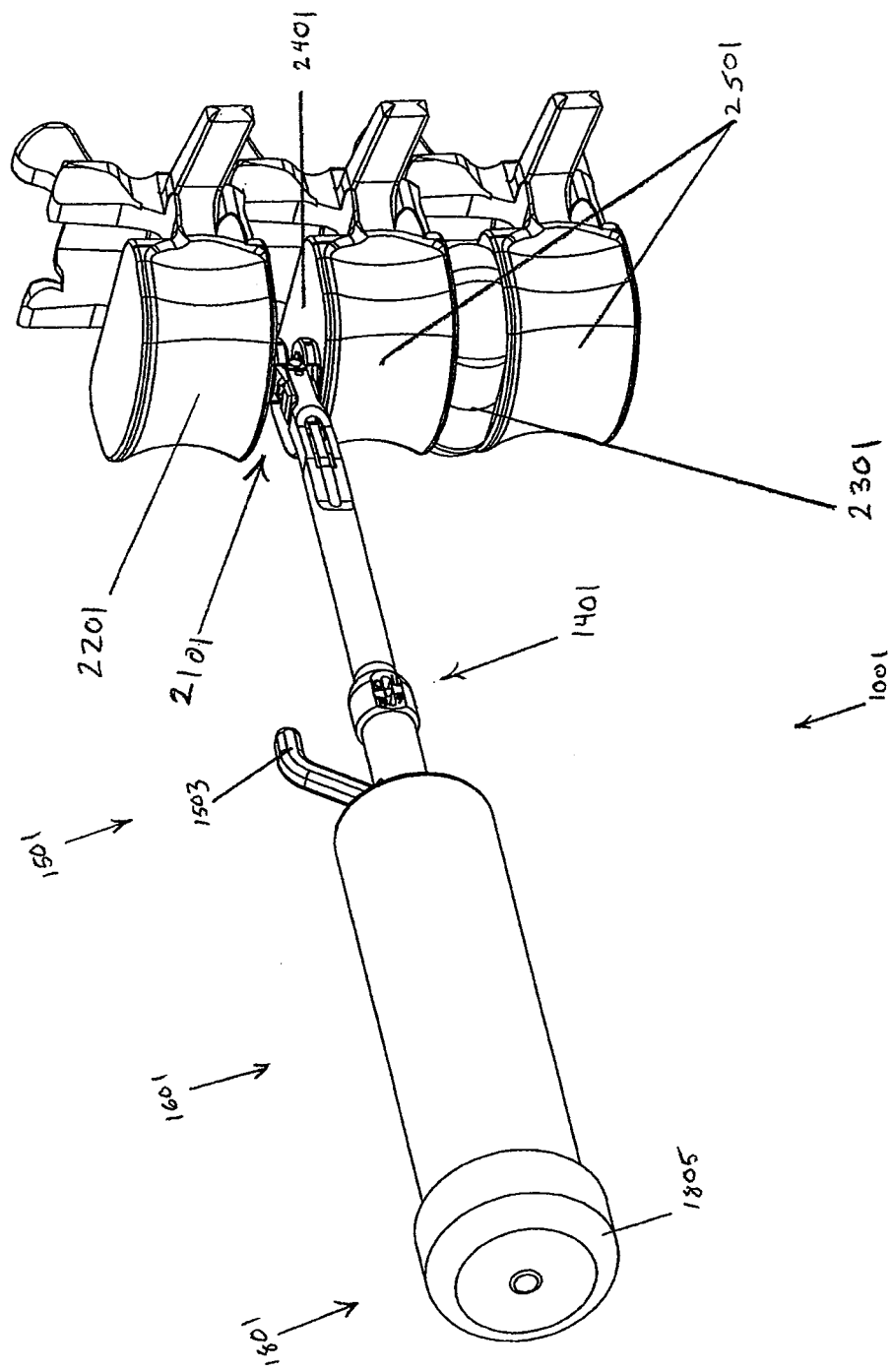
FIG. 91 is a perspective view of the expandable sizing instrument operating in the intervertebral space from a generally anterior insertion orientation, with the measuring head in the measuring configuration.

The expandable sizing instrument 1001 allows a precise amount of distraction force to be set by the force adjustment mechanism 1801 and the amount of intervertebral space 2101 can be measured by the spacer mechanism 1101, as shown in FIG. 69. The pads 1103 of measuring head 1100 of the inserter 1001 allow for measurement of varying angulations of endplates 2401 due anatomical differences of patients as shown in FIG. 80 and FIG. 91. All external surfaces of the inserter 1001 preferably are electropolished to improve the efficiency of cleaning and sterilization.

Figure 74:
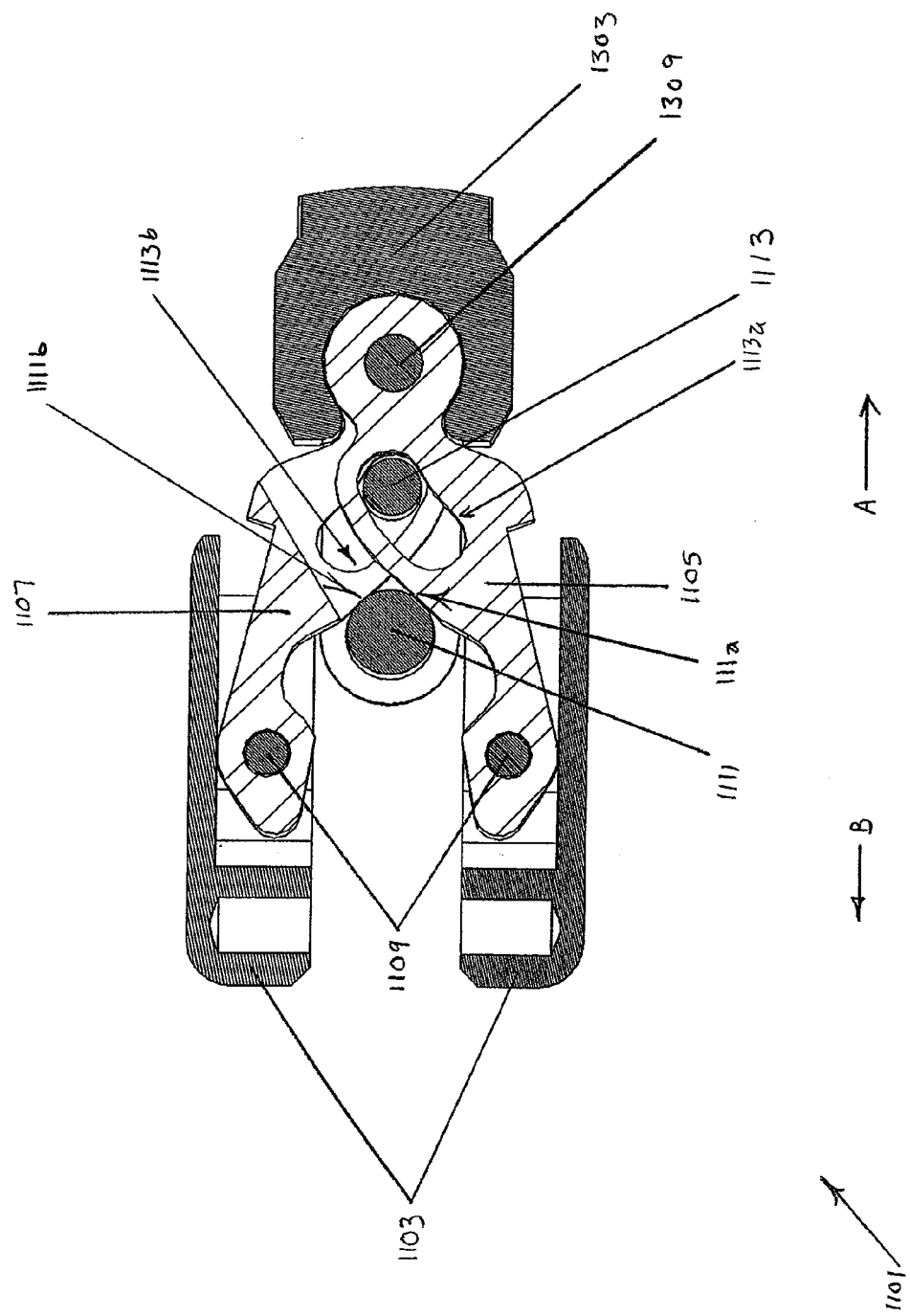
FIG. 74 is an enlarged, fragmentary cross-sectional view of the expandable sizing instrument measuring head in the opened configuration, showing upper and lower link members connecting the upper and lower pad members to the distal drive member via pin connections.
Figure 75:
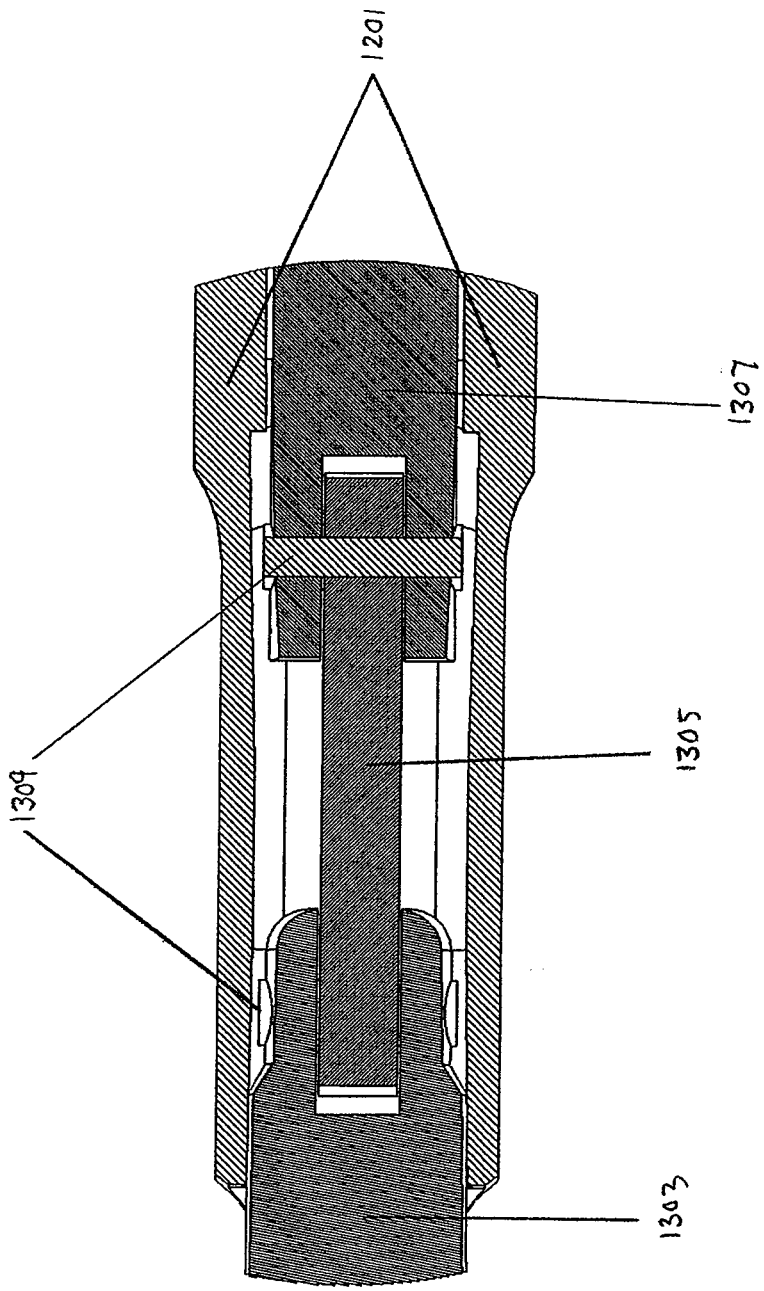
FIG. 75 is an enlarged, fragmentary cross-sectional view of a drive mechanism of the expandable sizing instrument, showing the connection of the inner shaft to the distal drive member via a linkage member.

The spacer mechanism 1101 is operable to measure the height of the intervertebral space 2101. The spacer mechanism 1101 expands from a closed position shown in FIG. 71 to an expanded open configuration shown in FIG. 72. The distance between the pads 1103 increases as the lever 1503 of the actuator mechanism 1501 is pulled in direction C. In a preferred form, the spacer mechanism 1101 has a height of 7 mm in a closed configuration and a maximum height of 11.5 mm in a fully open configuration. As shown in FIG. 74, the pads 1103 are connected to the inside linkage 1105 and outside linkage 1107 by the pad pins 1109.

As shown in FIG. 80, the pads 1103 are able to pivot on the inside linkage 1105 and outside linkage 1107 utilizing a pivotable bearing system 1114. The pivotable bearing system 1114 allow the pads 1103 to conform to the varying angulations of the inner endplate surfaces of adjacent vertebrae, which facilitates precise measurement of the intervertebral space. Further, because the pads 1103 can conform more closely to the inner endplate surfaces, the pads 1103 distribute distraction forces more evenly on the endplate surfaces. Consequently, the endplates are less likely to be damaged by the pads 1103 during distraction of the vertebrae and measurement of the intervertebral space.

The pivotable bearing system 1114 allows the pads 1103 to tilt about a plurality of different axes such that the pads have two degrees of freedom. The pads 1103 may tilt forwards and backwards about the longitudinal axis of pad pins 1109, as well as laterally from side to side as shown in FIG. 80. The pads 1103 may tilt forwards or backwards and simultaneously to one side or the other such that pads 1103 may tilt in any direction. This polyaxial articulation of the pads 1103 allows the pads to conform with the configuration of the endplates, regardless of surgical approach made with the tool. For example, the configuration of the endplates along an anterior approach will likely vary from the configuration of the endplates along a lateral approach. A sizing tool according to the present invention thus allows the surgeon to accurately measure the invertebral space from a plurality of different surgical approaches.

The polyaxial articulation of the pads 1103 is made possible through the configuration of the throughbores through which the pad pins 1109 are disposed and the bearing surfaces 1107a, 1107b, 1105a, 1105b of the upper and lower linkages 1107 and 1105. The pads 1103 rest on the inside bearing surfaces 1105a and the outside bearing surfaces 1107a when in a non-tilted orientation. However, should the endplates of the vertebrae be tilted at a lordotic angle β, which is typically the case, the pad bearing surfaces 1103a can tilt at the lordotic angle β so that the pads 1103 can conform closely to the contour of the endplates. Conforming to the contour of the endplates enables more accurate measurement of the intervertebral space. The inner bearing surfaces of the pads 1103c and the pad pins 1109 engage with the inside and outside bearing surfaces 1105b and 1107b, which are angled with respect to the non-tilted orientation of the pads 1103. The lordotic angle β can vary depending on the anatomy of the patient's vertebrae 2201. In a preferred form, the pads 1103 are configured to toggle independently to tilt at a minimum angle of 11 degrees in any direction when the pads 1103 are in an open configuration corresponding with a measurement of 8 mm. The pads 1103 may be tilted a greater amount when the pads 1103 are opened further than 8 mm, because the pad members 1103 do not interfere with one another when distracted further apart. In addition, the pads 1103 preferably do not toggle when positioned in a closed configuration.

The top pad 1102a and the bottom pad 1102b also pivot independently so that the top pad 1102a can have a lordotic angle which is different from the bottom pad 1102b. The spacer mechanism 1101 may be used to determine the lordotic angle because the pads 1103 tilt or pivot to conform to the lordotic angle of the endplates 2401 and an x-ray or fluoroscopy will clearly indicate the lordotic angle since the radiopaque pads 1103 will be readily visible on the x-ray or fluoroscopy films. The ability to measure different lordotic angles is especially important because the shape of the implant required will depend on the surgical approach taken by the surgeon, i.e. a posterior, anterior, or lateral approach. Preferably, the pads 1103 may pivot in any direction to conform to the lordotic angle of the vertebrae no matter what insertion approach is taken by the user. The pads 1103 may be pivotable to the same angle β in each direction, or the angle may vary in some directions. For example, in the embodiment shown in FIG. 74, the distal ends of pads 1103 may be pivoted towards one another at a greater angle than p so that the proximal ends of the pads are distracted far enough apart to allow access to the components of spacer mechanism 1101 for easier cleaning.

Figure 84:
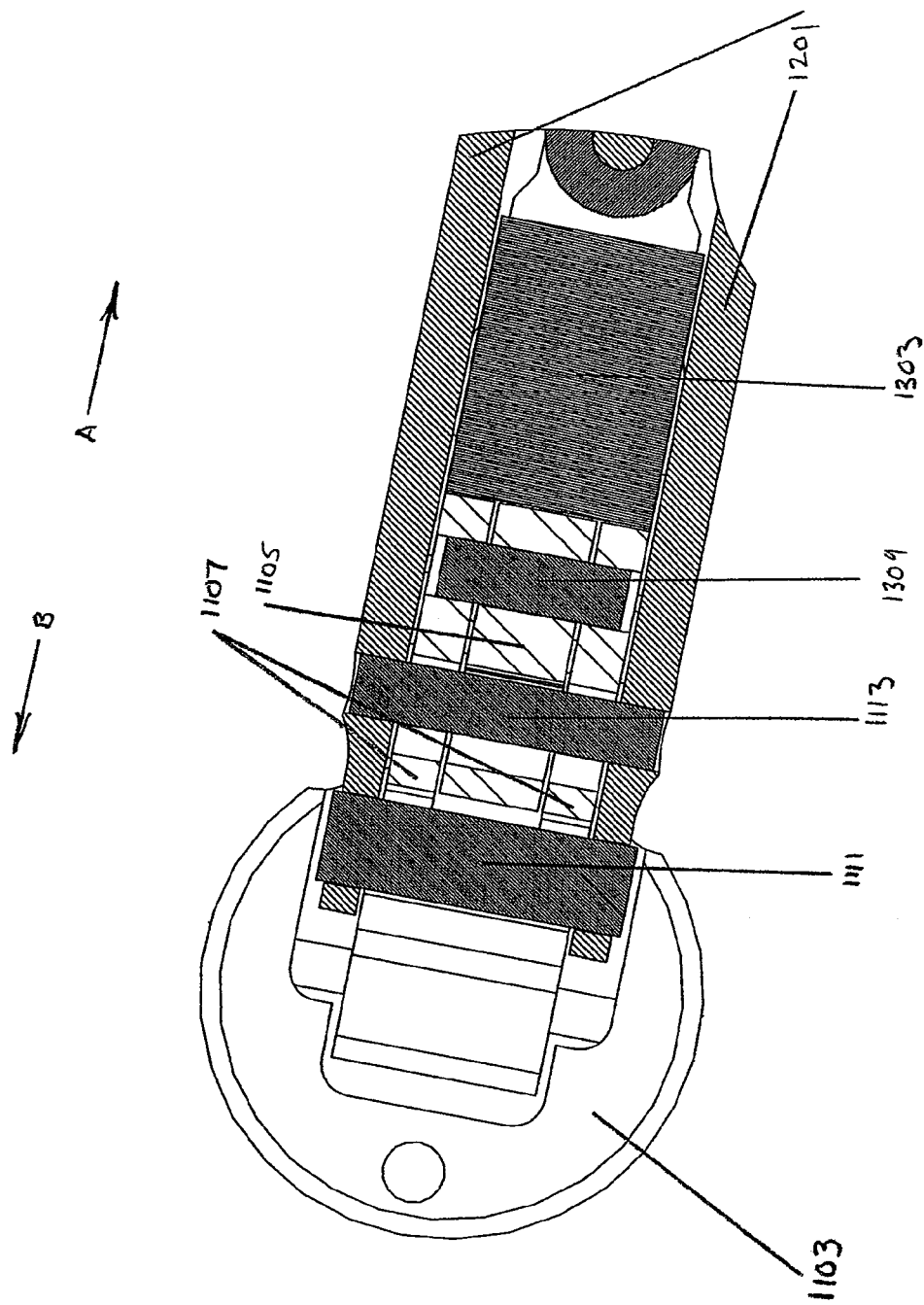
FIG. 84 is an enlarged, fragmentary cross-sectional view of the expandable sizing instrument measuring head in the opened configuration.
Figure 85:
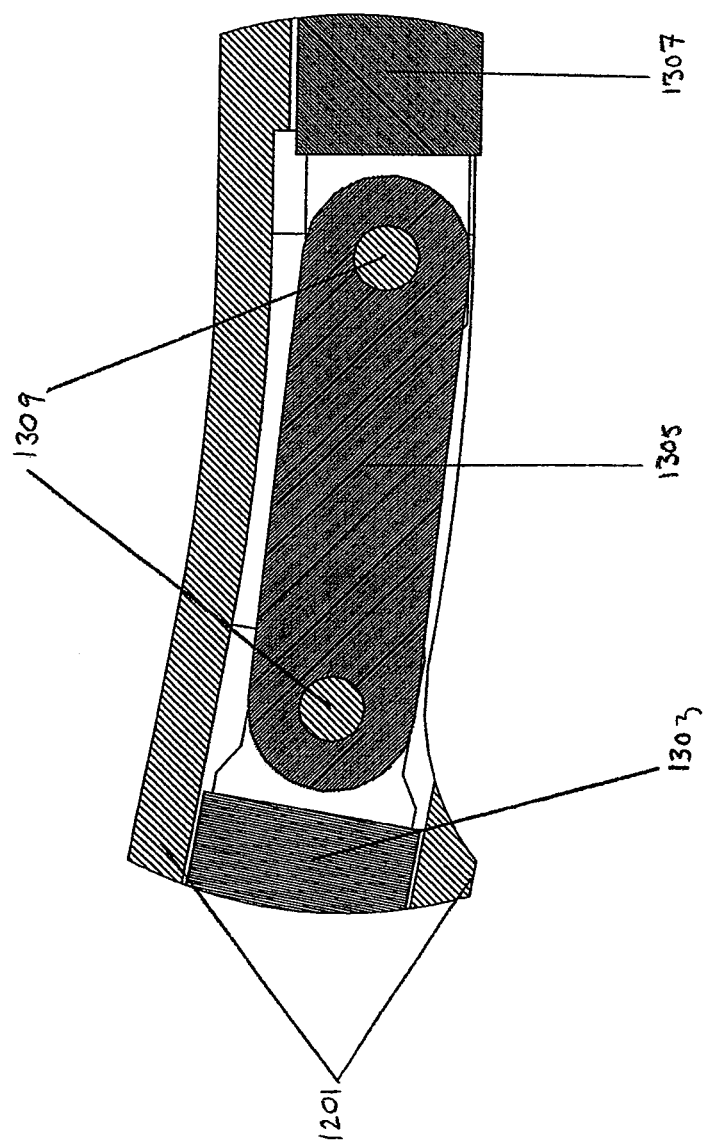
FIG. 85 is an enlarged, fragmentary cross-sectional view of the expandable sizing instrument in the opened configuration.

As shown in FIGS. 74 and 84, the spacer mechanism 1101 is shiftably connected to the distal drive member 1303 by the inside linkage 1105, and the outside linkage 1107. The opener pin 1111 connected to the outer shaft 1201 causes the inside linkage 1105, and the outside linkage 1107 to distract apart from each other when the distal drive member 1303 moves in the distal direction B because the inside linkage opening cam surface 1111a and the outside linkage opening cam surface 1111b slide along the stationary opener pin 1111. The opener pin 1111 effectively allows the spacer mechanism 1101 to be expandable within the intervertebral space 2101.

Similarly, when the distal drive member 1303 moves in the proximal direction A, the closer pin 1113 connected to the outer shaft 1201 closes the inside linkage 1105, and the outside linkage 1107. Closing cam surfaces 1113a, 1113b in the linkages 1105, 1107 provide a guide path that allows the linkages to slide along the closer pin 1113. As the linkages 1105, 1107 are retracted proximally, the stationary closer pin 1113 acts on the sloped closing cam surfaces 1113a, 1113b, providing the linkages 1105 with a closing force which causes the pads 1103 to retract and come together. The closer pin 1113 effectively allows the spacer mechanism 1101 to be collapsible within the intervertebral space 2101 as well as for allowing adjustments of position and removal of the inserter 1001

One benefit from the arrangement of the opener pin 1111 and closer pin 1113 and linkages 1105, 1107 is to maintain a substantially constant force distribution on the pads 1103. Once the desired distraction force is set by the knob 1805 of the force adjustment mechanism 1801, the pads are operable to provide the set distraction force to the adjacent vertebral bodies with which they are engaged. To provide a constant distraction force over the entire displacement range of the pads 1103, several factors are considered including spring choice, cam geometry, and pad size. Given a known surface area of the pads, the necessary distraction force for a given cam surface geometry may be calculated using known methods, such as three dimensional modeling software.

First, the force vectors, which are perpendicular to the closing cam surface 1111a, 1111b at the contact point between the opener pin 1111 and the closing cam surface 1111a, 1111b, are calculated. Next, the necessary input force is calculated for the initial closed configuration of the pads 1103. Once the input force for the initial closed configuration is determined, additional calculations for the input force at the halfway open configuration and fully open configuration of the pads 1103 are calculated. Based on the input forces at the three points, the spring constant needed at each point can be calculated based on the known displacement of the linkages 1105, 1007 in the proximal-distal direction. Once the spring constants are known for each of the three positions, the geometry of the closing cam surface 1111a and 1111b may be modified to obtain substantially identical spring constants for each of the three points. In a preferred form, the closing cam surfaces 1111a, 1111b have a generally sinusoidal contour along the portion thereof that the opener pin 1111 travels. The appropriate spring is then chosen based on the calculated spring constant. In a preferred form, the spring 1703 has a diameter of 0.975 inches and a length of 4 inches. The return spring 1511 preferably has a diameter of 0.281 inches and a length of 0.75 inches, with a spring constant of 9.2. Different springs may be used depending on the desired range of distraction force or pressure and the size of the pads 1103. For instance, if larger pads are used, larger or stronger springs may be used to maintain the desired amount of pressure to be exerted on the vertebral endplates, because the larger the surface area of the pads, the greater the exerted force must be to maintain a constant pressure. The amount of distraction force is adjustable to a set level through rotation of the knob 1805 of the force adjustment mechanism 1801, which is operable to selectively compress or allow expansion of spring 1703.

In a preferred form, the adjustable distraction force ranges from 20 PSI to 70 PSI and the pads 1103 have a surface area between 0.133 to 0.307 square inches. Different sized and shaped pad members may be used, depending on user preference, vertebral size, implant size or shape, insertion approach, and other factors. For instance, racetrack-shaped pad members may be used for sizing the intervertebral space for a similarly-shaped nuclear implant. In other forms, pads 1103 with a round configuration may preferable for use over pads with an elongate configuration, depending on the surgical approach used. For instance, pads with an elongate configuration may be better suited for lateral approaches, because a smaller incision may be made in the annulus to fit the narrow profile of the pads.

The spacer mechanism 1101 is preferably made of stainless steel. In its preferred embodiment, the inside linkage 1105 and the outside linkage 1107 are 440 stainless steel and provided with a low friction coating to allow smooth cam action by the opener pin 1111 and closer pin 1113 on the linkages 1105 and 1107. In a preferred form, the linkages 1105, 1107 are coated with chrome.

Figure 73:
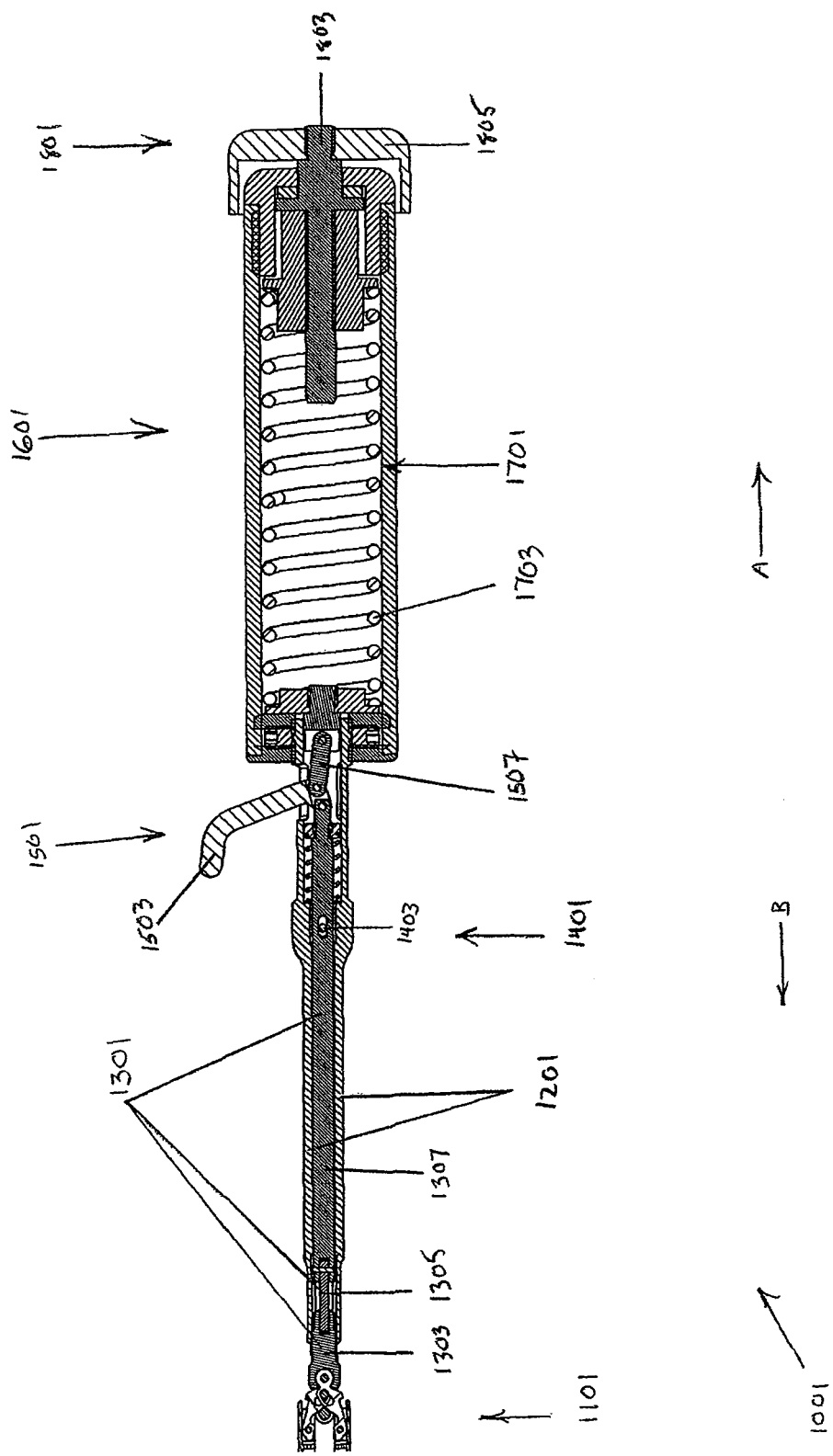
FIG. 73 is a cross-sectional view of the expandable sizing instrument of FIG. 72, showing the biasing member in the form of a coil spring and a force adjustment mechanism disposed in the handle portion of the instrument.
Figure 78:
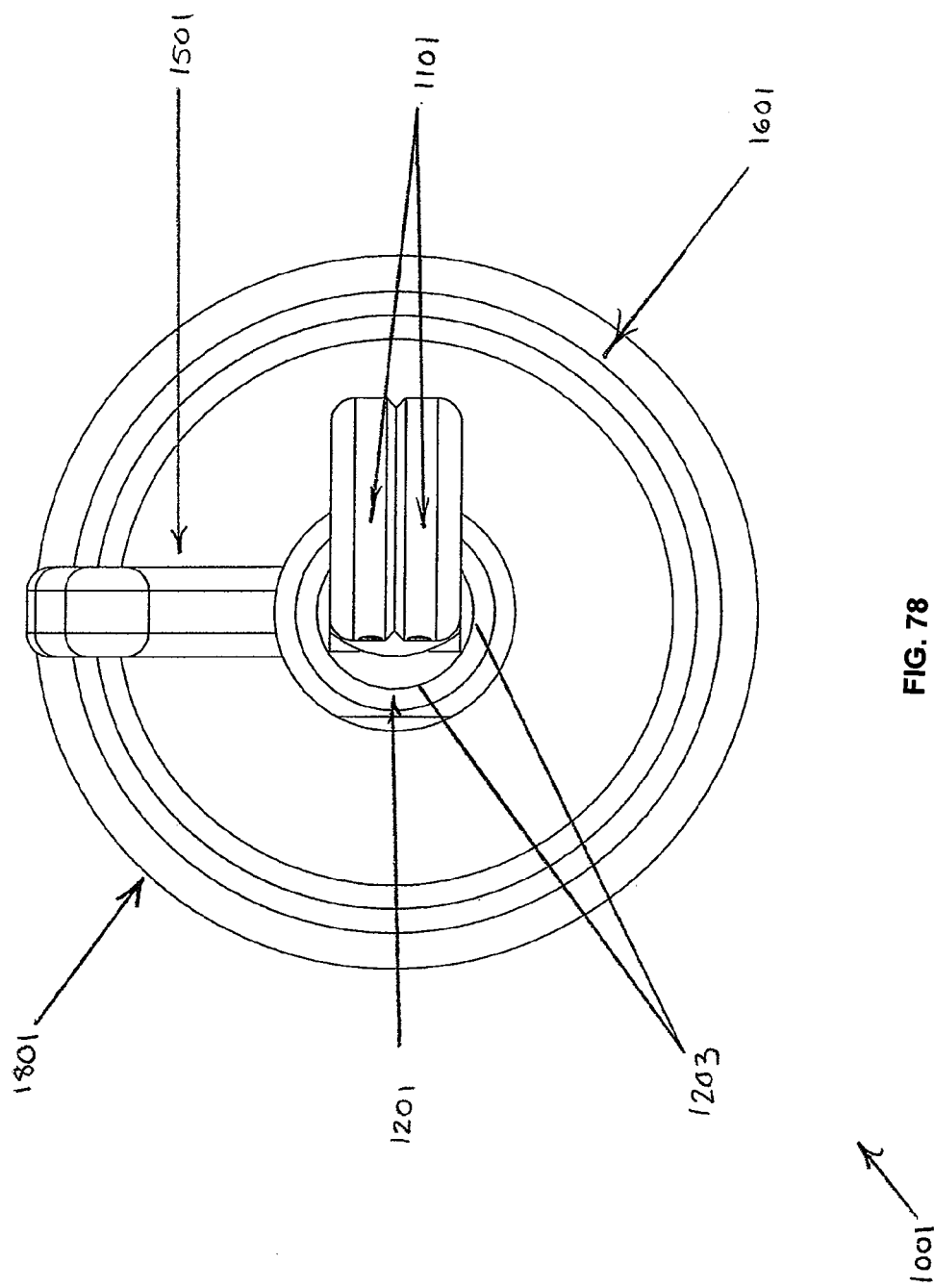
FIGS. 78 and 79 are elevational views of the measuring head of the expandable sizing instrument in the respective closed and opened configurations.
Figure 79:
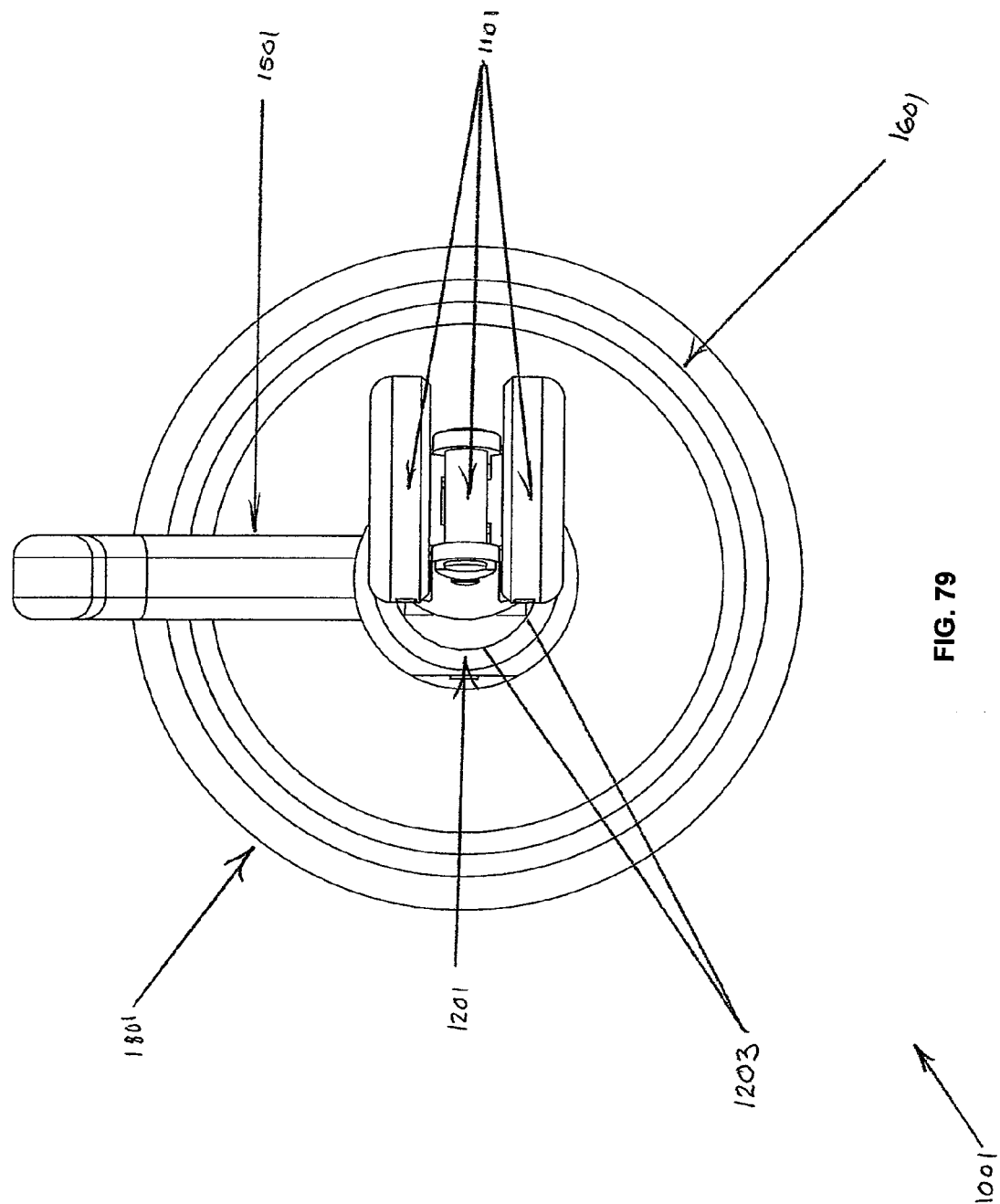

The outer shaft 1201 provides structural support for both the mechanical operation of the spacer mechanism 1101 previously described and for the drive mechanism 1301 as shown in FIG. 73. The outer shaft 1201 has a small diameter tubular configuration so that it has a narrow circular profile as shown in FIGS. 78 and 79. The narrow profile is desirable to fit within the narrow confines of the intervertebral space 2101 as shown in FIG. 91.

Figure 82:
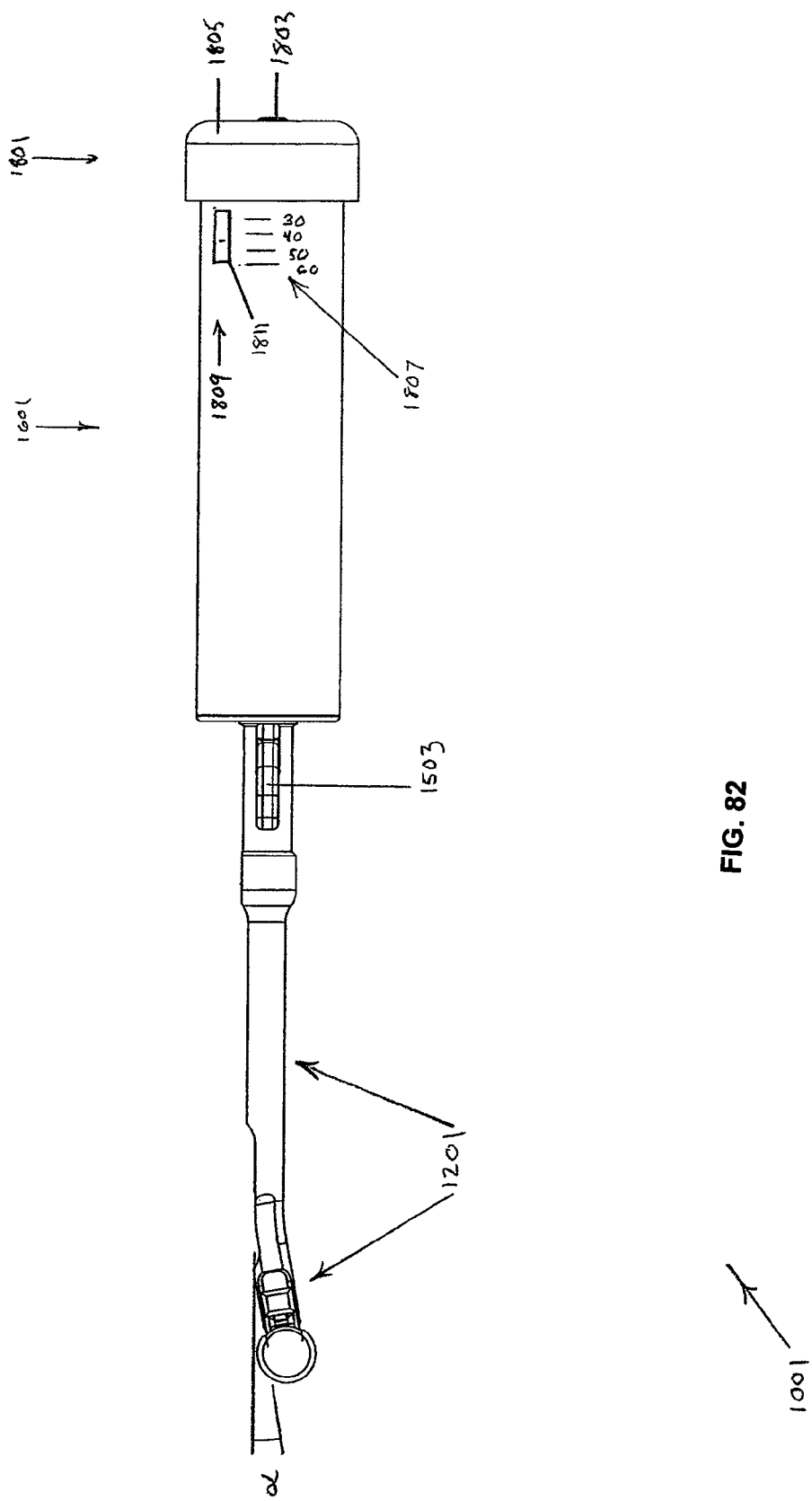
FIG. 82 is a plan view of the expandable sizing instrument measuring head in the open configuration.
Figure 83:
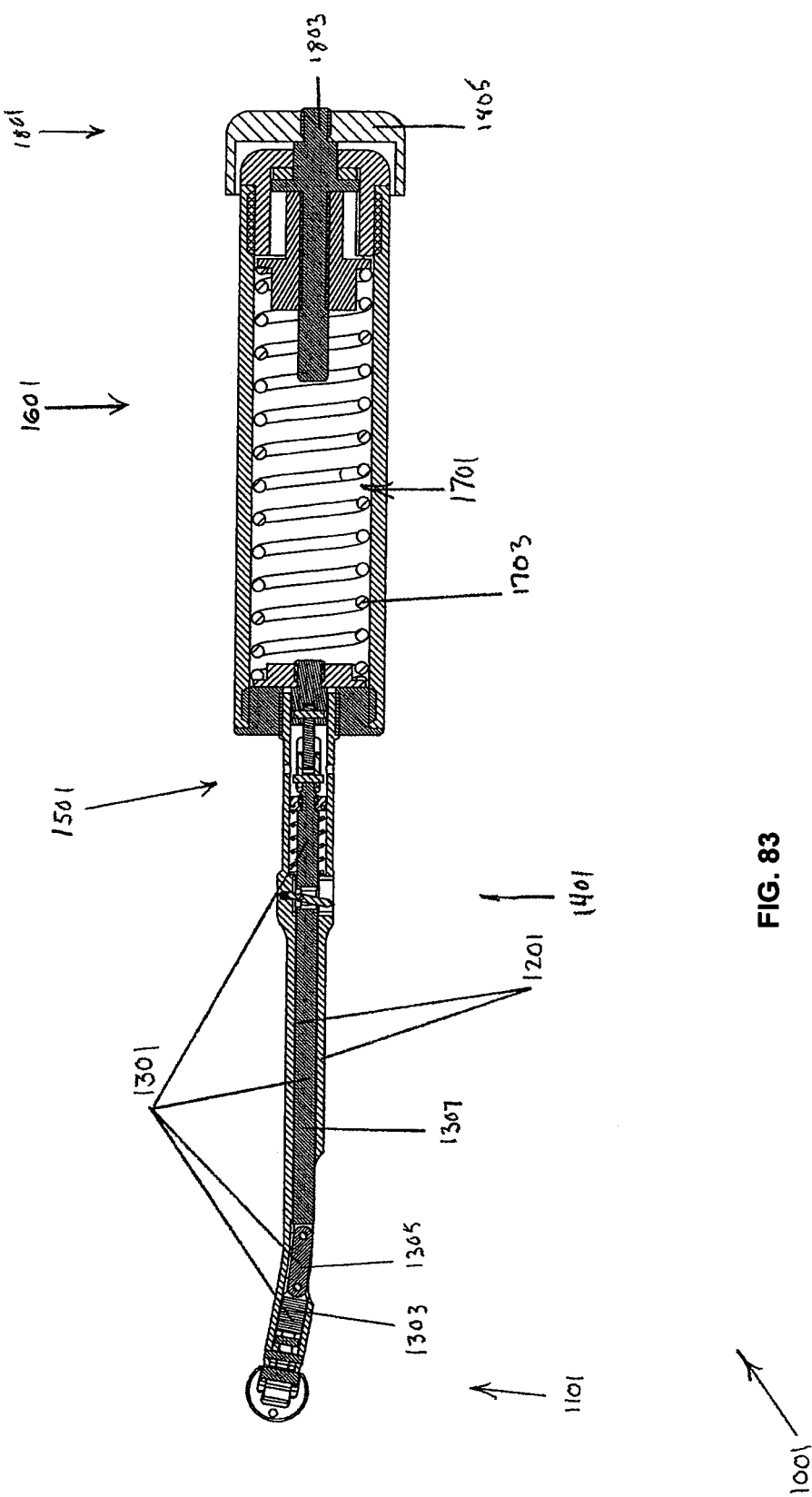
FIG. 83 is a top sectional view of the expandable sizing instrument measuring head in the opened configuration as shown in FIG. 81.

As shown in FIGS. 82 and 83, the outer shaft 1201 has a curve at angle α which is shown at approximately 10 degrees in the preferred embodiment. The curve at angle α of the outer shaft 1201 is configured to allow the inserter 1001 to reach the center of the vertebral body 2201 when the inserter 1001 is used from a posterior approach. Alternatively, the outer shaft 1201 could have a curve at angle α of zero or be straight for a conventional surgical approach.

The outer shaft 1201 also provides structural support to mechanically guide the drive mechanism 1301 as shown in FIGS. 73 and 83. The outer shaft 1201 constrains the distal drive member 1303 and linkage 1305 to move in the proximal and distal directions A and B upon actuation of the actuator mechanism 1501. The outer shaft 1201 also provides the structural connection by joining the spacer mechanism 1101 to the rest of the inserter 1001. The outer shaft 1201 is made of stainless steel in its preferred embodiment The drive mechanism 1301 provides mechanical linkage for the inserter 1001 apparatus and is the mechanism to transmit force from the actuator mechanism 1501 to the spacer mechanism 1101 as shown in FIGS. 73 and 83. The drive mechanism 1301 is mounted within the outer shaft 1201 to drive the spacer mechanism 1101.

The drive mechanism 1301 is composed of three shiftable shafts: distal drive member 1303, linkage 1305 and inner shaft 1307. The distal drive member 1303, linkage 1305 and inner shaft 1307 are mechanically connected by pins 1309 (shown in FIGS. 75 and 85) in order to provide force in the proximal and distal directions A and B at angle α (shown in FIGS. 81 and 82). The drive mechanism 1301 is made of stainless steel in its preferred embodiment.

The indicator mechanism 1401 provides an objective, accurate measurement of the height of the intervertebral space 2101 because the indicator mechanism 1401 is calibrated to the amount of displacement of the drive mechanism 1301 which, in turn, causes a specific known amount of expansion or compression of the spacer mechanism 1101. As shown in FIGS. 73, 76, 83 and 86, the indicator mechanism 1401 is mounted within the outer shaft 1201 and through the inner shaft 1307.

Figure 86:
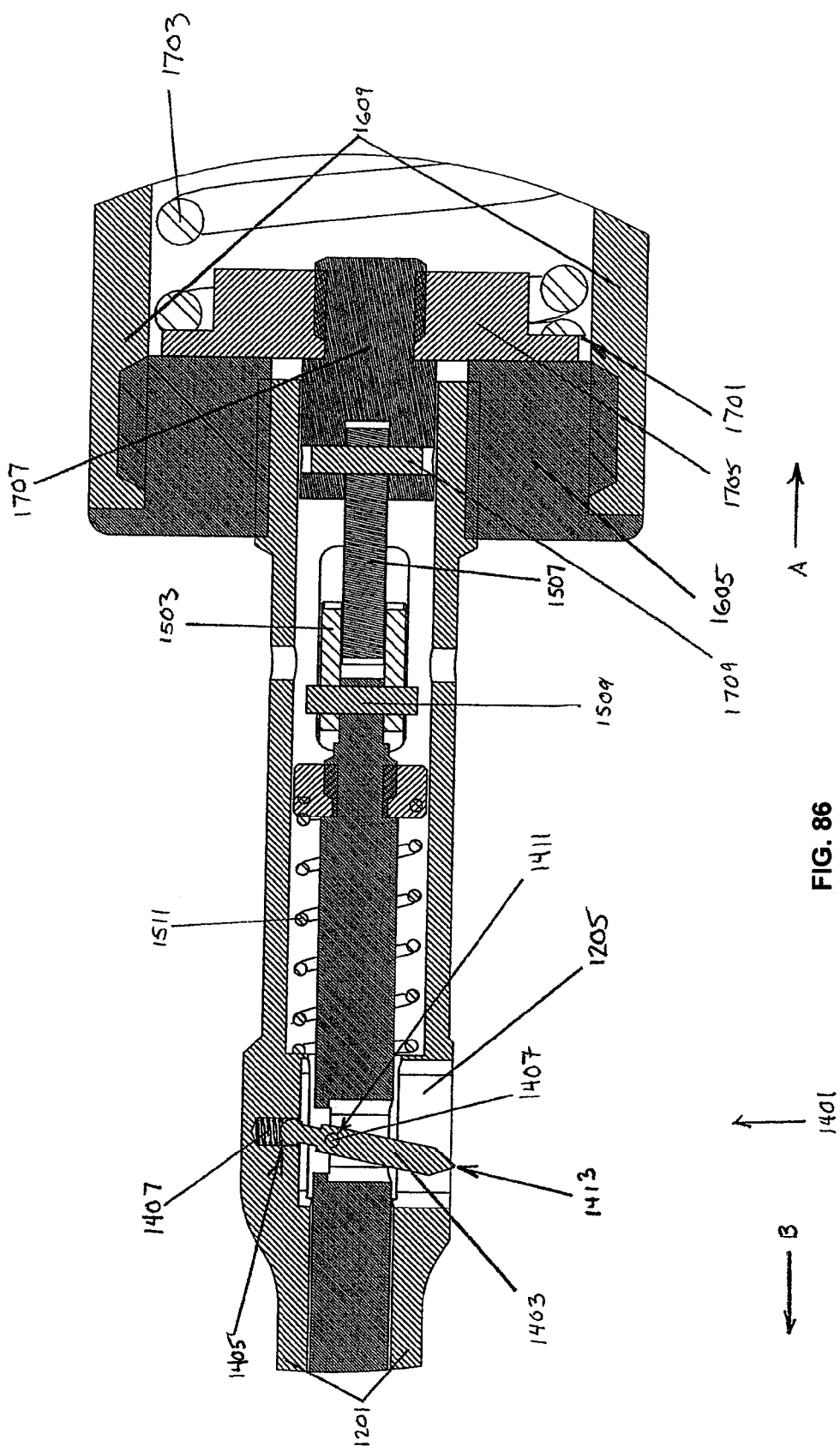
FIG. 86 is an enlarged, fragmentary cross-sectional view of the expandable sizing instrument showing the indicator mechanism and actuator mechanism.
Figure 92:
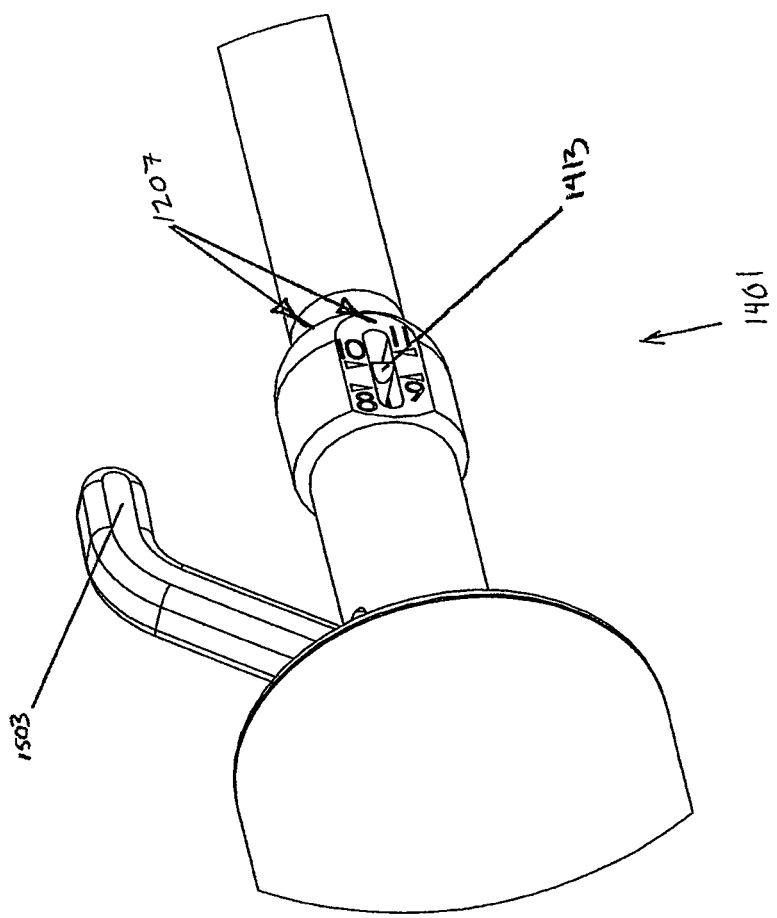
FIG. 92 is an enlarged, fragmentary perspective view of the sizing indicator for the expandable sizing instrument.
Figure 93:
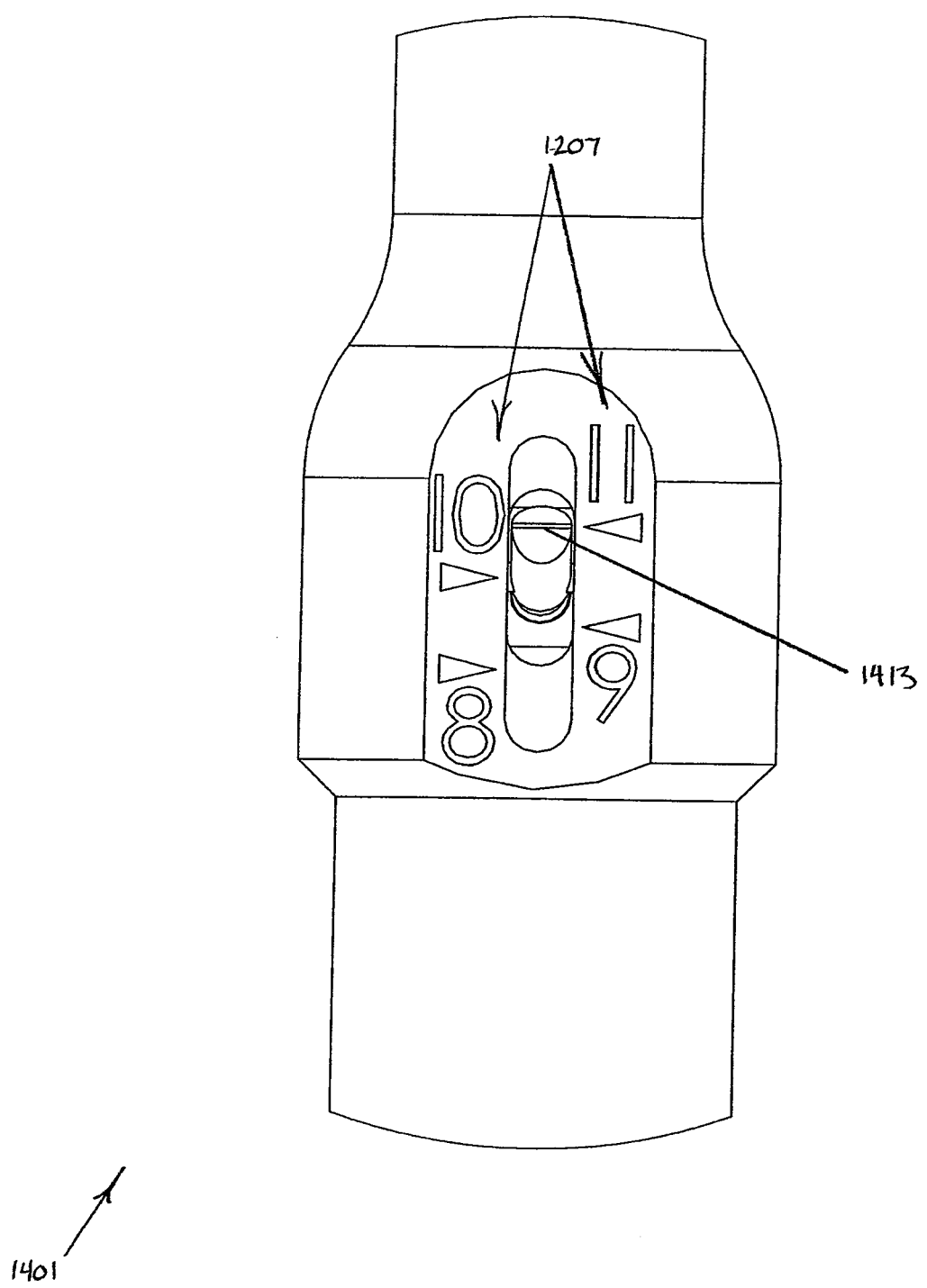
FIG. 93 is an enlarged, fragmentary side view of the sizing indicator for the expandable sizing instrument showing a measurement of 11 mm, corresponding with an opened position of the measuring head.

As shown in FIG. 86, the gauge 1403 has a spherical gauge surface 1405 engaged by a compressed gauge spring 1407 biasing the gauge 1403 into position. The spring force is resisted by the gauge pin bearing surfaces 1411 within the inner shaft 1307. When the inner shaft 1307 moves with the expansion or contraction of the spacer mechanism 1101 then the gauge 1403 will pivot or rotate about the spherical gauge surface 1405 to cause the gauge tip 1413 to shift to provide an indication of the size of the intervertebral space 2101. The gauge tip 1413 is free to tilt about the spherical gauge surface 1405 through the outer shaft cutout 1205. As shown in FIGS. 92 and 93, the gauge tip 1413 is visible to the operator, typically the surgeon. The indicator mechanism 1401 indicates with the gauge tip 1413 the amount of intervertebral space 2401 available for the implant, which corresponds to the vertical distance between the vertebrae 2501. The indicator mechanism 1401 is made of stainless steel in its preferred embodiment.

Figure 71:
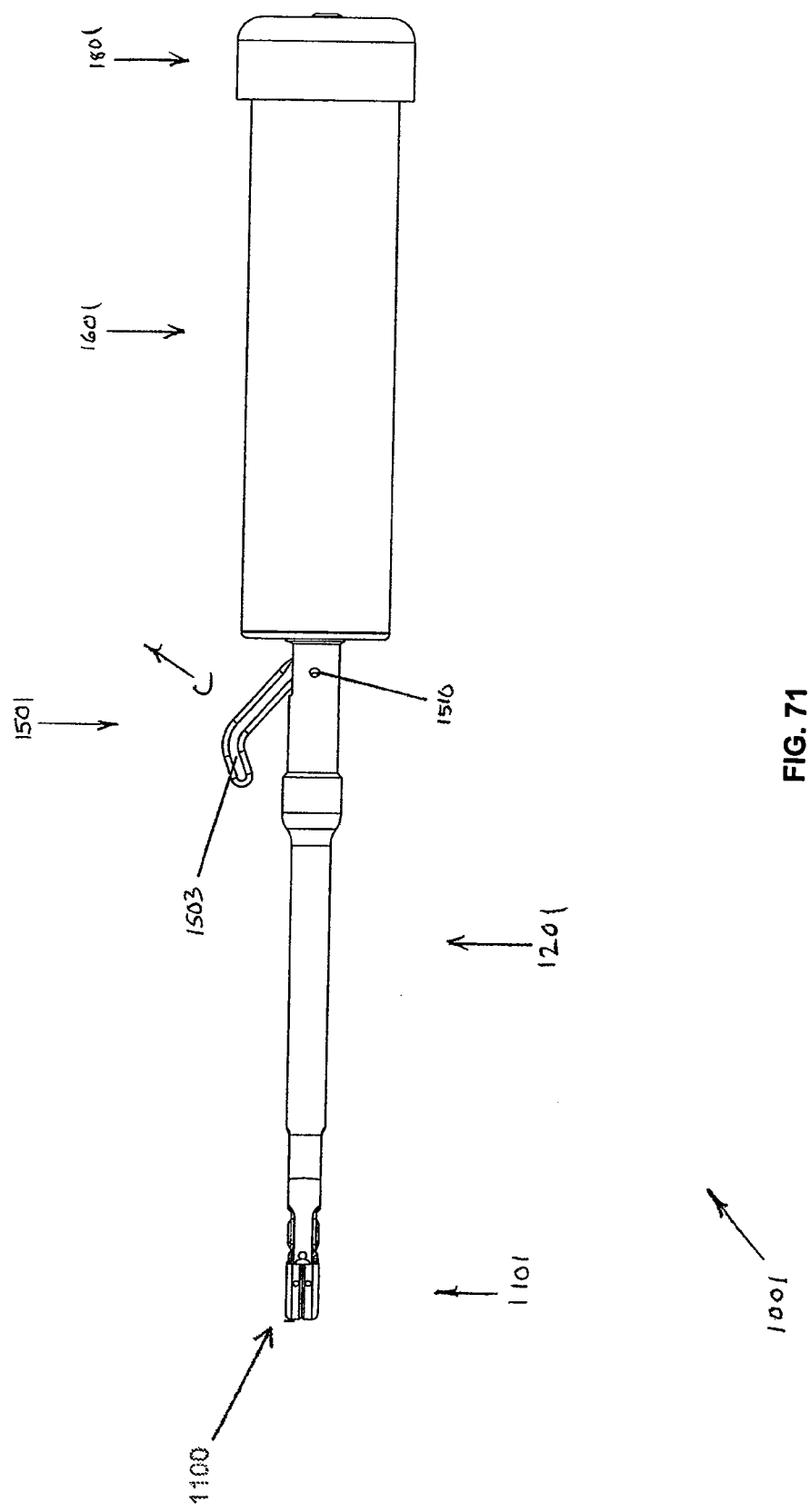
FIG. 71 is a side elevational view of the expandable sizing instrument showing the pad members in a closed configuration thereof, with the actuator in the forward orientation, which corresponds with an insertion and removal configuration of the sizing instrument.
Figure 72:
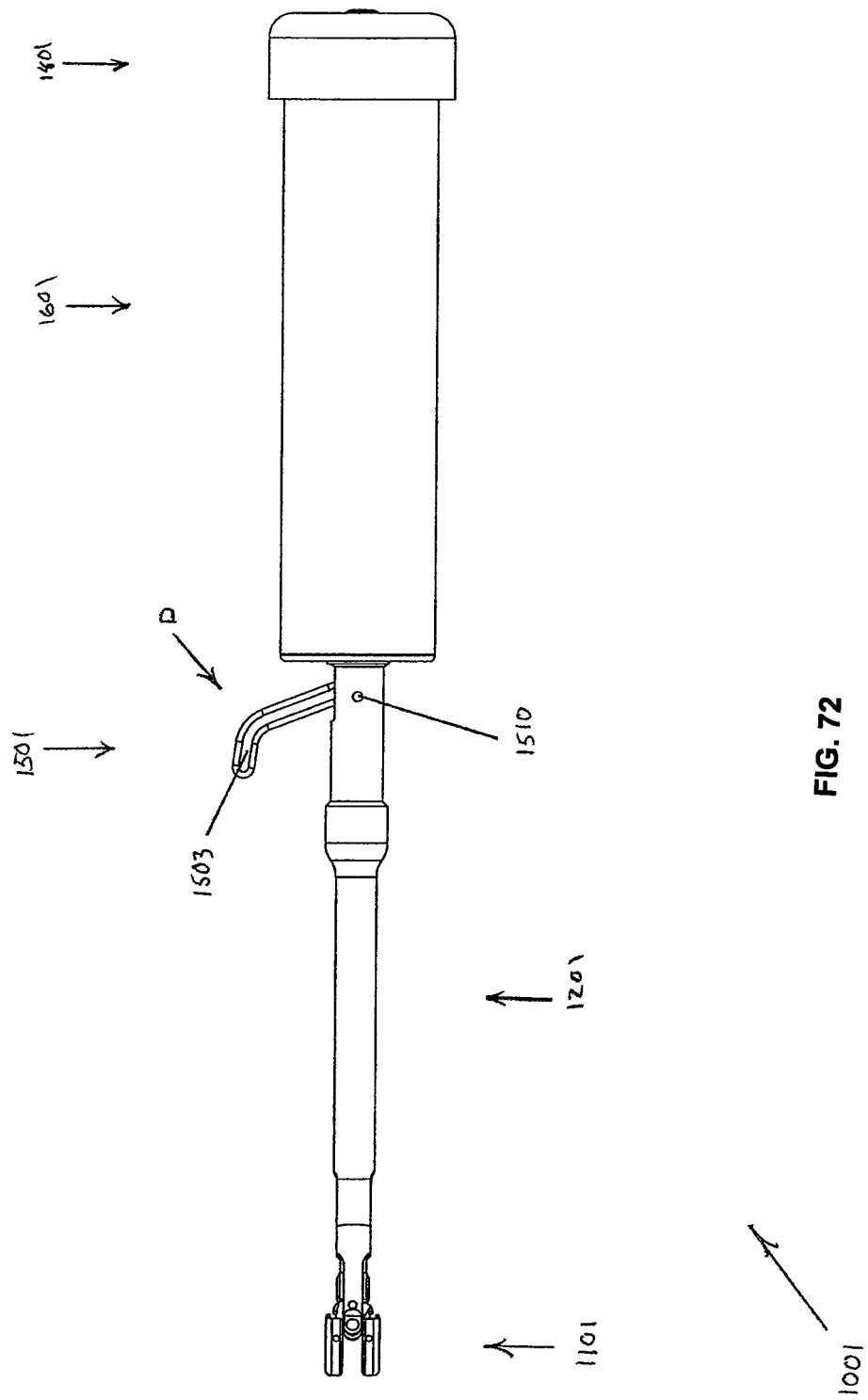
FIG. 72 is a side elevational view of the expandable sizing instrument showing the pad members in an opened configuration thereof, with the actuator in an intermediate rearward orientation, which corresponds with an opened configuration of the sizing instrument.

The actuator mechanism 1501 allows the operator to deploy the spacer mechanism 1101 from the compressed configuration shown in FIG. 71 to the expanded configuration shown in FIG. 72. As shown in FIG. 71, the operator expands the spacer mechanism 1101 by moving the lever 1503 generally upwardly away from shaft 1201 in direction C to measure the height of the intervertebral space 2101. As shown in FIG. 72, the operator compresses the spacer mechanism 1101 by moving the lever 1503 generally downwardly toward the shaft 1201 in direction D opposite to direction C in preparation for removing the inserter 1001 from an intervertebral space 2101. The lever 1503 is typically down, i.e. depressed in direction D, when inserting the inserter 1001 to provide the most compact configuration of the spacer mechanism 1101 possible during insertion into the narrow incision in the patient. The lever 1503 is mounted to the outer shaft 1201 by the shaft pin 1510.

Figure 76:
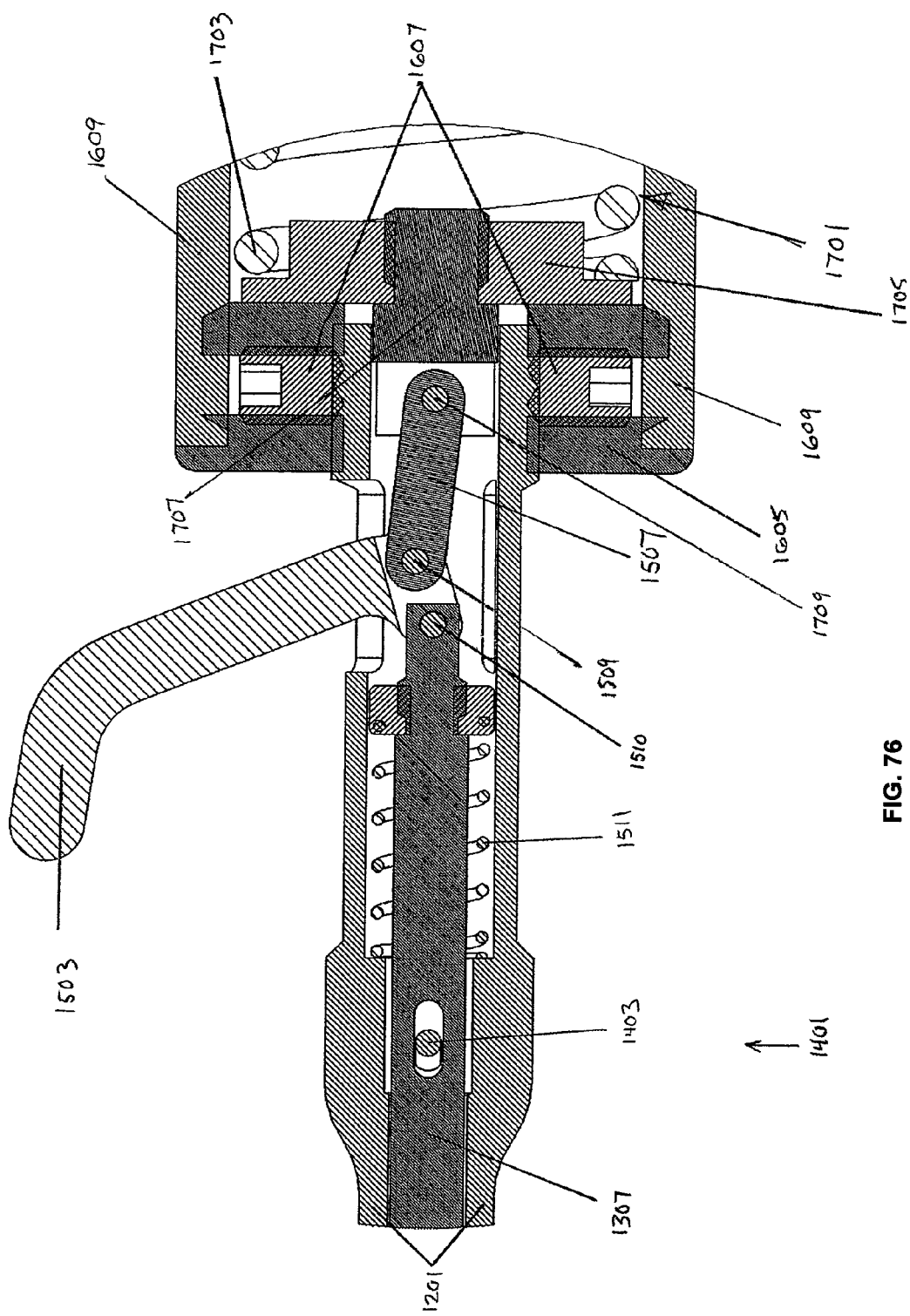
FIG. 76 is an enlarged, fragmentary cross-sectional view of the indicator and force applicator mechanism of the expandable sizing instrument, with the actuator in a forward position corresponding with a closed configuration of the measuring head.
Figure 94:
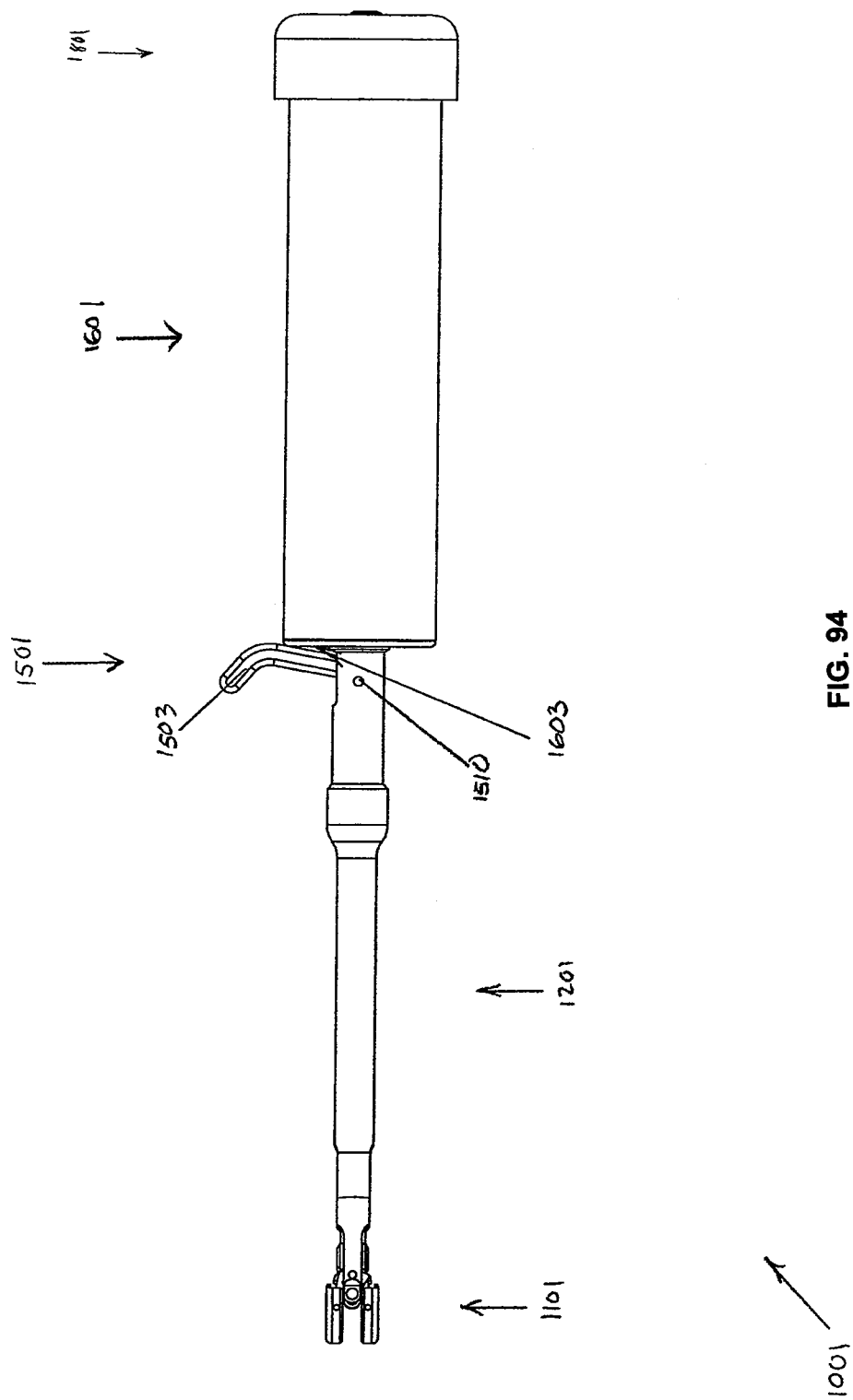
FIGS. 94 and 95 are respective side elevational and enlarged, fragmentary cross-sectional views of the expandable sizing instrument in the locked open configuration.
Figure 95:
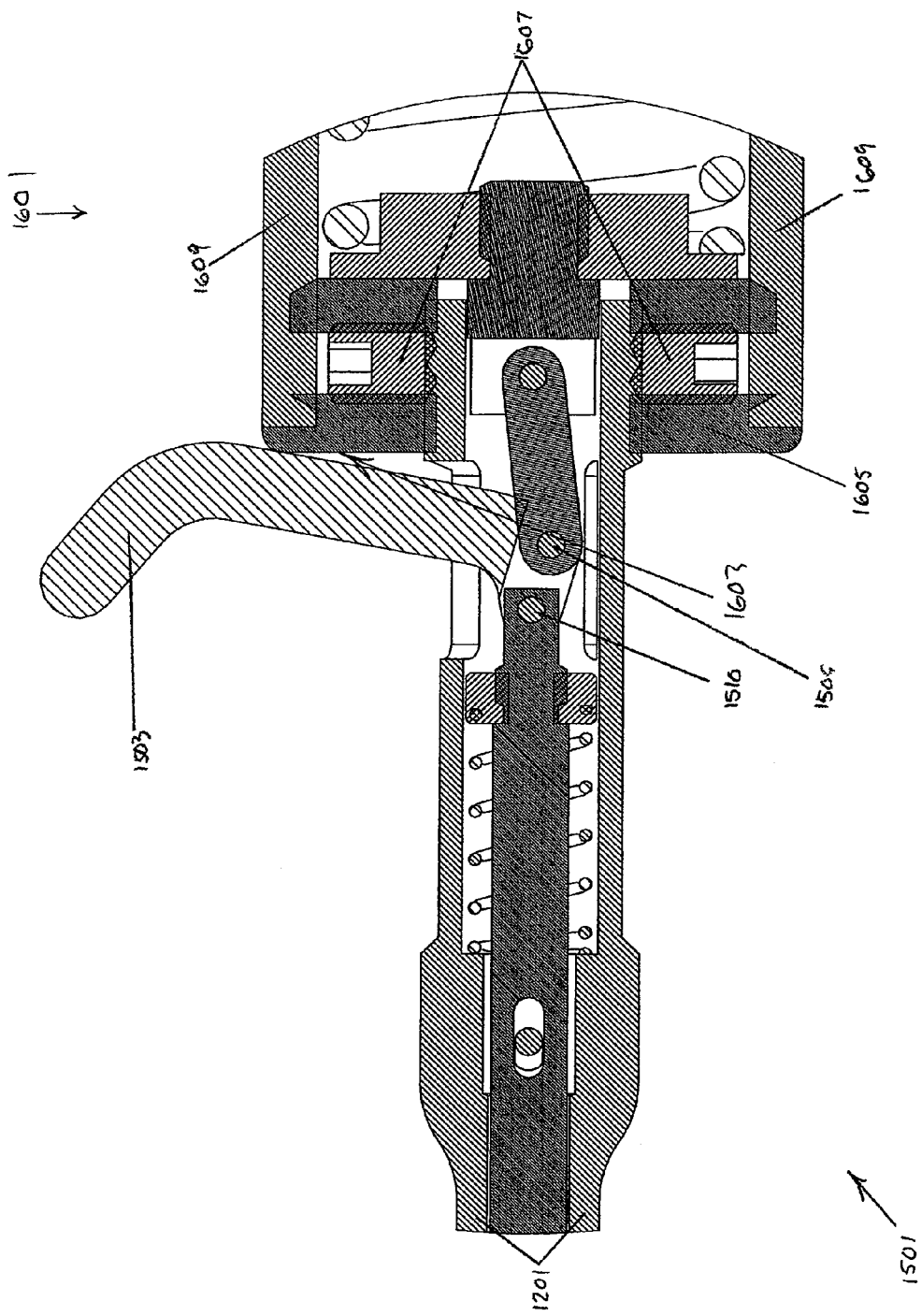

As shown in FIGS. 73, 76 and 86, the actuator in the form of lever 1503 is connected to the drive mechanism 1301 and force mechanism 1701 by a linkage 1507 with a lever pin 1509 and shaft pin 1510. The force on the drive mechanism 1301 created by the pressure of the patient's tissue on the spacer mechanism 1101 and the return spring 1511 is counterbalanced by the force created by the force mechanism 1701 as shown FIGS. 76 and 86. However, the lever 1503 can alter this balance as desired by the user. Finally, as shown in FIGS. 94 and 95, the lever 1503 can be locked open by depressing the lever 1503 until it reaches its locked position, which is caused by interference between the lever body 1503 and the linkage 1507, generally shown in FIG. 95. When the lever 1503 is in the locked open configuration, the spacer mechanism 1101 will be in the most expanded position. The actuator mechanism 1501 is made of stainless steel in its preferred embodiment.

The handle mechanism 1601 provides a handle grip 1609 for the operator and provides structural support when the inserter 1001 is grasped by the human hand. The handle mechanism 1601 provides increased distance for the operator especially while conducting x-rays or fluoroscopy. Direct radiation exposure can be minimized by the surgeon grasping the proximal end of the handle mechanism 1601.

As shown in FIGS. 76 and 86, the handle mechanism 1601 is connected to the outer shaft 1201 by the front handle cap 1605 and set screws 1607. The position of the outer shaft 1201 in relation to the force mechanism 1701 can be adjusted by the set screws 1607 to account for manufacturing error, i.e. stack up error, which occurs during the machining of the various parts. As shown in FIGS. 76, 77, 86 and 87, the front handle cap 1605, grip 1609, and end cap 1611 contains the force mechanism 1701 whose main component is a compression spring 1703. The end cap 1611 also provides a bushing for the adjustment shaft 1803.

The handle mechanism 1601 is made of stainless steel in its preferred embodiment. Alternatively, the handle mechanism 1601 can be made of Lexan or other clear strong plastics to allow visual feedback of the force mechanism 1701 which is contained within the handle mechanism 1601.

The force mechanism 1701 provides a generally constant distraction force through all phases of motion of the spacer mechanism 1101 during a sizing operation of the intervertebral space 2101 and does not require the operator to manually adjust the amount of force used. The force applicator mechanism 1701 automatically sets the distraction force without constant user intervention to maintain the distraction force at a set level.

The main component of the force mechanism 1701 is the large compression spring 1703 mounted within the handle mechanism 1601 and shown in FIGS. 73 and 83. As shown in FIGS. 76 and 86, the spring 1703 fits within and exerts a force on the adjustable fitting 1705. The adjustable fitting 1705 is threadably connected to the mechanical adaptor 1707 which in turn transmits a force (that varies with the compression of the spring 1703) to the connection pin 1709. The connection pin 1709 is then connected to the linkage 1507 of the actuator mechanism 1501 and the force exerted by the spring 1703 is transmitted all the way to the spacer mechanism 1101. Should the force exerted on the spacer mechanism 1101 by the vertebrae 2501 increase beyond the force of the spring 1703, then the pads 1103 and spring 1703 will collapse until an equilibrium is reached.

Figure 77:
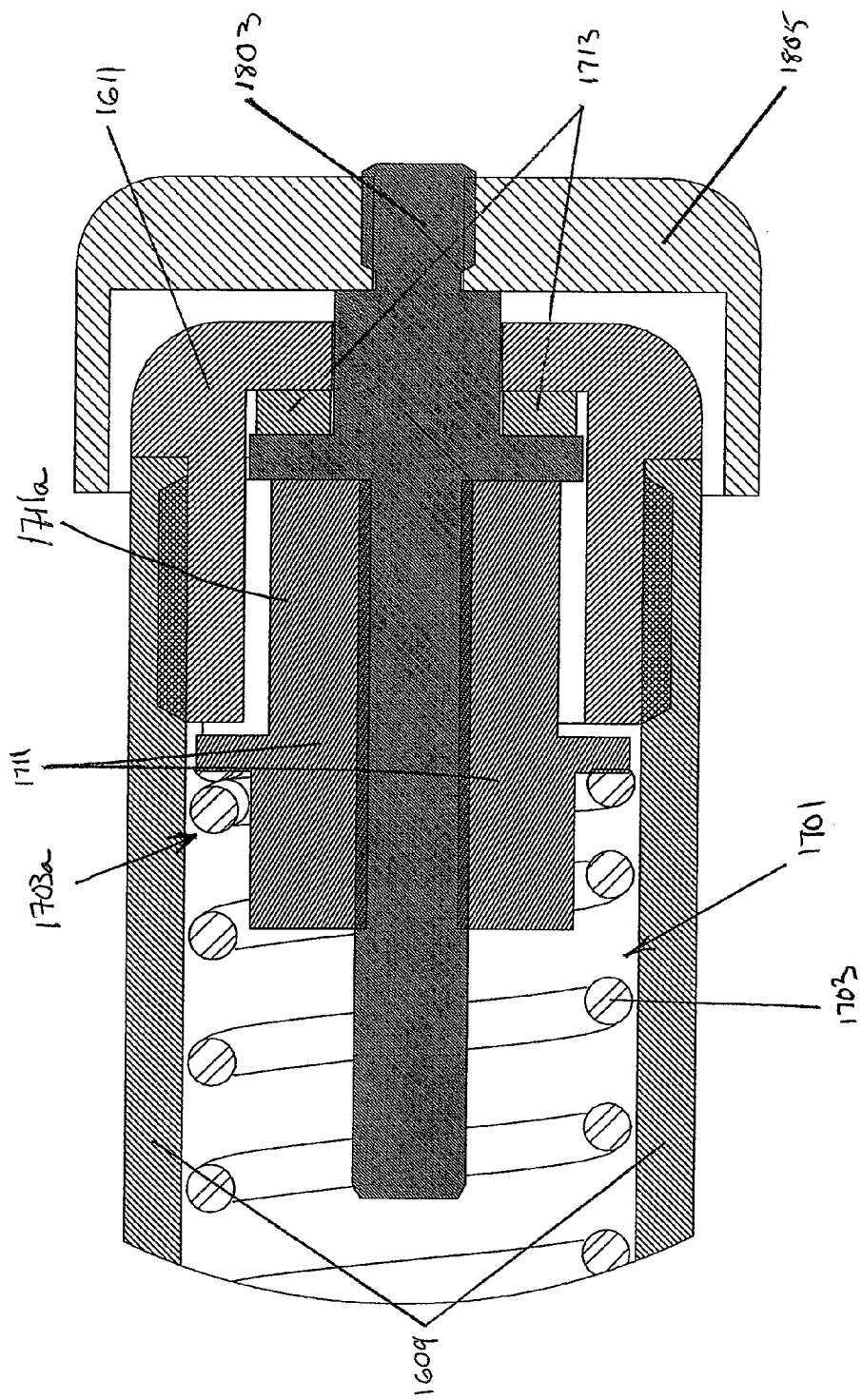
FIG. 77 is an enlarged, fragmentary cross-sectional view of the force applicator mechanism of the expandable sizing instrument, and particularly the force adjustment mechanism thereof, which is operable to adjust the amount of distraction force transmitted to the vertebrae via the pad members.
Figure 87:
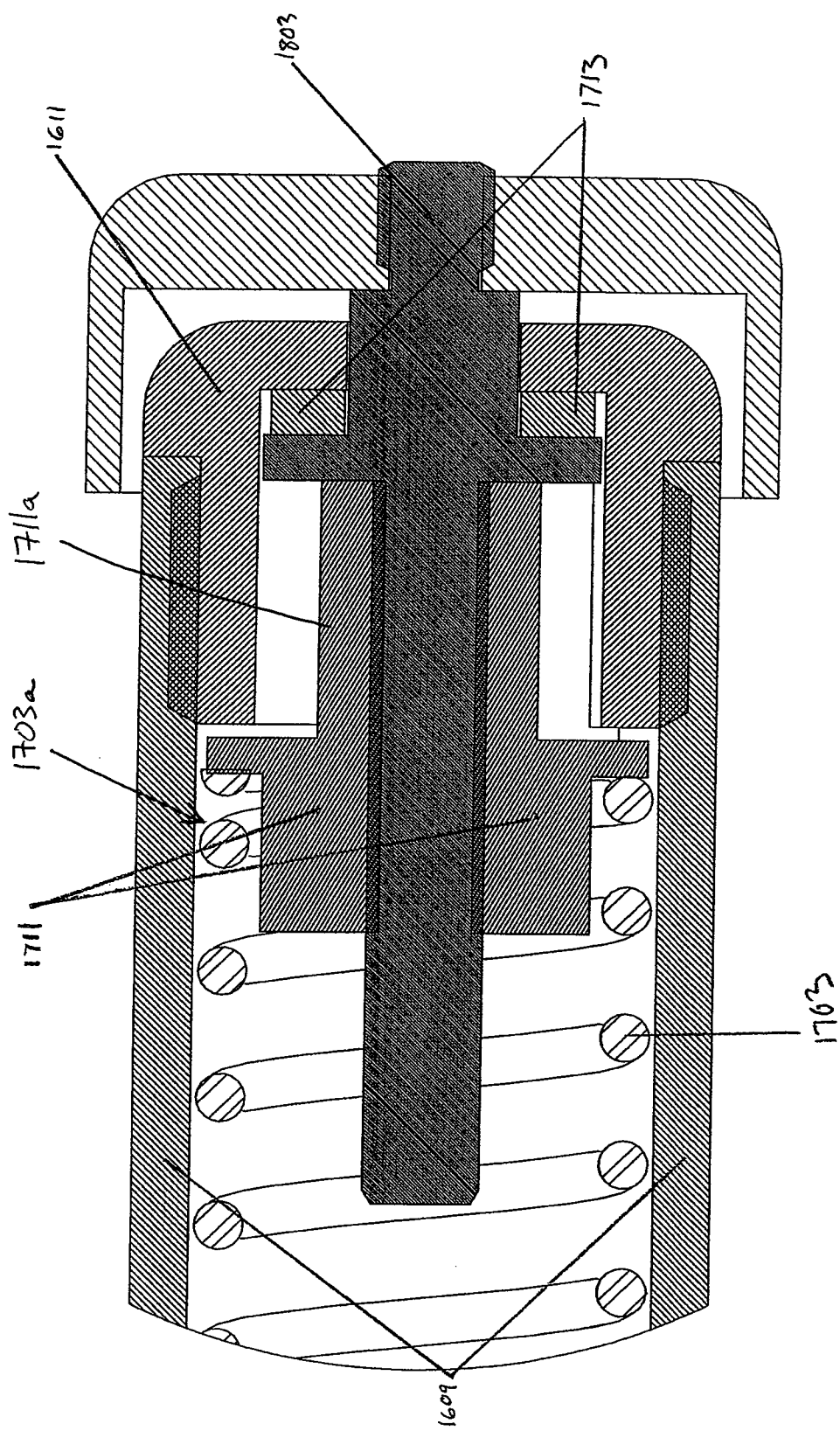
FIG. 87 is an enlarged, fragmentary cross-sectional view of the force adjustment mechanism.
Figure 90:
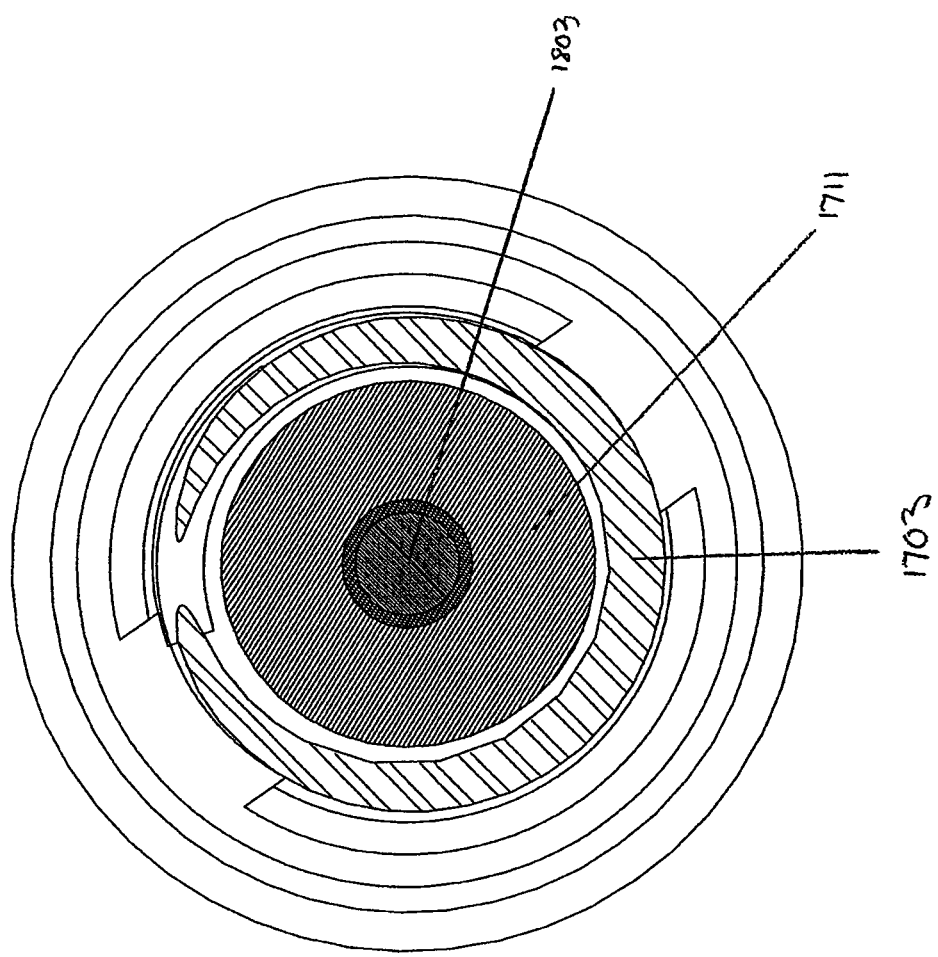
FIG. 90 is a rear cross-sectional view of the force adjustment member, the orientation plug, and the biasing member disposed within the handle.

The distraction force exerted on the vertebrae by the force mechanism 1701 can be fixed or adjusted as shown in FIGS. 77, 87, and 90. The compression spring 1703 is proximally fixed by the orientation plug 1711. The orientation plug 1711 fits within the proximal coils 1703a of spring 1703 and the end cap 1611. The orientation plug 1711 has radial flanges 1711a which fit within slots of the end cap 1611 to prevent the plug 1711 from rotating. The plug 1711 is threadably connected to the adjustment shaft 1803. Rotation of the adjustment shaft 1803 adjusts the force level of the compression spring 1703 by advancing or retracting orientation plug 1711 to respectively increase or reduce compression of the spring 1703. The rotation of the shaft 1803 is carried by the bearing 1713 which is preferably made of Teflon PFE to reduce the friction during rotation and adjustment of the shaft 1803. Finally, the variable force of the spring 1703 is adjustable via the knob 1805 of the force adjustment mechanism 1801. The components of the force mechanism 1701 are made of stainless steel in its preferred embodiment.

The force adjustment mechanism 1801 provides the element for controlling the amount of distraction force exerted by the inserter 1001 and to allow adjustment of the distraction force to a range of set levels for the user, preferably between 20 and 70 psi. The ability to control the amount of distraction is beneficial because different amounts of force may be needed to achieve the desired amount of distraction, which may depend on the portion of the spine 2001 in which the implant is to be inserted due to anatomical differences, i.e. the cervical region of the spine versus the lumbar portion of the spine. For example, the cervical region may require less distraction force than the larger lumbar region. Similarly, the amount of distraction force required depends on the degree of disc 2301 removal required for the implant.

Figure 89:
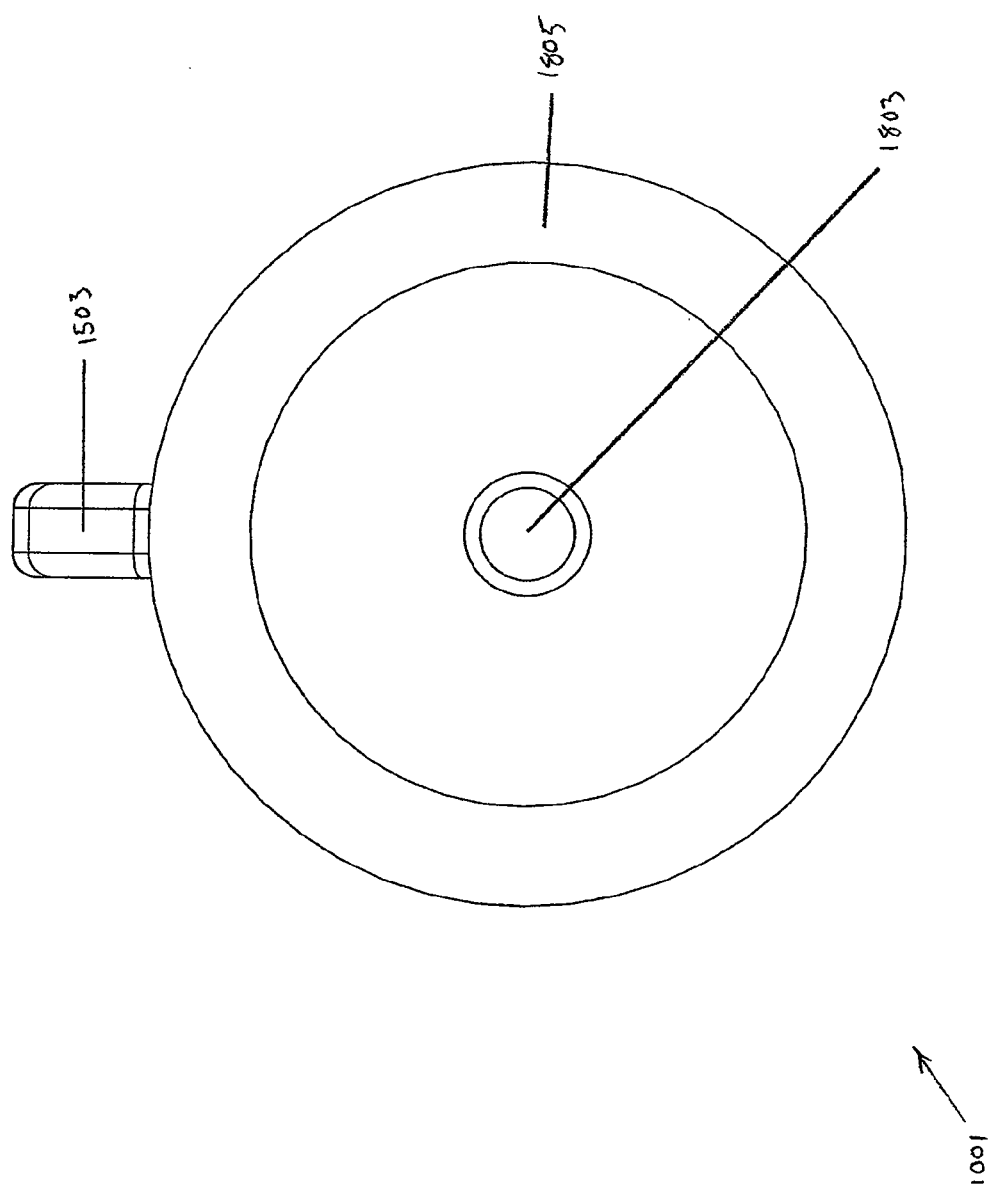

The force adjustment mechanism includes large knob 1805 mounted to the handle mechanism 1601 via the adjustment shaft 1803 shown in FIGS. 73 and 83. The knob 1805 is mounted on the most proximal end of the inserter 1001 as shown in FIGS. 88 and 89.

Figure 81:
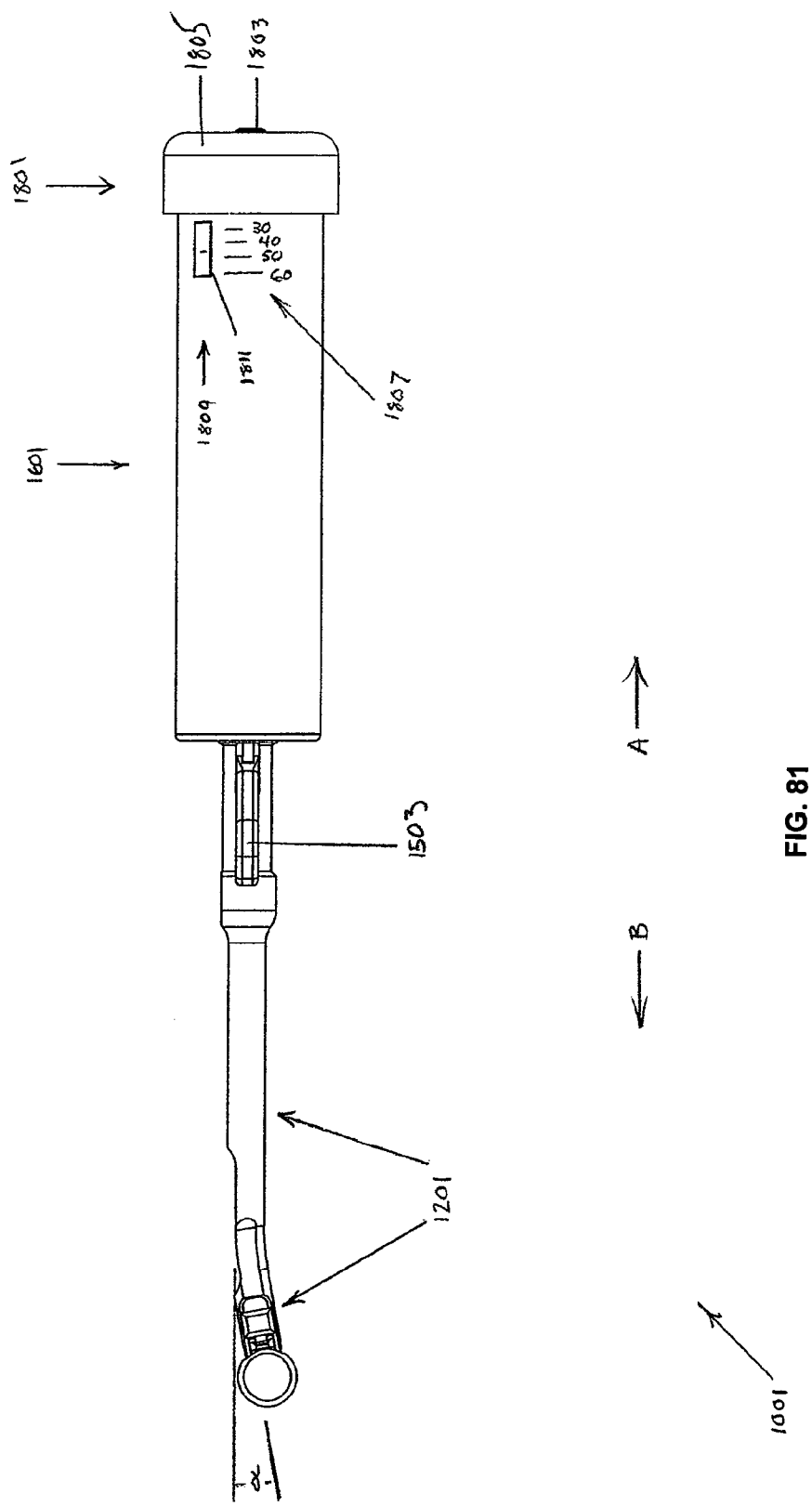
FIG. 81 is a plan view of the expandable sizing instrument showing the distraction force indicator disposed on the handle thereof.

As shown in FIGS. 81 and 82, the force adjustment knob 1805 utilizes handle markings 1807 to indicate the amount of distraction force. Preferably, the knob 1805 is rotated until the plug marking 1809 reaches the desired handle marking 1807 which corresponds to a precise amount of distraction force. The plug marking 1809 is preferably a laser etching on the orientation plug 1711 shown in FIGS. 77 and 87. The plug marking is visible through an aperture 1811 in the handle grip 1609 as shown in FIGS. 81 and 82.

As shown in FIGS. 77 and 87, the rotation of the knob 1805 causes the adjustment shaft 1803 to rotate and compress the spring 1703 and thus causes adjustment of the amount of force generated by the force mechanism 1701, as described above. The force adjustment mechanism 1801 is made of stainless steel in its preferred embodiment. Alternatively, an internal scale within the handle mechanism 1601 could be used.

The inserter 1001 can be manufactured by standard turning, milling, and Electro Discharge Machining (EDM). Alternatively, the inserter 1001 can be made from any suitable, structurally strong materials. The inserter 1001 can be constructed of suitable materials which are compatible with the uses and environments into which the device will be utilized. Preferably, the inserter 1001 is constructed of metallic materials such as stainless steel or titanium. The best mode of sterilizing the expandable space inserter 1001 is by sterilization through autoclave, i.e. steam.

The surgical procedure begins with sterilizing the surgical field and inserter 1001. Once the patient is anesthetized, a surgical incision is made in the patient from one of three basic approaches based on the surgeon's preference: 1) an anterior approach, i.e. from the front of the patient, 2) laterally, i.e. from the side of the patient, or 3) posteriorly, i.e. from the back of the patient. Once the incision is made the surrounding tissue is distracted or moved out of the way using standard instruments and methodology.

The installation site of the implant is prepared by removing the damaged tissue of the intervertebral disc 2301, i.e. a discectomy. The discectomy can be either a complete discectomy in which the entire disc is removed or a partial discectomy where the nucleus pulposus is removed and the annulus fibrosus is punctured. A full discectomy is more typical for the implantation of a spinal cage, Vertebral Body Replacement (VBR), or Interbody Fusion Device (IDF). A partial discectomy is more typical for the implantation of a DNP. In either procedure, the disc material is removed with a ring curette which cuts out the disc.

For the implantation of a DNP, the annulus fibrosus is punctured and the nucleus pulposus is removed. There typically is not surface preparation of the endplates 2401. For a VBR/IDF, the endplates of the vertebra are typically roughened with the use of a rasp because of the need to remove all disc material and to encourage blood flow and healing in the intervertebral space 2101. The roughening of the endplates 2401 flattens the surface of the vertebrae 2401 to conform to the surface of the implant thus reducing the risk that the implant will shift out of position.

The expandable sizing instrument 1001 surgical instrument is then deployed to determine the height and angles of the endplates 2401 in the intervertebral space 2101. The first step comprises adjusting the force adjustment mechanism 1801 by rotating the knob 1805 and setting the desired amount of distraction force as shown in FIG. 91. The distal end of the spacer mechanism 1101 is then inserted and positioned within the intervertebral space 2101. The actuator mechanism 1501 is deployed by moving the lever 1503 to cause the spacer mechanism 1101 to expand in the intervertebral space 2101. The operator of the inserter 1001, typically the surgeon, will then read the amount of intervertebral space, i.e. the distance between the vertebrae 2501, by viewing the indicator mechanism 1401. Alternatively, the force adjustment mechanism 1801 can be adjusted by rotating the knob 1805 while the spacer mechanism 1101 is within an intervertebral space 2101. Fluoroscopy can then be performed by taking and developing an x-ray or fluoroscopy image while the inserter 1001 is in a fixed position to determine the lordotic angle of the vertebrae 2501. After the invertebral space has been measured, the pads 1103 are retracted by pushing the actuator 1501 distally and the measuring head 1100 is removed from the intervertebral space. A properly sized implant is then selected and inserted as known in the art.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What we claim is:

1. An instrument for measuring the size of an intervertebral space, the instrument comprising: a handle portion; an elongate shaft portion having a proximal end, a distal end and a longitudinal axis extending therebetween, the elongate shaft portion is connected to the handle portion at the proximal end;
an actuator connected to the elongate shaft portion; and
upper and lower pad members each nonreleasably connected to the distal end of the elongate shaft portion via elongate link members such that the upper and lower pad members cannot be released from the elongate shaft portion while inserted within the intervertebral space for a measuring operation, the upper and lower pad members are configured for movement between an unexpanded orientation with the upper and lower pad members adjacent one another and a distracted orientation with the upper and lower pad members distracted apart to shift away from the longitudinal axis of the elongate shaft portion in a transverse direction relative thereto and from one another via actuation of the actuator in a first direction wherein the elongate shaft is slidably shifted along the longitudinal axis of the elongate shaft portion in a corresponding direction along the axis and causes the pads to distract apart from one another and the longitudinal axis via shifting in the transverse direction, and back to an unexpanded orientation via actuation of the actuator in a second direction opposite the first direction, wherein the elongate shaft is slidably shifted in the opposite direction along the longitudinal axis of the elongate shaft portion and causes the pads to retract toward one another and the longitudinal axis via shifting in the transverse direction; wherein each of the upper and lower pad members is connected to the respective elongate link member by a polyaxial connection such that the pad members are further configured for polyaxial movement relative to the distal end of the elongate shaft portion, with one of the upper and lower pad members configured to rotate in a first direction about a first axis and in a second direction about a second axis, wherein the first and second axes are different from one another, and the other of the upper and lower pad members configured to rotate in a third direction about a third axis and in a fourth direction about a fourth axis, wherein the third and fourth axes are different from one another and from the first and second axes, for allowing each pad member to shift polyaxially independent from movement of the other pad member and the handle portion such that each pad member is adapted for conforming with an endplate of an adjacent vertebra independent of the other pad member such that together the upper and lower pad members are adapted to determine the size of the intervertebral space and relative orientation of the endplates of the adjacent vertebrae from a plurality of different approaches relative to the intervertebral space.

2. The instrument of claim 1, wherein the first and second axes are transverse to one another, and the third and fourth axes are transverse to one another.

3. The instrument of claim 1, wherein the polyaxial connection includes each pad member being connected to the respective elongate link member with a pivotable pin member having two degrees of freedom, such that the one pad member configured to pivot about the first and second axes and the other pad member is configured to pivot about the third and fourth axes independently and simultaneously to conform with the endplates of the adjacent vertebra when the instrument is inserted into the intervertebral space at a plurality of approaches with respect thereto.

4. The instrument of claim 1, wherein the elongate link members are upper and lower link members connected to the upper and lower pad members via pin members, the link members being configured for moving the pad members between their unexpanded and distracted orientations.

5. The instrument of claim 4, wherein each of the elongate link members comprises a throughbore having central narrow portion and outer wider portions through which one of the pin members is disposed for allowing opposite ends of the pin member to pivot generally about the central narrow portion about an axis transverse to a longitudinal axis of the pin member for allowing each pad member to pivot generally about the central narrow portion and rotate about the longitudinal axis of the pin member.

6. The instrument of claim 1, wherein the pad members are sized and configured for insertion through an incision in an annulus when in the unexpanded orientation.

7. The instrument of claim 1, further comprising a biasing member in engagement with the upper and lower pad members which biases the upper and lower pad members towards a distracted orientation with a predetermined amount of distraction force.

8. The instrument of claim 7, further comprising an adjustable tensioning member connected to the biasing member, wherein the predetermined amount of force is selectable via adjustment of the force adjustment member between a first position, wherein the force adjustment member causes a first distraction force to be exerted by the biasing member and a second position, wherein the force adjustment member causes a second distraction force to be exerted by the biasing member.

9. The instrument of claim 1, further comprising a gauge connected to the upper and lower pad members for indicating the size of the intervertebral space corresponding with the distance between the upper and lower pad members.

10. The instrument of claim 4, further comprising an opener pin configured to engage with cam surfaces on each of the upper and lower link members to cause the upper and lower link members to shift the upper and lower pad members apart from one another when the elongate shaft portion is slidably shifted along the longitudinal axis.

* * * * *